(12) United States Patent
Klenke et al.

(10) Patent No.: US 9,556,165 B2
(45) Date of Patent: Jan. 31, 2017

(54) AMIDINE SUBSTITUTED β-LACTAM COMPOUNDS, THEIR PREPARATION AND USE AS ANTIBACTERIAL AGENTS

(71) Applicant: AiCuris GmbH & Co. KG, Wuppertal (DE)

(72) Inventors: Burkhard Klenke, Wuppertal (DE); Irith Wiegand, Wuppertal (DE); Guido Schiffer, Wuppertal (DE); Heike Broetz-Oesterhelt, Wuppertal (DE); Samarendra N. Maiti, Edmonton (CA); Jehangir Khan, Edmonton (CA); Andhe Reddy, Edmonton (CA); Zhixiang Yang, Edmonton (CA); Mostafa Hena, Edmonton (CA); Guofeng Jia, Edmonton (CA); Ou Ligong, Edmonton (CA); Hong Liang, Edmonton (CA); Judy Yip, Edmonton (CA); Chuanjun Gao, Edmonton (CA); Sabiha Tajammul, Edmonton (CA); Rahim Mohammad, Edmonton (CA); Ganguli Biswajeet, Edmonton (CA)

(73) Assignee: AiCuris GmbH & Co. KG, Wuppertal (DE)

( * ) Notice: Subject to any disclaimer, the term of this patent is extended or adjusted under 35 U.S.C. 154(b) by 0 days.

(21) Appl. No.: 14/374,325

(22) PCT Filed: Jan. 23, 2013

(86) PCT No.: PCT/EP2013/051217
§ 371 (c)(1),
(2) Date: Jul. 24, 2014

(87) PCT Pub. No.: WO2013/110643
PCT Pub. Date: Aug. 1, 2013

(65) Prior Publication Data
US 2015/0045340 A1 Feb. 12, 2015

(30) Foreign Application Priority Data
Jan. 24, 2012 (EP) ..................... 12152279

(51) Int. Cl.
| A61K 31/433 | (2006.01) |
| C07D 417/14 | (2006.01) |
| A61K 31/427 | (2006.01) |
| C07D 417/12 | (2006.01) |
| A61K 31/4178 | (2006.01) |
| A61K 31/4439 | (2006.01) |
| A61K 31/454 | (2006.01) |
| A61K 31/496 | (2006.01) |
| A61K 31/497 | (2006.01) |
| A61K 31/501 | (2006.01) |
| A61K 31/506 | (2006.01) |
| A61K 45/06 | (2006.01) |

(52) U.S. Cl.
CPC ......... *C07D 417/14* (2013.01); *A61K 31/4178* (2013.01); *A61K 31/427* (2013.01); *A61K 31/433* (2013.01); *A61K 31/4439* (2013.01); *A61K 31/454* (2013.01); *A61K 31/496* (2013.01); *A61K 31/497* (2013.01); *A61K 31/501* (2013.01); *A61K 31/506* (2013.01); *A61K 45/06* (2013.01); *C07D 417/12* (2013.01)

(58) Field of Classification Search
CPC . C07D 417/14; C07D 417/12; C07D 205/085; A61K 31/4439
See application file for complete search history.

(56) References Cited

U.S. PATENT DOCUMENTS

| 5,994,340 A | 11/1999 | Maiti et al. |
| 6,916,803 B2 | 7/2005 | Micetich et al. |
| 8,486,929 B2 | 7/2013 | Desarbre et al. |
| 2004/0019203 A1 | 1/2004 | Micetich et al. |
| 2010/0144699 A1 | 6/2010 | Desarbre et al. |
| 2013/0274238 A1 | 10/2013 | Desarbre et al. |

FOREIGN PATENT DOCUMENTS

| WO | 9910324 A1 | 3/1999 |
| WO | 0222613 A1 | 3/2002 |
| WO | 2008116813 A2 | 10/2008 |

OTHER PUBLICATIONS

Byrn, Stephen. Solid-State Chemistry of Drugs, 2nd edition (1999). Chapter 11 Hydrates and Solvates/hydrates, 233-247.*
Morissette, Sherry. Adv. Drug Delivery Rev. 2004, 56, 275-300.*
Rouhi, Maureen A. Chem. & Eng. News, (2003), 81(8), 32-35.*
MedicineNet.com. Brain Cancer. (2015) <http://www.medicinenet.com/brain_cancer/page9.htm>.*
Ryan, David. Livestrong.com. How to Prevent Bacterial Diseases. (2013). < http://www.livestrong.com/article/17349-prevent-bacterial-diseases/>.*
MedicineNet.com. Definition of Cancer. (2004). <http://www.medterms.com>.*
International Search Report for PCT/EP2013/051217 dated Feb. 26, 2013.

* cited by examiner

*Primary Examiner* — Golam M M Shameem
*Assistant Examiner* — Laura Daniel
(74) *Attorney, Agent, or Firm* — Millen White Zelano and Branigan, PC; John Sopp; Anthony Zelano

(57) ABSTRACT

The present invention relates to novel β-lactam compounds, their preparation and use. In particular, this invention relates to novel β-lactam compounds which are amidine substituted monobactam derivatives useful as antimicrobial agents and their preparation.

17 Claims, No Drawings

AMIDINE SUBSTITUTED β-LACTAM COMPOUNDS, THEIR PREPARATION AND USE AS ANTIBACTERIAL AGENTS

This invention relates to novel β-lactam compounds, their preparation and use. In particular, this invention relates to novel β-lactam compounds which are amidine substituted monobactam derivatives useful as antimicrobial agents and their preparation.

Public health experts and officials consider the emergence and spread of antibiotic resistant bacteria as one of the major public health problems of the 21st century. Although not a new phenomenon per se, the spread of antibiotic resistant bacteria has reached an unprecedented dimension. While the most resistant isolates continue to emerge in the hospital setting, physicians and epidemiologists are encountering increasing numbers of resistant bacteria in the community among people without previous healthcare contact. The number of patients who are dying from untreatable nosocomial infections continues to grow. Therapeutic options are especially limited for infections due to multi-drug-resistant Gram-negative pathogens including Enterobacteriaceae and non-fermenters, a situation made worse by the fact that the pipelines of the pharmaceutical industry contain few compounds with promising resistance breaking profiles (H. W. Boucher et al.; Bad bugs, no drugs: No ESKAPE! An update from the Infectious Diseases Society of America; Clin Inf Dis 2009, 48, 1-12).

The highly successful and well-tolerated class of β-lactam antibiotics has historically been one mainstay for the treatment of infections caused by Gram-negative pathogens. Among these especially 3rd-generation cephalosporins, carbapenems and monobactams are extensively used for the treatment of infections with Gram-negative bacteria. However, a vast array of more than 1000 β-lactamases (a constantly updated list of β-lactamases can be found under www.lahey.org/Studies/) and further resistance mechanisms severely endanger the mid-term usability of the current compounds in these subclasses. Especially extended-spectrum β-lactamases (ESBLs) and carbapenemases are important drivers of resistance. New β-lactams with resistance breaking properties are urgently needed to fill the gap.

With aztreonam as the single FDA approved monobactam used worldwide and a second analogue marketed exclusively in Japan (tigemonam), the monobactams are a clearly under-explored subclass among the β-lactams. Reviews on aztreonam are available: W. C. Hellinger, N. S. Brewer; Carbapenems and Monobactams-Imipenem, Meropenem and Aztreonam; Mayo Clin. Proc. 1999, 74, 420-434. R. B. Sykes, D. P. Bonner; Discovery and Development of the monobactams; Rev. Infect. Dis. 1985, 7 (Suppl. 4), 579-593.

The attempt to enhance the cellular uptake of the β-lactams by using iron-siderophore uptake systems in microorganisms is one concept that has been explored in the monobactam field by Basilea (WO 2007065288), Naeja Pharmaceuticals (WO 2002022613) and Squibb & Sons (U.S. Pat. No. 5,290,929, EP 531976, EP 484881). The heteroaryl units mimicing siderophores can also be attached to the side-chain as hydrazides as demonstrated by Squibb & Sons (U.S. Pat. No. 5,318,963, U.S. Pat. No. 5,112,968). Recently, Pfizer re-investigated monocarbams, monocyclic β-lactams that carry a sulfonylaminocarbonyl activating group at the N1-position (WO 2010070523). Additionally, in WO 2008116813 Basilea has described combination therapy approaches using a combination of monobactams with carbapenems.

In view of the increasing resistance development of pathogenic bacteria against known antibacterial agents, including multiple resistances, there is an ongoing need to find novel antibacterial substances, in particular compounds that have different structural motives.

The present invention relates to compounds of formula (I)

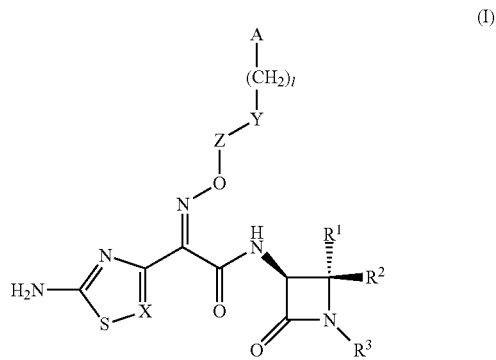

in which
R$^1$ and R$^2$ independently of one another represent hydrogen, aminocarbonyl or (C$_1$-C$_4$)-alkyl, or
R$^1$ and R$^2$ together with the carbon atom to which they are bonded form a (C$_3$-C$_8$)-cycloalkyl,
R$^3$ represents —(CH$_2$)$_m$—(SO$_2$)OH or —O—(CH$_2$)$_o$—(SO$_2$)OH,
  wherein m and o independently of one another represent an integer 0, 1, 2 or 3, and
  wherein any CH$_2$-group contained in the residues which R$^3$ represents may be substituted with one or two (C$_1$-C$_4$)-alkyl-residues,
X represents CR$^4$ or N,
R$^4$ represents hydrogen or halogen,
Z represents a bond or an alkyl-chain having one, two, three or four carbon atoms,
  whereby the alkyl-chain may be substituted with one, two, three or four substituents, selected independently of one another from the group consisting of carboxy, aminocarbonyl and (C$_1$-C$_4$)-alkyl,
  whereby alkyl in turn may be substituted with a substituent selected from the group consisting of hydroxy, carboxy and aminocarbonyl,
Y represents a bond, O, NH or S,
A represents (C$_6$-C$_{10}$)-aryl or 5- to 10-membered heteroaryl,
  whereby aryl and heteroaryl are substituted with a substituent of the following formula

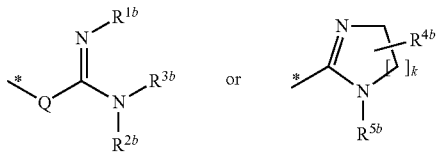

wherein
R$^{1b}$, R$^{2b}$ and R$^{3b}$ independently of one another represent hydrogen, amino, hydroxy, (C$_1$-C$_4$)-alkyl, (C$_1$-C$_4$)-alkoxy, (C$_3$-C$_6$)-cycloalkyl, 4-, 5-, 6- or 7-membered heterocyclyl or 5- or 6-membered heteroaryl, whereby amino and hydroxy may be substituted with one or two substituents selected independently of one another from the group consisting of carbonyl, ($C_1$-$C_4$)-alkylcarbonyl, mono- or di-($C_1$-$C_4$)-alkylaminocarbonyl, and ($C_1$-$C_4$)-alkyl,
whereby alkoxy, heterocyclyl and heteroaryl may be substituted with one, two or three substituents selected independently of one another from the group consisting of halogen, hydroxy, amino, carbonyl, carboxy, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)(NH$_2$), —C(=NH)CH$_3$ and ($C_1$-$C_4$)-alkyl, and
whereby alkyl and cycloalkyl may be substituted with one, two or three substituents selected independently of one another from the group consisting of halogen, hydroxy, amino, carbonyl, carboxy, carbonyloxy, aminocarbonyl, carbonylamino, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)(NH$_2$), —CH(=NH)CH$_3$, ($C_6$-$C_{10}$)-aryl, 5- or 6-membered heteroaryl and 5- or 6-membered heterocyclyl,
whereby heteroaryl and heterocyclyl in turn may be substituted with ($C_1$-$C_4$)-alkyl,
whereby amino in turn may be substituted with 5- or 6-membered heteroaryl, or
$R^{2b}$ and $R^{3b}$ together with the nitrogen atom to which they are bonded form a 5- to 7-membered heterocycle including one, two or three further heteroatoms selected from the series N, O and S and $R^{1b}$ is as defined above,
$R^{4b}$ represents hydrogen, amino, hydroxy, ($C_1$-$C_4$)-alkyl or ($C_1$-$C_4$)-alkoxy,
whereby amino and hydroxy may be substituted with one or two substituents selected independently of one another from the group consisting of ($C_1$-$C_4$)-alkylcarbonyl, mono- or di-($C_1$-$C_4$)-alkylaminocarbonyl and ($C_1$-$C_4$)-alkyl,
whereby alkoxy may be substituted with one, two or three substituents selected independently of one another from the group consisting of halogen, hydroxy, amino, carbonyl, carboxy, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)(NH$_2$), —CH(=NH)CH$_3$ and ($C_1$-$C_4$)-alkyl, and
whereby alkyl may be substituted with one, two or three substituents selected independently of one another from the group consisting of halogen, hydroxy, amino, carbonyl, carboxy, aminocarbonyl, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)(NH$_2$), —CH(=NH)CH$_3$, ($C_1$-$C_4$)-alkyl, ($C_6$-$C_{10}$)-aryl and 5- or 6-membered heteroaryl,
$R^{5b}$ represents hydrogen or ($C_1$-$C_4$)-alkyl,
Q represents a bond, CH$_2$ or NH,
k represents an integer 1 or 2, and
* is the linkage site to the residue represented by A, and
whereby aryl and heteroaryl further may be substituted with one or two substituents selected independently of one another from the group consisting of halogen, cyano, amino, hydroxy, ($C_1$-$C_4$)-alkyl, ($C_1$-$C_4$)-alkoxy, mono- or di-($C_1$-$C_4$)-alkylamino, amino-($C_1$-$C_4$)-alkyl, hydroxy-($C_1$-$C_4$)-alkyl or carboxy,
whereby alkyl, alkoxy, alkylamino, aminoalkyl, hydroxyalkyl and carboxy in turn may be substituted with a substituent selected from the group consisting of halogen, ($C_1$-$C_4$)-alkyl and carbonyl, and
l represents an integer 0, 1, 2 or 3,
and the salts thereof, the solvates thereof and the solvates of the salts thereof.

Compounds of the invention are the compounds of formula (I) and the salts, solvates and solvates of the salts thereof, as well as the compounds which are encompassed by formula (I) and are mentioned hereinafter as exemplary embodiment(s), and the salts, solvates and solvates of the salts thereof, insofar as the compounds encompassed by formula (I) and mentioned hereinafter are not already salts, solvates and solvates of the salts.

The compounds of the invention may, depending on their structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Examples of pharmaceutically acceptable salts of the compounds of formula (I) include salts of inorganic bases like ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethanolamine, diethylamine, triethylamine, ethylenediamine, procaine, morpholine, pyrroline, piperidine, N-ethylpiperidine, N-methylmorpholine, piperazine as the organic base; or salts with basic amino acids, in particular lysine, arginine, ornithine and histidine.

Examples of pharmaceutically acceptable salts of the compounds of formula (I) also include salts of inorganic acids like hydrochlorides, hydrobromides, sulfates, phosphates or phosphonates; salts of organic acids, in particular acetates, formates, propionates, lactates, citrates, fumarates, maleates, benzoates, tartrates, malates, methanesulfonates, ethanesulfonates, toluenesulfonates or benzenesulfonates; or salts with acidic amino acids, in particular aspartate or glutamate.

Solvates for the purposes of the invention refer to those forms of the compounds of the invention which in the solid or liquid state form a complex by coordination with solvent molecules. Hydrates are a specific form of solvates in which the coordination takes place with water.

In the context of this invention the substituents have the following definitions unless specified otherwise.

The term alkyl refers to branched or straight-chain ($C_1$-$C_6$)-alkyl, preferably ($C_1$-$C_4$)-alkyl, such as in particular methyl, ethyl, propyl, butyl, isopropyl, isobutyl and tert.-butyl. The term alkylamino refers to an alkyl substituent linked via an amino group. The term alkylcarbonyl refers to an alkyl substituent linked via a carbonyl group. The term alkylaminocarbonyl refers to an alkylamino substituent linked via a carbonyl group.

The term cycloalkyl refers to aliphatic $C_3$-$C_8$, preferably $C_3$-$C_6$, rings such as in particular cyclopropyl, cyclobutyl, cyclopentyl and cyclohexyl.

The term alkoxy refers to branched or straight-chain ($C_1$-$C_6$)-alkoxy, preferably ($C_1$-$C_4$)-alkoxy, such as in particular methoxy, ethoxy, propoxy, butoxy, isopropoxy, isobutoxy and tert.-butoxy. The term alkoxycarbonyl refers to an alkoxy substituent linked via a carbonyl group.

The term heteroaryl refers to cyclic heteroaromatic groups with 5-10 ring atoms, preferably with 5-6 ring atoms, and with up to 4, preferably with up to 2, heteroatoms selected from the group consisting of N, O, S, in which N can also form an N-oxide. Preferred are monocyclic heteroaryl groups with 5-6 ring atoms including up to 2 hetero atoms selected from the group consisting of N, O and S, such as in particular thiophene, benzothiophene, furan, benzofuran, pyrrole, pyrazole, imidazole, thiazole, thiadiazole, oxazole, isoxazole, pyridine, pyrazine, pyrimidine, pyridazine, indole, isoindole, purine, quinoline or isoquinoline. Many other suitable heteroaryl groups for the purpose of the invention are known to the person skilled in the art or can be readily found in the literature.

The term heterocyclyl refers to saturated or partially unsaturated heterocyclic groups with 4-10 ring atoms, preferably with 5-6 ring atoms, and with up to 3, preferably with up to 2, heteroatoms selected from the group consisting of N, O, S, SO and $SO_2$, in which N can also form an N-oxide. Preferred are saturated monocyclic heterocyclyl groups with 5-6 ring atoms including up to 2 hetero atoms selected from the group consisting of N, O and S, such as in particular pyrrolidine, pyrroline, tetrahydrofuran, tetrahydrothiophene, thiazolidine, imidazolidine, imidazoline, piperidine, pyran, tetrahydropyran, thiopyran, tetrahydrothiopyran, morpholine, thiomorpholine, piperazine, piperidazine. Many other suitable heterocyclyl groups for the purpose of the invention are known to the person skilled in the art or can be readily found in the literature.

The term halogen refers to fluorine, chlorine, bromine or iodine; preferably fluorine or chlorine.

The term aminocarbonyl refers to an amino group linked via a carbonyl group.

The term carbonylamino refers to a carbonyl group linked via an amino group.

The term carboxy refers to a carboxylic acid group, i.e. a —COOH group.

The term carbonyloxy refers to a carbonyl group linked via an oxygen.

The present invention also relates to compounds of formula (I) in which $R^1$ and $R^2$ independently of one another represent hydrogen or ($C_1$-$C_4$)-alkyl, or $R^1$ and $R^2$ together with the carbon atom to which they are bonded form a ($C_3$-$C_8$)-cycloalkyl, $R^3$ represents —$(CH_2)_m$—$(SO_2)OH$ or —O—$(CH_2)_o$—$(SO_2)OH$, wherein m and o independently of one another represent an integer 0, or 1 and wherein any $CH_2$-group contained in the residues which $R^3$ represents may be substituted with one or two ($C_1$-$C_4$)-alkyl-residues, X represents $CR^4$ or N, $R^4$ represents hydrogen or halogen, Z represents a bond or an alkyl-chain having one, two or three carbon atoms, whereby the alkyl-chain may be substituted with one, two or three substituents, selected independently of one another from the group consisting of carboxy, aminocarbonyl and ($C_1$-$C_4$)-alkyl, whereby alkyl in turn may be substituted with a substituent selected from the group consisting of hydroxy and carboxy, Y represents a bond, O, NH or S, A represents ($C_6$-$C_{10}$)-aryl or 5- to 10-membered heteroaryl, whereby aryl and heteroaryl are substituted with a substituent of the following formula

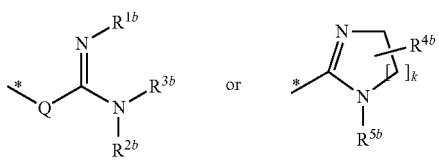

wherein $R^{1b}$, $R^{2b}$ and $R^{3b}$ independently of one another represent hydrogen, amino, hydroxy, ($C_1$-$C_4$)-alkyl, 4-, 5-, 6- or 7-membered heterocyclyl or 5- or 6-membered heteroaryl, whereby heterocyclyl and heteroaryl may be substituted with one, two or three substituents selected independently of one another from the group consisting of halogen, hydroxy, amino, carbonyl, carboxy, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)($NH_2$), —C(=NH)$CH_3$ and ($C_1$-$C_4$)-alkyl, and whereby alkyl may be substituted with one, two or three substituents selected independently of one another from the group consisting of halogen, hydroxy, amino, carbonyl, carboxy, carbonyloxy, aminocarbonyl, carbonylamino, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)($NH_2$), —CH(=NH)$CH_3$, ($C_6$-$C_{10}$)-aryl, 5- or 6-membered heteroaryl and 5- or 6-membered heterocyclyl, whereby heteroaryl and heterocyclyl in turn may be substituted with ($C_1$-$C_4$)-alkyl, or $R^{2b}$ and $R^{3b}$ together with the nitrogen atom to which they are bonded form a 5- to 7-membered heterocycle including one, two or three further heteroatoms selected from the series N, O and S and $R^{1b}$ is as defined above, $R^{4b}$ represents hydrogen, amino, hydroxy, ($C_1$-$C_4$)-alkyl or ($C_1$-$C_4$)-alkoxy, whereby amino and hydroxy may be substituted with one or two substituents selected independently of one another from the group consisting of ($C_1$-$C_4$)-alkylcarbonyl, mono- or di-($C_1$-$C_4$)-alkylaminocarbonyl and ($C_1$-$C_4$)-alkyl, and whereby alkyl may be substituted with one, two or three substituents selected independently of one another from the group consisting of halogen, hydroxy, amino, carbonyl, carboxy, aminocarbonyl, ($C_1$-$C_4$)-alkylcarbonyl, ($C_1$-$C_4$)-alkoxy, mono- or di-($C_1$-$C_4$)-alkylamino, mono- or di-($C_1$-$C_4$)-alkylaminocarbonyl, —NH—CH(=NH), —NH—C(=NH)($NH_2$), —CH(=NH)$CH_3$, ($C_1$-$C_4$)-alkyl, ($C_6$-$C_{10}$)-aryl and 5- or 6-membered heteroaryl, $R^{5b}$ represents hydrogen or $(C_1-C_4)$-alkyl,
Q represents a bond, $CH_2$ or NH,
k represents an integer 1 or 2, and
* is the linkage site to the residue represented by A, and
whereby aryl and heteroaryl further may be substituted with one or two substituents selected independently of one another from the group consisting of halogen, cyano, amino, hydroxy, $(C_1-C_4)$-alkyl, $(C_1-C_4)$-alkoxy, mono- or di-$(C_1-C_4)$-alkylamino, amino-$(C_1-C_4)$-alkyl, hydroxy-$(C_1-C_4)$-alkyl or carboxy,
whereby alkyl, alkoxy, alkylamino, aminoalkyl, hydroxyalkyl and carboxy in turn may be substituted with a substituent selected from the group consisting of halogen, $(C_1-C_4)$-alkyl and carbonyl, and
l represents an integer 0 or 1
and the salts thereof, the solvates thereof and the solvates of the salts thereof.

The present invention also relates to compounds of formula (I) in which
$R^1$ and $R^2$ independently of one another represent hydrogen or $(C_1-C_4)$-alkyl, or
$R^1$ and $R^2$ together with the carbon atom to which they are bonded form a $(C_3-C_8)$-cycloalkyl,
$R^3$ represents —$(SO_2)OH$ or —O—$(CH_2)_o$—$(SO_2)OH$,
wherein o is an integer 0 or 1, and
wherein any $CH_2$-group contained in the residues which $R^3$ represents may be substituted with one or two $(C_1-C_4)$-alkyl-residues,
X represents CH,
Z represents an alkyl-chain having two or three carbon atoms,
whereby the alkyl-chain may be substituted with one or two substituents selected independently of one another from the group consisting of carboxy, aminocarbonyl, methyl, hydroxymethyl, hydroxyethyl,
Y represents O
A represents phenyl or 5- or 6-membered heteroaryl,
whereby phenyl and heteroaryl are substituted with a substituent of the following formula

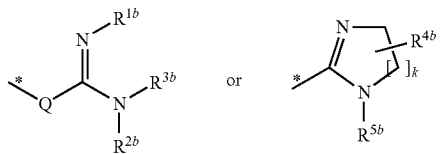

wherein
$R^{1b}$, $R^{2b}$ and $R^{3b}$ independently of one another represent hydrogen, amino, hydroxy, $(C_1-C_4)$-alkyl or 4-, 5-, 6- or 7-membered heterocyclyl,
whereby heterocyclyl may be substituted with one or two substituents selected independently of one another from the group consisting of amino, carboxy, mono- or di-$(C_1-C_4)$-alkylamino, and $(C_1-C_4)$-alkyl, and
whereby alkyl may be substituted with one or two substituents selected independently of one another from the group consisting of hydroxy, amino, carboxy, carbonyloxy, aminocarbonyl, carbonylamino, mono- or di-$(C_1-C_4)$-alkylamino, mono- or di-$(C_1-C_4)$-alkylaminocarbonyl, —NH—CH(=NH), —NH—C(=NH)—($NH_2$), phenyl, 6-membered heteroaryl and 5- or 6-membered heterocyclyl, or $R^{2b}$ and $R^{3b}$ together with the nitrogen atom to which they are bonded form a 6-membered heterocycle including one or two nitrogen atoms and $R^{1b}$ is hydrogen,
$R^{4b}$ represents hydrogen or amino,
whereby amino may be substituted with one or two $(C_1-C_4)$-alkyl substituents,
$R^{5b}$ represents hydrogen,
Q represents a bond,
k represents an integer 1 or 2, and
* is the linkage site to the residue represented by A, and
whereby phenyl and heteroaryl further may be substituted with one or two substituents selected independently of one another from the group consisting of halogen, cyano, amino, hydroxy, $(C_1-C_4)$-alkyl or hydroxy-$(C_1-C_4)$-alkyl,
whereby hydroxyalkyl in turn may be substituted with a carbonyl substituent, and
l represents 0
and the salts thereof, the solvates thereof and the solvates of the salts thereof.

The present invention also relates to compounds of formula (I) in which
$R^1$ and $R^2$ independently of one another represent hydrogen or methyl,
$R^3$ represents —$(SO_2)OH$ or —O—$(SO_2)OH$,
X represents CH,
Z represents an alkyl-chain having two or three carbon atoms,
whereby the alkyl-chain may be substituted with one or two substituents, selected independently of one another from the group consisting of carboxy and methyl,
Y represents O,
A represents phenyl or 6-membered heteroaryl,
whereby phenyl and heteroaryl are substituted with a substituent of the following formula

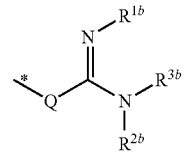

wherein
$R^{1b}$ and $R^{2b}$ represent hydrogen,
$R^{3b}$ represents hydrogen, amino, hydroxy, $(C_1-C_4)$-alkyl or 4-, 5- or 6-membered nitrogen-containing heterocyclyl,
whereby alkyl may be substituted with a substituent selected from the group consisting of hydroxy, amino, carboxy, carbonyloxy, mono- or di-$(C_1-C_4)$-alkylamino, —NH—CH(=NH), —NH—C(=NH)($NH_2$), 5- or 6-membered nitrogen-containing heteroaryl and 5- or 6-membered nitrogen-containing heterocyclyl,
Q represents a bond,
* is the linkage site to the residue represented by A, and
whereby aryl and heteroaryl further may be substituted with one substituent selected from the group consisting of halogen, cyano, amino, hydroxy, $(C_1-C_4)$-alkyl or hydroxy-$(C_1-C_4)$-alkyl
l represents 0
and the salts thereof, the solvates thereof and the solvates of the salts thereof.

The present invention also relates to compounds of formula (I) in which
R¹ and R² represent methyl,
R³ represents —O—(SO₂)OH,
X represents CH,
Z represents an alkyl-chain having two carbon atoms, whereby the alkyl-chain may be substituted with a carboxy substituent,
Y represents O,
A represents phenyl substituted with a substituent of the following formula

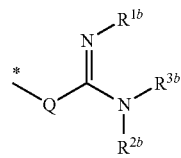

wherein
$R^{1b}$ and $R^{2b}$ represent hydrogen,
$R^{3b}$ represents aminoethyl, azetidine, pyrrolidine or piperidine,
Q represents a bond,
* is the linkage site to the residue represented by A, and
l represents 0
and the salts thereof, the solvates thereof and the solvates of the salts thereof.

The present invention also relates to compounds of formula (I) in which
R¹ and R² represent methyl,
R³ represents —O—(SO₂)OH,
X represents CH,
Z represents a two carbon alkyl-chain, substituted with a carboxy substituent,
Y represents O,
A represents phenyl substituted with a substituent of the following formula

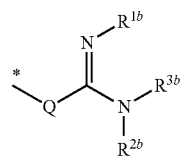

wherein
$R^{1b}$ and $R^{2b}$ represent hydrogen,
$R^{3b}$ represents aminoethyl, azetidine, pyrrolidine or piperidine,
Q represents a bond,
* is the linkage site to the residue represented by A, and
l represents 0
and the salts thereof, the solvates thereof and the solvates of the salts thereof.

In particular the present invention relates to compounds of formula (I) in which
A represents a group selected from the following formulae

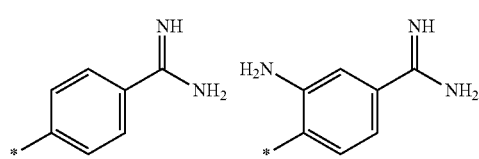

-continued

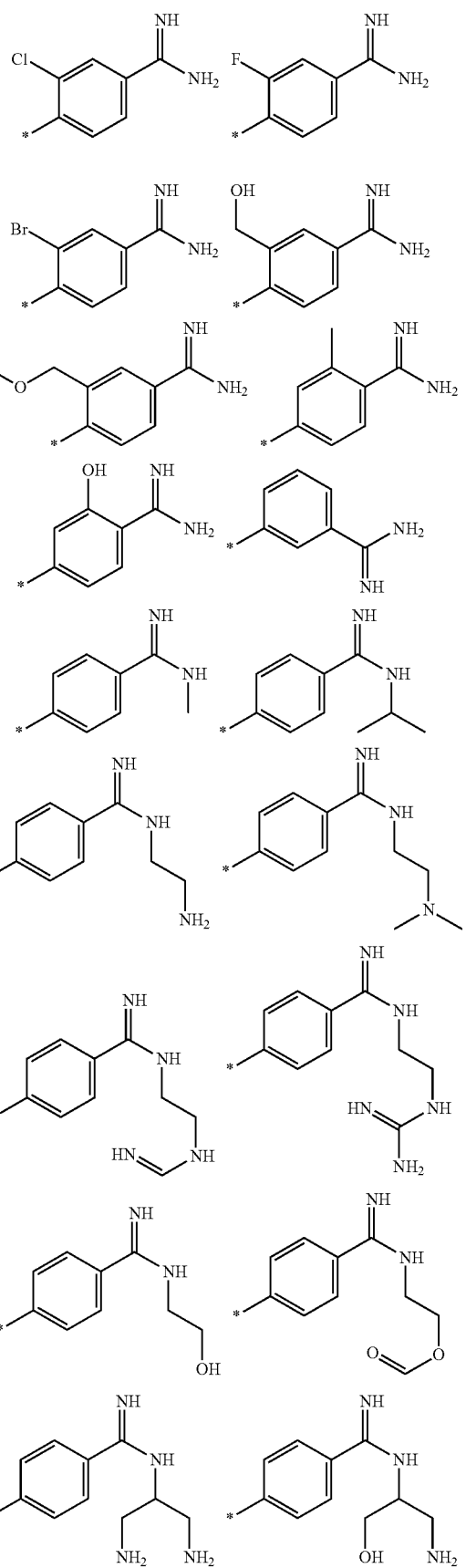

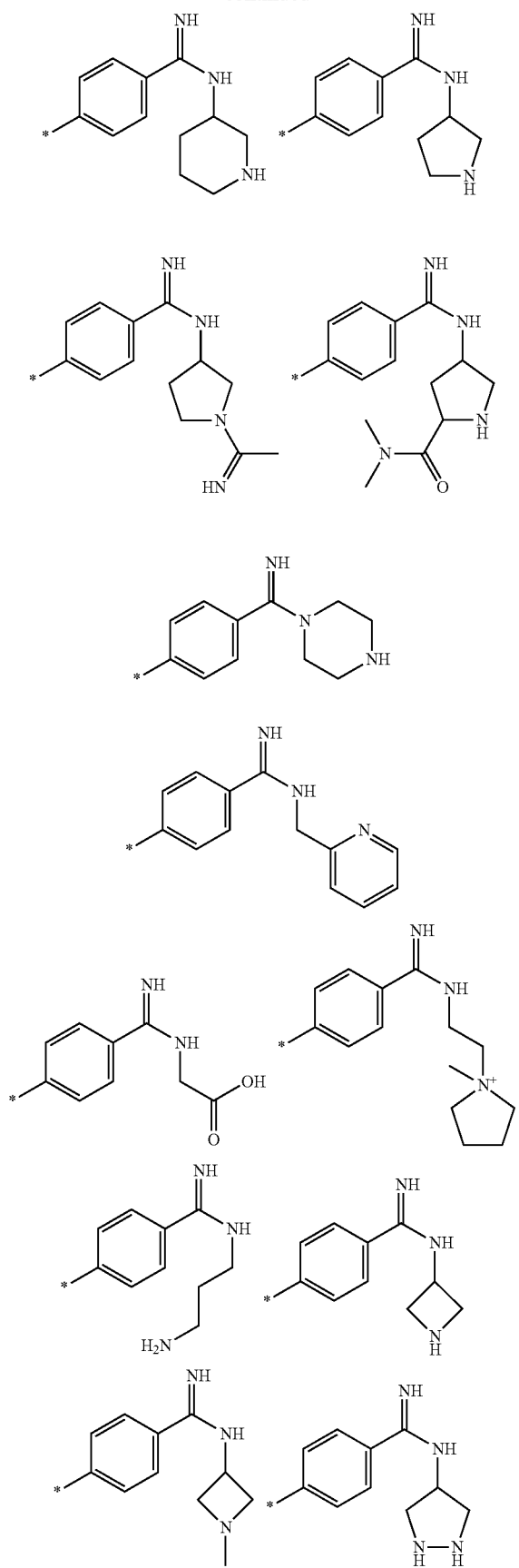
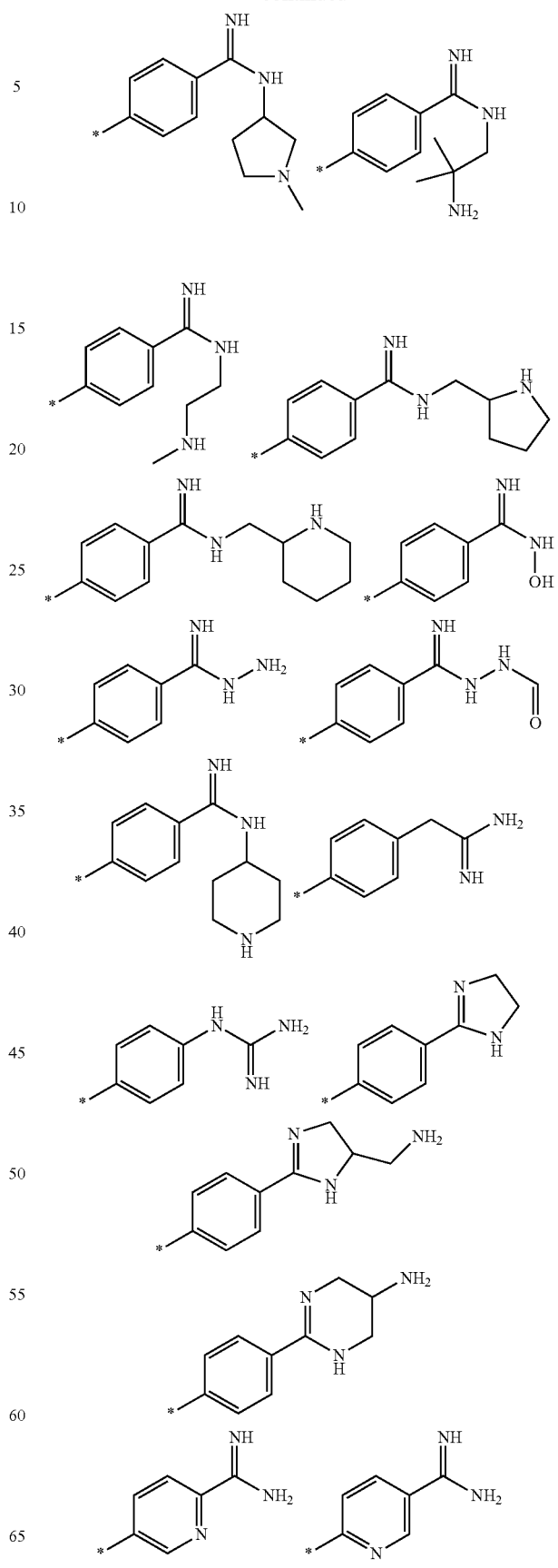

-continued

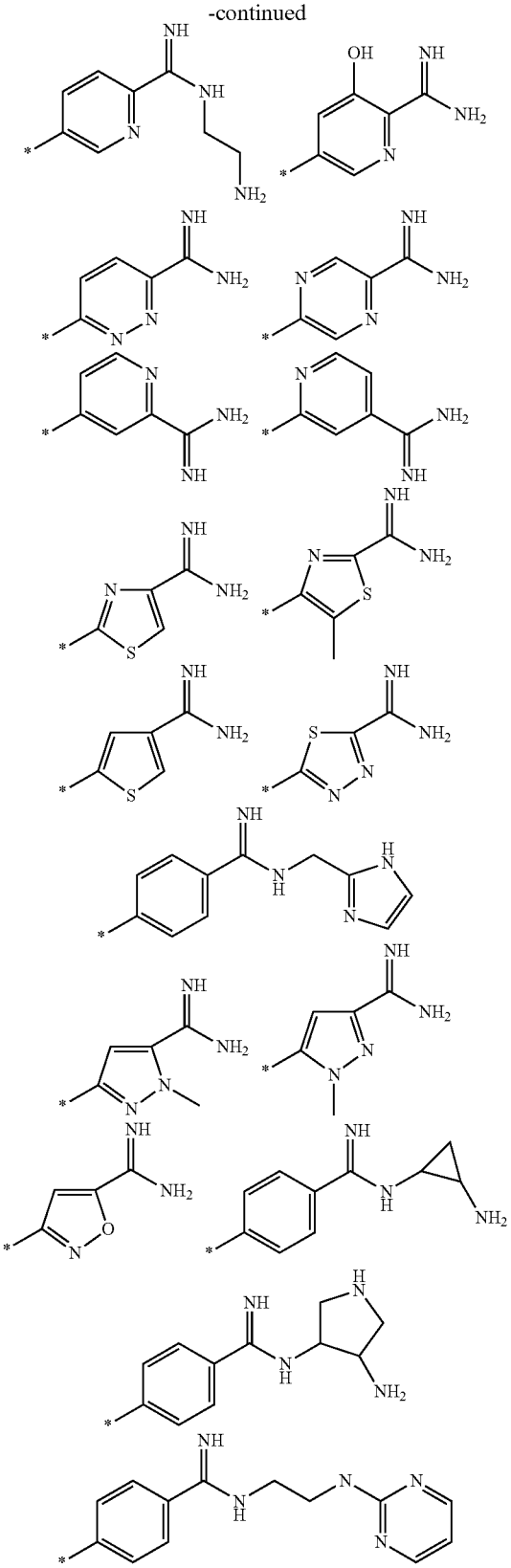

and the salts thereof, the solvates thereof and the solvates of the salts thereof.

The present invention also relates to methods for the preparation of compounds of formula (I). The compounds of the present invention may be prepared by removing the protecting group from compounds of formula

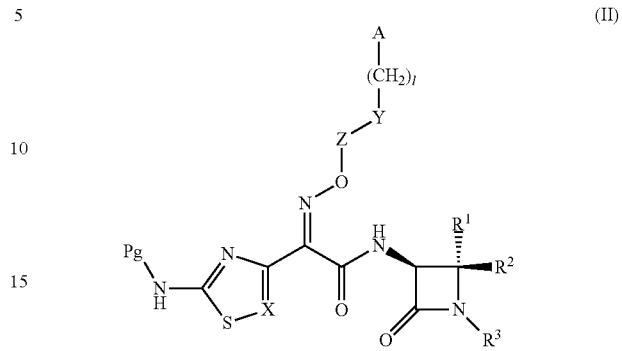

(II)

in which Pg represents a protecting group and $R^1$-$R^3$, A, l, X, Y and Z are as defined above, under acidic conditions.

Acidic conditions may involve treating the compounds of formula (II) with formic acid, acetic acid, trifluoroacetic acid or hydrochloric acid at temperatures ranging from 0° C. to 100° C. for a time ranging from 10 min to 16 hours, preferably with 90% formic acid at a temperature of 30-60° C. for 30-60 min.

The compounds of formula (II) can be synthesized by reacting compounds of formula

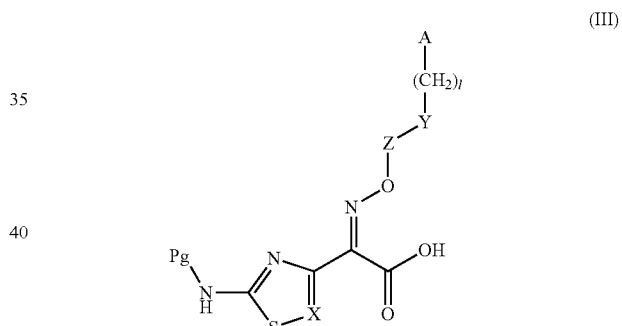

(III)

in which Pg represents a protecting group and A, l, X, Y and Z are as defined above,
with compounds of formula

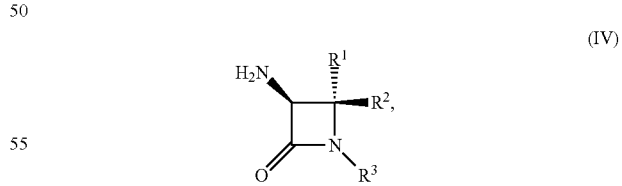

(IV)

in which $R^1$, $R^2$ and $R^3$ are as defined above.

The reaction generally takes place in inert solvents in the presence of a coupling reagent and where applicable with addition of a base at a temperature ranging from −20° C. to 80° C. for 1-24 hours, preferably at a temperature of 20-30° C. overnight. Inert solvents are for example dichloromethane (DCM), trichloromethane, benzene, toluene, tetrahydrofuran (THF), 1,4-dioxane, N,N-dimethylformamide (DMF), N,N-dimethylacetamide (DMA), N-methylpyrrolidin-2-one (NMP) and acetonitrile as well as mixtures of the aforementioned solvents. A preferred solvent is N,N-dimethylformamide.

Suitable coupling reagents are for example carbodiimides such as N,N'-diethyl-, N,N,'-dipropyl-, N,N'-diisopropyl-, N,N'-dicyclohexylcarbodiimide, N-(3-di-methylaminoisopropyl)-N'-ethylcarbodiimid-hydrochloride (EDC), N-cyclohexylcarbodiimid-N'-propyloxymethyl-polystyrene (PS-Carbodiimide) or carbonyl compounds such as carbonyldiimidazole (CDI), or 1,2-oxazolium compounds such as 2-ethyl-5-phenyl-1,2-oxazolium-3-sulfate or 2-tert.-butyl-5-methyl-isoxazolium-perchlorate, or acylamino compounds such as 2-ethoxy-1-ethoxycarbonyl-1,2-dihydrochinoline, or propanphosphonic acid anhydride, or isobutylchloroformate, or bis-(2-oxo-3-oxazolidinyl)-phosphorylchloride, or O-(benzotriazol-1-yl)-N,N,N',N'-tetramethyluroniumhexafluorophosphate (HBTU), 2-(2-oxo-1-(2H)-pyridyl)-1,1,3,3-tetramethyluroniumtetrafluoroborate (TPTU) or O-(7-azabenzotriazol-1-yl)-N,N,N',N'-tetramethyluroniumhexafluorophosphate (HATU), or 1-hydroxybenzotriazole (HOBt), or benzotriazol-1-yloxytris(dimethylamino)-phosphoniumhexafluorophosphate (BOP), or benzotriazol-1-yloxytris(pyrrolidino)-phosphoniumhexafluorophosphate (PyBOP), or N-hydroxysuccinimide as well as mixtures of the aforementioned coupling reagents with or without the addition of a base. In the latter case both inorganic and organic bases may be used. Suitable bases are for example carbonates and bicarbonates, triethylamine, diisopropylethylamine, N-methylmorpholine, N-methylpiperidine or 4-dimethylaminopyridine. Preferably, reactions are carried out with a mixture of a carbodiimide and 1-hydroxybenzotriazole with or without the addition of sodium bicarbonate as base.

The compounds of formula (III) can be prepared selectively with the preferred Z-orientation of the oxime by reacting compounds of formula

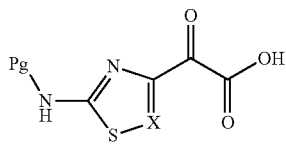

(V)

in which Pg represents a protecting group,
and X is as defined above
with compounds of formula

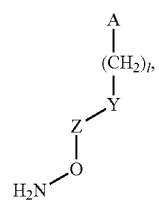

(VI)

in which A, l, Y and Z are as defined above.

The reaction generally takes place in protic solvents or in solvent mixtures containing at least one protic solvent at a temperature ranging from 0° C. to 100° C. for 1-24 hours. Suitable protic solvents are for example methanol, ethanol, iso-propanol, tert.-butanol, water or acetic acid. Solvents suitable to form mixtures are for example dichloromethane, trichloromethane, tetrahydrofuran, 1,4-dioxane, acetonitrile and N,N-dimethylformamide. Preferably, the reaction is carried out in a mixture of anhydrous ethanol and chloroform at 20-30° C. overnight.

Compounds of formula (IV) can be synthesized according to the following literature references: J. Org. Chem. 1982, 47 (26), 5160-5167; WO 2007/65288; J. Antibiotics 1985, 38 (11), 1536-1549; WO 2008/116813; Org. Proc. Res. Dev. 2002, 6 (6), 863-868; EP 336667; DE 3336262; BE 904699 or by adapting the referenced procedures in a way known to a person skilled in the art.

Compounds of formula (V) can be synthesized according to the following literature references: Chem. & Pharm. Bull., 1990, 38(12), 3476-3479; Bioorg. Med. Chem., 2007, 38 (21), 6716-6732; Chem. & Pharm. Bull., 1990, 38(12), 3476-3479 or Bioorg. Med. Chem., 2007, 38(21), 6716-6732.

The compounds of formula (VI) can be prepared by deprotecting compounds of formula

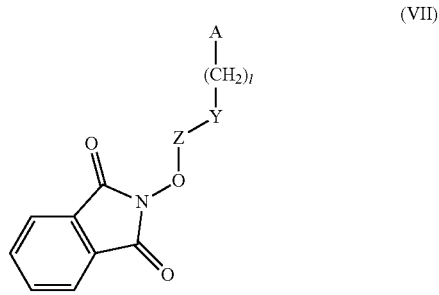

(VII)

in which A, l, Y and Z are as defined above.

The deprotection reaction generally takes place with hydrazine, ammonia or methylamine or a salt or a solvate thereof in protic solvents or in solvent mixtures containing at least one protic solvent at a temperature ranging from 0° C. to 100° C. for 1-24 hours. Protic solvents are for example methanol, ethanol, iso-propanol, tert.-butanol, water or acetic acid. Suitable solvents to form mixtures are for example dichloromethane, trichloromethane, tetrahydrofuran, 1,4-dioxane, acetonitrile and N,N-dimethylformamide. Preferably, the reactions are carried out with hydrazine monohydrate in anhydrous ethanol at 20-30° C. for 2-6 hours.

The compounds of formula (VII) can be prepared by reacting compounds of formula

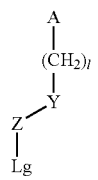

(VIII)

in which Lg represents a leaving group and A, l, Y and Z are as defined above
with N-hydroxy-phthalimide.

The reaction can be performed as an alkylation type (Lg=halide, mesylate, tosylate, triflate or similar) or a Mitsunobu type (Lg=OH) reaction. Alkylation type reactions generally take place in the presence of an inorganic or organic base in aprotic solvents at a temperature ranging from 0° C. to 100° C. for 1-24 hours.

Mitsunobu type reactions are generally carried out in the presence of triphenylphosphine and an alkyl azodicarboxylate in aprotic solvents at a temperature ranging from 0° C. to 100° C. for 1-24 hours. Suitable aprotic solvents are for example acetonitrile, tetrahydrofuran, dichloromethane, trichloromethane, 1,4-dioxane, N,N-dimethylformamide, N,N-dimethylacetamide and N-methyl-pyrolidin-2-one. Preferably, the reaction takes place under Mitsunobu conditions (Lg=OH) in the presence of triphenylphosphine and diisopropyl azodicarboxylate in anhydrous tetrahydrofuran at 0° C. to 30° C. for 2-6 hours.

In an alternative preferred method the reaction takes place under alkylation conditions in the presence of potassium carbonate or 1,8-diazabicyclo[5.4.0]undec-7-ene (DBU) in acetonitrile or N,N-dimethylformamide at 20° C. to 80° C. for 2-16 hours. Examples for preferred compounds of formula (VIII) are compounds of formulae

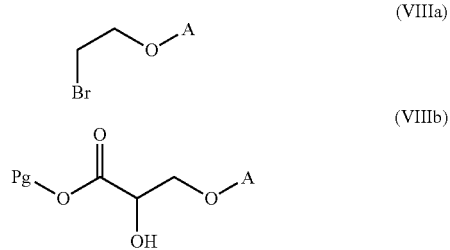

in which Pg represents an alkyl- or arylalkylester protecting group and A is as defined above.

The compounds of formula (VIIIa) and (VIIIb) can be synthesised by converting the cyano group in compounds of formula

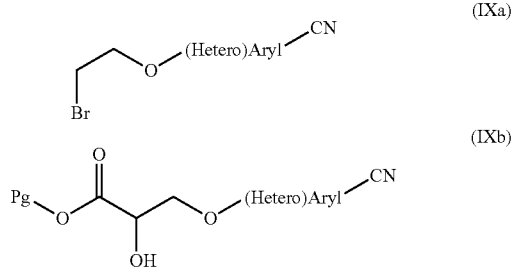

in which Pg represents an alkyl- or arylalkylester protecting group
into the required substituted or unsubstituted amidine functionality.

The conversion of the cyano(hetero)aryl to the corresponding amidine can be achieved under a range of different acidic and alkaline conditions.

One possibility is to treat the cyano(hetero)aryl with hydrochloric acid gas in a protic solvent, like methanol or ethanol, at 0° C. to 30° C. for 2-24 hours. The formed O-alkyl amidate intermediate is then treated with an ammonia solution or an amine in the same solvent at 20° C. to 50° C. for 1-16 hours. Hydrochloric acid gas may also be formed in-situ from acetylchloride or thionylchloride; ammonium chloride in the presence of a base like triethylamine or diisopropylethylamine may also be used instead of an ammonia solution.

A further possibility is to react the cyano(hetero)aryl with an amine, ammonium chloride or an amine salt in the presence of trimethylaluminium in a non-protic solvent, like toluene or dichlorobenzene, at 20° C. to 120° C. for 1-16 hours.

A further option is to treat the cyano(hetero)aryl with hydroxylamine in polar solvents, like ethanol, water or dimethylsulfoxide or a mixture of the aforementioned solvents, at 20° C. to 80° C. for 1-16 hours. The formed amidoxime intermediate is then de-oxygenated using hydrogen over palladium on carbon in acetic acid at 20° C. to 50° C. for 4-24 hours. Hydroxylamine hydrochloride in the presence of triethylamine or diisopropylethylamine may be used instead of hydroxylamine; the de-oxygenation may also be carried out using a co-solvent, like methanol, ethanol or 1,4-dioxane, or with the additional acetic acid anhydride.

A further option is to treat the cyano(hetero)aryl with sodium alkoxide in the corresponding alcohol, preferably with sodium methoxide in methanol, at 20° C. to 50° C. for 2-20 hours. The formed O-alkyl amidate intermediate is then treated with an ammonia solution or an amine as described above.

A further option is to treat the cyano(hetero)aryl with lithium hexamethyldisilazide in an inert solvent like tetrahydrofuran at 0° C. to 20° C. for 2-20 hours. The formed silyl protected amidine intermediate is then de-protected by treating with an acid in a polar solvent, preferably with hydrochloric acid in ethanol, at 0° C. to 20° C. for 1-16 h. The lithium hexamethyldisilazide may thereby be formed in-situ e.g. from n-butyl lithium and hexamethyldisilazane.

Compounds of formula (IXa) and (IXb) can be synthesized from compounds of formula

by adapting alkylation procedures reported in the literature, e.g. in *J. Am. Chem. Soc.* 2009, 131 (10), 3762-3771 and WO 2008096189, or by adapting epoxide ring opening procedures reported in the literature, e.g. in *Chem Med Chem.* 2007, 2 (5), 641-654; *Heterocycles* 2005, 65 (11), 2667-2674 and *Tetrahedron Lett.* 2001, 42 (50), 8743-8745.

Before carrying out the alkylation or epoxide opening, compounds of formula (X) may also first be converted to the corresponding amidine using the methods detailed above.

The compounds of the invention show a valuable range of pharmacological effects which could not have been predicted.

They are therefore suitable for use as medicaments for the treatment and/or prophylaxis of diseases in humans and animals.

The compounds of the present invention are distinguished in particular by an advantageous range of antibacterial effects.

The present invention therefore further relates to the use of the compounds of the invention for the treatment and/or prophylaxis of diseases caused by bacteria, especially gram-negative bacteria.

The present invention further relates to the use of the compounds of the invention for the treatment and/or prophylaxis of diseases, especially of the diseases mentioned below.

The present invention further relates to the use of the compounds of the invention for the manufacture of a medicament for the treatment and/or prophylaxis of diseases, especially of bacterial infections and in particular the diseases mentioned below.

The present invention further relates to a method for the treatment and/or prophylaxis of diseases, especially of bacterial infections and in particular the diseases mentioned below, using a therapeutically effective amount of the compounds of the invention.

The compounds of the invention exhibit an antibacterial spectrum against gram-negative bacteria and selected gram-positive bacteria combined with low toxicity. Compounds of this invention are particularly useful in human and veterinary medicine for the prophylaxis and treatment of local and systemic infections which are caused for example by the following pathogens or by mixtures of the following pathogens:

Aerobic gram-positive bacteria: Including but not limited to *Staphylococcus* spp. (*S. aureus*), *Streptococcus* spp. (*S. pneumoniae, S. pyogenes, S. agalactiae, Streptococcus* group C and G) as well as *Bacillus* spp. and *Listeria monocytogenes*.

Aerobic gram-negative bacteria: Enterobacteriaceae, including but not limited to *Escherichia* spp. (*E. coli*), *Citrobacter* spp. (*C. freundii, C. diversus*), *Klebsiella* spp. (*K. pneumoniae, K. oxytoca*), *Enterobacter* spp. (*E. cloacae, E. aerogenes*), *Morganella morganii, Hafnia alvei, Serratia* spp. (*S. marcescens*), *Proteus* spp. (*P. mirabilis, P. vulgaris, P. penneri*), *Providencia* spp. (*P. stuartii, P. rettgeri*), *Yersinia* spp. (*Y. enterocolitica, Y. pseudotuberculosis*), *Salmonella* spp., *Shigella* spp. and also non-fermenters including but not limited to *Pseudomonas* spp. (*P. aeruginosa*), *Burkholderia* spp. (*B. cepacia*), *Stenotrophomonas maltophilia*, and *Acinetobacter* spp. (*A. baumannii, Acinetobacter* gen. sp. 13TU, *Acinetobacter* gen. sp. 3) as well as *Bordetella* spp. (*B. bronchiseptica*), *Moraxella catarrhalis* and *Legionella pneumophila*; furthermore, *Aeromonas* spp., *Haemophilus* spp. (*H. influenzae*), *Neisseria* spp. (*N. gonorrhoeae, N. meningitidis*) as well as *Alcaligenes* spp. (including *A. xylosoxidans*), *Pasteurella* spp. (*P. multocida*), Vibro spp. (*V. cholerae*), *Campylobacter jejuni* and *Helicobacter pylori*.

Moreover, the antibacterial spectrum also covers strictly anaerobic bacteria including but not limited to *Bacteroides* spp. (*B. fragilis*), *Peptostreptococcus* spp. (*P. anaerobius*), *Prevotella* spp., *Brucella* spp. (*B. abortus*), *Porphyromonas* spp., and *Clostridium* spp. (*Clostridium perfringens*).

The above listing of pathogens is merely exemplary and in no way to be regarded as limiting. Examples of diseases which may be caused by the said pathogens and which may be prevented, improved or cured by the compounds according to the invention are, for example:

Respiratory tract infections such as lower respiratory tract infections, lung infection in cystic fibrosis patients, acute exacerbation of chronic bronchitis, community acquired pneumonia (CAP), nosocomial pneumonia (including ventilator-associated pneumonia (VAP)), diseases of the upper airways, diffuse panbronchiolitis, tonsillitis, pharyngitis, acute sinusitis and otitis including mastoiditis; urinary tract and genital infections for example cystitis, uretritis, pyelonephritis, endometritis, prostatitis, salpingitis and epididymitis; ocular infections such as conjunctivitis, corneal ulcer, iridocyclitis and post-operative infection in radial keratotomy surgery patients; blood infections, for example septicaemia; infections of the skin and soft tissues, for example infective dermatitis, infected wounds, infected burns, phlegmon, folliculitis and impetigo; bone and joint infections such as osteomyelitis and septic arthritis; gastro-intestinal infections, for example dysentery, enteritis, colitis, necrotising enterocolitis and anorectal infections; intraabdominal infections such as typhoid fever, infectious diarrhea, peritonitis with appendicitis, pelviperitonitis, and intraabdominal abscesses; infections in the oral region for example infections after dental operations; other infections for example, meliodosis, infectious endocarditis, hepatic abscesses, cholecystitis, cholangitis, mastitis as well as meningitis and infections of the nervous systems.

In addition to humans, bacterial infections can also be treated in animals, such as primates, pigs, ruminants (cow, sheep, goat), horses, cats, dogs, poultry (such as hen, turkey, quail, pigeon, ornamental birds) as well as productive and ornamental fish, reptiles and amphibians.

The compounds of the invention may act systemically and/or locally. They can for this purpose be administered in a suitable way, such as, for example, parenterally, pulmonarily, nasally, sublingually, lingually, buccally, rectally, dermally, transdermally, conjunctivally, otically or as an implant or stent.

For these administration routes the compounds of the invention can be administered in suitable administration forms.

Parenteral administration can take place with avoidance of an absorption step (e.g. intravenous, intraarterial, intracardiac, intraspinal or intralumbar) or with inclusion of an absorption step (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays; tablets, films/wafers or capsules, for lingual, sublingual or buccal administration, suppositories, preparations for ears or eyes, vaginal capsules, aqueous suspensions (lotions, shaking mixtures), lipophilic suspensions, ointments, creams, transdermal therapeutic systems (such as for example patches), milk, pastes, foams, dusting powders, implants or stents.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The present invention further relates to medicaments which comprise at least one compound of the invention, usually together with one or more inert, non-toxic, pharmaceutically acceptable excipients, as well as to their use for the aforementioned purposes.

The present invention further relates to medicaments which comprise at least one compound of the invention in combination with at least one further active compound, as well as to their use for the aforementioned purposes.

Examples for the further active compound include—lactamase inhibitors.

Examples for suitable—lactamase inhibitors to be used in combination with the compounds of the invention include clavulanic acid, tazobactam, sulbactam, avibac-tam (NXL-104), and MK-7655.

The minimum amount of the compounds of the invention to be administered is a therapeutically effective amount. The term "therapeutically effective amount" means an amount of compound which prevents the onset of, alleviates the symptoms of, stops the progression of, and/or eliminates a bacterial infection in humans or animals.

Typically, an effective dosing schedule of the compounds of the invention for adults is about 50 mg to about 3000 mg of a compound of formula (I) in a single dose; in another embodiment, an effective single dose is about 100 mg to about 2000 mg. In another embodiment, an effective single dose is about 500 mg to about 1200 mg. Typically the dosages are given 1 to 4 times per day. In one embodiment, the dosages are given 3 times per day. In some cases, it may be necessary to use dosages outside these limits.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. In the case of an administration of larger amounts, it may be advisable to distribute these in a plurality of single doses over the day.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

EXAMPLES

Abbreviations

: chemical shift in ppm
br s: broad singlet in NMR
$CDCl_3$: deuterated chloroform
d: doublet in NMR
dd: doublet of doublet in NMR
DCM: dichloromethane
DMF: N,N-dimethylformamide
DMSO: dimethyl sulfoxide
EtOAc: ethyl acetate
ES$^-$: negative ion mode in electrospray ionization mass spectrometry
ES$^+$: positive ion mode in electrospray ionization mass spectrometry
g: gram(s)
h: hour(s)
HPLC: high performance liquid chromatography
Hz: hertz
J: coupling constant in NMR
L: liter(s)
M: molarity
m: multiplet in NMR
mg: milligram(s)
MHz: megahertz
min: minute(s)
mL: milliliter(s)
mmol: millimole(s)
mol: mole(s)
MS: mass spectrometry
N: normality
NMR: nuclear magnetic resonance
q: quartet in NMR
s: singlet in NMR
t: triplet in NMR
t-BuOH: tert-butyl alcohol
TFA: trifluoroacetic acid
THF: tetrahydrofuran
TLC: thin layer chromatography
TMS: tetramethylsilane Analytical Methods All $^1$H and $^{19}$F NMR spectra were recorded on a Varian Oxford AS 400 NMR operating at 400 MHz for $^1$H, and 376 MHz for $^{19}$F respectively. NMR data is recorded in chemical shifts relative to tetramethylsilane (TMS) as internal standard. NMR spectra were run either in $CDCl_3$ containing 0.05% TMS, $CD_3OD$ containing 0.05% TMS, or DMSO-$d_6$ containing 0.03% TMS.

HPLC analyses were performed using a Waters 2695 Separation Module and a Waters 2996 Photodiode Array Detector system or a Waters 600 Controller including a Waters 717plus Autosampler and a Waters 2996 Photodiode Array Detector system on an Atlantis T3-C18-3 m-4.6×150 mm column with an acetonitrile/aqueous 0.1% $H_3PO_4$ gradient at 22° C., and a flow rate of 1 mL/minute.

Preparative HPLC was performed on a Waters Prep LC 2767 System utilizing a Waters Prep HPLC Controller, and a Waters 2487 Dual Wave Absorbance Detector on a Gem-C-18-10 m-50×100 mm (flow rate of 70 mL/minute), X-Bridge-C-18-5 m-30×100 mm (flow rate of 42 mL/minute), Ace-C-18-5 m-30×250 mm (flow rate of 40 mL/minute), or GemNX-C-18-10 m-50×250 mm (flow rate of 80 mL/minute) column, using an acetonitrile/aqueous 0.1% trifluoroacetic acid gradient or an acetonitrile/aqueous 0.1% formic acid gradient at 22° C.

Mass spectra were recorded on a Waters 2795 Separation Module using either ES$^-$ or ES$^+$ ionization modes.

Column chromatography was performed using Desican Inc. Silica Gel: CC Grade (230-400 Mesh).

Commercial solvents and reagents were generally used without further purification. All products were dried before characterization and use in subsequent synthetic steps.

General Synthetic Methods

1. Synthesis of the β-lactam building blocks 1.1
(3S,4S)-3-Amino-4-methyl-2-oxoazetidine-1-sulfonic acid

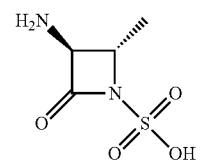

1_1_1

Compound 1_1_1 was synthesized according to David M. Floyd, Alan W. Fritz, Josip Pluscec, Eugene R. Weaver, Christopher M. Cimarusti *J. Org. Chem.*, 1982, 47 (26), 5160-5167.

1.2 (3S,4S)-3-Amino-4-methyl-1-(sulfooxy)azetidin-2-one

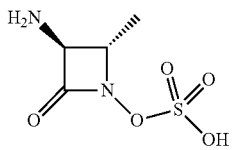

1_2_1

Compound 1_2_1 was synthesized according to WO 2007/65288

1.3 (3S,4R)-3-Amino-4-methyl-2-oxoazetidine-1-sulfonic acid

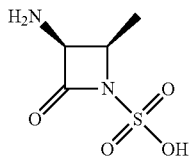

1_3_1

Compound 1_3_1 was synthesized according to David M. Floyd, Alan W. Fritz, Josip Pluscec, Eugene R. Weaver, Christopher M. Cimarusti *J. Org. Chem.*, 1982, 47 (26), 5160-5167.

1.4 (3S,4R)-3-Amino-4-methyl-1-(sulfooxy)azetidin-2-one

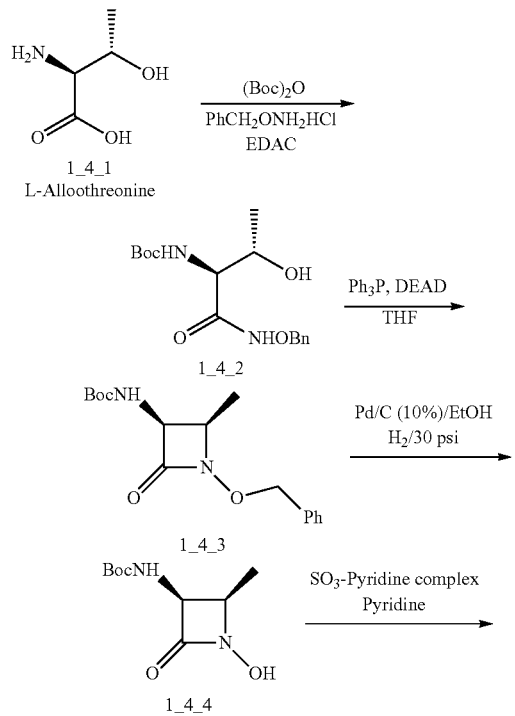

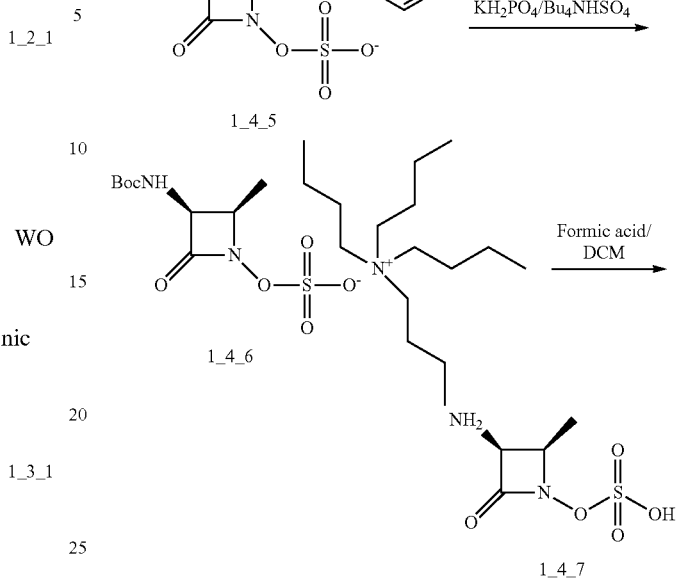

To a solution of potassium hydroxide (2.53 g, 45.1 mmol, in 28 mL of water) at room temperature was added L-allo-threonine (3.0 μm, 25.1 mmol) and the mixture was cooled to 24° C. using an ice-bath. A di-tert-butyl dicarbonate solution ($Boc_2O$, 6.02 g in 15 mL of t-BuOH) was then added portionwise over 20 minutes to the colorless reaction mixture without cooling to form a white cloudy solution. The reaction mixture was then stirred at room temperature for 5 h until TLC (acetonitrile/acetone/acetic acid, 15:15:1) indicated the absence of any starting material. O-benzyloxy-hydroxylamine hydrochloride (6.0 g, 37.6 mmol) was then added in portions over 7 min, 6.0 N HCl (4 mL) was then added in portions maintaining pH 4 (white fumes), 1-ethyl-3-(3-dimethylaminopropyl)carbodiimide hydrochloride (4.81 g, 25.1 mmol) was then added in portions to the reaction mixture while cooling. The reaction mixture was left stirring at room temperature overnight, saturated with sodium chloride and extracted with ethyl acetate (2×200 mL). The organic extracts were combined, dried over $MgSO_4$, filtered, evaporated to dryness and dried under vacuum to afford 1_4_2 (6.5 g, 79.5%) as viscous oil.

$^1$H NMR (400 MHz, DMSO-$d_6$): δ=1.02 (d, J=5.8 Hz, 3H), 1.36 (s, 9H), 3.49-3.83 (m, 1H), 3.56-3.70 (m, 1H), 4.70-4.81 (m, 2H), 4.86 (d, J=4.6 Hz, 1H), 6.73 (d, J=8.5 Hz, 1H), 7.29-7.42 (m, 5H), 11.09 (s, 1H).

Diethyl azodicarboxylate (DEAD, 0.51 mL. 3.08 mmol) was added dropwise to a solution of compound 1_4_2 (1.0 g, 3.08 mmol) and triphenylphosphine (0.81 g, 3.08 mmol) in THF (40 mL) at room temperature over 5 min. The reaction mixture was heated at 50° C. for 6 h and concentrated to give a viscous oil which was purified by column chromatography eluting with ethyl acetate/hexane (40:60) to give compound 1_4_3 (0.30 g, 31.7%).

$^1$H NMR (400 MHz, DMSO-$d_6$): δ=1.01 (d, J=5.8 Hz, 3H), 1.38 (s, 9H), 3.87-4.11 (m, 1H), 4.62 (dd, J=9.3 and 5.1 Hz, 1H), 4.78-5.02 (m, 2H), 7.21-7.51 (m, 5H), 7.64 (d, J=9.3 Hz, 1H).

10% Pd/C (100 mg, wet) was added to a solution of compound 1_4_3 (1.0 g, 3.26 mmol) in ethanol (100 mL)

and the mixture was hydrogenated at 30 psi for 3 h. TLC (1:1, ethyl acetate in hexanes) showed completion of the reaction. The catalyst was removed by filtration through a bed of celite and was washed with methanol (2×50 mL). The filtrate was concentrated under vacuum resulting in compound 1_4_4 as a solid (0.7 g, 99%) which was used in the next step without further purification.

$^1$H NMR (400 MHz, DMSO-$d_6$): δ=1.05 (d, J=6.2 Hz, 3H), 1.37 (s, 9H), 3.69-4.09 (m, 1H), 4.60 (dd, J=8.9 and 5.1 Hz, 1H), 7.62 (d, J=9.3 Hz, 1H), 9.92-10.40 (m, 1H).

Sulfur trioxide-pyridine complex (1.76 g, 11.09 mmol) was added to a solution of compound 1_4_4 (2.0 g, 9.24 mmol) in anhydrous pyridine (20 mL) and the mixture was stirred at room temperature for 2 h. The mixture was concentrated under vacuum resulting in a foam, which was triturated with dichloromethane (10 mL) and hexane (30 mL) to give compound 1_4_5 as a white solid (3.46 g) which was used directly for the next step.

Compound 1_4_5 (3.46 g, 9.21 mmol) was dissolved in a 0.5 M solution of potassium dihydrogen phosphate (100 mL), extracted with ethyl acetate (2×100 mL), and the ethyl acetate extract was discarded. Tetra-n-butyl ammonium sulfate (3.13 g, 9.21 mmol) was added to the aqueous layer in one portion. The mixture was stirred at room temperature for 1 h and extracted with dichloromethane (2×50 mL). The combined organic layers were washed with brine, dried over sodium sulfate, filtered and concentrated under vacuum resulting in compound 1_4_6 as a foam (4.0 g) which was used directly for the next step.

Compound 1_4_6 (4.00 g, 7.41 mmol) was dissolved in 98% formic acid (16 mL) and the mixture was stirred at room temperature for 3 h. A white precipitate began to form after few minutes. Dichloromethane (30 mL) was added to the reaction mixture and the mixture was cooled to 0-5° C., and kept overnight in the fridge. The white precipitate formed was isolated by filtration and dried under vacuum to give compound 1_4_7 (1.00 g, 75.8%).

$^1$H NMR (400 MHz, DMSO-$d_6$): δ=1.32 (d, J=6.2 Hz, 3H), 4.30-4.42 (m, 1H), 4.50 (d, J=5.0 Hz, 1H), 8.31-9.20 (m, 3H).

1.5 (3S)-3-Amino-4,4-dimethyl-1-(sulfooxy)azetidin-2-one

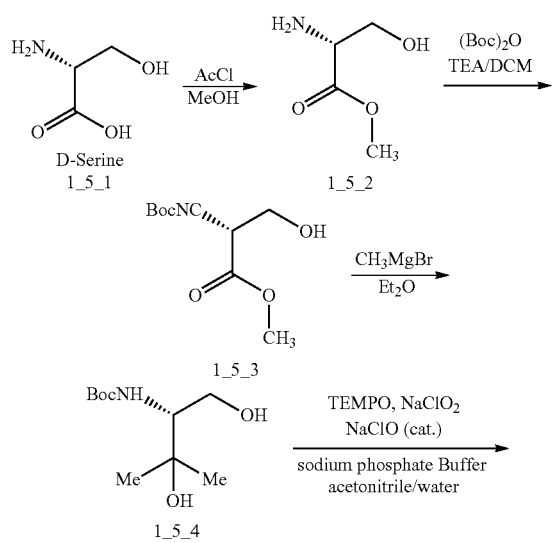

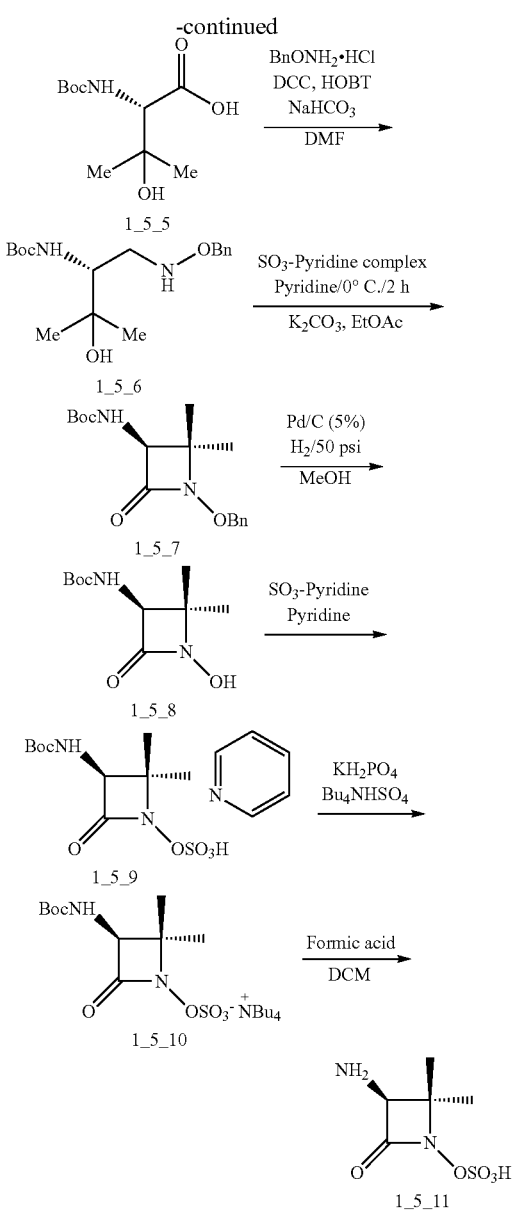

Acetyl chloride (AcCl, 96.0 mL, 1.35 mol) was added dropwise over 15 min to pre-cooled methanol (650 mL) at 0° C. The solution was stirred for an additional 5 min, and then solid D-serine (51.0 g, 0.49 mol) was added in portions. The resulting mixture was heated under reflux for 2 h, then cooled to room temperature and the solvent was removed under reduced pressure. The solid obtained was triturated with 3:1 hexane/ether (300 mL) to give compound 1_5_2 as an off-white solid, which was thoroughly dried overnight in an oven under vacuum to give compound 1_5_2 (87.0 g, 99%) as a white solid.

$^1$H NMR (400 MHz, Methanol-$d_4$): δ=3.72 (s, 3H), 3.81 (br. s, 2H), 4.07 (s, 1H), 5.6 (br. s, 1H), 8.78 (br. s, 2H).

Triethylamine (TEA, 183 mL, 1.3 mol) was added dropwise to a solution of compound 1_5_2 (94.0 g, 0.605 mol) in THF (3 L) at 0° C. To the resulting thick white suspension a solution of di-tert-butyldicarbonate (135.0 g, 0.65 mol) in THF (500 mL) was added dropwise over a period of 1.5 h at the same temperature. The reaction mixture was stirred at room temperature for 16 h. The solvent was removed under reduced pressure and the residue was partitioned between diethyl ether (3 L) and a saturated aqueous sodium bicarbonate solution (3 L). The aqueous layer was extracted with diethyl ether (3×2 L), the organic extracts were combined and dried over sodium sulfate, filtered and the filtrate was concentrated under reduced pressure to give compound 1_5_3 (134.0 g, 75%) as a viscous oil.

$^1$H NMR (400 MHz, CDCl$_3$): δ=1.42 (s, 9H), 3.80 (s, 3H), 3.90 (m, 2H), 4.38 (br. s, 1H), 5.44 (br. s, 1H).

A 3.0 M solution of MeMgBr in diethyl ether (450 mL, 1.35 mol) was added dropwise to a cooled solution of compound 1_5_3 (50.0 g, 0.23 mol) in diethyl ether (2 L) at −78° C. The reaction mixture was allowed to reach room temperature, stirred at room temperature for 1 h, and then poured into a saturated aqueous ammonium chloride solution (2.5 L). The organic layer was separated and the aqueous layer was extracted with ethyl acetate (3×2 L). The combined organic layers were washed with brine, dried over sodium sulfate, filtered, and concentrated under reduced pressure. The residue was triturated with diethyl ether/hexane (1:2, 500 mL) and cooled in an ice bath. The precipitated solid was isolated by filtration to give compound 1_5_4 (33.0 g, 66%) as a colorless solid.

$^1$H NMR (400 MHz, CDCl$_3$): δ=1.25 (s, 3H), 1.35 (s, 3H), 1.43-1.48 (m, 9H), 2.49 (br. s, 1H), 2.62 (br. s, 1H), 3.47 (d, J=8.9 Hz, 1H), 3.76-3.86 (m, 1H), 3.98-4.09 (m, 1H), 5.37 (br. s, 1H).

2,2,6,6-Tetramethylpiperidine 1-oxyl (TEMPO, 2.3 g, 15 mmol) was added to a mixture of compound 1_5_4 (33.0 g, 150 mmol) in acetonitrile (750 mL) and sodium phosphate buffer (600 mL, 0.7 M solution, pH 6-7) and the resulting mixture was heated to 35° C. The mixture was then treated by a simultaneous addition of a sodium chlorite solution (34.2 g in 150 mL of water) and 60 drops of a very dilute sodium hypochlorite solution (3 mL of commercial solution in 100 mL of water). The mixture was stirred at 35° C. overnight, cooled to room temperature, treated with citric acid (~15 g, pH 3), saturated with sodium chloride and extracted with ethyl acetate (3×2 L). The organic extracts were combined and concentrated under reduced pressure. The residue was dissolved in 1.5 L of a 2M sodium carbonate solution and washed with ethyl acetate (2×2 L). The aqueous layer was cooled to 0° C., the pH was adjusted to 3.0 using a 2 M solution of H$_3$PO$_4$ and the solution was saturated with sodium chloride. The resulting mixture was extracted with ethyl acetate (3×2 L), the organic phases were combined, dried, filtered and concentrated under reduced pressure to give compound 1_5_5 (28.4 g, 81%) as a colorless solid.

$^1$H NMR (400 MHz, DMSO-d$_6$): δ=1.15 (s, 3H), 1.17 (s, 3H), 1.39 (s, 9H), 3.86 (d, J=8.6 Hz, 1H) 6.52 (d, J=8.9 Hz, 1H).

Dicyclohexylcarbodiimide (DCC, 19.5 g, 94.3 mmol) was added to a solution of compound 1_5_5 (20.0 g, 85.7 mmol) in N,N-dimethylformamide at room temperature followed by 1-hydroxybenzotriazole (HOBt, 12.7 g, 94.3 mmol). The resulting mixture was stirred at room temperature for 30 min, and O-benzylhydroxylamine hydrochloride (15.1 g, 94.3 mmol) was added followed by sodium bicarbonate (18.0 g, 214.3 mmol). The reaction mixture was stirred at room temperature for 24 h and filtered through a celite bed, washed with ethyl acetate (2×50 mL), and concentrated under reduced pressure. The residue was purified by column chromatography eluting with 30-40% ethyl acetate in hexane to give compound 1_5_6 (24.5 g, 84.5%) as a colorless solid.

$^1$H NMR (400 MHz, DMSO-d$_6$): δ=1.05 (s, 3H), 1.08 (s, 3H), 1.26 (s, 9H), 3.74 (d, J=9.3 Hz, 1H), 4.62 (br. s, 1H), 4.72 (s, 2H), 6.42 (d, J=8.9 Hz, 1H), 7.26-7.47 (m, 5H), 11.03 (br. s, 1H).

Sulfur trioxide-pyridine complex (58.7 g, 0.368 mol) was added to a solution of compound 1_5_6 (96.0 g, 0.283 mol) in pyridine (1 L) at 0° C. in portions and the mixture was stirred for 2 h. The pyridine was removed under vacuum and the residue was triturated with diethyl ether/hexanes (1:10, 1 L) to remove the major portion of the pyridine. A solution of potassium carbonate (240 g in 1.2 L of water) and 500 mL of ethyl acetate were added to the solid intermediate. The resulting mixture was heated under reflux for 2 h, cooled down to room temperature and the ethyl acetate layer was separated. The aqueous layer was extracted with ethyl acetate (2×200 mL) and the combined ethyl acetate layers were washed with brine, dried over sodium sulfate, filtered and concentrated. The residue was purified by column chromatography eluting with 30-40% ethyl acetate in hexanes. The desired fractions were combined and concentrated. The residue was triturated with 10% ether in hexane (~400 mL) to give compound 1_5_7 (58.1 g, 64%) as a colorless solid.

$^1$H NMR (400 MHz, CDCl$_3$): δ=1.08 (s, 3H), 1.32 (s, 3H), 1.43 (s, 9H), 4.30 (d, J=6.8 Hz, 1H), 4.96 (s, 2H), 7.40 (m, 5H).

5% Pd/C (6.0 g, wet, ~50% water) was added to a solution of compound 1_5_7 (30.0 g, 93.6 mmol) in methanol (600 mL) and the mixture was hydrogenated at 50 psi for 1 h. TLC (1:1, ethyl acetate in hexanes) showed completion of the reaction. The catalyst was removed by filtration through a bed of celite and was washed with methanol (2×100 mL). The filtrate was concentrated under vacuum and the resulting solid was triturated with 10% ether in hexanes (100 mL), filtered and dried in vacuum to give compound 1_5_8 (21.9 g, quant.) as a colorless solid.

$^1$H NMR (400 MHz, DMSO-d$_6$): δ=1.17 (s, 3H), 1.31 (s, 3H), 1.41 (s, 9H), 4.21 (d, J=6.8 Hz, 1H), 7.71 (d, J=6.8 Hz, 1H), 10.01 (br. s, 1H).

Sulfur trioxide-pyridine complex (39.7 g, 0.249 mol) was added to a solution of compound 1_5_8 (50.0 g, 0.217 mol) in pyridine (500 mL) at 0° C. The resulting mixture was stirred at room temperature for 1.5 h and concentrated under vacuum to give compound 1_5_9 (106.0 g) as a foam, which was dissolved in 4 L of a 0.5 M solution of KH$_2$PO$_4$ and extracted with dichloromethane (2×400 mL). The aqueous layer was cooled to 0° C. and tetra-n-butyl ammonium sulfate (84.8 g, 0.249 mol) was added. The resulting mixture was stirred at 0-5° C. for 1 h and extracted with dichloromethane (5×500 mL). The combined dichloromethane layers were washed with brine, dried over sodium sulfate, filtered and concentrated under vacuum to give intermediate 1_5_10 (115.0 g) as a foam which was dissolved in 96% formic acid (500 mL) and the resulting mixture was stirred at room temperature for 4 h. A white precipitate began to form after few minutes. Dichloromethane (500 mL) was added to the reaction mixture and the mixture was cooled to 0-5° C., and kept in the fridge over the weekend. The white precipitate was isolated by filtration and dried under vacuum to afford compound 1_5_11 (24.5 g, 53% over 3 steps) as a colorless solid.

$^1$H NMR (400 MHz, DMSO-d$_6$): δ=1.42 (s, 3H), 1.43 (s, 3H), 4.15 (s, 1H), 8.80 (br. s, 2H).

1.6 {[(3S,4S)-3-Amino-4-methyl-2-oxoazetidin-1-yl]oxy}methanesulfonic acid

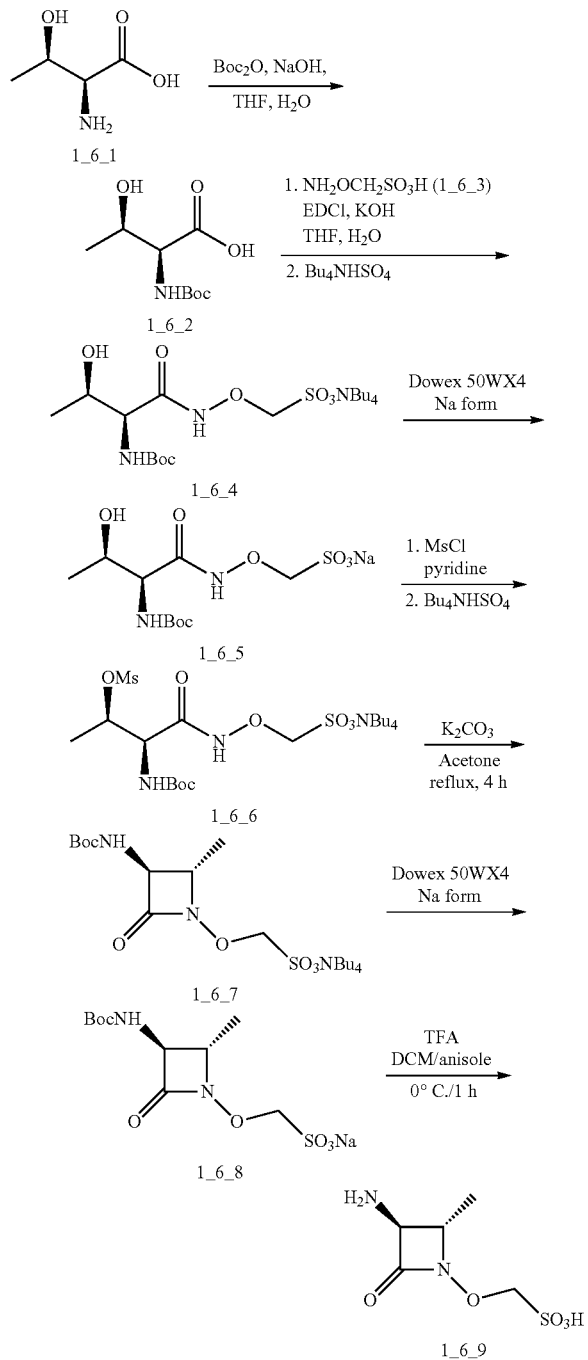

Di-tert-butyl dicarbonate (56.7 g, 59.7 mL, 0.23 mol, Aldrich) was added dropwise to a solution of L-threonine 1_6_1 (23.8 g, 0.2 mol) in THF (200 mL) and a 2 N aqueous sodium hydroxide solution (120 mL) at 0° C. The resulting mixture was stirred at 0° C. to room temperature overnight and concentrated under reduced pressure to remove the solvent. The residue was saturated with solid ammonium chloride, cooled to 0° C., acidified with 1 N hydrochloric acid to pH 3, and extracted with ethyl acetate (3×100 mL). The combined organic layers were washed with water (200 mL) and brine (200 mL), dried over sodium sulfate and concentrated under reduced pressure. The residue was treated with hexane (300 mL) and filtered to give 1_6_2 (39.7 g, 91%) as a colorless solid.

$^1$H NMR (400 MHz, DMSO-d$_6$): δ=1.06 (d, J=6.2 Hz, 3H), 1.37 (s, 9H), 3.86 (dd, J=9.1 and 3.3 Hz, 1H), 3.98-4.08 (m, 1H), 6.29 (d, J=9.3 Hz, 1H).

(Aminooxy)methanesulfonic acid compound 1_6_3 (5.9 g, 46.4 mmol) was added to a solution of compound 1_6_2 (9.4 g, 42.9 mmol) in THF (50 mL) and water (100 mL) at 0° C., the pH of the mixture was adjusted to 4.5 using a 1N aqueous potassium hydroxide solution, and a solution of N-(3-dimethylaminopropyl)-N-ethylcarbodiimide hydrochloride (EDCI, 9.3 g, 47.1 mmol) in water (30 mL) was added slowly over 20 min. The resulting mixture was stirred at room temperature for 3 h while adjusting to pH 4.0-4.5 with 1N sulfuric acid. Tetrabutylammonium hydrogensulfate (14.5 g, 42.9 mmol, Aldrich) was added, the pH was adjusted to 3 using 1N sulfuric acid and the mixture was extracted with chloroform (5×100 mL). The combined chloroform layers were dried over sodium sulfate and concentrated under reduced pressure to give crude compound 1_6_4 (17.5 g) which was dissolved in water (20 mL) and purified on a Dowex 50WX4 Na form ion exchange resin (200 mL) column eluting with water. The first 400 mL of water fractions were collected and lyophilized to give 1_6_5 (6.93 g, 46%) as a yellow solid.

$^1$H NMR (400 MHz, DMSO-d$_6$): δ=1.01 (d, J=6.2 Hz, 3H), 1.38 (s, 9H), 3.72-3.91 (m, 2H), 4.24 (s, 2H), 4.85 (br. s, 1H), 6.37 (d, J=8.6 Hz, 1H), 7.40 (s, 1H), 11.25 (br. s, 1H).

Methanesulfonyl chloride (MsCl, 0.72 g, 6.3 mmol) was added dropwise via a syringe to a solution of 1_6_5 (2.0 g, 5.71 mmol) in pyridine (60 mL) at 0° C. The resulting mixture was stirred at room temperature overnight and concentrated under reduced pressure. The residue was dissolved in water (10 mL), tetrabutylammonium hydrogensulfate (1.87 g, 5.5 mmol) was added, the pH was adjusted to 3 with 1N sulfuric acid, and the mixture was extracted with chloroform (5×30 mL). The combined chloroform layers were dried over sodium sulfate and concentrated under reduced pressure to give a light brown solid. MS indicated that the product obtained was a mixture of compound 1_6_6, a N,N,N-tributylbutan-1-amonium salt of compound 1_6_5 and a di-Ms by-product. The mixture was used in the next step without further purification.

A solution of 1_6_6 (3.1 g, 4.8 mmol) in acetone (10 mL) was added dropwise to a suspension of potassium carbonate (3.0 g, 21.7 mmol) in acetone (90 mL) under reflux. The resulting mixture was kept under reflux for 4 h. After cooling to room temperature, the reaction mixture was filtered. The filtrate was concentrated under reduced pressure to give crude intermediate 1_6_7 which was dissolved in a 0.5 M aqueous KH$_2$PO$_4$ solution (15 mL), the pH was adjusted to 3 using 1N sulfuric acid, and the mixture was extracted with dichloromethane (6×50 mL). The combined dichloromethane layers were dried over sodium sulfate and concentrated under reduced pressure. The residue was dissolved in water (10 mL) and purified on a Dowex 50WX4 Na form ion exchange resin (200 mL) column eluting with water. The first 500 mL of water fractions were collected and lyophilized to give 1.3 g of crude product as a yellow solid. MS indicated that the product obtained was a mixture of compound 1_6_8 and compound 1_6_5. This mixture was used in the next step without further purification.

Trifluoroacetic acid (TFA, 10 mL) was added to a suspension of compound 1_6_8 from the previous step as mixture (1.2 g, 3.6 mmol) in dichloromethane (5 mL) and anisole (5 mL) at 0° C. The resulting mixture was stirred at 0° C. for 1 h and concentrated under reduced pressure. The residue was stirred with benzene (10 mL) and evaporated twice, washed with dichloromethane, and dried in vacuum to give crude compound 1_6_9 (1.6 g, quant, with small amount of residual trifluoroacetic acid). This material was used as 47% pure in next step without further purification.

The $^1$H NMR was complex as the product obtained was a mixture of compound 1_6_9 and compound 1_6_5.

MS (ES$^-$) m/z: [M-Na]$^-$ calcd for $C_5H_9N_2O_5S$: 209.02. Found: 209.11.

1.7 {[(3S)-3-Amino-4,4-dimethyl-2-oxoazetidin-1-yl]oxy}methanesulfonic acid

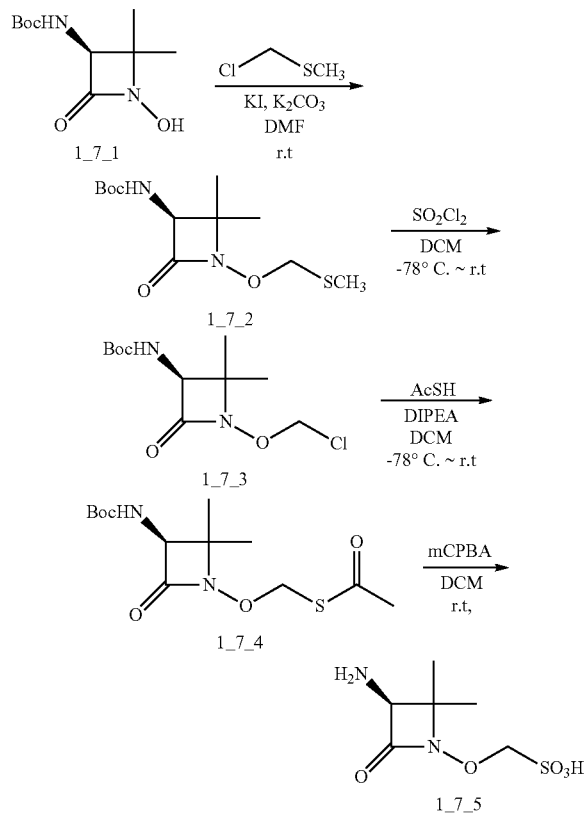

Chloromethyl methyl sulfide (1.15 mL, 13.8 mmol) was added dropwise to a solution of potassium iodide (2.29 g, 13.8 mmol) in N,N-dimethylformamide (40 mL) at room temperature. The resulting mixture was stirred at room temperature for 0.5 h, and tert-butyl {(3S)-4,4-dimethyl-1-hydroxy-2-oxoazetidin-3-yl}carbamate 1_7_1 (1.60 g, 6.94 mmol) was added followed by potassium carbonate (1.90 g, 13.8 mmol). The resulting mixture was stirred at room temperature overnight. The mixture was poured into ice water (200 mL) and extracted with ethyl acetate (3×30 mL). The combined ethyl acetate layers were washed with water and brine, dried (sodium sulfate) and concentrated under reduced pressure. The residue was purified by silica gel column chromatography eluting with 6:1-3:1 hexane-ethyl acetate to give compound 1_7_2 (1.73 g, 86%) as a yellow oil.

$^1$H NMR (400 MHz, CDCl$_3$): δ=1.33 (s, 3H), 1.45 (s, 9H), 1.54 (s, 3H), 2.28 (s, 3H), 4.39 (d, J=6.6 Hz, 1H), 4.96 (s, 2H), 5.10 (d, J=6.6 Hz, 1H).

Sulfuryl dichloride (0.71 mL, 8.78 mmol) was added dropwise to a solution of compound 1_7_2 (1.70 g, 5.85 mmol) in dichloromethane (50 mL) at -78° C. The resulting mixture was stirred at -78° C. for 15 min and then at room temperature for 15 min. The reaction mixture was cooled to -78° C. and N-ethyldiisopropylamine (DIPEA, 10.1 mL, 58.5 mmol) was added dropwise followed by thioacetic acid (AcSH, 2.1 mL, 29.3 mmol). The resulting mixture was stirred at -78° C. for 15 min and then at -78° C. to room temperature for 1 hour. The reaction mixture was poured into a saturated aqueous sodium bicarbonate solution (200 mL) and extracted with dichloromethane (3×50 mL). The combined dichloromethane layers were dried over sodium sulfate and concentrated under reduced pressure. The residue was purified by silica gel column chromatography eluting with 6:1-3:1 hexane-ethyl acetate to give compound 1_7_4 (1.25 g, 67%) as a yellow solid.

$^1$H NMR (400 MHz, CDCl$_3$): δ=1.32 (s, 3H), 1.45 (s, 9H), 1.52 (s, 3H), 2.42 (s, 3H), 4.36 (d, J=6.6 Hz, 2H), 5.03 (d, J=6.6 Hz, 1H), 5.36 (s, 2H).

Compound 1_7_4 (1.10 g, 3.45 mmol) was added to a solution of 3-chloroperoxybenzoic acid (mCPBA, 4.0 g, 13.8 mmol) in dichloromethane (50 mL). The resulting mixture was stirred at room temperature overnight and concentrated under reduced pressure. The residue was treated with formic acid (96%, 20 mL) and stirred at room temperature for 4 h. The solid was filtered off and the filtrate was concentrated under reduced pressure. The residue was treated with dichloromethane (50 mL), stirred at room temperature for 0.5 h and filtered. The filtrate was concentrated under reduced pressure to give crude compound 1_7_5 (0.9 g, 100%, 0.77 g expected) as a pale yellow solid which was used as it is in the next step.

$^1$H NMR (400 MHz, DMSO-d$_6$): δ=1.46 (s, 3H), 1.48 (s, 3H), 4.14 (s, 1H), 4.42 (AB, J=8.0 and 32.0 Hz, 2H), 8.72 (br s, 1H).

1.8 3-Amino-1-(sulfooxy)-1-azaspiro[3.4]octan-2-one

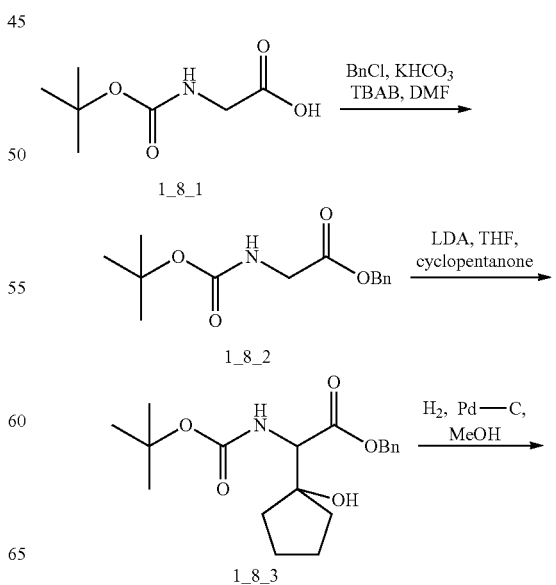

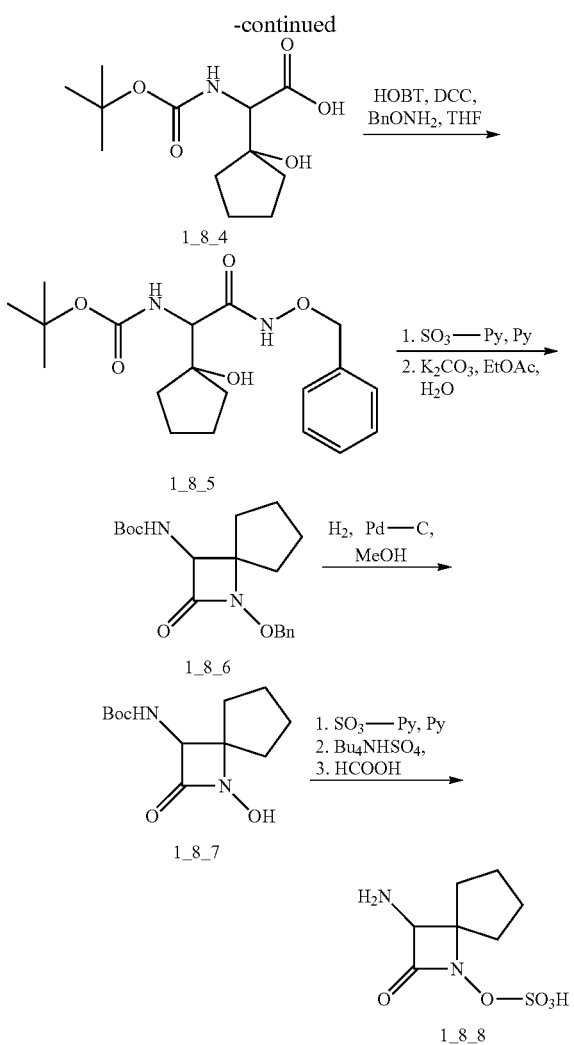

trated. The residue was purified by column chromatography to give compound 1_8_3 (5.65 g, 79%).

$^1$H NMR (400 MHz, DMSO-d$_6$): ε=1.40 (s, 9H), 1.50-1.90 (m, 8H), 2.20 (s, 1H), 4.25 (d, J=7.7 Hz, 1H), 5.20 (m, 2H), 5.50 (d, J=7.7 Hz, 1H), 7.40 (m, 5H).

10% Pd/C (0.52 g) was added to a degassed solution of compound 1_8_3 (5.65 g, 16.19 mmol) in methanol (100 mL). The mixture was stirred under a hydrogen balloon for 3 h and filtered through a pad of celite. The filtrate was concentrated to give compound 1_8_4 (4.1 g) which was used in the next step without further purification.

$^1$H NMR (400 MHz, DMSO-d$_6$): ε=1.40 (s, 9H), 1.50-2.00 (m, 8H), 4.20 (br. s, 1H), 5.95 (br. s, 1H).

1-Hydroxybenzotriazole (HOBT, 2.19 g, 16.19 mmol) and dicyclohexylcarbodiimide (DCC, 3.34 g, 16.19 mmol) was added to a cooled (0° C.) solution of compound 1_8_4 (4.1 g) in THF (20 mL). The mixture was stirred at 0° C. for 2 hours. A solution of O-benzyl hydroxylamine (made from 7.76 g of its corresponding hydrogen chloride salt and an aqueous sodium hydroxide solution, 47.89 mmol) in THF (10 mL) was added and the mixture was stirred at room temperature for 5 h and filtered. The filtrate was concentrated and the residue was purified by column chromatography to give compound 1_8_5 (4.7 g, 80%)

$^1$H NMR (400 MHz, CDCl$_3$): δ=1.40 (s, 9H), 1.50-2.00 (m, 8H), 3.60 (d, J=7.8 Hz, 1H), 3.90 (s, 1H), 4.90 (s, 2H), 5.62 (d, J=7.8 Hz, 1H), 7.40 (m, 5H), 9.02 (s, 1H).

A mixture of compound 1_8_5 (4.66 g, 12.80 mmol) and sulfur trioxide-pyridine complex (3.71 g, 23.25 mmol) in pyridine (50 mL) was heated at 50-55° C. for 2 h and concentrated. The residue was diluted with acetonitrile (20 mL) and concentrated. The residue was dried under high vacuum for 2 h, diluted with ethyl acetate (150 mL) and treated with a solution of potassium carbonate (19.67 g, 143 mmol) in water (54 mL). The resulting mixture was refluxed for 2 h, cooled to room temperature and the phases were separated. The organic phase was washed with a 5% aqueous sodium hydrogen sulfate solution (20 mL), dried and concentrated. The residue was purified by column chromatography to give compound 1_8_6 (2.5 g, 56%) as colorless solid.

$^1$H NMR (400 MHz, CDCl$_3$): δ=1.42 (s, 9H), 1.43-2.00 (m, 8H), 4.43 (d, J=8.0 Hz, 1H), 4.90-5.00 (m, 3H), 7.40 (m, 5H).

10% Pd—C (100 mg) was added to a degassed solution of compound 1_8_6 (1.0 g, 2.89 mmol) in methanol (20 mL). The mixture was stirred under a hydrogen balloon for 1 h and filtered through a pad of celite. The filtrate was concentrated to give compound 1_8_7 (0.70 g, 100%) which was used in the next step without further purification.

$^1$H NMR (400 MHz, DMSO-d$_6$): ε=1.39 (s, 9H), 1.50-2.00 (m, 8H), 4.28 (d, J=7.9 Hz, 1H), 7.72 (d, J=7.9 Hz, 1H).

A mixture of compound 1_8_7 (0.74 g, 2.89 mmol) and sulfur trioxide-pyridine complex (1.43 g, 8.96 mmol) in pyridine (20 mL) was stirred at room temperature for 2 h, and concentrated. The residue was treated with a 10% aqueous potassium dihy-drogenphosphate solution (10 mL) and the mixture was stirred with tetra-n-butylammonium hydrogensulfate (1.08 g, 3.18 mmol) at 0° C. for 30 min. The reaction mixture was extracted with dichloromethane (3×50 mL) and the combined organic phases were concentrated. The residue was dissolved in 98% formic aid (10 mL) and stirred at room temperature for 4 h, diluted with dichloromethane (30 mL) and left in the fridge for 16 h. The solid was collected and dried to give compound 1_8_8 (380 mg, 56%).

A mixture of N-(tert-butoxycarbonyl)glycine 1_8_1 (10 g, 57.14 mmol), benzyl chloride (BnCl, 7.30 mL, 62.85 mmol), tetra-n-butylammonium bromide (TBAB, 0.19 g, 0.57 mmol) and potassium bicarbonate (6.87 g, 68.57 mmol) in N,N-dimethylformamide (100 mL) was stirred at room temperature for 72 hours and filtered. The filtrate was concentrated under vacuum. The residue was treated with water and the solid was collected and dried to give compound 1_8_2 (10 g, 67%).

$^1$H NMR (400 MHz, DMSO-d$_6$): δ=1.40 (s, 9H), 3.75 (d, J=6.8 Hz, 2H), 5.10 (s, 2H), 7.20 (t, J=6.8 Hz, 1H), 7.33 (m, 5H).

n-Butyl lithium (35.85 mL, 1.6 M in hexane) was added to a cooled (−40° C.) solution of di-isopropylamine (7.23 mL, 51.23 mmol) in THF (40 mL). The mixture was stirred at −40° C. for 30 min to form lithium diisopropylamide (LDA). A solution of compound 1_8_2 (5.43 g, 20.49 mmol) in THF (20 mL) was added at −78° C. The mixture was stirred at −78° C. for 30 min and cyclopentanone (dried over molecular sieves, 2.07 mL, 24.59 mmol) was added. The resulting mixture was stirred at −78° C. for 20 min, gradually warmed up to −20° C. over 30 min and then to 0° C. over 20 min, quenched with a solution of acetic acid (2.70 mL, 47.13 mmol) in THF (10 mL), poured into water (50 mL), extracted with ethyl acetate (200 mL), dried and concen- $^1$H NMR (400 MHz, DMSO-d$_6$): ϵ=1.40-2.00 (m, 6H), 2.20 (m, 2H), 4.37 (s, 1H).

1.9 (3S,4S)-3-Amino-4-(aminocarbonyl)-2-oxo-1-azetidinesulfonic acid

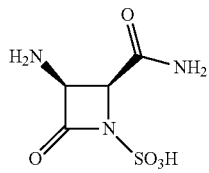

1_9_1

Compound 1_9_1 was synthesized according to M. Sendai, S. Hashiguchi, M. Tomimoto, S. Kishimoto, T. Matsuo, M. Ochiai; *Chemical & Pharmaceutical Bulletin* 1985, 33 (9), 3798-3810 and EP 73061.

2. Synthesis of amino-thiazole and amino-thiadiazole building blocks 2.1 Oxo[2-(tritylamino)-1,3-thiazol-4-yl]acetic acid

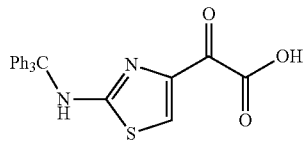

2_1_1

Compound 2_1_1 was synthesized according to Sakagami, Kenji; Iwamatsu, Katsuyoshi; Atsumi, Kunio; Hatanaka, Minoru; *Chemical & Pharmaceutical Bulletin*, 1990, 38(12), 3476-3479.

2.2 {5-[(tert-Butoxycarbonyl)amino]-1,2,4-thiadiazol-3-yl}(oxo)acetic acid

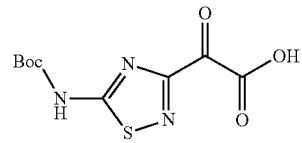

2_2_1

Compound 2_2_1 was synthesized according to Yamawaki, Kenji; Nomura, Takashi; Yasukata, Tatsuro; Uotani, Koichi; Miwa, Hideaki; Takeda, Kei; Nishitani, Yasuhiro; *Bioorganic & Medicinal Chemistry*, 2007, 38 (21), 6716-6732.

2.3 [5-Chloro-2-(tritylamino)-1,3-thiazol-4-yl](oxo)acetic acid

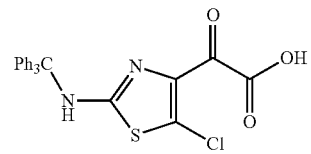

2_3_1

Compound 2_3_1 was synthesized according to:
a) Sakagami, Kenji; Iwamatsu, Katsuyoshi; Atsumi, Kunio; Hatanaka, Minoru; *Chemical & Pharmaceutical Bulletin*, 1990, 38(12), 3476-3479.
b) Yamawaki, Kenji; Nomura, Takashi; Yasukata, Tatsuro; Uotani, Koichi; Miwa, Hideaki; Takeda, Kei; Nishitani, Yasuhiro; *Bioorganic & Medicinal Chemistry*, 2007, 38(21), 6716-6732.

3. Synthesis of aryl and heteroaryl amidine side chains 3.1 4-[2-(Aminooxy)ethoxy]benzenecarboximidamide

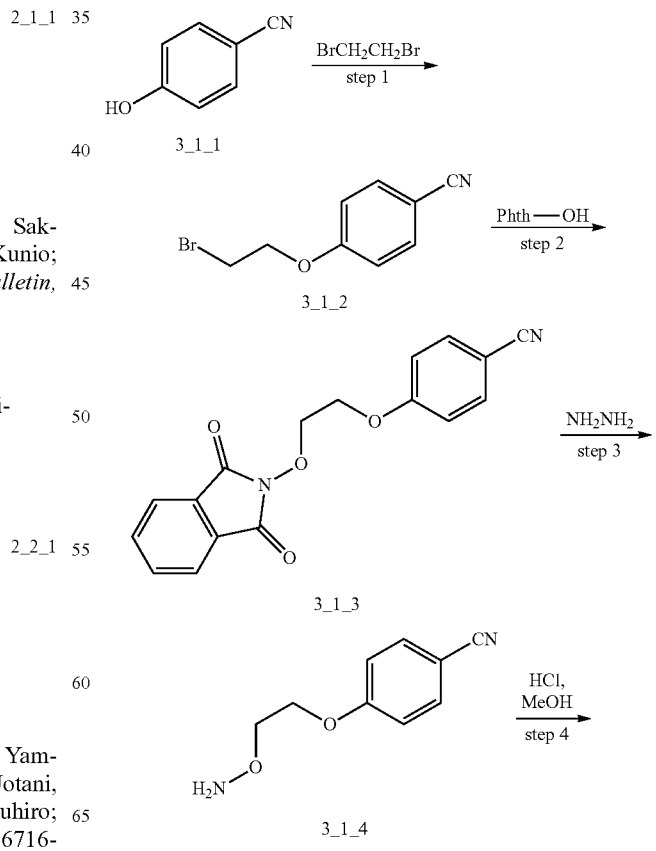

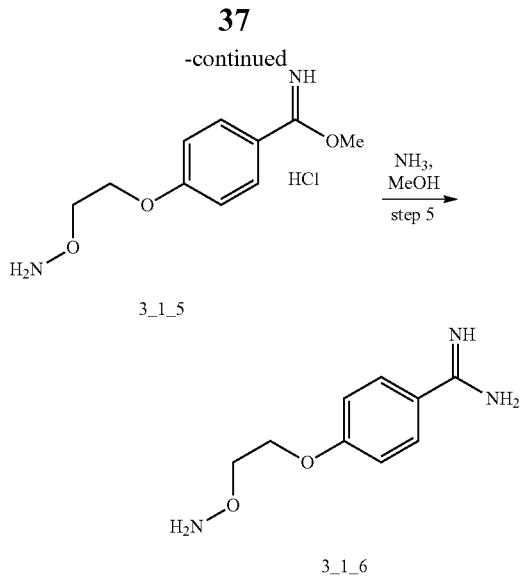

Step 1: 4-(2-Bromoethoxyl)benzonitrile (3_1_2)

1,2-Dibromoethane (471 g, 2.52 mol) and potassium carbonate (232 g, 1.68 mol) were added to a solution of 4-hydroxybenzonitrile 3_1_1 (100 g, 0.84 mol) in acetonitrile (4 L). The mixture was refluxed for 18 hours, the solid was removed by filtration and the filtrate was concentrated to give a residue which was purified by chromatography (3:1 hexanes/ethyl acetate) to give compound 3_1_2 (74.4 g, 40% yield) as a solid.

$^1$H NMR (400 MHz, CDCl$_3$): δ=3.66 (t, J=6.0 Hz, 2H), 4.34 (t, J=6.2 Hz, 2H), 6.97 (d, J=8.9 Hz, 2H), 7.61 (d, J=8.9 Hz, 2H).

Step 2: 4-{2-[(1,3-Dioxo-1,3-dihydro-2H-isoindol-2-yl)oxy]ethoxy}benzonitrile (3_1_3)

1,8-Diazabicyclo[5.4.0]undec-7-ene (49.4 mL, 0.33 mmol) was added slowly over 20 minutes to a solution of compound 3_1_2 (74.3 g, 0.33 mol) and N-hydroxyphthalimide (Phth-OH, 53.6 g, 0.33 mol) in N,N-dimethylformamide (470 mL) and the mixture was heated at 46° C. for 6 hours. After removal of the solvent, the residue was treated with 1N HCl (1 L) which resulted in a precipitate. The precipitate was collected by filtration, washed with water and dried to give compound 3_1_3 (98.0 g, 96% yield) as a white solid.

$^1$H NMR (400 MHz, CDCl$_3$): δ=4.31-4.43 (m, 2H), 4.51-4.63 (m, 2H), 6.91 (m, J=8.5 Hz, 2H), 7.57 (m, J=8.5 Hz, 2H), 7.75-7.87 (m, 4H).

Step 3: 4-[2-(Aminooxy)ethoxy]benzonitrile (3_1_4)

Hydrazine hydrate (11.5 mL, 0.236 mol) was added to a suspension of compound 3_1_3 (72.7 g, 0.236 mol) in ethanol (800 mL) and the mixture was stirred at 45° C. for 14 hours. The solid was removed by filtration and the filtrate was concentrated. The residue was diluted with ethyl acetate (300 mL), the solid was removed by filtration and the filtrate was concentrated to give compound 3_1_4 (40.0 g, 96% yield) as a white solid.

$^1$H NMR (400 MHz, CDCl$_3$): δ=4.03 (t, J=4.8 Hz, 2H), 4.21 (t, J=4.8 Hz, 2H), 5.58 (s, 2H), 6.98 (d, J=6.0 Hz, 2H), 7.59 (d, J=6.0 Hz, 2H).

Step 4: Methyl 4-[2-(aminooxy)ethoxy]benzenecarboximidoate (3_1_5)

Hydrogen chloride gas was bubbled through a solution of compound 3_1_4 (15.0 g, 84.7 mmol) in dry methanol (330 mL) at 0° C. for 1 hour and the mixture was stirred at room temperature for 14 hours (NMR showed 50% conversion). Hydrogen chloride gas was bubbled through the solution for another 40 minutes at 0° C., and the reaction mixture was stirred for 24 hours to give a suspension. Compound 3_1_5 (23.0 g, 96% yield, hydrochloride salt) was collected by filtration as a white solid.

$^1$H NMR (400 MHz, CDCl$_3$): δ=3.95-4.08 (m, 2H), 4.13-4.25 (m, 2H), 5.55 (br s, 2H), 6.99 (m, J=8.5 Hz, 2H), 7.26 (s, 1H), 7.59 (m, J=8.5 Hz, 2H).

Step 5: 4-[2-(Aminooxy)ethoxy]benzenecarboximidamide (3_1_6)

Ammonia (7 N in methanol, 53.3 mL) was added to a solution of compound 3_1_5 (11.5 g, 37.3 mmol) in dry methanol (150 mL). The mixture was stirred at 50° C. for 2 hours and at room temperature for 14 hours. After removal of the solvent, the residue was purified by chromatography to give compound 3_1_6 (6.2 g, 85% yield) as a solid.

$^1$H NMR (400 MHz, Methanol-d$_4$): δ=3.97-4.05 (m, 2H), 4.24-4.37 (m, 2H), 7.16 (d, J=8.9 Hz, 2H), 7.79 (d, J=8.9 Hz, 2H).

Using the conditions described above under 3.1 the following amidine side chains were prepared:

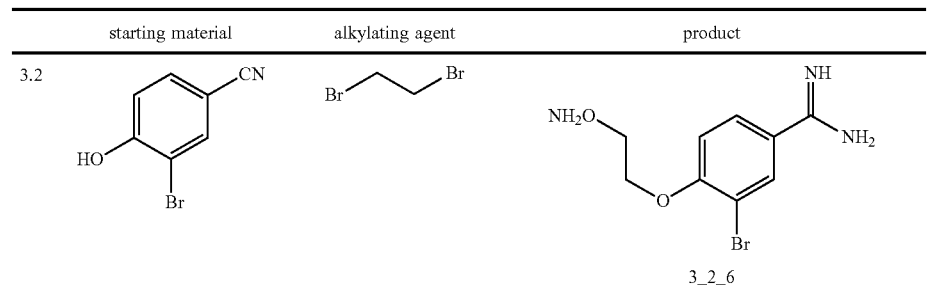

| starting material | alkylating agent | product |
|---|---|---|
| 3.2 | | |

-continued

| | starting material | alkylating agent | product |
|---|---|---|---|
| 3.3 | 3-hydroxybenzonitrile | Br-CH2CH2-Br | 3_3_6: 3-(2-aminooxyethoxy)benzamidine |
| 3.4 | 3-chloro-4-hydroxybenzonitrile | Br-CH2CH2-Br | 3_4_6: 4-(2-aminooxyethoxy)-3-chlorobenzamidine |
| 3.5 | 4-hydroxyphenylacetonitrile | Br-CH2CH2-Br | 3_5_6: 2-[4-(2-aminooxyethoxy)phenyl]acetamidine |
| 3.6 | 3-fluoro-4-hydroxybenzonitrile | Br-CH2CH2-Br | 3_6_6: 4-(2-aminooxyethoxy)-3-fluorobenzamidine |
| 3.7 | 4-hydroxybenzonitrile | Br-CH2CH2CH2-Br | 3_7_6: 4-(3-aminooxypropoxy)benzamidine |

3.8 tert-Butyl {({4-[2-(aminooxy)ethoxy]phenyl}amino)[(tert-butoxycarbonyl)-amino]methylidene}carbamate

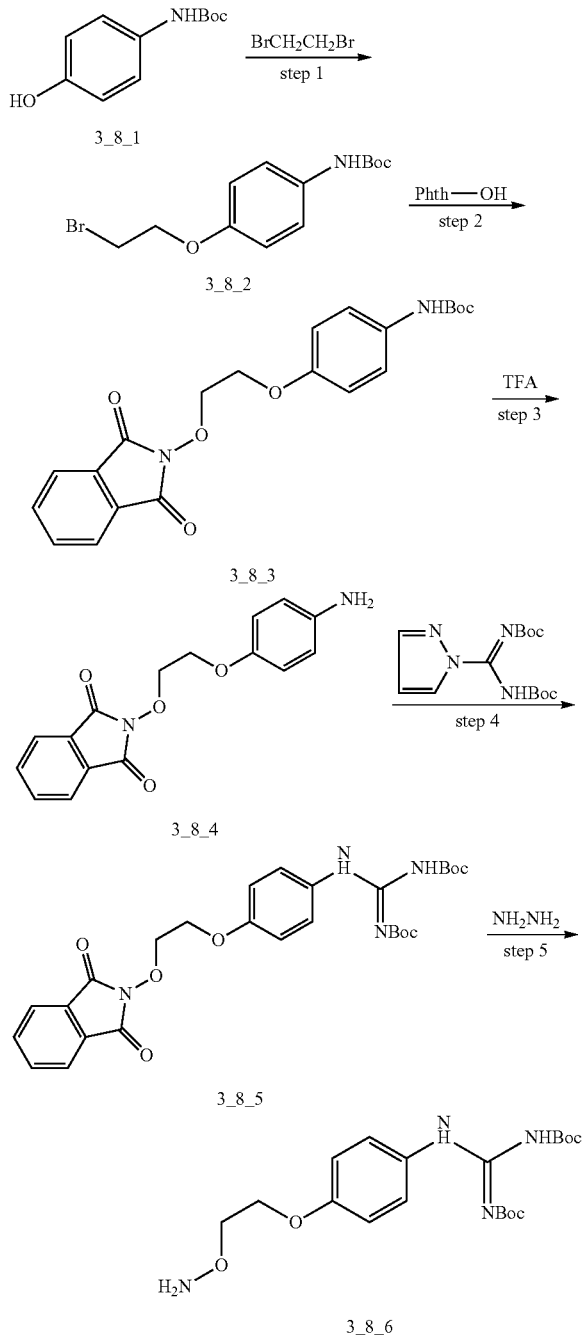

Step 1: tert-Butyl [4-(2-bromoethoxyl)phenyl]carbamate (3_8_2)

A mixture of tert-butyl(4-hydroxyphenyl)carbamate 3_8_1 (25 g, 119.6 mmol), 1,2-dibromoethane (41 mL, 478.5 mmol) and potassium carbonate (33 g, 239.2 mmol) in acetonitrile (500 mL) was refluxed for 24 hours (TLC showed 50% conversion). Additional 1,2-dibromoethane (20 mL, 239 mmol) and potassium carbonate (16 g, 120 mmol) was added and the mixture was refluxed for another 23 hours. Further potassium carbonate (16 g, 120 mmol) was added and the mixture was refluxed for another 5 hours. The solid was removed by filtration and the filtrate was concentrated to give a residue. The residue was purified by chromatography to give compound 3_8_2 (15.6 g, 41% yield) as a solid.

$^1$H NMR (CDCl$_3$): δ=1.51 (s, 9H), 3.61 (t, J=6.0 Hz, 2H), 4.26 (t, J=6.0 Hz, 2H), 4.26 (t, J=6.0 Hz, 2H), 6.34 (s, 1H), 6.85 (d, J=8.8 Hz, 2H), 7.27 (d, J=8.8 Hz, 2H).

Step 2: tert-Butyl (4-{2-[(1,3-dioxo-1,3-dihydro-2H-isoindol-2-yl)oxy]ethoxy}phenyl)carbamate (3_8_3)

1,8-Diazabicyclo[5.4.0]-undec-7-ene (9 mL, 59.3 mmol) was added to a solution of compound 3_8_2 (15.6 g, 49.4 mmol) and N-hydroxyphalimide (Phth-OH, 12.1 g, 74 mmol) in N,N-dimethylformamide (80 mL) at room temperature. The mixture was stirred at 45° C. for 15 hours, concentrated, extracted with ethyl acetate, washed with a saturated sodium bicarbonate solution, 1N hydrochloric acid and brine, dried over sodium sulfate, filtered and concentrated. The residue was triturated with hexanes and the solid was collected to give compound 3_8_3 (17.1 g, 86% yield) as a white solid.

$^1$H NMR (CDCl$_3$): δ=1.50 (s, 9H), 4.32 (t, J=6.4 Hz, 2H), 4.56 (t, J=6.4 Hz, 2H), 6.33 (s, 1H), 6.75 (d, J=8.8 Hz, 2H), 7.22 (d, J=8.8H, 2H), 7.83 (m, 2H), 7.52 (m, 2H).

Step 3: 2-[2-(4-Aminophenoxyl)ethoxy]-1H-isoindole-1,3(2H)-dione (3_8_4)

Trifluoroacetic acid (TFA, 14.3 mL) was added to a solution of compound 3_8_3 (7.4 g, 18.6 mmol) in dichloromethane (150 mL). The mixture was stirred for 2.5 hours at room temperature, and concentrated. The residue was then triturated with diethyl ether and the solid was collected to give the desired compound 3_8_4 (7.5 g, 97% yield, trifluoroacetic acid salt) as a pink solid.

$^1$H NMR (MeOH-d$_4$): δ=4.36 (m, 2H), 4.55 (m, 2H), 6.98 (d, J=8.8 Hz, 2H), 7.26 (d, J=8.8 Hz, 2H), 7.83 (s, 4H).

Step 4: tert-Butyl {(E)-[(tert-butoxycarbonyl)amino][(4-{2-[(1,3-dioxo-1,3-dihydro-2H-isoindol-2-yl)oxy]ethoxy}phenyl)amino]methylidene}carbamate (3_8_5)

Trifluoroacetic acid (6 mL, 43.2 mmol) was added to a suspension of compound 3_8_4 (7.4 g, 14.1 mmol) in acetonitrile (200 mL), and the mixture was stirred for 30 minutes at room temperature. Di-tert-butyl [(Z)-1H-pyrazol-1-ylmethylylidene]biscarbamate (3.2 g, 10.8 mmol) was added and the mixture was stirred for 15 hours at room temperature, concentrated and the residue was extracted with ethyl acetate, washed with brine, filtered and concentrated to give a residue. The residue was purified by chromatography to give compound 3_8_5 (3.82 g, 50% yield) as a solid.

$^1$H NMR (CDCl$_3$): δ=1.49 (s, 9H), 1.53 (s, 9H), 4.32 (t, J=4.4 Hz, 2H), 4.57 (t, J=4.4 Hz, 2H), 6.78 (d, J=8.8 Hz, 2H), 7.45 (d, J=8.8 Hz, 2H), 7.84 (m, 2H), 7.75 (m, 2H), 10.18 (s, 1H), 11.63 (s, 1H).

Step 5: tert-Butyl {({4-[2-(aminooxy)ethoxy]phenyl}amino)[(tert-butoxycarbonyl)amino]methylidene}carbamate (3_8_6)

Hydrazine hydrate (0.35 mL, 7.1 mmol) was added to a suspension of compound 3_8_5 (3.82 g, 7.1 mmol) in ethanol (200 mL) and the mixture was stirred at 35° C. for 18 hours. The solid was removed by filtration and the filtrate was concentrated to give a residue. The residue was purified by chromatography (1:1 ethyl acetate/hexanes) to give a crude product (3.1 g), which was washed with dichloromethane and filtered. The filtrate was concentrated to give pure product 3_8_6 (2.7 g, 97% yield) as a white solid.

$^1$H NMR (CDCl$_3$): δ=1.49 (s, 9H), 1.53 (s, 9H), 4.01 (t, J=4.4 Hz, 2H), 4.14 (t, J=4.4 Hz, 2H), 5.54 (s, 2H), 6.89 (d, J=9.2 Hz, 2H), 7.49 (d, J=9.2 Hz, 2H), 10.19 (s, 1H), 11.64 (s, 1H).

3.9 tert-Butyl {({4-[2-(aminooxy)propoxy]phenyl}amino)[(tert-butoxycarbonyl)amino]methylidene}carbamate

3_9_6

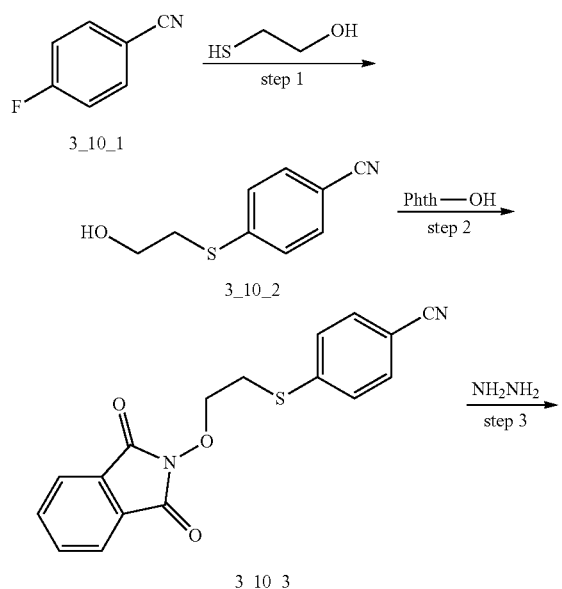

Compound 3_9_6 was prepared using the procedure described above for compound 3_8_6 using 1,3-dibromopropane instead of 1,2-dibromoethane in step 1.

3.10 4-{[2-(Aminooxy)ethyl]sulfanyl}benzenecarboximidamide

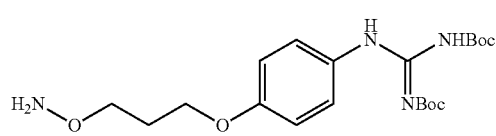

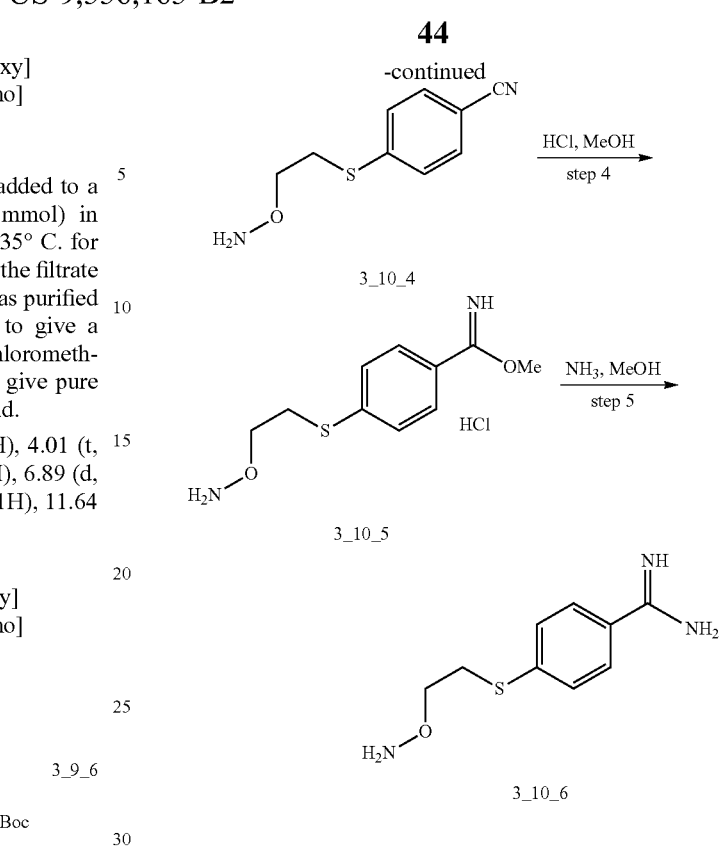

Step 1: 4-[(2-Hydroxyethyl)sulfanyl]benzonitrile (3_10_2)

2-Mercaptoethanol (4.10 g, 0.0525 mmol) and potassium carbonate (7.25 g, 0.0525 mol) was added to a solution of 4-fluorobenzonitrile 3_10_1 (4.22 g, 0.035 mol) in acetonitrile (50 mL) and the mixture was stirred at room temperature for 18 hours. The solid was removed by filtration and the filtrate was concentrated to give a residue, which was purified by column chromatography to give compound 3_10_2 (4.0 g, 64% yield) as an oil.

$^1$H NMR (400 MHz, CDCl$_3$): δ=1.92 (t, J=6.1 Hz, 1H), 3.22 (t, J=5.9 Hz, 2H), 3.86 (q, J=6.0 Hz, 2H), 7.38 (m, J=8.6 Hz, 2H), 7.55 (m, J=8.2 Hz, 2H).

Step 2: 4-{[2-(1,3-Dioxo-1,3-dihydro-2H-isoindol-2-yl)ethyl]sulfanyl}benzonitrile (3_10_3)

Triphenyl phosphine (5.85 g, 0.0223 mol) was added to a solution of compound 3_10_2 (4.00 g, 0.0223 mol) and N-hydroxyphalimide (Phth.OH, 3.64 g, 0.223 mol) in tetrahydrofuran (100 mL), followed by diethyl azodicarboxylate (3.66 mL, 0.0223 mol) slowly over 20 minutes. The mixture was stirred at room temperature for 24 hours then concentrated to give a residue. The residue was purified by column chromatography to afford compound 3_10_3 (4.6 g, 62% yield).

$^1$H NMR (400 MHz, CDCl$_3$): δ=3.42 (s, 2H), 4.38 (s, 2H), 7.41 (m, J=8.2 Hz, 2H), 7.56 (m, J=8.2 Hz, 2H), 7.79 (d, J=3.1 Hz, 2H), 7.85 (br s, 2H).

Step 3: 4-{[2-(Aminooxy)ethyl]sulfanyl}benzonitrile (3_10_4)

Hydrazine (0.804 mL, 0.0256 mol) was added to a suspension of compound 3_10_3 (4.6 g, 0.0256 mol) in ethanol (100 mL) and the mixture was stirred at 45° C. for 14 hours. The solid was removed by filtration and the filtrate was concentrated. The residue was diluted with dichloromethane (20 mL) and the solid was removed by filtration. The filtrate was concentrated to give compound 3_10_4 (3.5 g, 70% yield) as an oil.

$^1$H NMR (400 MHz, CDCl$_3$): δ=3.25 (t, J=6.6 Hz, 2H), 3.88 (t, J=6.6 Hz, 2H), 5.49 (br s., 2H), 7.37 (m, J=8.2 Hz, 2H), 7.54 (m, J=8.6 Hz, 2H).

Step 4: 4-{-[2-(Aminooxy)ethyl]sulfanyl}benzenecarboximidoate (3_10_5)

Hydrogen chloride gas was bubbled through a solution of compound 3_10_4 (3.5 g, 0.0180 mol) in dry methanol (100 mL) at 0° C. for 10 minutes. The mixture was stirred at room temperature for 14 hours to give a suspension. The white solid (3.0 g, 74% yield, hydrochloride salt) was collected by filtration.

$^1$H NMR (400 MHz, MeOH-d$_4$): δ=3.47 (s, 2H), 4.27-4.40 (m, 5H), 7.57 (d, J=9.0 Hz, 2H), 7.98 (d, J=8.6 Hz, 2H).

Step 5: 4-{[2-(Aminooxy)ethyl]sulfanyl}benzenecarboximidamide (3_10_6)

Ammonia (7N in methanol, 10 mL) was added to a solution of compound 3_10_5 (3.0 g, 73.7 mol) in dry methanol (20 mL) and the mixture was heated at 50° C. for 2 hours. After removal of the solvent, the residue was purified by chromatography to give compound 3_10_6 (1.5 g, 54% yield) as a solid.

$^1$H NMR (400 MHz, MeOH-d$_4$): δ=3.32 (br s, 2H), 3.86 (s, 2H), 7.53 (m, J=8.6 Hz, 2H) 7.71 (m, J=8.60 Hz, 2H).

3.11 4-[2-(Aminooxy)ethoxy]-N-(propan-2-yl)benzenecarboximidamide

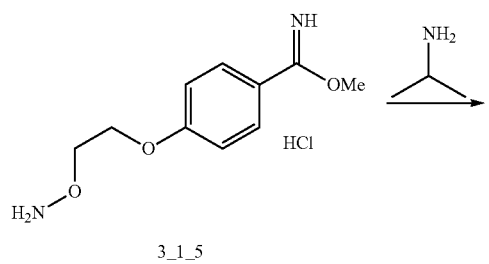

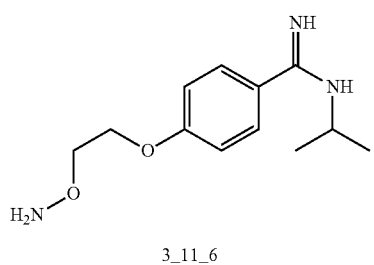

Isopropylamine (2 mL) was added dropwise at 0° C. to a suspension of compound 3_1_5 (1 g, 3.57 mmol) in methanol (10 mL) in a sealed tube and the mixture was heated at 50° C. for 16 hours. The solvent was removed under reduced pressure and the residue was partitioned between water (50 mL) and ethyl acetate (50 mL). The aqueous layer was lyophilized to give compound 3_11_6 (1.0 g, 75% yield) as a yellow foam.

3.12 4-[2-(Aminooxy)ethoxy]-N-methylbenzenecarboximidamide

Compound 3_12_6 was prepared using the procedure described above for compound 3_11_6 using methylamine instead of isopropylamine.

3.13 4-[2-(Aminooxy)ethoxy]-N-(2-hydroxyethyl)benzenecarboximidamide

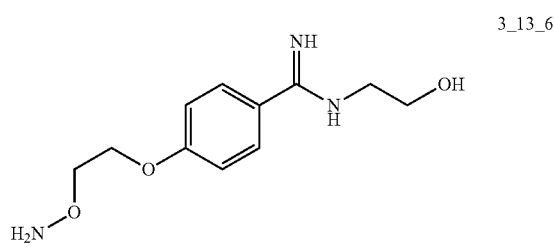 [SMILES: N=C(NCCO)c1ccc(OCCON)cc1]

Compound 3_13_6 was prepared using the procedure described above for compound 3_11_6 using 2-aminoethanol instead of isopropylamine.

3.14 2-{[{4-[2-(Aminooxy)ethoxy]phenyl}(imino)methyl]amino}ethyl formate

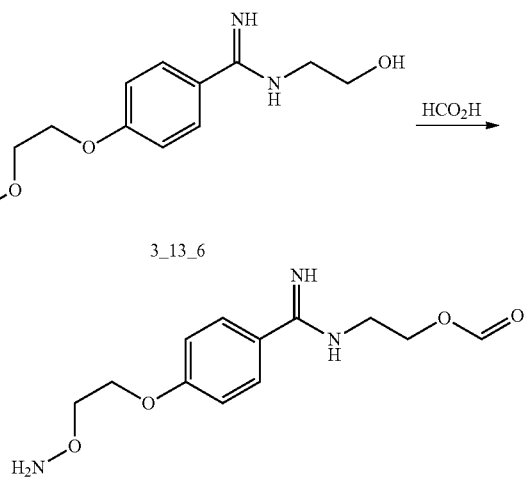

Compound 3_14_7 was prepared from compound 3_13_6 using a standard literature reported formylation method using formic acid, see e.g. *Chem. Commun.* 2007, (28), 2977-2979.

3.15 N-(2-(tert-Butoxycarbonylamino)ethyl)-4-[2-(aminooxy)ethoxy]benzenecarboximidamide

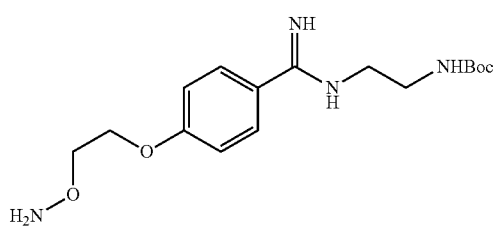

3_15_6

Compound 3_15_6 was prepared using the procedure described above for compound 3_11_6 using tert-butyl 2-aminoethylcarbamate instead of isopropylamine.

3.16 4-[2-(Aminooxy)ethoxy]-N-(3-(tert-butoxycarbonylamino)propyl)benzenecarboximidamide

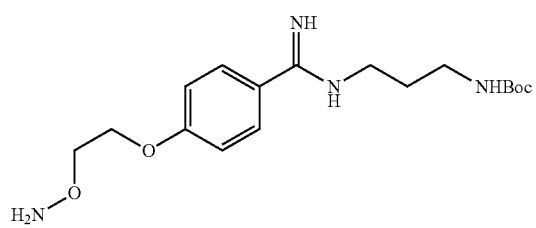

3_16_6

Compound 3_16_6 was prepared using the procedure described above for compound 3_11_6 using tert-butyl 2-aminopropylcarbamate instead of isopropylamine.

3.17 4-[2-(Aminooxy)ethoxy]-N-(pyridin-2-ylmethyl)benzenecarboximidamide

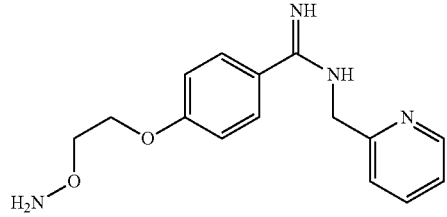

3_17_6

Compound 3_17_6 was prepared using the procedure described above for compound 3_11_6 using 2-aminomethyl pyridine instead of isopropylamine.

3.18 1-{4-[2-(Aminooxy)ethoxy]phenyl}-[4-(tert-butoxycarbonylpiperazin-1-yl)]-methanimine

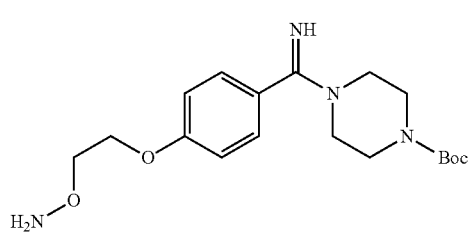

3_18_16

Compound 3_18_6 was prepared using the procedure described above for compound 3_11_6 using N-Boc protected piperizane instead of isopropylamine.

3.19 4-[2-(Aminooxy)ethoxy]-N-[2-(dimethylamino)ethyl]benzenecarboximidamide

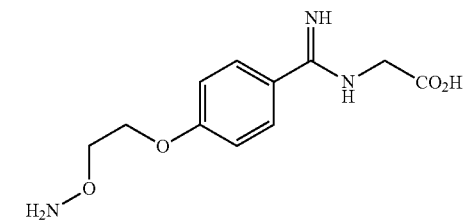

3_19_6

Compound 3_19_6 was prepared using the procedure described above for compound 3_11_6 using 2-(N,N-dimethylamino)ethylamine instead of isopropylamine.

3.20 N-[{4-[2-(Aminooxy)ethoxy]phenyl}(imino)methyl]glycine

3_20_6

Compound 3_20_6 was prepared using the procedure described above for compound 3_11_6 using amino acetic acid instead of isopropylamine.

3.21 4-[2-(Aminooxy)ethoxy]-N-(1,3-di(tert-butoxycarbonylamino)propan-2-yl)benzenecarboximidamide

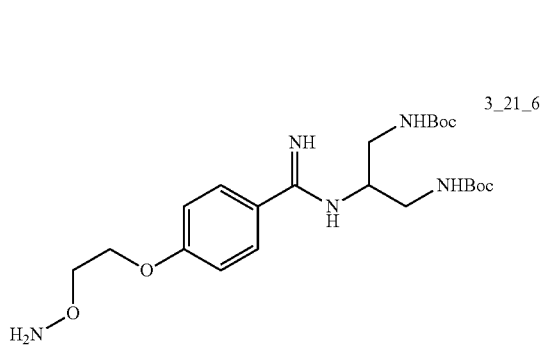 [SMILES: CC(C)(C)OC(=O)NCC(CNC(=O)OC(C)(C)C)NC(=N)c1ccc(OCCON)cc1]

Compound 3_21_6 was prepared using the procedure described above for compound 3_11_6 using di-tert-butyl (2-aminopropane-1,3-diyl)biscarbamate instead of isopropylamine.

3.22 N-(1-(tert-butoxycarbonylamino)-3-hydroxypropan-2-yl)-4-[2-(aminooxy)ethoxy]benzenecarboximidamide

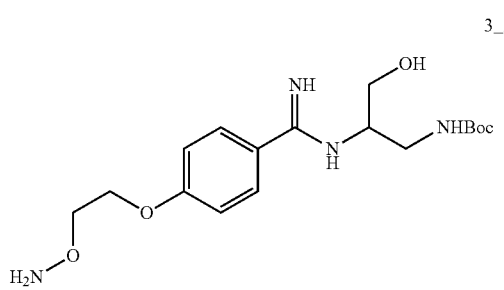

Compound 3_22_6 was prepared using the procedure described above for compound 3_11_6 using tert-butyl (2-amino-3-{[tert-butyl(dimethyl)silyl]oxy}propyl)carbamate instead of isopropylamine.

3.23 4-(2-Aminooxy-ethoxy)-N-hydroxy-benzamidine

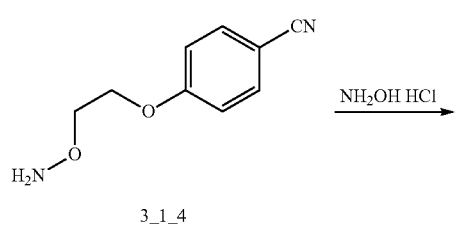

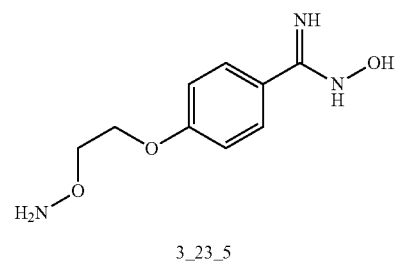

Hydroxylamine hydrogen chloride (1.36 g, 19.6 mmol) was added to a mixture of compound 3_1_4 (1 g, 5.61 mmol) and sodium carbonate (1.07 g, 10.1 mmol) in ethanol/water (3 mL: 23 mL). The reaction mixture was stirred at room temperature for 72 hours, diluted with brine (40 mL), extracted into ethyl acetate (3×100 mL) and the combined organic extracts were washed with water, dried over anhydrous sodium sulfate and evaporated. The residue was triturated with dichloromethane, filtered, rinsed with dichloromethane and dried in vacuum to give compound 3_23_5 (0.3 g, 25% yield) as a white powder.

$^1$H NMR (400 MHz, DMSO-d$_6$): δ=3.82 (br s, 2H), 4.11 (br s, 2H), 5.69 (s, 2H), 6.08 (s, 2H), 6.91 (d, J=8.99 Hz, 2H), 7.57 (d, J=8.99 Hz, 2H), 9.42 (s, 1H).

MS: m/z (ES$^+$, %) 212 (M+H, 100), 179 (5), 153 (10), 124 (15), 103 (25).

3.24 4-[(Aminooxy)methyl]benzenecarboximidamide

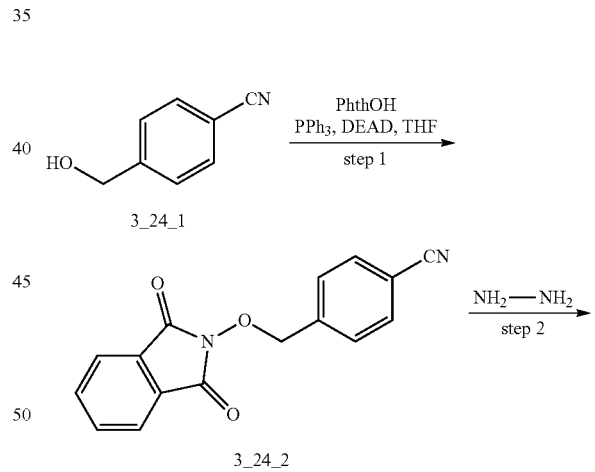

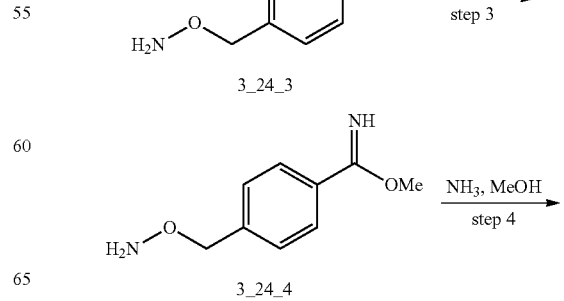

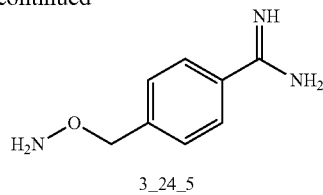

3_24_5

Step 1: 4-{[(1,3-Dioxo-1,3-dihydro-2H-isoindol-2-yl)oxy]methyl}benzonitrile (3_24_2)

N-Hydroxyphthalimide (PhthOH, 7.12 g, 55 mmol), triphenylphosphine (14.41 g, 55 mmol) and diethyl azodicarboxylate (DEAD, 9 mL, 55 mmol) were slowly added to a solution of 4-hydroxymethyl benzonitrile 3_24_1 (8.15 g, 50 mmol) in tetrahydrofuran (100 mL). The mixture was stirred at room temperature for 15 hours. The solid was collected by filtration, washed with tetrahydrofuran and dried to give compound 3_24_2 (10 g, 72% yield) as a solid.

Step 2: 4-[(Aminooxy)methyl]benzonitrile (3_24_3)

Hydrazine hydrate (0.336 g, 6.2 mmol) was added to a suspension of compound 3_24_2 (1.55 g, 5.6 mmol) in ethanol (20 mL) and the mixture was stirred at room temperature for 15 hours. The solid was removed by filtration and the filtrate was concentrated. The residue was diluted with dichloromethane (30 mL), the solid was removed by filtration and the filtrate was concentrated to give compound 3_24_3 (0.88 g, 100% yield) as a solid.

Step 3: Methyl 4-[(aminooxy)methyl]benzenecarboximidoate (3_24_4)

Hydrogen chloride gas was bubbled through a solution of compound 3_24_3 (0.88 g, 5.6 mmol) in methanol (30 mL) at 0° C. for 5 minutes and the mixture was stirred at room temperature for 20 hours. The solid was collected by filtration, washed with methanol and dried to give compound 3_24_4 (0.54 g, 38% yield) as a white solid.

Step 4: 4-[(Aminooxy)methyl]benzenecarboximidamide (3_24_5)

Compound 3_24_4 (0.54 g, 2.13 mmol) in methanol (5 mL) was added slowly to a solution of ammonia (7N in methanol, 7 mL, 21 mmol) in methanol (10 mL) and the mixture was stirred at room temperature for 18 hours. After removal of the solvent, the residue was diluted with dichloromethane (30 mL), and the solid was collected by filtration to give compound 3_24_5 (0.42 g, 83% yield) as a white solid.

3.25 4-{[2-(Aminooxy)ethyl]amino}benzenecarboximidamide

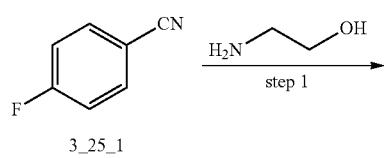

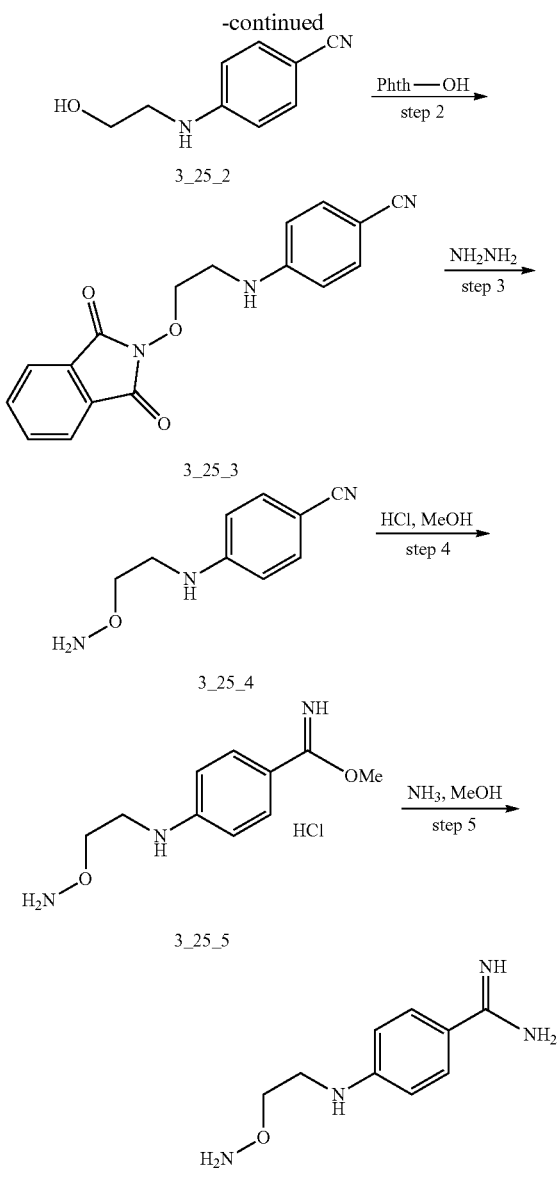

Step 1: 4-[(2-Hydroxyethyl)amino]benzonitrile (3_25_2)

2-Aminoethanol (3.0 mL, 49.48 mmol) and potassium carbonate (6.84 g, 49.48 mmol) were added to a solution of 4-fluorobenzonitrile 3_25_1 (5.0 g, 41.24 mmol) in dimethyl sulfoxide (30 mL). The mixture was stirred at 100° C. for 18 hours, poured onto ice-water (100 mL) and extracted with ethyl acetate (3×100 mL). The combined extracts were washed with brine (50 mL), dried over magnesium sulfate, and concentrated to give a residue which was purified by column chromatography to give compound 3_25_2 (3.0 g, 45% yield) as an oil.

$^1$H NMR (400 MHz, CDCl$_3$): δ=1.80 (t, J=5.3 Hz, 1H), 3.34 (q, J=5.5 Hz, 2H), 3.87 (q, J=5.2 Hz, 2H), 4.61 (br s., 1H), 6.60 (d, J=8.6 Hz, 2H), 7.42 (d, J=8.6 Hz, 2H).

Step 2: 4-({2-[(1,3-Dioxo-1,3-dihydro-2H-isoindol-2-yl)oxy]ethyl}amino)benzonitrile (3_25_3)

Triphenylphosphine (1.61 g, 6.16 mmol) was added to a solution of compound 3_25_2 (1.00 g, 6.16 mmol) and N-hydroxyphthalimide (Phth-OH, 1.05 g, 6.16 mmol) in tetrahydrofuran (100 mL), followed by the slow addition of diethyl azodicarboxylate (1.02 mL, 6.16 mmol) over 20 minutes. The mixture was stirred at room temperature for 24 hours and concentrated to yield a residue which was purified by column chromatography to afford compound 3_25_3 (1.1 g, 58% yield).

$^1$H NMR (400 MHz, DMSO-$d_6$): δ=3.50 (d, J=5.5 Hz, 2H), 4.29 (t, J=5.47 Hz, 2H), 6.71 (d, J=8.6 Hz, 2H), 6.79 (s, 1H), 7.47 (d, J=8.6 Hz, 2H), 7.86 (s, 4H).

Step 3: 4-{-[2-(Aminooxy)ethyl]amino}benzonitrile (3_25_4)

Hydrazine hydrate (0.255 mL, 10.90 mmol) was added to a suspension of compound 3_25_3 (3.35 g, 10.90 mmol) in ethanol (80 mL) and the mixture was stirred at 45° C. for 14 hours. The solid was removed by filtration and the filtrate was concentrated. The residue was diluted with dichloromethane (20 mL). The solid was removed by filtration and the filtrate was concentrated to give compound 3_25_4 (1.9 g, 97% yield) as an oil.

$^1$H NMR (400 MHz, DMSO-$d_6$): δ=3.27 (d, J=5.7 Hz, 2H), 3.58-3.71 (m, 2H), 6.04 (s, 2H), 6.66 (d, J=8. Hz, 3H), 7.43 (d, J=8.9 Hz, 2H).

Step 4: 4-{[2-(Aminooxy)ethyl]amino}benzenecarboximidoate (3_25_5)

Hydrogen chloride gas was bubbled through a solution of compound 3_25_4 (1.9 g, 10.72 mmol) in dry methanol (50 mL) at 0° C. for 10 minutes. The mixture was stirred at room temperature for 14 hours to give compound 3_25_5 as a white solid (1.0 g, 45% yield, hydrochloride salt) which was collected by filtration.

$^1$H NMR (400 MHz, MeOH-$d_4$): δ=3.60 (s, 2H), 4.18-4.30 (m, 5H), 6.79 (d, J=8.9 Hz, 2H), 7.86 (d, J=8.9 Hz, 2H).

Step 5: 4-{-[2-(Aminooxy)ethyl]amino}benzenecarboximidamide (3_25_6)

Ammonia (7N in methanol, 5 mL) was added to a solution of compound 3_25_5 (1.0 g, 4.78 mmol) in dry methanol (10 mL) and the mixture was heated at 50° C. for 2 hours. After removal of the solvent, the obtained product (930 mg, 100% yield) was used without further purification.

$^1$H NMR (400 MHz, MeOH-$d_4$): δ=6 3.40 (t, J=5.5 Hz, 2H), 3.82 (t, J=5.5 Hz, 2H), 6.74 (d, J=9.0 Hz, 2H), 7.61 (d, J=8.6 Hz, 2H).

3.26 5-{[2-(Aminooxy)ethoxy]methyl}thiophene-3-carboximidamide

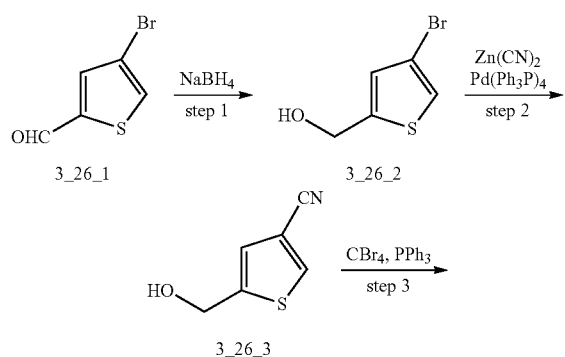

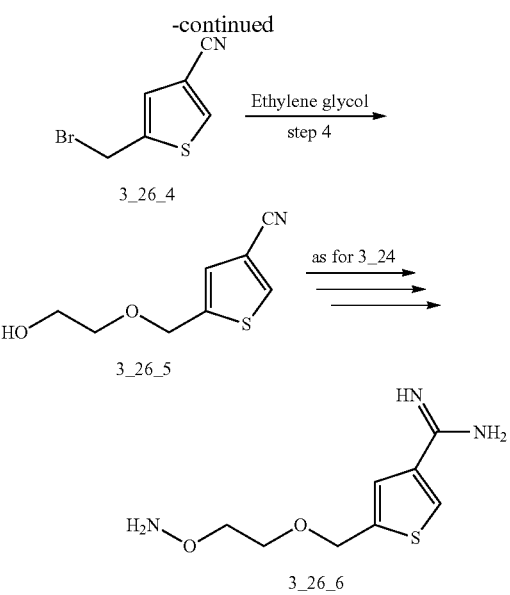

Step 1: (4-Bromothiophen-2-yl)methanol (3_26_2)

Sodium borohydride (5.20 g, 0.137 mol) was added to a solution of 4-bromo-thiophene-2-carbaldehyde 3_26_1 (25.0 g, 0.131 mol) in anhydrous tetrahydrofuran (400 mL) at room temperature and the resulting mixture was stirred at room temperature for 1.5 hours. The reaction was quenched by carefully adding a saturated ammonium chloride solution (100 mL) at room temperature. The mixture was extracted into ethyl acetate and the extract was washed with brine, dried over sodium sulfate, and concentrated to give the product (25.02 g, 99% yield) which was used in the next step without further purification.

$^1$H NMR (400 MHz, CDCl$_3$): δ=1.93 (br. s., 1H), 4.79 (s, 2H), 6.93 (s, 1H), 7.18 (d, J=1.5 Hz, 1H).

Step 2: 5-(Hydroxymethyl)thiophene-3-carbonitrile (3_26_3)

Zinc cyanide (15.2 g, 0.129 mmol) was added to a solution of (4-bromothiophen-2-yl)-methanol 3_26_2 (25.0 g, 0.129 mol) in N,N-dimethylformamide (150 mL). After degassing for 10 minutes, tetrakis(triphenylphosphine)palladium(0) (7.48 g, 6.47 mmol) was added and the reaction mixture was stirred at 80° C. for 4 hours. After cooling to room temperature, the mixture was filtered and the filtrate was concentrated to dryness. The residue was purified by column chromatography to give the desired product (13.67 g, 76% yield).

$^1$H NMR (400 MHz, CDCl$_3$): δ=1.98 (t, 1H), 4.86 (d, J=6.1 Hz, 2H), 7.17 (d, J=1.2 Hz, 1H), 7.88 (d, J=1.2 Hz, 1H).

Step 3: 5-(Bromomethyl)thiophene-3-carbonitrile (3_26_4)

Triphenylphosphine (9.9 g, 37.7 mmol) and carbon tetrabromide (12.59 g, 37.7 mmol) were added to a solution of 5-hydroxymethyl-thiophene-3-carbonitrile 3_26_3 (5.0 g, 35.9 mmol) in tetrahydrofuran (150 mL), at room temperature. After stirring for 4 hours, the mixture was concentrated to dryness. The residue was purified by column chromatography to give the desired product (4.85 g, 67% yield) as a colorless oil.

Step 4: 5-[(2-Hydroxyethoxy)methyl]thiophene-3-carbonitrile (3_26_5)

Sodium (0.824 g, 35.8 mmol) was added to a solution of ethylene glycol (14.8 g, 0.239 mol) in tetrahydrofuran (20 mL) at room temperature. After all the sodium was consumed, 5-bromomethyl-thiophene-3-carbonitrile 3_26_4 (4.83 g, 23.9 mmol) in tetrahydrofuran (20 mL) was added at −10° C. and the reaction mixture was stirred at room temperature for 9.5 hours. The reaction mixture was neutralized to pH 7 using diluted hydrochloric acid at 0° C. and the mixture was extracted with ethyl acetate and the extract was washed with brine, dried over sodium sulfate and concentrated to dryness to give the product (4.12 g, 9% yield) as a colorless oil.

$^1$H NMR (400 MHz, CDCl$_3$): δ=1.90 (t, 1H), 3.58-3.65 (m, 2H), 3.73-3.88 (m, 2H), 4.62-4.81 (m, 2H), 7.18 (d, J=1.2 Hz, 1H), 7.90 (d, J=1.5 Hz, 1H).

MS (ES$^+$) m/z: [M+H]$^+$ calcd for C$_8$H$_{10}$NO$_2$S: 184.23. Found: 184.93.

Following the procedures as described under 3_24 and using 5-(2-hydroxy-ethoxymethyl)-thiophene-3-carbonitrile (3_26_5) in place of 4-hydroxymethyl benzonitrile (3_24_1), compound 3_26_6 was prepared.

3.27
5-[(Aminooxy)methyl]thiophene-3-carboximidamide

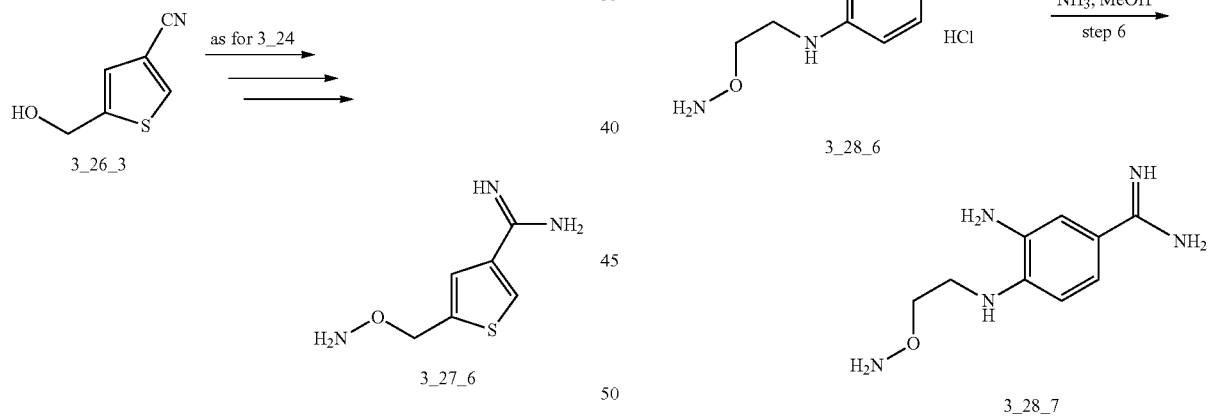

Following the procedures as described under 3_24 and using 5-(hydroxymethyl)-thiophene-3-carbonitrile (3_26_3) in place of 4-hydroxymethyl benzonitrile (3_24_1), compound 3_27_6 was prepared.

3.28 3-Amino-4-(2-aminooxy-ethoxy)-benzamidine

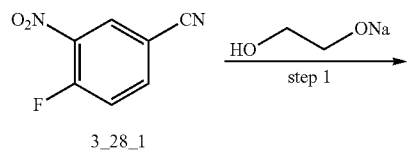

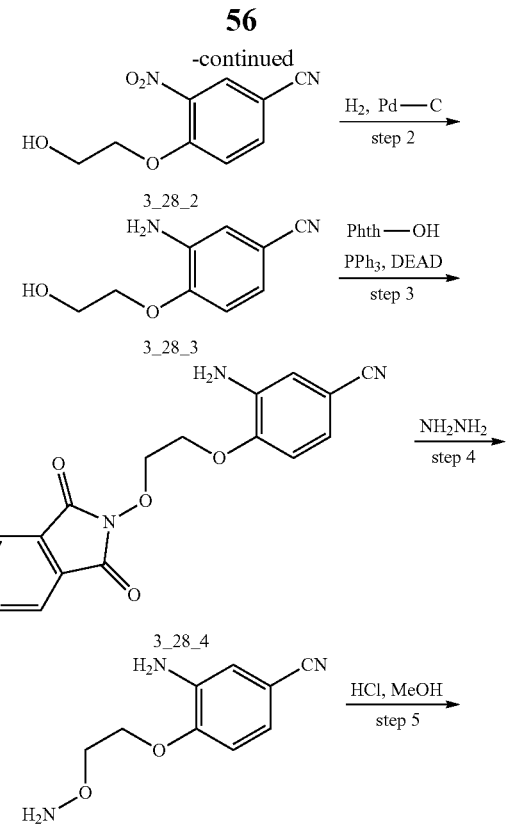

Step 1: 4-(2-Hydroxy-ethoxy)-3-nitro-benzonitrile (3_28_2)

Sodium (1.038 g, 45.2 mmol) was added to a mixture of ethylene glycol (28.03 g, 0.451 mol) in tetrahydrofuran (20 mL) at room temperature. After all sodium was consumed, 4-fluoro-3-nitro-benzonitrile 3_28_1 (5.0 g, 30.1 mmol) in tetrahydrofuran (10 mL) was added at −10° C. and the reaction mixture was stirred at room temperature for 3 hours. The reaction mixture was quenched by adding ice-water and neutralized to pH 7 using dilute hydrochloric acid at 0° C. The mixture was extracted with ethyl acetate and the extract was washed with brine, dried over sodium sulfate and concentrated to dryness. The residue was purified by crystallization from ethyl acetate/hexanes to give the desired product (4.45 g, 71% yield) as a light yellow solid.

$^1$H NMR (400 MHz, DMSO-d$_6$): δ=3.60-3.79 (m, 2H), 4.17-4.37 (m, 2H), 4.94 (t, J=5.3 Hz, 1H), 7.56 (d, J=8.8 Hz, 1H), 8.09 (dd, J=8.9, 2.2 Hz, 1H), 8.45 (d, J=2.0 Hz, 1H).

MS (ES$^-$) m/z: [M–H]$^-$ calcd for C$_9$H$_7$N$_2$O$_4$: 207.18. Found: 206.90.

Step 2: 3-Amino-4-(2-hydroxy-ethoxy)-benzonitrile (3_28_3)

Palladium on charcoal (10%, 0.4 g) was added to a solution of 4-(2-hydroxy-ethoxy)-3-nitro-benzonitrile 3_28_2 (2.7 g, 12.97 mmol) in ethanol (40 mL) and tetrahydrofuran (40 mL). The mixture was hydrogenated on a Parr Shaker apparatus at room temperature for 3 hours. After filtration, the filtrate was concentrated and the residue was purified by flash column chromatography to give the desired product (1.50 g, 65% yield) as a white solid.

$^1$H NMR (400 MHz, DMSO-d$_6$): ε=3.71 (m, 2H), 3.98 (t, J=4.7 Hz, 2H), 4.93 (t, J=6.3 Hz, 1H), 5.30 (s, 2H), 6.77-6.98 (m, 3H).

MS (ES$^+$) m/z: [M+H]$^+$ calcd for C$_9$H$_{11}$N$_2$O$_2$: 179.19. Found: 178.99.

Step 3: 3-Amino-4-[2-(1,3-dioxo-1,3-dihydro-isoindol-2-yloxy)-ethoxy]-benzonitrile (3_28_4)

N-Hydroxyphthalimide (Phth-OH, 1.44 g, 8.83 mmol) and triphenylphosphine (2.53 g, 9.63 mmol) were added to a solution of 3-amino-4-(2-hydroxy-ethoxy)-benzonitrile 3_28_3 (1.43 g, 8.02 mmol) in anhydrous tetrahydrofuran (40 mL) at room temperature. Diethyl azodicarboxylate (1.68 g, 9.63 mmol) was added dropwise to the resulting solution at 20° C. and the resulting mixture was stirred at room temperature overnight. After the evaporation of the tetrahydrofuran, the residue was dissolved in acetone (25 mL) and diluted with hexanes (33 mL). The white precipitate was collected and washed with a minimum amount of acetone to give the desired product (1.91 g, 74% yield) as a white solid.

$^1$H NMR (400 MHz, DMSO-d$_6$): δ=4.34 (m, 2H), 4.54 (ddd, J=3.9, 2.2, 2.0 Hz, 2H), 5.21 (s, 2H), 6.83-7.03 (m, 3H), 7.86 (s, 4H).

Step 4: 3-Amino-4-(2-aminooxy-ethoxy)-benzonitrile (3_28_5)

Hydrazine monohydrate (0.338 g, 6.76 mmol) was added to a solution of 3-amino-4-[2-(1,3-dioxo-1,3-dihydro-isoindol-2-yloxy)-ethoxy]-benzonitrile 3_28_4 (1.90 g, 5.88 mmol) in anhydrous ethanol (15 mL) and tetrahydrofuran (30 mL) at 0° C. and the resulting mixture was stirred at room temperature for 6.5 hours. After concentration, the residue was stirred with ether (40 mL) for 1 hour and filtered. The filtrate was concentrated to give crude compound 3_28_5 (1.31 g, crude) as a white solid.

$^1$H NMR (400 MHz, DMSO-d$_6$): ε=3.77-3.91 (m, 2H), 4.12-4.22 (m, 2H), 5.13 (s, 2H), 6.09 (br s., 2H), 6.82-7.00 (m, 3H).

Step 5: 3-Amino-4-(2-aminooxy-ethoxy)-benzimidic acid methyl ester dihydrochloric acid salt (3_28_6)

Hydrogen chloride gas was introduced into a solution of 3-amino-4-(2-aminooxy-ethoxy)-benzonitrile 3_28_5 (1.30 g, 6.73 mmol) in anhydrous methanol (200 mL) at 0° C. for 15 minutes and the resulting mixture was stirred at room temperature overnight. After concentration, the residue was stirred with ether (60 mL) for 0.5 hour and the precipitate was collected and dried to give the desired product (1.33 g, 66% yield) as a white solid.

$^1$H NMR (400 MHz, DMSO-d$_6$): ε=4.23 (s, 3H), 4.34-4.51 (m, 8H), 7.12 (d, J=8.8 Hz, 1H), 7.43 (d, J=1.5 Hz, 1H), 7.61 (br s., 1H), 8.05 (br s., 1H).

Step 6: 3-Amino-4-(2-aminooxy-ethoxy)-benzamidine (3_28_7)

Ammonia (7N in methanol, 9.6 mL, 66.9 mol) was added to a suspension of 3-amino-4-(2-aminooxy-ethoxy)-benzimidic acid methyl ester dihydrochloric acid salt 3_28_6 (1.33 g, 4.46 mmol) in anhydrous methanol (35 mL) at 0° C. and the resulting mixture was stirred at 50° C. for 3 hours. After concentration, the residue was stirred with ethanol for 1 hour. After filtration, the filtrate was concentrated to dryness to afford the desired product (1.2 g, >100% yield) as a white solid, which was used without further purification.

3.29 4-[2-(Aminooxy)ethoxy]-3-(hydroxymethyl)benzenecarboximidamide

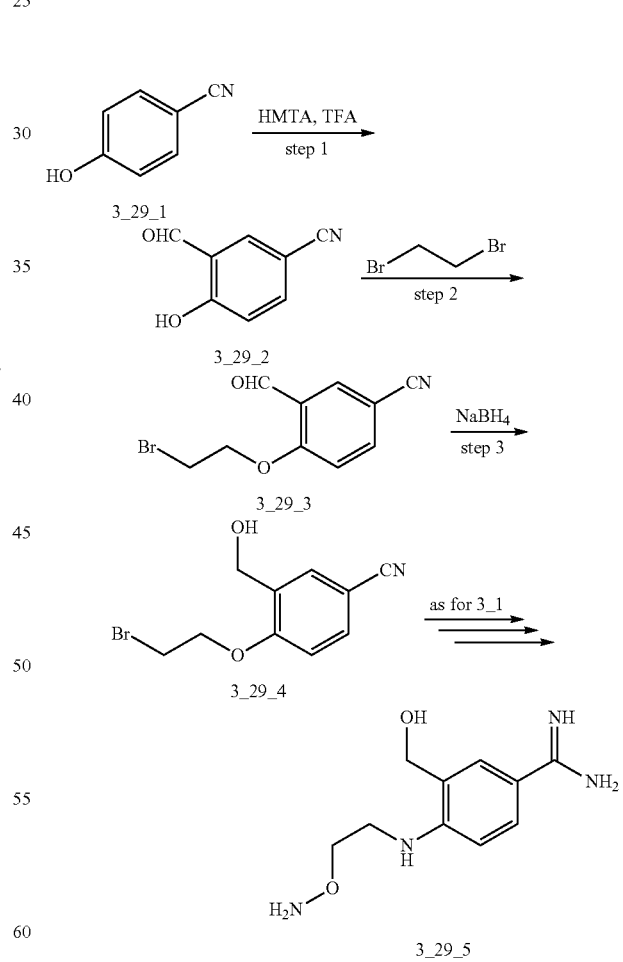

Step 1: 3-Formyl-4-hydroxybenzonitrile (3_29_2)

Hexamethylenetetramine (HMTA, 117.6 g, 840 mmol) was added to a cooled (0° C.) solution of 4-cyanophenol 3_29_1 (50 g, 420 mmol) in trifluoroacetic acid (TFA, 340 mL). After the addition, the mixture was heated at 100° C. for 16 hours, cooled to room temperature, quenched with 50% sulfuric acid (210 mL) and water (1260 mL), extracted with ethyl acetate, dried and concentrated. The residue was purified by chromatography to give compound 3_29_2 (12 g, 19% yield) as an off-white solid.

Step 2: 4-(2-Bromoethoxy)-3-formylbenzonitrile (3_29_3)

A mixture of compound 3_29_2 (0.5 g, 3.4 mmol), 1,2-dibromoethane (0.85 mL, 10.20 mmol) and $K_2CO_3$ (2.35 g, 17 mmol) in acetonitrile was refluxed for 2 h, cooled to RT, filtered and concentrated. The residue was purified by chromatography to give compound 3_29_3 (650 mg, 76% yield) as a colorless oil.

Step 3: 4-(2-Bromoethoxy)-3-(hydroxymethyl)benzonitrile (3_29_4)

Sodium borohydride (67 mg, 1.77 mmol) was added in portions to a cooled (0° C.) solution of compound 3_29_3 (224 mg, 0.89 mmol) in methanol (5 mL). After the addition, the mixture was stirred at 0° C. for 40 minutes, quenched with a saturated ammonium chloride solution, diluted with ethyl acetate (30 mL), washed with water (5 mL), dried over sodium sulfate and concentrated to give compound 3_29_4 (170 mg, 75% yield) as a gum.

Following the procedures as described under 3_1 and using 4-(2-bromoethoxy)-3-(hydroxymethyl)benzonitrile (3_29_4) instead of 4-(2-bromoethoxy)benzonitrile (3_1_2), compound 3_29_5 was prepared.

3.30 tert-Butyl [{6-[2-(aminooxy)ethoxy]pyridazin-3-yl}(imino)methyl]carbamate

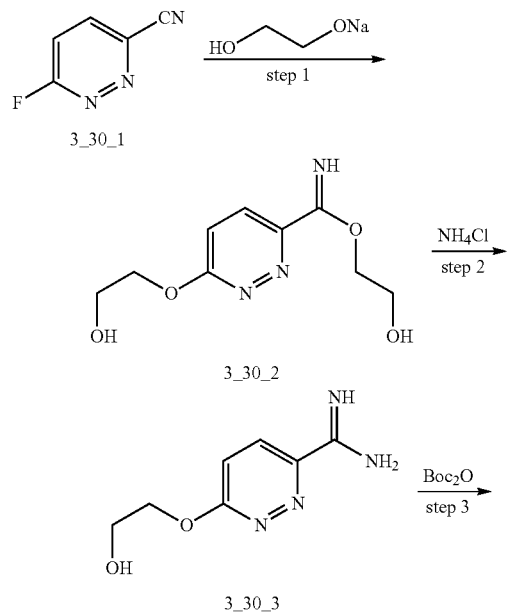

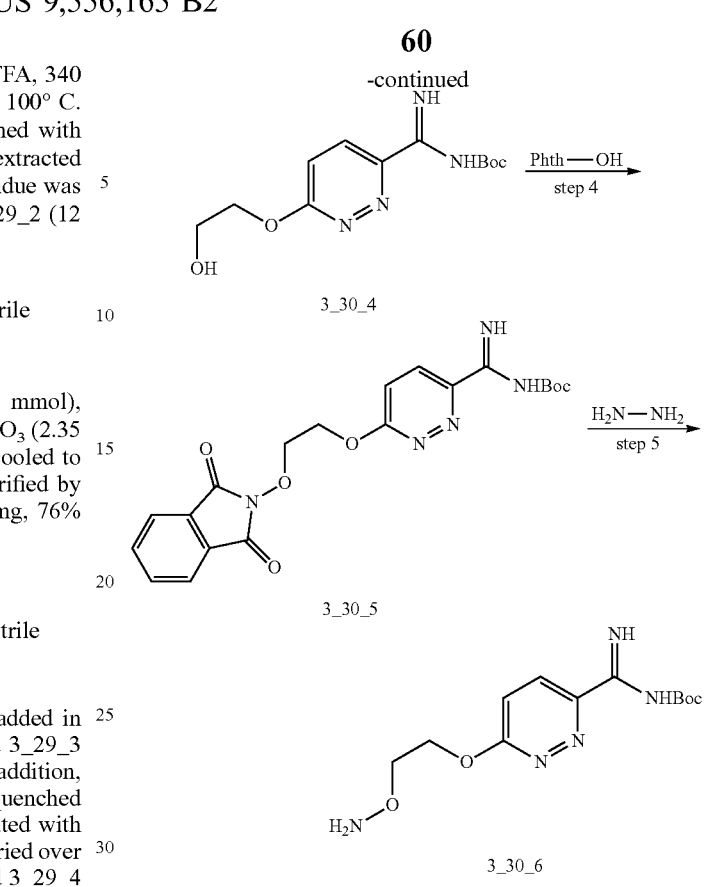

Step 1: 6-(2-Hydroxyethoxyl)pyridazine-3-carboximidic acid 2-hydroxy-ethyl ester (3_30_2)

Sodium (0.593 g, 0.0258 mmol) was added to a flask containing ethylene glycol (13.34 g, 0.215 mol) at 0° C. After all sodium was consumed, 6-fluoro-pyridazine-3-carbonitrile 3_30_1 (3.0 g, 0.0215 mmol) in tetrahydrofuran (10 mL) was added at 0° C. and the reaction mixture was stirred at room temperature overnight. The reaction mixture was filtered and the filter cake was washed with cold tetrahydrofuran and dried to afford the desired product 3_30_2 (4.32 g, 88% yield) as a white solid.

$^1$H NMR (400 MHz, DMSO-$d_6$): ϵ=3.65-3.86 (m, 4H), 4.23-4.34 (m, 2H), 4.47-4.57 (m, 2H), 4.82-5.03 (m, 2H), 7.37 (d, J=9.0 Hz, 1H), 8.04 (d, J=9.0 Hz, 1H), 9.23 (s, 1H).

MS (ES$^+$) m/z: [M+H]$^+$ calcd for $C_9H_{14}N_3O_4$: 228.22. Found: 228.07.

Step 2: 6-(2-Hydroxyethoxyl)pyridazine-3-carboxamidine (3_30_3)

Ammonium chloride (0.899 g, 16.8 mmol) was added to a mixture of 6-(2-hydroxy-ethoxy)-pyridazine-3-carboximidic acid 2-hydroxy-ethyl ester 3_30_2 (3.185 g, 14.0 mmol) in methanol (120 mL). The mixture was refluxed overnight and then concentrated to dryness. The residue was dissolved in water, neutralized to pH 9 using a saturated sodium bicarbonate solution and lyophilized to give the crude product. The material was purified by flash column chromatography to give the desired product (2.1 g, 82% yield) as a white solid.

$^1$H NMR (400 MHz, DMSO-d$_6$): δ=3.78 (m, 2H), 4.41-4.57 (m, 2H), 4.88-4.99 (m, 1H), 6.87 (br. s., 3H), 7.29 (d, J=9.1 Hz, 1H), 8.24 (d, J=9.4 Hz, 1H).

Step 3: tert-Butyl {[6-(2-hydroxyethoxyl)pyridazin-3-yl](imino)methyl}carbamate (3_30_4)

A saturated sodium bicarbonate solution (8 mL) and a solution of di-tert-butyldicarbonate (BOC$_2$O, 2.753 g, 12.6 mmol) in 1,4-dioxane (10 mL) were added to a solution of 6-(2-hydroxy-ethoxy)-pyridazine-3-carboxamidine 3_30_3 (1.915 g, 10.5 mmol) in water (10 mL) at room temperature. After stirring at room temperature overnight, more di-tert-butyldicarbonate (1.0 g) was added and the mixture was stirred for another 16 hours. The resulting mixture was concentrated and the white solid was collected, washed with water and dried to give the desired product (1.29 g, 44% yield) as an off-white solid.

$^1$H NMR (400 MHz, DMSO-d$_6$): δ=1.45 (s, 9H), 3.68-3.89 (m, 2H), 4.41-4.61 (m, 2H), 4.95 (t, J=5.4 Hz, 1H), 7.32 (d, J=9.4 Hz, 1H), 8.22 (d, J=9.1 Hz, 1H), 9.03 (br s., 2H).

MS (ES$^+$) m/z: [M+H]$^+$ calcd for C$_{12}$H$_{19}$N$_4$O$_4$: 283.30 Found: 283.25.

Step 4: tert-Butyl [(6-{2-[(1,3-dioxo-1,3-dihydro-2H-isoindol-2-yl)oxy]ethoxy}pyridazin-3-yl)(imino)methyl]carbamate (3_30_5)

N-Hydroxyphthalimide (Phth-OH, 0.814 g, 4.99 mmol) and triphenylphosphine (1.427 g, 5.44 mmol) were added to a solution of {[6-(2-hydroxy-ethoxy)-pyridazin-3-yl]-imino-methyl}-carbamic acid tert-butyl ester 3_30_4 (1.28 g, 4.53 mmol) in anhydrous tetrahydrofuran (40 mL) at room temperature and a solution of diethyl azodicarboxylate (0.948 g, 5.44 mmol) in tetrahydrofuran (20 mL) was added dropwise to the resulting solution at 20° C. The resulting mixture was stirred at room temperature for 2 hours. After evaporation of half of the tetrahydrofuran, the white precipitate was collected, washed with a small volume of cold tetrahydrofuran and dried to afford the product 3_30_5 (1.412 g, 73% yield) as a white solid.

$^1$H NMR (400 MHz, DMSO-d$_6$): δ=1.53 (s, 9H), 4.50-4.66 (m, 2H), 4.73-4.89 (m, 2H), 7.29 (d, J=9.1 Hz, 1H), 7.86 (s, 4H), 8.23 (d, J=9.1 Hz, 1H), 9.03 (br s., 2H).

MS (ES$^+$) m/z: [M+H]$^+$ calcd for C$_{20}$H$_{22}$N$_5$O$_6$: 428.42. Found: 428.22.

Step 5: tert-Butyl [{6-[2-(aminooxy)ethoxy]pyridazin-3-yl}(imino)methyl]carbamate (3_30_6)

Hydrazine monohydrate (0.178 g, 3.55 mmol) was added to a solution of ({6-[2-(1,3-dioxo-1,3-dihydro-isoindol-2-yloxy)-ethoxy]-pyridazin-3-yl}-imino-methyl)-carbamic acid tert-butyl ester 3_30_5 (1.381 g, 3.23 mmol) in anhydrous ethanol (20 mL) and tetrahydrofuran (20 mL) at 0° C. and the resulting mixture was stirred at room temperature for 2.5 hours. After concentration, the residue was purified by flash column chromatography to give compound 3_30_6 (0.960 g, 100%) as a white solid.

$^1$H NMR (400 MHz, DMSO-d$_6$): δ=1.44 (s, 9H), 3.80-3.96 (m, 2H), 4.58-4.70 (m, 2H), 6.12 (s, 2H), 7.31 (d, J=9.4 Hz, 1H), 8.19 (d, J=9.1 Hz, 1H).

MS (ES$^+$) m/z: [M+H]$^+$ calcd for C$_{12}$H$_{20}$N$_5$O$_4$: 298.32. Found: 298.27.

3.31 tert-Butyl [{5-[2-(Aminooxy)ethoxy]pyrazine-2-yl}(imino)methyl]carbamate

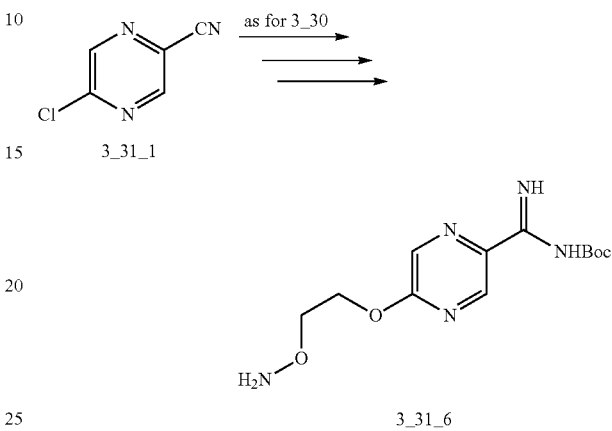

Using the procedure as described under 3.30 but using 5-chloro-pyrazine-2-carbonitrile (3_31_1) instead of 6-fluoro-pyridazine-3-carbonitrile (3_30_1), compound 3_31_6 was prepared.

3.32 5-[2-(Aminooxy)ethoxy]pyridine-2-carboximidamide

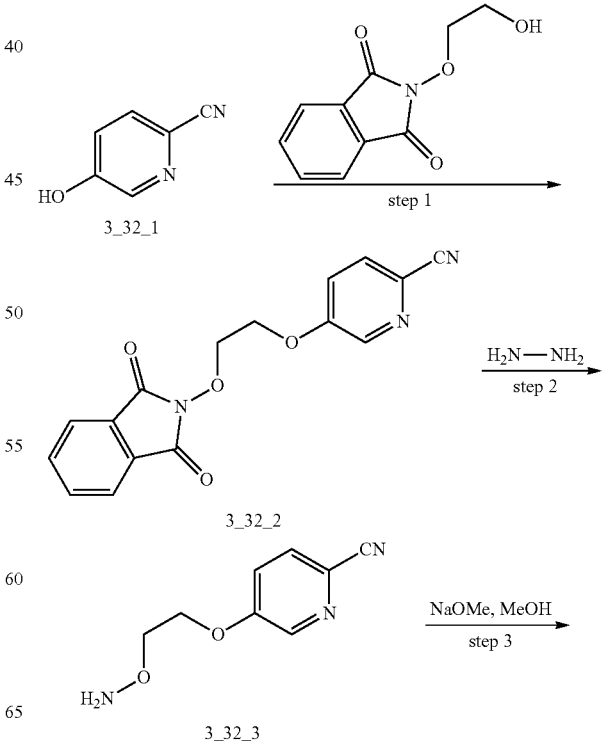

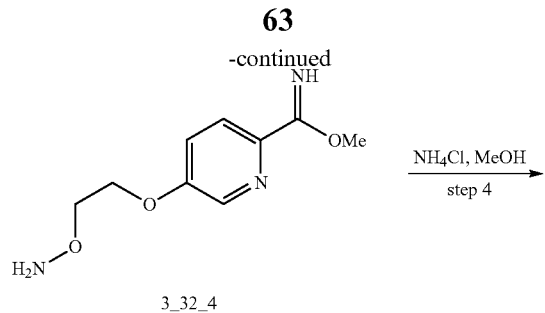

Step 4: 5-(2-Aminooxy-ethoxy)-pyridine-2-carboxamidine (3_32_5)

Ammonium chloride (31 mg, 0.568 mmol) was added to a solution of 3_32_4 (100 mg, 0.437 mmol) in methanol (5 mL) and the mixture was stirred at room temperature for 6 hours. After the removal of the solvent, the residue was washed with tert-butyl methyl ether (10 mL), and stirred with ammonia (6N in methanol, 1 mL) for 1 hour. The solvents were then evaporated to give compound 3_32_5 (0.10 g, crude) as a solid.

$^1$H NMR (400 MHz, DMSO-d$_6$): ϵ=4.31 (b. s., 2H), 4.35-4.43 (m, H), 6.01 (br. s., 2H), 7.42-7.51 (m, 1H), 7.74-7.82 (m, 1H), 8.30 (br s., 1H).

3.33 tert-Butyl (2-{[{5-[2-(aminooxy)ethoxy]pyridin-2-yl}-(imino)methyl]amino}ethyl)-carbamate

Step 1: 5-[2-(1,3-Dioxo-1,3-dihydro-isoindol-2-yloxy)-ethoxy]-pyridine-2-carbonitrile (3_32_2)

Triphenylphosphine (4.36 g, 16.65 mmol) was added to a solution of N-(2-hydroxyethoxyl)phthalimide (3.45 g, 16.65 mmol) and 2-cyano-5-hydroxypyridine 3_32_1 (2.0 g, 16.65 mmol) in tetrahydrofuran (200 mL), followed by the slow addition of diethyl azodicarboxylate (2.73 mL, 16.65 mmol) over 20 minutes and the mixture was stirred at room temperature for 24 hours. After removal of the solvent, the residue was purified by crystallization from tetrahydrofuran to afford compound 3_32_2 (3.0 g, 58% yield).

$^1$H NMR (400 MHz, DMSO-d$_6$): δ=4.51 (dd, J=17.5, 5.7 Hz, 4H), 7.60 (dd, J=8.9, 2.9 Hz, 1H), 7.87 (s, 4H), 8.02 (d, J=8.9 Hz, 1H), 8.39 (d, J=2.9 Hz, 1H).

Step 2: 5-(2-Aminooxy-ethoxy)-pyridine-2-carbonitrile (3_32_3)

Hydrazine hydrate (0.310 mL, 9.69 mmol) was added to a suspension of compound 3_32_2 (3.0 g, 9.69 mmol) in ethanol (100 mL) and the mixture was stirred at 45° C. for 14 hours. The solid was removed by filtration and the filtrate was concentrated. The residue was diluted with dichloromethane (20 mL), the solid was removed by filtration and the filtrate was concentrated to give compound 3_32_3 (1.3 g, 75% yield) as an oil.

$^1$H NMR (400 MHz, DMSO-d$_6$): ϵ=3.80-3.90 (m, 2H), 4.24-4.34 (m, 2H), 6.13 (s, 2H), 7.61 (dd, J=8.7, 3.0 Hz, 1H), 8.00 (d, J=8.6 Hz, 1H), 8.45 (d, J=2.5 Hz, 1H).

Step 3: 5-(2-Aminooxy-ethoxy)-pyridine-2-carboximidic acid methyl ester (3_32_4)

Sodium methoxide (23 mg, 0.418 mmol) was added to a solution of compound 3_32_3 (150 mg, 0.837 mmol) in 5 mL of dry MeOH. The mixture was stirred at room temperature for 16 hours, and the solvent was evaporated to give compound 3_32_4 as a white solid (0.176 mg, 100% yield).

$^1$H NMR (400 MHz, MeOH-d$_4$): δ=3.94 (s, 3H), 3.93-4.03 (m, 2H), 4.19-4.38 (m, 2H), 7.45 (dd, J=8.6, 2.74 Hz, 1H), 7.84 (d, J=8.6 Hz, 1H), 8.35 (d, J=2.7 Hz, 1H).

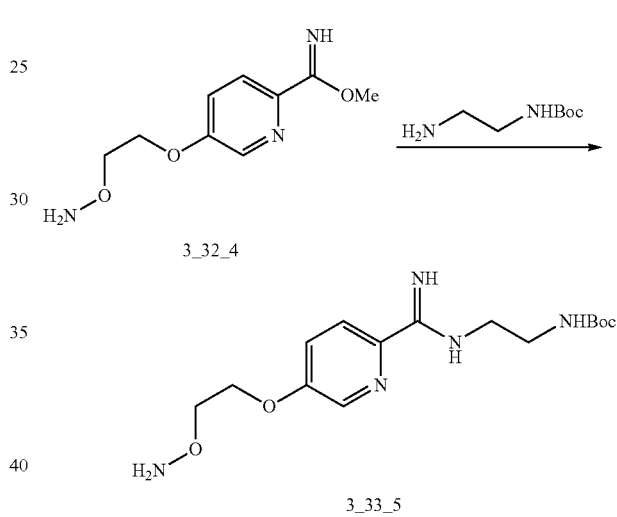

Following the procedure described under 3.32 but using N-Boc-diethylamine instead of ammonium chloride compound 3_33_5 was prepared.

3.34 6-[2-(Aminooxy)ethoxy]pyridine-3-carboximidamide

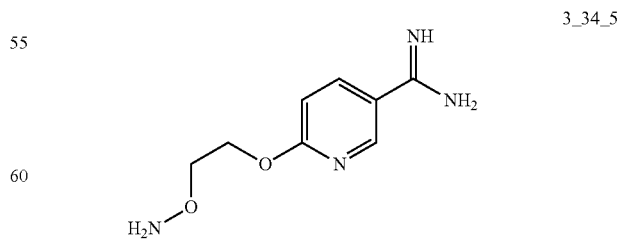

Following the procedure described under 3.32 but using 5-cyano-2-hydroxypyridine instead of 2-cyano-5-hydroxypyridine (3_32_1) compound 3_34_5 was prepared.

3.35 tert-Butyl 2-[{5-[2-(aminooxy)ethoxy]phenyl}(imino)methyl]hydrazinecarboxylate

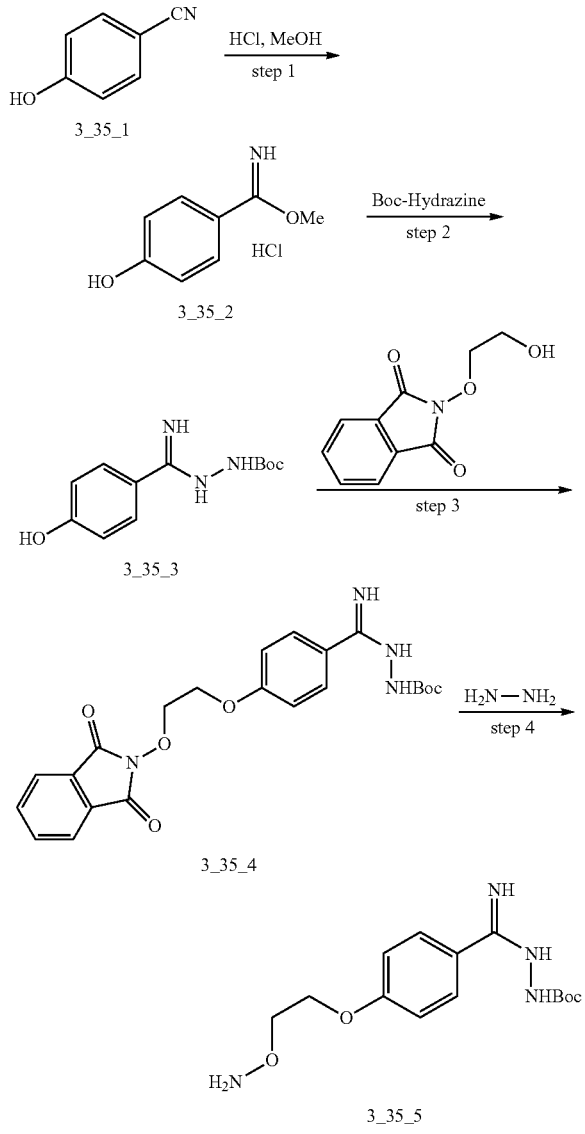

Step 1: 4-Hydroxy benzenecarboximidoate (3_35_2)

A suspension of 4-cyanophenol 3_35_1 (20.0 g, 167.9 mmol) in methanol (300 mL) was cooled to 0° C. and a stream of hydrogen chloride gas was passed through until the solution became saturated. The reaction mixture was stirred overnight at room temperature and the solid was collected by filtration to obtain compound 3_35_2 (28.6 g, 90% yield, hydrochloride salt) as a white solid.

$^1$H NMR (400 MHz, DMSO-d$_6$): δ=4.22 (s, 3H), 6.99 (d, J=8.6 Hz, 2H), 8.02 (d, J=9.0 Hz, 2H), 11.18 (br s, 1H), 11.68 (br s, 1H).

MS (ES$^+$) m/z: [M+H]$^+$ calcd for C$_8$H$_{10}$NO$_2$: 152.07. found: 152.13.

Step 2: tert-Butyl 2-[(5-hydroxyphenyl)(imino)methyl]hydrazinecarboxylate (3_35_3)

Triethylamine (5.42 g, 53.3 mmol) was added to a suspension of compound 3_35_2 (10.0 g, 53.3 mmol) in methanol (200 mL) followed by tert-butyl hydrazinecarboxylate (Boc-Hydrazine, 14.1 g, 106.6 mmol). The resulting clear solution was heated at 40° C. for 2 hours, it was then evaporated and purified by column chromatography to obtain compound 3_35_3 (9.2 g, 69% yield) as a white solid.

$^1$H NMR (400 MHz, DMSO-d$_6$): δ=1.42 (s, 9H), 6.08 (br s, 2H), 6.71 (d, J=8.6 Hz, 2H), 7.53 (d, J=8.6 Hz, 2H), 8.80 (br s, 1H), 9.60 (s, 1H).

MS (ES$^+$) m/z: [M+H]$^+$ calcd for C$_{12}$H$_{18}$N$_3$O$_3$: 252.13. found: 252.17.

Step 3: tert-Butyl 2-[(5-{2-[(1,3-dioxo-1,3-dihydro-2H-isoindol-2-yl)oxy]ethoxy}phenyl)-(imino)methyl]hydrazinecarboxylate (3_35_4)

To a suspension of compound 3_35_3 (3.2 g, 12.8 mmol), triphenylphosphine (3.7 g, 14.1 mmol), and N-(2-hydroxyethoxyl)phthalimide (2.9 g, 14.1 mmol) in tetrahydrofuran (20 mL) was added diisopropyl azodicarboxylate (2.8 g, 14.1 mmol) dropwise with sonication in an ultrasonic bath. The mixture was sonicated for an additional 15 minutes, stirred overnight at room temperature, evaporated and purified by column chromatography to obtain compound 3_35_4 (4.4 g, 79% yield) as a white solid.

$^1$H NMR (400 MHz, DMSO-d$_6$): δ=1.43 (s, 9H), 4.18-4.37 (m, 2H), 4.37-4.57 (m, 2H), 6.15 (s, 2H), 6.81 (d, J=8.6 Hz, 2H), 7.62 (d, J=9.0 Hz, 2H), 7.85 (s, 4H), 8.86 (br s, 1H).

MS (ES$^+$) m/z: [M+H]$^+$ calcd for C$_{22}$H$_{25}$N$_4$O$_6$: 441.18. found: 441.20.

Step 4: tert-Butyl 2-[{5-[2-(aminooxy)ethoxy]phenyl}(imino)methyl]hydrazinecarboxylate (3_35_5)

Hydrazine hydrate (0.68 g, 20.2 mmol) was added to a suspension of compound 3_35_4 (4.5 g, 10.1 mmol) in ethanol and the resulting mixture was slowly heated to 45° C. with vigorous stirring until a precipitate formed. The slurry was allowed to cool to room temperature and stirred for 4 hours. After the solid was removed by filtration, the filtrate was evaporated and purified by column chromatography to obtain compound 3_35_5 (2.7 g, 87% yield).

$^1$H NMR (400 MHz, DMSO-d$_6$): ε=1.42 (s, 9H), 3.82 (d, J=4.44 Hz, 2H), 4.11 (d, J=4.8 Hz, 2H), 6.08 (s, 2H), 6.15 (br s, 2H), 6.90 (d, J=8.9 Hz, 2H), 7.64 (d, J=8.9 Hz, 2H), 8.86 (br s, 1H).

3.36 4-(2-Aminooxy-2-methyl-propoxy)-benzamidine

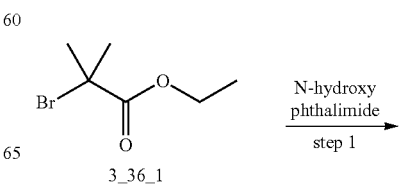

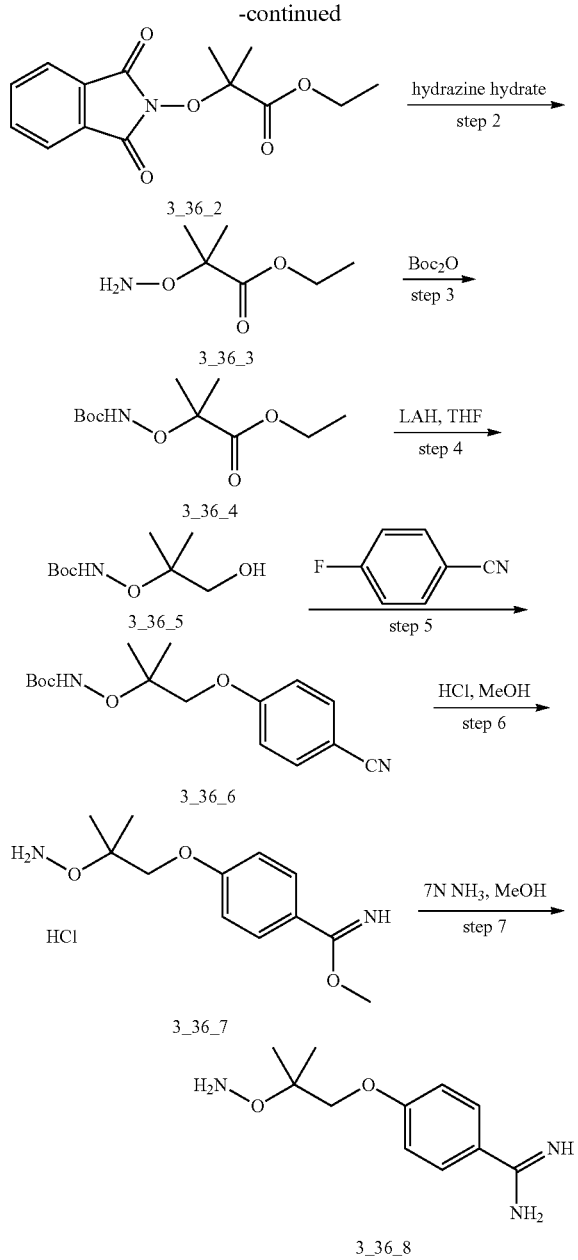

Step 1: 2-(1,3-Dioxo-1,3-dihydro-isoindol-2-yloxy)-2-methyl-propionic acid ethyl ester (3_36_2)

N-Hydroxyphthalimide (8.36 g, 51.27 mmol) was added dropwise to a solution of compound 3_36_1 (10.0 g, 51.26 mmol) in dry N,N-dimethylformamide (70 mL) followed by 1,8-diazabicyclo[5.4.0]undec-7-ene (7.7 mL, 51.27 mmol) during 20 minutes. The mixture was stirred at 35° C. for 3 days, concentrated under vacuum and the residue was suspended in ethyl acetate (200 mL) and washed successively with cold 0.5 M hydrochloric acid, water and brine. The organic extract was dried over anhydrous sodium sulfate and evaporated to afford the title compound 3_36_2 (14.0 g, 98% yield), which was used in the next step without further purification.

$^1$H NMR (400 MHz, DMSO-d$_6$): δ=1.21 (t, J=7.0 Hz, 3H), 1.50 (s, 6H), 4.12 (d, J=7.0 Hz, 2H), 7.86 (s, 4H).

MS: m/z (ES$^+$%) 278 (M+H, 35) 204 (100), 186 (20), 164 (3S), 115 (4S).

Step 2: 2-Aminooxy-2-methyl-propionic acid ethyl ester (3_36_3)

Hydrazine hydrate (1.01 mL, 18.7 mmol) was added to a suspension of compound 3_36_2 (4.95 g, 17.8 mmol) in absolute ethanol (50 mL) and the mixture was stirred at 40° C. for 2 hours. The suspension was cooled to 20° C., filtered, washed with ethanol and the filtrate was evaporated. The residue obtained was triturated with ethyl acetate (50 mL) and filtered. The filtrate was concentrated to obtain compound 3_36_3 (1.9 g, 73% yield) as a white solid.

$^1$H NMR (400 MHz, DMSO-d$_6$): δ=1.18 (t, J=7.1 Hz, 3H), 1.25 (s, 6H), 4.06 (q, J=70 Hz, 2H), 5.81 (br s, 2H).

MS: m/z (ES$^+$, %) 148 (M+H, 100)

Step 3: N-Boc-2-Aminooxy-2-methyl-propionic acid ethyl ester (3_36_4)

Di-tert-butyldicarbonate (BOC$_2$O, 2.82 g, 12.92 mmol) was added to a solution of compound 3_36_3 (1.9 g, 12.92 mmol) in dry tetrahydrofuran (25 mL) and the mixture was stirred at room temperature for 16 hours and evaporated under vacuum. The residue obtained was purified by chromatography to obtain compound 3_36_4 (2.3 g, 72% yield) as a clear thick oil.

$^1$H NMR (400 MHz, DMSO-d$_6$): δ=1.10-1.29 (m, 3H), 1.32 (s, 3H), 1.39 (s, 3H), 1.47 (s, 9H), 3.96-4.19 (m, 2H), 9.55 (s, 1H).

MS: m/z (ES$^-$, %) 248 (M+H, 60), 192 (100), 175 (8), 115 (18).

Step 4: N-Boc-2-Aminooxy-2-methyl-propan-1-ol (3_36_5)

Lithium aluminium hydride (LAH, 1M in tetrahydrofuran, 13.45 mL, 11.33 mmol) was added dropwise to a cold (0° C.) solution of compound 3_36_4 (1.9 g, 7.68 mmol) in dry diethyl ether (35 mL) over 15 minutes. The reaction mixture was stirred at 0° C. for 5 hours and quenched by pouring into a cold (0° C.) saturated ammonium chloride solution. The aqueous phase was extracted with ethyl acetate (2×75 mL) and the combined organic extracts were filtered through Celite, washed with water, brine, dried over anhydrous sodium sulfate and evaporated to yield compound 3_36_5 (1.1 g, 70% yield) as a solid.

$^1$H NMR (400 MHz, DMSO-d$_6$): δ=1.05 (s, 6H), 1.40 (s, 9H), 3.21 (d, J=6.6 Hz, 2H), 4.43 (t, J=6.6 Hz, 2H), 9.58 (d, J=3.9 Hz, 1H).

Step 5: N-Boc-4-(2-Aminooxy-2-methyl-propoxy)-benzonitrile (3_36_6)

Sodium hydride (60% in mineral oil, 0.41 g, 10.24 mmol) was added in portions to a cold (10° C.) solution of compound 3_36_5 (0.7 g, 3.41 mmol) in dry tetrahydrofuran (9 mL) under a nitrogen atmosphere. After stirring for 15 minutes 4-fluorobenzonitrile (0.496 g, 4.09 mmol) was added dropwise and the mixture was refluxed for 3 hours, stirred at 50° C. for 16 hours, cooled to room temperature, poured into cold water, acidified with acetic acid (1.5 mL) and extracted into ethyl acetate (3×75 mL). The combined organic extracts were filtered through Celite, washed with water and brine, dried over anhydrous sodium sulfate, evaporated and the residue was purified by column chromatography to obtain compound 3_36_6 (0.75 g, 72% yield) as an off-white solid.

$^1$H NMR (400 MHz, DMSO-d$_6$): δ=1.23 (s, 6H), 1.37 (s, 9H), 3.94 (s, 2H), 7.09 (m, J=8.9 Hz, 2H), 7.76 (m, J=8.9 Hz, 2H), 9.55 (s, 1H).

MS: m/z (ES$^-$, %) 305 (M+H, 98), 218 (100), 204 (8).

Step 6:
4-(2-Aminooxy-2-methyl-propoxy)-benzimidic acid methyl ester hydrochloride salt (3_36_7)

A solution of compound 3_36_6 (0.75 g, 2.45 mmol) in anhydrous methanol (20 mL) in a pressure reaction vessel (100 mL) at −10° C. was saturated with dry hydrogen gas and the sealed vessel was stirred at room temperature for 18 hours. The reaction mixture was concentrated to half the volume, diluted with diethyl ether (75 mL), stirred, filtered, washed with diethyl ether and dried under vacuum to obtain compound 3_36_7 (0.7 g, 70% yield) as a white powder, which was used in the next step without purification.

$^1$H NMR (400 MHz, DMSO-d$_6$): ϵ=1.44 (s, 6H), 4.14 (br s, 3H), 4.22-4.38 (m, 2H), 7.24 (m, J=8.9 Hz, 2H), 8.16 (m, J=8.9 Hz, 2H), 11.08 (br s, 3H).

MS: m/z (ES$^+$%) 239 (M$^+$H, 45), 206 (100), 174 (15), 152 (90), 104 (30)

Step 7:
4-(2-Aminooxy-2-methyl-propoxy)-benzamidine (3_36_8)

Ammonia (7N in methanol, 3.0 mL) was added to a suspension of compound 3_36_7 (0.70 g, 2.55 mmol) in anhydrous methanol (10 mL) at 20° C. and the mixture was stirred at room temperature for 1 hour. The reaction mixture was concentrated and the residue was triturated with hexanes/ether (1:1, 50 mL), filtered, washed with hexanes/ether (1:1) and dried under vacuum to obtain the title compound 3_36_8 (0.55 g, quant.) as a white powder.

$^1$H NMR (400 MHz, DMSO-d$_6$): δ=1.17 (s, 6H), 3.99 (s, 2H), 7.15 (d, J=9.0 Hz, 2H), 7.82 (d, J=9.0 Hz, 2H), 8.96 (br s, 2H), 9.19 (br s, 1H).

MS: m/z (ES$^+$%) 224 (M$^+$ H, 100), 199 (74), 191 (82), 137 (7).

3.37
4-(2-Aminooxy-1,1-dimethyl-ethoxy)-benzamidine

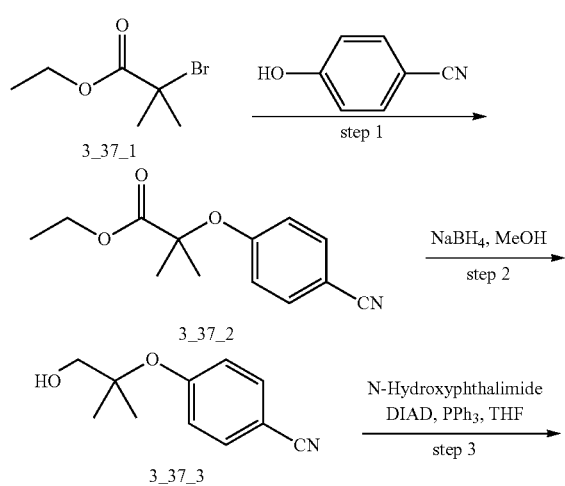

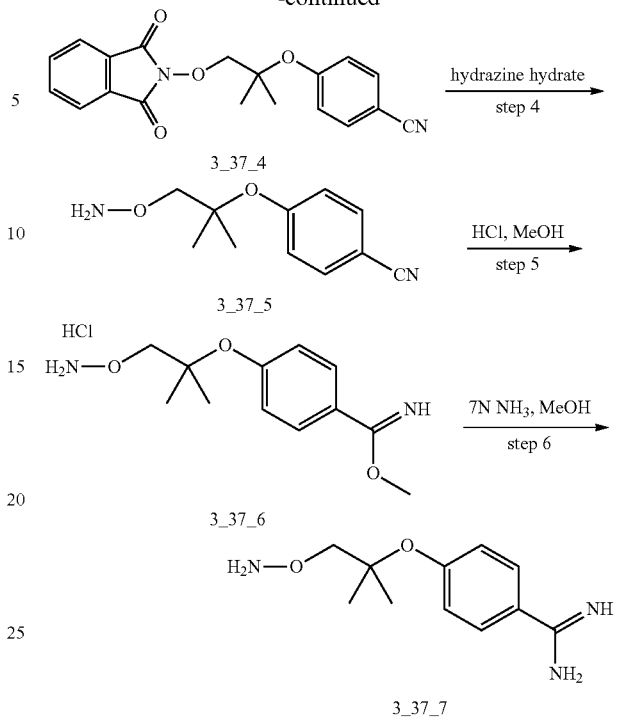

Step 1: 2-(4-Cyano-phenoxy)-2-methyl-propionic acid ethyl ester (3_37_2)

Potassium carbonate (14.16 g. 102.5 mmol) was added to a solution of compound 3_37_1 (10.0 g, 51.27 mmol) in dry N,N-dimethylformamide (70 mL) followed by 4-cyanophenol (6.7 g, 61.52 mmol) at room temperature and the reaction mixture was heated at 60° C. for 16 hours. The reaction mixture was cooled to room temperature, filtered, washed with N,N-dimethylformamide and the filtrate was concentrated under vacuum. The residue was dissolved in ethyl acetate (300 mL), washed with a cold, aqueous 0.5 M sodium hydroxide solution (3×30 mL), water and brine, dried over anhydrous sodium sulfate and evaporated. The crude product was purified by column chromatography to afford compound 3_37_2 (3.1 g, 26% yield) as a clear liquid.

$^1$H NMR (400 MHz, DMSO-d$_6$): δ=1.12 (t, J=7.03 Hz, 3H), 1.58 (s, 6H), 4.15 (d, J=7.0 Hz, 2H), 6.89 (d, J=9.0 Hz, 2H), 7.73 (d, J=9.0 Hz, 2H).

Step 2:
4-(2-Hydroxy-1,1-dimethyl-ethoxy)-benzonitrile (3_37_3)

Sodium borohydride (2.3 g, 60.76 mmol) was added in portions to a cold (5° C.) solution of compound 3_37_2 (4.7 g, 20.17 mmol) in anhydrous methanol (50 mL) over 10 minutes. The mixture was stirred at room temperature for 16 hours and the suspension was concentrated to remove most of the methanol. The residue was partitioned between a cold saturated ammonium chloride solution and ethyl acetate (150 mL each). The organic layer was separated and the aqueous layer was extracted with ethyl acetate (50 mL). The combined organic extracts were washed with water and brine, dried over anhydrous sodium sulfate and evaporated.

The crude product obtained was purified by column chromatography to give compound 3_37_3 (3.2 g, 79% yield) as a colorless liquid.

$^1$H NMR (400 MHz, DMSO-d$_6$): δ=1.26 (s, 6H), 3.41 (d, J=5.86 Hz, 2H), 5.00 (t, 1H), 7.16 (d, J=8.6 Hz, 2H), 7.72 (d, J=8.6 Hz, 2H).

Step 3: 4-[2-(1,3-Dioxo-1,3-dihydro-isoindol-2-yloxy)-1,1-dimethyl-ethoxy]-benzonitrile (3_37_4)

Triphenylphosphine (2.31 g, 8.79 mmol) was added to a mixture of compound 3_37_3 (1.6 g, 8.37 mmol) and N-hydroxyphthalimide (1.43 g, 8.79 mmol) in tetrahydrofuran (20 mL), and the mixture was sonicated for 20 minutes, and treated with diisopropyl azodicarboxylate (DIAD, 1.73 mL, 8.79 mmol). The reaction mixture was stirred at room temperature for 20 hours, concentrated and the residue was purified by column chromatography to give compound 3_37_4 (1.6 g, 57% yield) as an off-white solid, which was used in the next step without further purification.

Step 4: 4-(2-Aminooxy-1,1-dimethyl-ethoxy)-benzonitrile (3_37_5)

Hydrazine hydrate (0.24 mL, 4.99 mmol) was added to a solution of compound 3_37_4 (1.6 g, 4.75 mmol) in absolute ethanol (30 mL) and the mixture was stirred at 35° C. for 2 hours. The resulting suspension was cooled to 20° C., filtered, washed with ethanol and evaporated. The residue was triturated in ethyl acetate (50 mL), filtered and the filtrate was evaporated to obtain compound 3_37_5 (1.0 g, 100% yield), which was used in the next step without purification.

$^1$H NMR (400 MHz, DMSO-d$_6$): δ=1.29 (s, 6H), 3.61 (s, 2H), 6.17 (s, 2H), 7.16 (d, J=8.6 Hz, 2H), 7.72 (d, J=8.6 Hz, 2H).

Step 5: 4-(2-Aminooxy-1,1-dimethyl-ethoxy)-benzimidic acid methyl ester (3_37_6)

A solution of compound 3_37_5 (1.6 g, 4.85 mmol) in anhydrous methanol (20 mL) at −10° C. was saturated with dry hydrogen chloride gas and the sealed vessel was stirred at room temperature for 18 hours. The reaction mixture was concentrated to half the volume, diluted with diethyl ether (75 mL), stirred, filtered, washed with diethyl ether and dried under vacuum to obtain compound 3_37_6 (1.6 g, >100% yield) as a white powder, which was used in the next step without purification.

$^1$H NMR (400 MHz, DMSO-d$_6$): δ=1.37 (s, 6H), 4.13 (s, 2H), 4.24 (s, 3H), 7.27 (d, J=8.9 Hz, 2H), 8.07 (d, J=8.9 Hz, 2H).

Step 6: 4-(2-Aminooxy-1,1-dimethyl-ethoxy)-benzamidine (3_37_7)

Ammonia (7 N in methanol (7.5 mL, 52.5 mmol) was added to a suspension of compound 3_37_6 (1.6 g, 4.85 mmol) in anhydrous methanol (150 mL) at 20° C. and the mixture was stirred at 35° C. for 1.5 hours and concentrated. The residue was triturated in a mixture of hexanes/ether (50 mL, 1:1), filtered, washed with hexanes/ether (1:1) and dried under vacuum to afford compound 3_37_7 (1.0 g, 93% yield) as a white powder.

3.38 tert-Butyl [{2-[2-(aminooxy)ethoxy]-1,3-thiazol-4-yl}(imino)methyl]carbamate

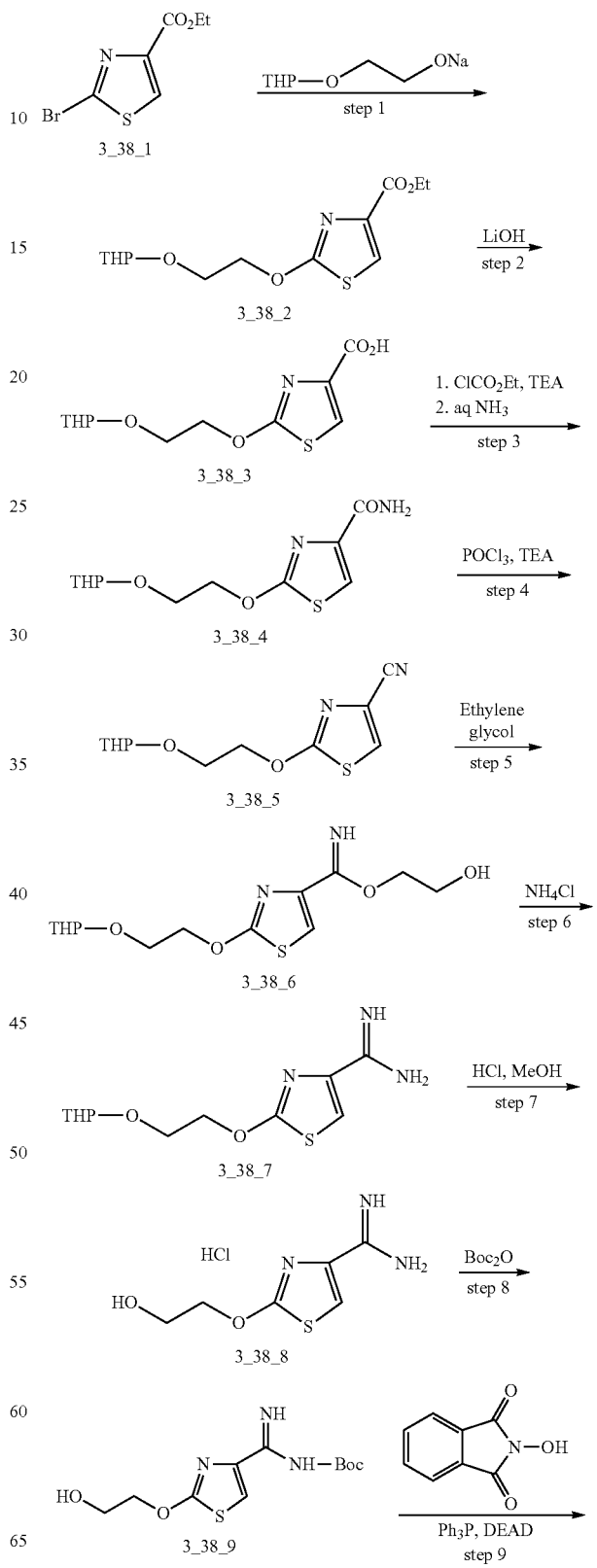

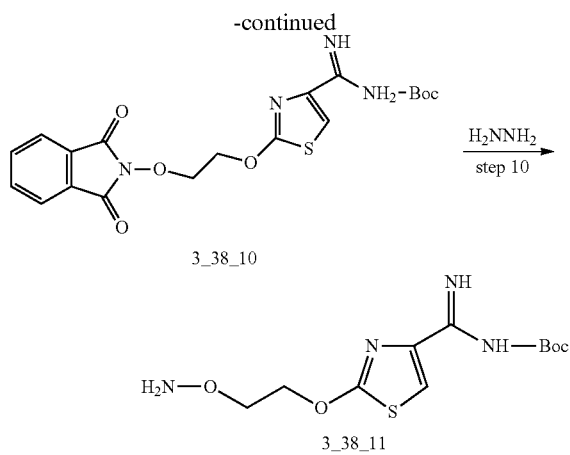

3_38_10

3_38_11

Step 1: 2-[2-(Tetrahydro-pyran-2-yloxy)-ethoxy]-thiazole-4-carboxylic acid ethyl ester (3_38_2)

Sodium hydride (60% dispersion in oil, 1.69 g, 42.4 mmol) was added to a solution of 2-(tetrahydro-pyran-2-yloxy)-ethanol (6.19 g, 42.4 mmol) in N,N-dimethylformamide (20 mL). After stirring at 0° C. for 1 hour, 2-bromo-thiazole-4-carboxylic acid ethyl ester 3_38_1 (10.0 g, 42.4 mmol) in N,N-dimethylformamide (10 mL) was added at 0° C. and the resulting mixture was stirred at 0° C. for 2.5 hours. The reaction mixture was neutralized to pH 7 using acetic acid at 0° C., diluted with ethyl acetate (150 mL) and washed with brine. The organic layer was dried over sodium sulfate and concentrated. The residue was purified by column chromatography to give the desired product (99.4 g, 73% yield) as a white solid.

$^1$H NMR (400 MHz, DMSO-$d_6$): $\epsilon$=1.28 (t, J=7.2 Hz, 3H), 1.37-1.53 (m, 4H), 1.56-1.78 (m, 2H), 3.38-3.48 (m, 1H), 3.66-3.80 (m, 2H), 3.85-3.98 (m, 1H), 4.26 (q, J=7.0 Hz, 2H), 4.37-4.46 (m, 1H), 4.52-4.59 (m, 1H), 4.64 (br s, 1H), 7.93 (s, 1H).

Step 2: 2-[2-(Tetrahydro-pyran-2-yloxy)-ethoxy]-thiazole-4-carboxylic acid (3_38_3)

A solution of lithium hydroxide (1.26 g, 52.6 mmol) in water (35 mL) was added to a solution of 2-[2-(tetrahydro-pyran-2-yloxy)-ethoxy]-thiazole-4-carboxylic acid ethyl ester 3_38_2 (3.17 g, 10.5 mmol) in tetrahydrofuran (45 mL). After stirring at room temperature for 2 hours, the reaction mixture was neutralized to pH 7 using dilute hydrochloric acid at 0° C., diluted with ethyl acetate (150 mL) and washed with brine. The organic layer was dried over sodium sulfate and concentrated. The residue was purified by column chromatography to give the desired product (2.9 g, 100% yield) as a white solid.

$^1$H NMR (400 MHz, DMSO-$d_6$): δ=1.35-1.54 (m, 4H), 1.57-1.76 (m, 2H), 3.39-3.47 (m, 1H), 3.67-3.81 (m, 2H), 3.90-3.98 (m, 1H), 4.50-4.58 (m, 2H), 4.64 (br s, 1H), 7.85 (s, 1H).

Step 3: 2-[2-(Tetrahydro-pyran-2-yloxy)-ethoxy]-thiazole-4-carboxylic acid amide (3_38_4)

Triethylamine (TEA, 1.22 g, 12.07 mmol) was added to a solution of 2-[2-(tetrahydro-pyran-2-yloxy)-ethoxy]-thiazole-4-carboxylic acid 3_38_3 (3.0 g, 11.0 mmol) in tetrahydrofuran (60 mL), followed by ethyl chloroformate (1.31 g, 12.07 mmol) slowly at −10° C. After stirring at room temperature for 1.5 hour, concentrated ammonium hydroxide (0.80 g, 13.17 mmol) was slowly added to the reaction mixture at 0° C. and the resulting mixture was stirred at room temperature for 1 hour. The reaction mixture was concentrated, diluted with ethyl acetate (150 mL) and washed with brine. The organic layer was dried over sodium sulfate and concentrated. The residue was purified by column chromatography to give the desired product (1.76 g, 59% yield) as a white solid.

$^1$H NMR (400 MHz, DMSO-$d_6$): $\epsilon$=1.33-1.53 (m, 4H), 1.55-1.79 (m, 2H), 3.38-3.51 (m, 1H), 3.66-3.82 (m, 2H), 3.87-4.00 (m, 1H), 4.43-4.74 (m, 3H), 7.44-7.57 (m, 2H), 7.62 (s, 1H).

MS (ES$^+$) m/z: [M+H]$^+$ calcd for $C_{11}H_{17}N_2O_4S$: 273.33. Found: 273.24.

Step 4: 2-[2-(Tetrahydro-pyran-2-yloxy)-ethoxy]-thiazole-4-carbonitrile (3_38_5)

Triethylamine (TEA, 7.625 g, 75.3 mmol) was added to a solution of 2-[2-(tetrahydro-pyran-2-yloxy)-ethoxy]-thiazole-4-carboxylic acid amide 3_38_4 (1.71 g, 6.28 mmol) in dichloromethane (50 mL) at 0° C. Phosphorus oxychloride (2.407 g, 15.70 mmol) was slowly added to the reaction mixture at 0° C. and the resulting mixture was stirred at room temperature for 1 hour. The reaction mixture was quenched with ice-water (20 mL), extracted with ethyl acetate and the extract was washed with brine, dried over sodium sulfate and concentrated. The residue was purified by silica gel column to give the desired product (1.42 g, 88.9%) as a white solid.

$^1$H NMR (400 MHz, DMSO-$d_6$): δ=1.38-1.55 (m, 4H), 1.57-1.79 (m, 2H), 3.38-3.51 (m, 1H), 3.67-3.79 (m, 2H), 3.87-4.00 (m, 1H), 4.49-4.71 (m, 3H), 8.25 (s, 1H).

MS (ES$^+$) m/z: [M+H]$^+$ calcd for $C_{11}H_{15}N_2O_3S$: 255.31. Found: 255.20.

Step 5: 2-[2-(Tetrahydro-pyran-2-yloxy)-ethoxy]-thiazole-4-carboximidic acid 2-hydroxy-ethyl ester (3_38_6)

Sodium (0.036 g, 1.56 mmol) was added to a flask containing ethylene glycol (1.33 g, 5.23 mmol) at room temperature. After all sodium was consumed, 2-[2-(tetrahydro-pyran-2-yloxy)-ethoxy]-thiazole-4-carbonitrile 3_38_5 (1.33 g, 5.23 mmol) in tetrahydrofuran (10 mL) was added at 0° C. and the reaction mixture was stirred at room temperature overnight. The reaction mixture was neutralized to pH 7 using acetic acid and diluted with ethyl acetate. The mixture was washed with brine, dried and concentrated to afford the desired product (1.52 g, 92% yield) as a white solid, which was used without purification.

$^1$H NMR (400 MHz, DMSO-$d_6$): $\epsilon$=1.35-1.53 (m, 4H), 1.58-1.76 (m, 2H), 3.41-3.48 (m, 1H), 3.66-3.79 (m, 4H), 3.89-3.98 (m, 1H), 4.19 (t, J=5.0 Hz, 2H), 4.54-4.61 (m, 3H), 4.64 (d, J=2.9 Hz, 2H), 7.48 (s, 1H), 8.31 (br s, 1H).

MS (ES$^+$) m/z: [M+H]$^+$ calcd for $C_{13}H_{21}N_2O_5$: 317.38. Found: 317.27.

Step 6: 2-[2-(Tetrahydro-pyran-2-yloxy)-ethoxy]-thiazole-4-carboxamidine (3_38_7)

Ammonium chloride (0.302 g, 5.65 mmol) was added to a mixture of 2-[2-(tetrahydro-pyran-2-yloxy)-ethoxy]-thiazole-4-carboximidic acid 2-hydroxy-ethyl ester 3_38_6 (1.49 g, 4.71 mmol) in methanol (40 mL) and the mixture was refluxed for 6.5 hours and concentrated to dryness to afford the crude product which was purified by column chromatography to give the desired product (1.35 g, 100%) as a white solid.

$^1$H NMR (400 MHz, DMSO-d$_6$): ε=1.44 (m, 4H), 1.54-1.79 (m, 2H), 3.38-3.48 (m, H), 3.66-3.80 (m, H), 3.85-4.00 (m, 1H), 4.54-4.73 (m, 3H), 8.39 (s, 1H), 9.20 (br s, 4H).

MS (ES$^+$) m/z: [M+H]$^+$ calcd for C$_{11}$H$_{18}$N$_3$O$_3$S: 272.34. Found: 272.23.

Step 7: 2-(2-Hydroxy-ethoxy)-thiazole-4-carboxamidine hydrochloric acid (3_38_8)

Concentrated hydrochloric acid (0.1 mL) was added to a mixture of 2-[2-(tetrahydro-pyran-2-yloxy)-ethoxy]-thiazole-4-carboxamidine 3_38_7 (1.25 g, 4.61 mmol) in methanol (10 mL) and the mixture was stirred at room temperature for 1 hour and concentrated to dryness to afford compound 3_38_8 as crude product (0.92 g, 91% yield) as a white solid.

$^1$H NMR (400 MHz, DMSO-d$_6$): δ=3.67-3.77 (m, 2H), 4.43-4.53 (m, 2H), 8.40 (s, 1H), 9.14 (s, H), 9.24 (s, 2H).

MS (ES$^+$) m/z: [M+H]$^+$ calcd for C$_6$H$_{10}$N$_3$O$_2$S: 188.22. Found: 188.20.

Step 8: {[2-(2-Hydroxy-ethoxy)-thiazol-4-yl]-iminomethyl}-carbamic acid tert-butyl ester (3_38_9)

A saturated sodium bicarbonate solution (15 mL) and a solution of di-tert-butyldicarbonate (BOC$_2$O, 1.346 g, 6.17 mmol) in 1,4-dioxane (10 mL) were added to a solution of 2-(2-hydroxy-ethoxy)-thiazole-4-carboxamidine hydrochloric acid 3_38_8 (0.92 g, 4.11 mmol) in water (5 mL) at room temperature. After stirring at room temperature overnight, the resulting mixture was concentrated and the residue was extracted with ethyl acetate. The extract was washed with brine, dried over sodium sulfate and concentrated to dryness. The crude product was purified by column chromatography to give the desired product (0.68 g, 58% yield) as a white solid.

$^1$H NMR (400 MHz, DMSO-d$_6$): δ=1.42 (s, 9H), 3.65-3.78 (m, 2H), 4.47 (t, J=4.7 Hz, 2H), 4.96 (t, J=5.4 Hz, 1H), 7.79 (s, 1H), 8.32 (br s, 1H), 9.09 (br s, 1H).

MS (ES$^+$) m/z: [M+H]$^+$ calcd for C$_{11}$H$_{18}$N$_3$O$_4$S: 288.34. Found: 288.20.

Step 9: ({2-[2-(1,3-Dioxo-1,3-dihydro-isoindol-2-yloxy)-ethoxy]-thiazol-4-yl}-imino-methyl)-carbamic acid tert-butyl ester (3_38_10)

N-Hydroxyphthalimide (0.393 g, 2.41 mmol) and triphenylphosphine (0.690 g, 2.63 mmol) were added to a solution of {[2-(2-hydroxy-ethoxy)-thiazol-4-yl]-imino-methyl}-carbamic acid tert-butyl ester 3_38_9 (0.63 g, 2.19 mmol) in anhydrous tetrahydrofuran (40 mL) at room temperature. A solution of diethyl azodicarboxylate (DEAD, 0.458 g, 2.63 mmol) in tetrahydrofuran (20 mL) was added dropwise to the resulting solution at 20° C. and the resulting mixture was stirred at room temperature overnight. After evaporation of the tetrahydrofuran, the crude product was purified by column chromatography to give the desired product (1.02 g, 100% yield) as a white solid.

$^1$H NMR (400 MHz, DMSO-d$_6$): ε=1.41 (s, 9H), 4.53-4.65 (m, 2H), 4.70-4.83 (m, 2H), 7.81 (s, 1H), 7.85 (s, 4H).

MS (ES$^+$) m/z: [M+H]$^+$ calcd for C$_{19}$H$_{21}$N$_4$O$_6$S: 433.46. Found: 433.34.

Step 10: 3.38. tert-Butyl [{2-[2-(aminooxy)ethoxy]-1,3-thiazol-4-yl}(imino)methyl]carbamate (3_38_11)

Hydrazine monohydrate (0.127 g, 2.54 mmol) was added to a solution of ({2-[2-(1,3-dioxo-1,3-dihydro-isoindol-2-yloxy)-ethoxy]-thiazol-4-yl}-imino-methyl)-carbamic acid tert-butyl ester 3_38_10 (1.0 g, 2.31 mmol) in anhydrous ethanol (15 mL) and tetrahydrofuran (10 mL) at 0° C. and the resulting mixture was stirred at room temperature for 2.5 hours. After concentration, the residue was stirred with ethyl acetate/hexanes (2:1, 20 mL) and filtered. The filtrate was concentrated to afford the desired product (0.6 g, 86% yield) as a white solid.

$^1$H NMR (400 MHz, DMSO-d$_6$): δ=1.42 (s, 9H), 3.78-3.89 (m, 2H), 4.57-4.64 (m, 2H), 6.12 (s, 2H), 7.79 (s, 1H), 8.36 (br s, 1H), 9.09 (br s, 1H).

3.39 tert-Butyl [{5-[2-(aminooxy)ethoxy]-1,3,4-thiadiazol-2-yl}(imino)methyl]-carbamate

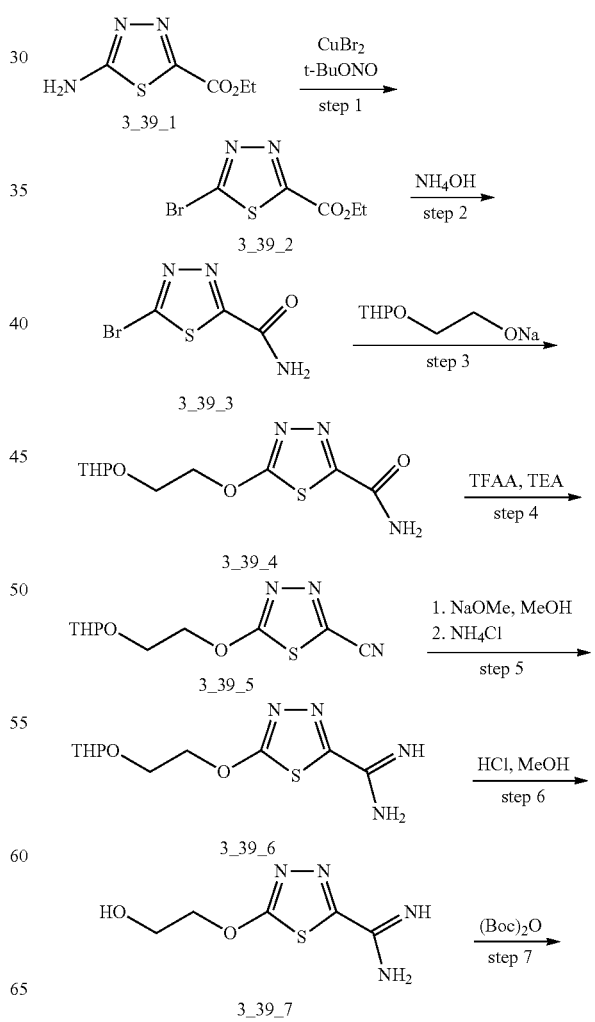

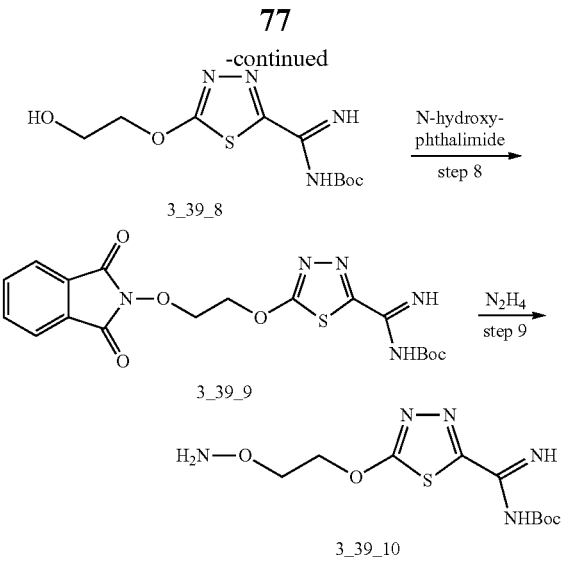

Step 1: 5-Bromo-[1,3,4]thiadiazole-2-carboxylic acid ethyl ester (3_39_2)

CuBr₂ (18.06 g, 80.1 mmol) was added to a suspension of 5-amino-[1,3,4]thiadiazole-2-carboxylic acid ethyl ester 3_39_1 (7 g, 40.5 mmol) in 150 mL of acetonitrile, the mixture was stirred for 15 min, t-BuONO (9.6 mL, 80.1 mmol) was added over 20 min., and the mixture was heated at 60° C. for 0.5 h. Water and ethyl acetate were added, the mixture was stirred until the dark color disappeared and filtered through celite, and the organic layer was washed with brine, dried over Na₂SO₄, filtrated and concentrated to give compound 3_39_2 (7.56 g, 79% yield) as a yellow solid.

¹H NMR (400 MHz, DMSO-d₆): δ=1.32 (t, J=7.14 Hz, 3H), 4.41 (q, J=7.30 Hz, 2H);

Step 2: 5-Bromo-[1,3,4]thiadiazole-2-carboxylic acid amide (3_39_3)

NH₄OH (50% aq solution, 6.45 mL) was added to a solution of compound 3_39_2 (7.56 g, 31.8 mol) in 70 mL of tetrahydrofuran, and the mixture was stirred at room temperature for 16 h and concentrated to give a solid, which was triturated with ether, filtered, and dried to give compound 3_39_3 (6.5 g, 98% yield) as a yellow solid.

¹H NMR (400 MHz, DMSO-d₆): δ=8.26 (br. s., 1H), 8.64 (br. s., 1H).

Step 3: 5-[2-(Tetrahydro-pyran-2-yloxy)-ethoxy]-[1,3,4]thiadiazole-2-carboxylic acid amide (3_39_4)

NaH (1.6 g, 40.2 mmol) was added to a solution of compound 3_39_3 (4.16 g, 20.1 mmol) in 20 mL of N,N-dimethylformamide, and the mixture was stirred at room temperature for 20 min. 2-(Tetrahydro-pyran-2-yloxy)-ethanol (3.81 mL, 26.1 mmol) was added, and the mixture was heated at 50-60° C. for 3 h, concentrated, diluted with ethyl acetate, washed with brine, dried over Na₂SO₄, filtered and concentrated to give a residue, which was purified by column chromatography to give compound 3_39_4 (2.15 g, 40% yield) as a gum.

¹H NMR (400 MHz, CDCl₃): δ=1.45-1.70 (m, 4H), 1.69-1.92 (m, 2H), 3.54 (m, 1H), 3.79-3.94 (m, 2H), 4.05-4.15 (m, 1H), 4.68 (t, J=3.49 Hz, 1H), 4.77 (dt, J=6.03, 3.01 Hz, 2H), 5.90 (br. s., 1H), 7.08 (br. s., 1H).

Step 4: 5-[2-(Tetrahydro-pyran-2-yloxy)-ethoxy]-[1,3,4]thiadiazole-2-carbonitrile (3_39_5)

Trifluoroacetic anhydride (TFAA, 1.13 mL, 8.46 mmol) was added to a solution of compound 3_39_4 (2.1 g, 7.69 mmol) and triethylamine (TEA, 1.13 mL, 8.64 mmol) in tetrahydrofuran (20 mL) at 0° C., and the mixture was warmed to room temperature, and stirred for 1 hour. Additional 0.4 mL of trifluoroacetic anhydride and 3 mL of triethylamine were added and the mixture was stirred at room temperature for 16 h, diluted with ethyl acetate, washed with a saturated sodium bicarbonate solution and brine, dried over Na₂SO₄, filtered, and concentrated to give a residue. The residue was purified by column chromatography to give compound 3_39_5 (1.3 g, 68% yield) as a yellow oil.

¹H NMR (400 MHz, CDCl₃): δ=1.48-1.66 (m, 4H), 1.68-1.88 (m, 2H), 3.55 (t, J=5.39 Hz, 1H), 3.81-3.91 (m, 2H), 4.06-4.17 (m, 1H), 4.67 (t, J=2.86 Hz, 1H), 4.78-4.93 (m, 2H).

Step 5: 5-[2-(Tetrahydro-pyran-2-yloxy)-ethoxy]-[1,3,4]thiadiazole-2-carboxamidine (3_39_6)

NaOMe (0.08 g, 1.5 mmol) was added to solution of compound 3_39_5 (0.77 g, 3.02 mmol) in 15 mL of dry MeOH, and the mixture was stirred at room temperature for 0.5 h. NH₄Cl (7.6 g, 30.1 mmol) was added, and the reaction mixture was refluxed for 20 h, concentrated, diluted with ethyl acetate, washed with a saturated sodium bicarbonate solution and brine, dried over Na₂SO₄, filtered and concentrated to give compound 3_39_6 (0.41 g 50% yield) as a brown gum.

¹H NMR (400 MHz, DMSO-d₆ with one drop of trifluroacetic acid): δ=1.32-1.52 (m, 4H), 1.53-1.72 (m, 2H), 3.42 (m, 1H), 3.67-3.87 (m, 2H), 3.93-4.04 (m, 1H), 4.59-4.69 (m, 1H), 4.75 (m, 2H), 9.66 (br. s., 2H), 9.87 (br. s., 2H).

Step 6: 5-(2-Hydroxy-ethoxy)-[1,3,4]thiadiazole-2-carboxamidine (3_39_7)

3 mL of 1N HCl were added to a solution of compound 3_39_6 (0.41 g, 1.5 mmol) in 15 mL of MeOH at 0° C., and the mixture was stirred at 20° C. for 2 h, concentrated and lyophilized to give crude compound 3_39_7 (0.51 g, >100% yield) as a solid, which was used in the next step without purification.

¹H NMR (400 MHz, DMSO-d₆ with one drop of trifluroacetic acid): δ=3.77 (d, J=4.12 Hz, 2H), 4.59 (t, J=4.44 Hz, 2H), 9.64 (br. s., 2H), 9.88 (br. s., 2H).

Step 7: {[5-(2-Hydroxy-ethoxy)-[1,3,4]thiadiazol-2-yl]-imino-methyl}-carbamic acid tert-butyl ester (3_39_8)

Di-tert-butyldicarbonate (Boc₂O, 0.5 g, 2.25 mmol) was added to a solution of compound 3_39_7 (0.5 g crude as obtained above) in 3 mL of a saturated sodium bicarbonate solution, 5 mL of dioxane and 2.5 mL of water, and the mixture was stirred for 16 h at room temperature, concentrated, diluted with ethyl acetate, washed with brine, dried over Na₂SO₄, filtered, and concentrated to give compound 3_39_8 (0.3 g, 69% yield over two steps) as a brown oil.

$^1$H NMR (400 MHz, DMSO-d$_6$): δ=1.42 (s, 9H), 3.75 (d, J=4.12 Hz, 2H), 4.52 (d, J=4.12 Hz, 2H), 5.06 (s, 1H).

Step 8: ({5-[2-(1,3-Dioxo-1,3-dihydro-isoindol-2-yloxy)-ethoxy]-[1,3,4]thiadiazol-2-yl}-iminomethyl)-carbamic acid tert-butyl ester (3_39_9)

Triphenylphosphine (0.37 g, 1.5 mmol) and diisopropyl azodicarboxylate (0.3 mL, 1.5 mmol) were added to a solution of compound 3_39_8 (0.3 g, 1 mmol) and N-hydroxyphalimide (0.17 g, 1 mmol) in 10 mL of tetrahydrofuran, at 0° C., and the mixture was stirred at room temperature for 1.5 h, diluted with ethyl acetate, washed with a saturated sodium bicarbonate solution and brine, dried over Na$_2$SO$_4$, filtered and concentrated to give a residue. The residue was purified by column chromatography to give compound 3_39_9 (0.4 g, 92% yield).

$^1$H NMR (400 MHz, CDCl$_3$): δ=1.55 (s, 9H), 4.55-4.67 (m, 2H), 4.88-5.00 (m, 2H), 7.70-7.91 (m, 4H).

Step 9: tert-Butyl [{5-[2-(aminooxy)ethoxy]-1,3,4-thiadiazol-2-yl}(imino)methyl]carbamate (3_39_10)

Hydrazine hydrate (0.1 mL, 2 mmol) was added to a suspension of compound 3_39_9 (1.5 g, 2 mmol) in 6 mL of EtOH, and the mixture was stirred at room temperature for 4 h. The solid was removed by filtration, and the filtrate was concentrated to give a residue. The residue was dissolved in dichloromethane, filtered to remove the solid, and the filtrate was concentrated to give compound 3_39_10 (0.43 g, 71% yield) as an oil.

$^1$H NMR (400 MHz, CDCl$_3$): δ=1.54 (s, 9H), 4.04 (d, J=4.44 Hz, 2H), 4.79 (d, J=4.12 Hz, 2H), 6.34 (br. s., 2H).

3.40 tert-Butyl [{3-[2-(aminooxy)ethoxy]-1,2-oxazol-5-yl}(imino)methyl]carbamate

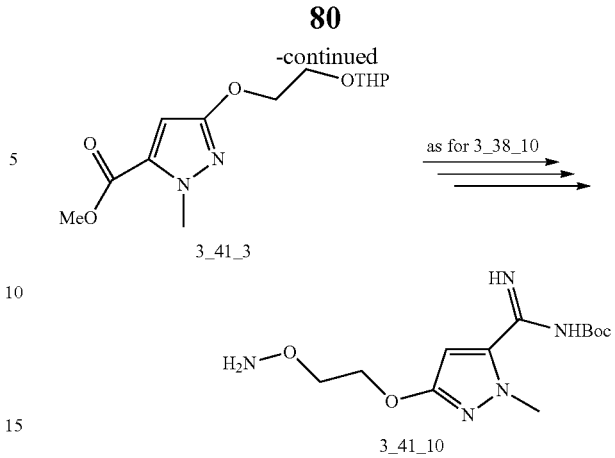

Following the procedure as described above under 3.38 but using ethyl 3-bromo-isoxazole-5-carboxylate instead of ethyl 2-bromo-thiazole-4-carboxylate 3_38_1 compound 3_40_10 was prepared.

3.41 tert-Butyl [{3-[2-(aminooxy)ethoxy]-1-methyl-1H-pyrazol-5-yl}(imino)methyl]-carbamate

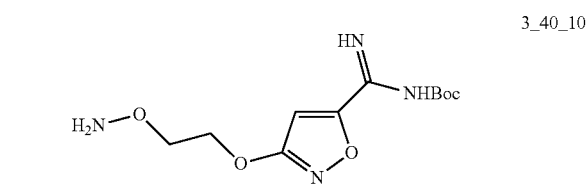 [SMILES: CC(C)(C)OC(=O)NC(=N)c1cc(OCCON)no1]

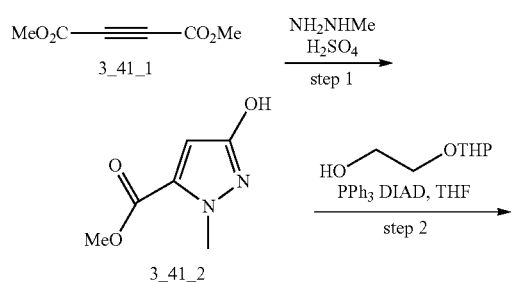

Step 1: Methyl 3-hydroxy-1-methyl-1H-pyrazole-5-carboxylate (3_41_2)

Triethylamine (66 mL, 474.4 mmol) was added to a solution of methylhy-drazine sulfuric acid salt (30.4 g, 211 mmol) in water (150 mL) and methanol (300 mL) at room temperature. The mixture was stirred for 0.5 hour at room temperature, but-2-ynedioic acid dimethyl ester (30 g, 211 mmol) was added and the mixture was stirred for 18 hours at 70° C. The reaction mixture was kept at room temperature for two days and the solid was collected by filtration and dried to give 12 g of the desired compound. The filtrate was concentrated, treated with ice and the solid was collected by filtration, and dried to give an additional 5 g of the desired compound 3_41_2 (17 g, 52% yield) as a yellow solid.

$^1$H NMR (400 MHz, DMSO-d$_6$): δ=3.79 (s, 3H), 3.88 (s, 3H), 6.01 (s, 1H), 10.05 (s, 1H).

Step 2: 2-Methyl-5-[2-(tetrahydro-pyran-2-yloxy)-ethoxy]-2H-pyrazole-3-carboxylic acid ethyl ester (3_41_3)

Diisopropyl azodicarboxylate (DIAD, 41.6 mL, 205.8 mmol) was added to a solution of 3_41_2 (10.7 g, 68.6 mmol), 2-(tetrahydro-pyran-2-yloxy)-ethanol (17 mL, 102.9 mmol) and triphenylphosphine (53.9 g, 205.8 mmol) at 0° C., and the mixture was stirred at room temperature for 16 hours. The reaction mixture was heated at 80° C. for 16 hours, more 2-(tetrahydro-pyran-2-yloxy)-ethanol (3.75 mL), triphenylphosphine (5.3 g) and diisopropyl azodicarboxylate (3 mL) were added, and the reaction mixture was refluxed for 16 hours, concentrated and treated with diethyl ether and hexanes (2:3, 500 mL) to give a precipitate, which was removed by filtration. The filtrate was concentrated and the residue obtained was purified by column chromatography to give compound 3_41_3 (26.6 g, >100% yield, contaminated with diisopropyl azodicarboxylate) as a yellow oil.

$^1$H NMR (400 MHz, CDCl$_3$): δ=1.45-1.90 (m, 6H), 3.52 (d, J=11.4 Hz, 1H), 3.79-3.92 (m, 5H), 3.95-4.10 (m, 5H), 4.31 (t, J=4.9 Hz, 2H), 4.69 (t, J=3.5 Hz, 1H), 6.21 (s, 1H).

Following the procedure as described above under 3.38 intermediate 3_41_3 was converted to compound 3_41_10.

3.42 tert-Butyl [{5-[2-(aminooxy)ethoxy]-1-methyl-1H-pyrazol-3-yl}(imino)methyl]-carbamate

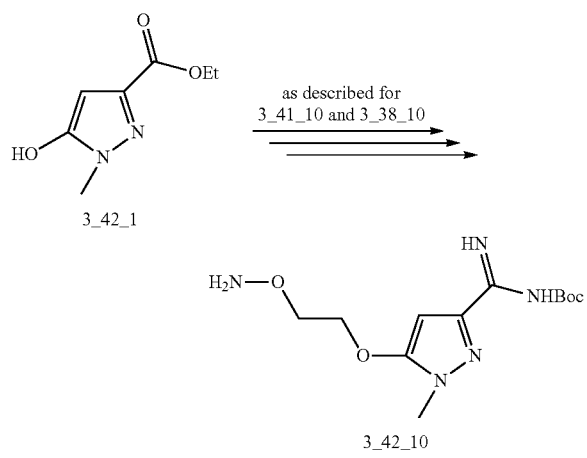

Using ethyl 5-hydroxy-1-methyl-1H-pyrazole-3-carboxylate 3_42_1 (EP 1990336, 2008) as the starting material and following the conditions described under 3.41 and 3.38 compound 3_42_10 was prepared.

3.43 4-[2-(Aminooxy)ethoxy]-5-methyl-1,3-thiazole-2-carboximidamide

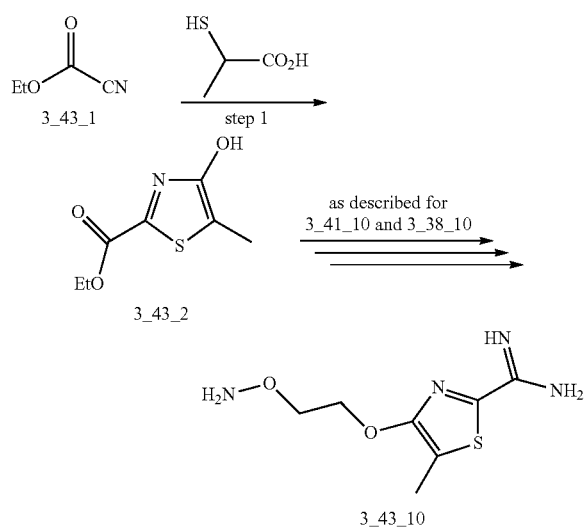

Step 1: 5-Hydroxy-1-methyl-1H-pyrazole-3-carboxylic acid ethyl ester (3_43_2)

Pyridine (2 mL) was slowly added to a mixture of 2-mercaptopropionic acid (10 g, 94 mmol) and nitriloacetic acid ethyl ester 3_43_1 (8.77 g, 94 mmol) at 0° C., and the mixture was stirred for 1 hour and then heated at 100° C. for 2 hours. After cooling, ethanol (100 mL) was added and the reaction mixture was stirred at room temperature for 1 hour to give a suspension, which was collected by filtration, washed with diethyl ether, and dried to give compound 3_43_2 (104 g, 60% yield) as a white solid.

$^1$H NMR (400 MHz, DMSO-d$_6$): δ=1.27 (td, J=7.2, 1.9 Hz, 3H), 2.23 (d, J=1.9 Hz, 3H), 4.29 (dd, J=7.0, 1.9 Hz, 2H).

Following the conditions as described under 3.41 and 3.38 the intermediate 3_43_2 was converted to compound 3_43_10.

3.44 4-[2-(Aminooxy)ethoxy]-2-hydroxybenzenecarboximidamide

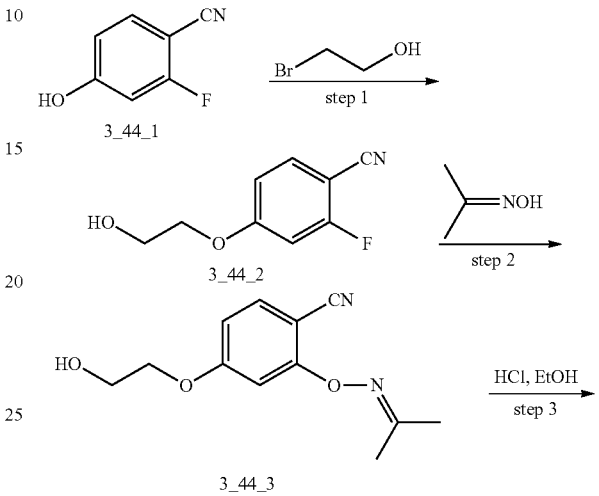

Step 1: 2-Fluoro-4-(2-hydroxy-ethoxy)-benzonitrile (3_44_2)

Anhydrous potassium carbonate (10.0 g, 72.4 mmol) was added to a solution of 2-fluoro-4-hydroxy-benzonitrile 3_44_1 (5.0 g, 36.5 mmol) in N,N-diemthylformamide (50 mL). The resulting mixture was stirred at room temperature for 10 minutes, and 2-bromoethanol (13.5 g, 7.7 mL, 108.0 mmol) was added dropwise over 15 minutes. The resulting mixture was stirred at room temperature for 3 days. TLC showed the reaction was incomplete. Additional 2-bromoethanol (3 mL) was added and the reaction mixture was stirred for another day, poured into water (300 mL) and extracted with ethyl acetate (3×50 mL). The combined ethyl acetate layers were washed with a saturated sodium bicarbonate solution, water and brine, dried over sodium sulfate and concentrated under reduced pressure. The residue was purified by column chromatography to give compound 3_44_2 (5.0 g, 76% yield) as a white solid.

¹H NMR (CDCl₃, 400 MHz): δ=3.99-4.01 (m, 2H), 4.02-4.14 (m, 2H), 6.73-6.81 (m, 2H), 7.51-7.55 (m, 12H).

Step 2 and 3:
2-(3-Amino-benzo[d]isoxazol-6-yloxy)-ethanol (3_44_4)

Potassium tert-butoxide (6.5 g, 58.0 mmol) was added in portions to a solution of acetone oxime (4.2 g, 58.05 mmol) in N,N-dimethylformamide (100 mL). The resulting mixture was stirred at room temperature for 1 hour, and a solution of compound 3_44_2 (5.0 g, 27.6 mmol) in N,N-dimethylformamide (20 mL) was added dropwise. The resulting mixture was stirred at room temperature for 3 hours. The reaction mixture was poured into a saturated ammonium chloride solution (600 mL) and extracted with ethyl acetate (3×100 mL). The combined ethyl acetate layers were washed with water and brine, dried over sodium sulfate and concentrated under reduced pressure to give crude intermediate 3_44_3 (5.3 g, yellow oil). The intermediate 3_44_3 was dissolved in ethanol (100 mL) and 2N hydrochloric acid solution (100 mL) and heated under reflux for 2 hours. The reaction mixture was concentrated under reduced pressure and the residue was dissolved in ethyl acetate (200 mL), and washed with a saturated sodium bicarbonate solution, water and brine, dried over sodium sulfate and concentrated under reduced pressure. The residue was purified by column chromatography to give 3_44_4 (1.9 g, 35% yield) as a white solid.

¹H NMR (MeOH-d₄, 400 MHz): δ=3.90 (t, J=4.8 Hz, 2H), 4.11 (t, J=4.8 Hz, 2H), 6.87-6.93 (m, 2H), 7.45 (d, J=8.4 Hz, 1H).

Step 4:
2-Hydroxy-4-(2-hydroxy-ethoxy)-benzamidine (3_44_5)

Palladium on charcoal (5% wet, 1.5 g, ~50% water) was added to a solution of compound 3_44_4 (1.9 g, 7.7 mmol) in methanol (100 mL) and the mixture was hydrogenated at 1 atmosphere with a balloon for 31 hours. TLC showed completion of the reaction. The catalyst was removed by filtration through a bed of celite and washed with methanol (2×10 mL). The filtrate was concentrated under reduced pressure to give compound 3_44_5 (1.4 g, 73% yield) as an off-white solid which was used without further purification.

¹H NMR (MeOH-d₄, 400 MHz): δ=3.84 (t, J=4.8 Hz, 2H), 4.03 (t, J=4.8 Hz 2H), 6.14-6.19 (m, 2H), 7.45 (d, J=8.8 Hz, 1H).

MS: m/z (ES⁺, %) 197 (M⁺⁺ H, 100).

Following the conditions described in the previous examples intermediate 3_44_5 was converted via a Mitsunobu reaction with N-hydroxyphthalimide and consecutive phthalimide deprotection to compound 3_44_6.

3.45 Diphenylmethyl 2-(aminooxy)-3-{4-[N-(tert-butoxycarbonyl)carbamimidoyl]-phenoxy}propanoate

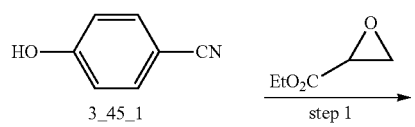

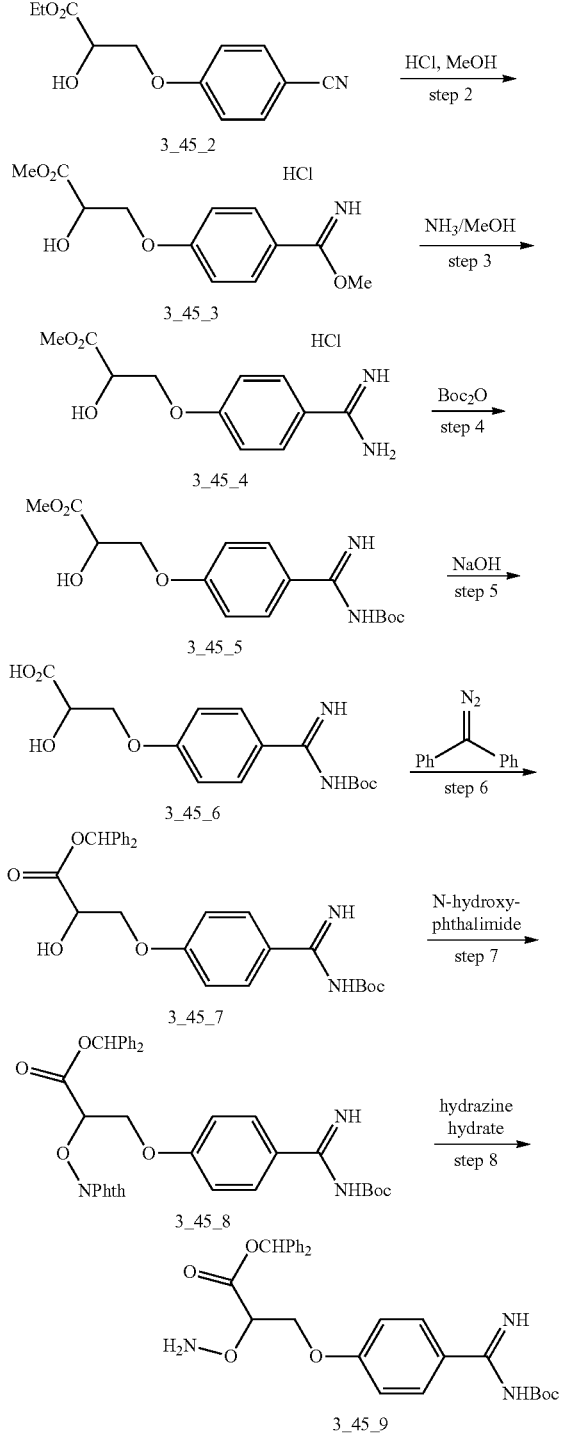

Step 1: 3-(4-Cyano-phenoxy)-2-hydroxy-propionic acid ethyl ester (3_45_2)

Potassium carbonate (10.705 g, 77.5 mmol), lithium perchlorate (5.497 g, 51.7 mmol) and ethyl 2,3-epoxypropanoate (3.0 g, 25.8 mmol) were added to a solution of 4-hydroxybenzonitrile 3_45_1 (12.31 g, 0.103 mmol) in acetonitrile (100 mL). After refluxing for 4 hours, the resulting mixture was cooled and filtered. The filtrate was diluted with ice-water and neutralized to pH 7 using dilute hydrochloric acid and extracted with ethyl acetate. The extract was washed with brine, dried over sodium sulfate and concentrated. The residue was purified by column chromatography to give the desired compound 3_45_2 (2.92 g, 48% yield) as a thick colorless oil.

$^1$H NMR (400 MHz, DMSO-d$_6$): δ=1.18 (t, J=1.7 Hz, 3H), 4.03-4.19 (m, 2H), 4.25 (d, J=4.4 Hz, 2H), 4.38-4.51 (m, 1H), 5.89 (d, J=5.9 Hz, 1H), 7.11 (d, J=8.8 Hz, 2H), 7.77 (d, J=8.8 Hz, 2H).

MS (ES$^+$) m/z: [M+H]$^+$ calcd for C$_{12}$H$_{14}$NO$_4$: 236.24. Found: 236.16.

Step 2: 2-Hydroxy-3-(4-methoxycarbonimidoyl-phenoxy)-propionic acid methyl ester hydrochloric acid salt (3_45_3)

Hydrogen chloride gas was introduced into a solution of 3-(4-cyano-phenoxy)-2-hydroxy-propionic acid ethyl ester 3_45_2 (2.10 g, 8.93 mmol) in anhydrous methanol (70 mL) at 0° C. for 10 minutes and the resulting mixture was stirred at room temperature overnight. After concentration, the residue was stirred with diethyl ether (20 mL) for 0.5 hour and the precipitate was collected and dried to give the desired product (2.43 g, 94% yield) as a white solid.

$^1$H NMR (400 MHz, DMSO-d$_6$): δ=3.66 (s, 3H), 4.24 (s, 3H), 4.27-4.30 (m, 2H), 4.48 (t, J=4.4 Hz, 1H), 7.16 (d, J=9.1 Hz, 2H), 8.09 (d, J=9.1 Hz, 2H).

Step 3: 3-(4-Carbamimidoyl-phenoxy)-2-hydroxy-propionic acid methyl ester (3_45_4)

Ammonia (7N in methanol, 3.0 mL, 20.97 mmol) was added to a mixture of 2-hydroxy-3-(4-methoxycarbonimidoyl-phenoxy)-propionic acid methyl ester hydrochloric acid salt 3_45_3 (2.43 g, 8.39 mmol) in anhydrous methanol (30 mL) at 0° C. and the resulting mixture was stirred at 40° C. for 5 hours. The reaction mixture was concentrated to dryness to give the crude product of compound 3_45_4 (2.39 g, >100% yield) as a white solid which was used without purification.

$^1$H NMR (400 MHz, DMSO-d$_6$): δ=3.65 (s, 3H), 4.22-4.31 (m, 2H), 4.47 (q, J=4.7 Hz, 1H), 5.99 (d, J=5.9 Hz, 1H), 7.13 (d, J=8.9 Hz, 2H), 7.85 (d, J=8.9 Hz, 2H), 9.16 (br. s., 3H).

MS (ES$^+$) m/z: [M+H]$^+$ calcd for C$_{11}$H$_{15}$N$_2$O$_4$: 239.25. Found: 239.23.

Step 4: 3-[4-(tert-Butoxycarbonylamino-imino-methyl)-phenoxy]-2-hydroxy-propionic acid methyl ester (3_45_5)

A saturated sodium carbonate solution (10 mL) and di-tert-butyldicarbonate (BOC$_2$O, 2.197 g, 10.07 mmol) were added to a solution of 3-(4-carbamimidoyl-phenoxy)-2-hydroxy-propionic acid methyl ester 3_45_4 (2.35 g, crude material from previous step, 8.39 mmol) in tetrahydrofuran (30 mL) at room temperature. After stirring at room temperature for 3.5 hours, the resulting mixture was extracted with ethyl acetate. The extract was washed with brine, dried and concentrated. The residue was purified by column chromatography to give the desired product (2.0 g, 66% yield) as a white solid.

$^1$H NMR (400 MHz, DMSO-d$_6$): δ=1.42 (s, 9H), 3.66 (s, 3H), 4.14-4.25 (m, 2H), 4.45 (t, J=4.4 Hz, 1H), 5.88 (d, 1H), 6.98 (d, J=8.8 Hz, 2H), 7.92 (d, J=8.8 Hz, 2H).

Step 5: 3-[4-(tert-Butoxycarbonylamino-imino-methyl)-phenoxy]-2-hydroxy-propionic acid (3_45_6)

A solution of sodium hydroxide (0.189 g, 4.73 mmol) in water (4 mL) was added to a solution of 3-[4-(tert-butoxycarbonylamino-imino-methyl)-phenoxy]-2-hydroxy-propionic acid methyl ester 3_45_5 (0.8 g, 2.36 mmol) in tetrahydrofuran (10 mL) at 0° C. After stirring at this temperature for 15 minutes, the reaction mixture was neutralized to pH 7 using acetic acid and concentrated to dryness to afford the crude desired product (1.12 g) as a white solid.

$^1$H NMR (400 MHz, DMSO-d$_6$): δ=3.77-3.79 (m, 2H), 3.84-3.95 (m, 1H), 4.13-4.29 (m, 1H), 6.94 (d, J=7.9 Hz, 2H), 7.90 (d, J=8.2 Hz, 2H).

MS (ES$^+$) m/z: [M+H]$^+$ calcd for C$_{15}$H$_{21}$N$_2$O$_6$: 325.34. Found: 325.22.

Step 6: 3-[4-(tert-Butoxycarbonylamino-imino-methyl)-phenoxy]-2-hydroxy-propionic acid benzhydryl ester (3_45_7)

A solution of diazo(diphenyl)methane (0.459 g, 2.36 mmol) was slowly added to a solution of 3-[4-(tert-butoxycarbonylamino-imino-methyl)-phenoxy]-2-hydroxy-propionic acid 3_45_6 (1.12 g, crude, 2.36 mmol) in methanol (10 mL). The resulting mixture was stirred at room temperature overnight and concentrated to dryness. The residue was purified by column chromatography to give the desired product (0.571 g, 49% yield) as a white solid.

$^1$H NMR (400 MHz, DMSO-d$_6$): ε=1.42 (s, 9H), 4.20-4.30 (m, 1H), 4.30-4.43 (m, 1H), 4.61 (d, J=4.4 Hz, 1H), 6.00 (d, J=4.4 Hz, 1H), 6.85 (s, 1H), 6.95 (d, J=9.1 Hz, 2H), 7.20-7.45 (m, 10H), 7.93 (d, J=8.8 Hz, 2H).

MS (ES$^+$) m/z: [M+H]$^+$ calcd for C$_{28}$H$_{31}$N$_2$O$_6$: 491.56. Found: 491.23.

Step 7: 3-[4-(tert-Butoxycarbonylamino-imino-methyl)-phenoxy]-2-(1,3-dioxo-1,3-dihydro-isoindol-2-yloxy)-propionic acid benzhydryl ester (3_45_8)

N-Hydroxyphthalimide (0.205 g, 1.26 mmol) and triphenylphosphine (0.359 g, 1.37 mmol) were added to a solution of 3-[4-(tert-butoxycarbonylamino-imino-methyl)-phenoxy]-2-hydroxy-propionic acid benzhydryl ester 3_45_7 (0.56 g, 1.14 mmol) in anhydrous tetrahydrofuran (10 mL) at room temperature. A solution of diethyl azodicarboxylate (0.238 g, 1.37 mmol) in tetrahydrofuran (5 mL) was added dropwise to the resulting solution at 20° C. and the resulting mixture was stirred at room temperature overnight. After evaporation of the tetrahydrofuran, the crude product was purified by column chromatography to give the desired product (0.79 g, 88% yield) as a white solid.

$^1$H NMR (400 MHz, DMSO-d$_6$): δ=1.43 (s, 9H), 4.51-4.66 (m, 2H), 5.43 (t, J=3.2 Hz, 1H), 6.92 (s, 1H), 6.95 (d, J=2.6 Hz, 2H), 7.19-7.46 (m, 10H), 7.85 (s, 4H), 7.94 (d, J=8.8 Hz, 2H), 8.98 (br s, 2H).

MS (ES$^+$) m/z: [M+H]$^+$ calcd for C$_{36}$H$_{34}$N$_3$O$_8$: 366.68. Found: 366.34.

Step 8: Diphenylmethyl 2-(aminooxy)-3-{4-[N-(tert-butoxycarbonyl)carbamimidoyl]-phenoxy}propanoate (3_45_9)

Hydrazine monohydrate (0.067 g, 1.35 mmol) was added to a solution of 3-[4-(tert-butoxycarbonylamino-iminomethyl)-phenoxy]-2-(1,3-dioxo-1,3-dihydro-isoindol-2-yloxy)-propionic acid benzhydryl ester 3_45_8 (0.78 g, 1.23 mmol) in anhydrous ethanol (15 mL) and tetrahydrofuran (10 mL) at 0° C. and the resulting mixture was stirred at room temperature for 2 hours. After concentration, the residue was stirred with dichloromethane (10 mL) and filtered. The filtrate was concentrated to afford the desired product (0.76 g, >100% yield) as a white solid, which was used without purification.

$^1$H NMR (400 MHz, DMSO-$d_6$): δ=1.42 (s, 9H), 4.28-4.46 (m, 2H), 4.60 (t, J=4.1 Hz, 1H), 6.43 (s, 2H), 6.89 (s, 1H), 6.94 (d, J=8.5 Hz, 2H), 7.19-7.47 (m, 10H), 7.92 (d, J=8.8 Hz, 2H), 8.98 (br s, 2H).

3.46 4-[2-(Aminooxy)ethoxy]-2-methylbenzenecarboximidamide

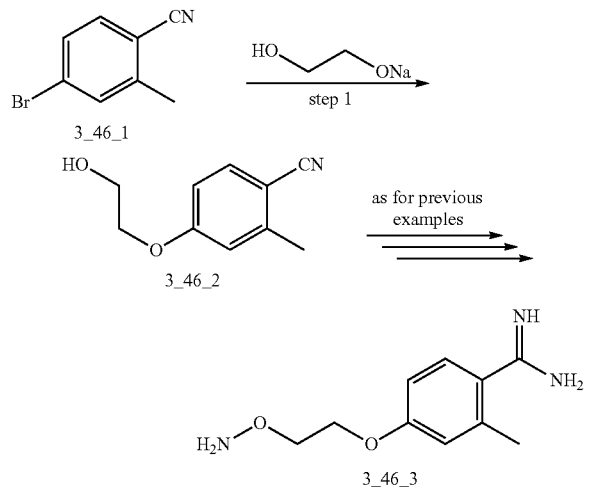

Step 1: 4-(2-Hydroxyethoxy)-2-methylbenzonitrile (3_46_2)

Sodium hydride (60%, 0.62 g, 40.8 mmol) was added slowly to ethylene glycol (40 mL) and the resulting mixture was stirred at room temperature for 0.5 hour. 4-Bromo-2-methylbenzonitrile 3_46_1 (2.0 g, 10.2 mmol) was then added followed by cop-per(I) bromide (0.44 g, 3.06 mmol) and the reaction mixture was heated at 120° C. for 2 hours, cooled to room temperature, poured into water (300 mL), and extracted with ethyl acetate (3×100 mL). The combined ethyl acetate layers were washed with water (2×200 mL) and brine (1×200 mL), dried over sodium sulfate and concentrated under reduced pressure. The residue was purified by column chromatography to give compound 3_46_2 (1.6 g, 88% yield) as a pale yellow solid.

$^1$H NMR (400 MHz, CDCl$_3$): δ=2.51 (s, 3H), 3.94-4.04 (m, 2H), 4.07-4.15 (m, 2H), 6.74-6.87 (m, 2H), 7.53 (d, J=8.6 Hz, 1H).

Using intermediate 3_46_2 and following the conditions as described in the previous examples, compound 3_46_3 was prepared.

3.47 tert-Butyl [{4-[2-(aminooxy)ethoxy]pyridin-2-yl}(imino)methyl]carbamate

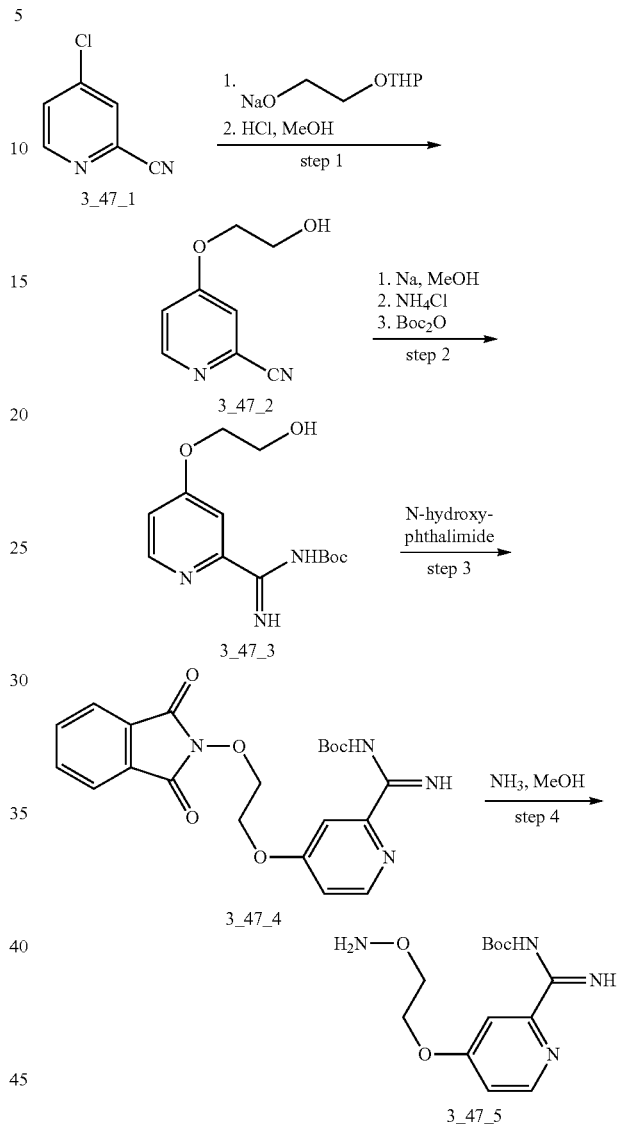

Step 1: 4-(2-Hydroxyethoxy)-pyridine-2-carbonitrile (3_47_2)

2-(Tetrahydropyran-2-yloxy)ethanol (3.50 g, 22 mmol) was added dropwise to a cooled (0° C.) suspension of sodium hydride (530 mg, 60% in mineral oil, 21 mmol) in N,N-dimethylformamide. After the addition was over, the mixture was stirred at room temperature for 10 minutes. The reaction mixture was cooled to 0° C. and 4-chloro-pyridine-2-carbonitrile 3_47_1 (2.77 g, 20 mmol) was added in one portion. The resulting mixture was stirred at room temperature for 2 hours and the mixture was quenched with a saturated aqueous ammonium chloride solution, extracted with ethyl acetate, washed with water, dried and concentrated. The residue was dissolved in methanol (30 mL) and treated with a 1N hydrochloric acid solution (10 mL) at 0° C. The mixture was stirred at room temperature for 2 hours, extracted with ethyl acetate (150 mL), dried and concentrated. The residue was purified by column chromatography to give 3_47_2 (2.04 g, 62% yield) as a white solid.

$^1$H NMR (CDCl$_3$, 400 MHz): δ=8.60 (d, 1H), 7.25 (s, 1H), 7.03 (d, 1H), 4.27 (m, 2H), 4.00 (m, 2H), 2.00 (t, 1H).

Step 2: {[4-(2-Hydroxyethoxy)-pyridin-2-yl]-iminomethyl}carbamic acid tert-butyl ester (3_47_3)

A solution of compound 3_47_2 (1.0 g, 6.10 mmol) in methanol (10 mL) was added to a freshly prepared solution of sodium methoxide (0.28 g of sodium in methanol (10 mL) at 0° C. and the reaction mixture was stirred at room temperature for 90 minutes. Ammonium chloride (1.30 g, 24.4 mmol) was added and the reaction mixture was heated at reflux for 16 hours. A saturated aqueous sodium bicarbonate solution (20 mL) and di-tert-butyl dicarbonate (Boc$_2$O, 4.17 g, 18.3 mmol) were added to the cooled (0° C.) mixture. The resulting mixture was stirred at room temperature for 16 hours, extracted with ethyl acetate (150 mL), dried and concentrated. The residue was purified by column chromatography to give compound 3_47_3 (1.53 g, 90% yield) as viscous oil.

$^1$H NMR (CDCl$_3$, 400 MHz): δ=9.40 (br s, 1H), 8.44 (d, 2H), 8.00 (s, 1H), 7.00 (d, 1H), 4.30 (d, 2H), 4.00 (m, 2H), 2.00 (br s, 1H), 1.60 (s, 9H).

Step 3: ({4-[2-(1,3-Dioxo-1,3-dihydro-isoindol-2-yloxy)-ethoxy]-pyridin-2-yl}-imino-methyl)carbamic acid tert-butyl ester (3_47_4)

Diisopropyl azodicarboxylate (1.28 mL, 6.53 mmol) was added dropwise to a cooled mixture of compound 3_47_3 (1.53 g, 5.44 mmol), N-hydroxyphthalimide (0.98 g, 5.98 mmol) and triphenylphosphine (1.71 g, 6.53 mmol) in tetrahydrofuran. After the addition, the mixture was stirred at room temperature for 16 hours and concentrated. The residue was purified by column chromatography to give compound 3_47_4 (1.66 g, 72% yield) as a white solid.

$^1$H NMR (CDCl$_3$, 400 MHz): δ=9.40 (br s, 1H), 8.37 (d, 2H), 7.91 (s, 1H), 7.85 (m, 2H), 7.78 (m, 2H), 6.91 (d, 1H), 4.90 (m, 2H), 4.49 (m, 2H).

Step 4: tert-Butyl [{4-[2-(aminooxy)ethoxy]pyridin-2-yl}(imino)methyl]carbamate (3_47_5)

Ammonia (2.5 mL, 2N in methanol) was added to a solution of compound 3_47_4 (210 mg, 0.5 mmol) in methanol (1 mL). The mixture was stirred for 16 hours, filtered and the filtrate was concentrated. The residue was diluted with dichloromethane and filtered. The filtrate was concentrated to give compound 3_47_5 (160 mg, >100% yield) which was used in the next step without further purification.

$^1$H NMR (CDCl$_3$, 400 MHz): δ=9.30 (br s, 1H), 8.40 (m, 2H), 8.00 (s, 1H), 7.00 (d, 1H), 5.60 (s, 2H), 4.40 (m, H), 4.10 (m, 2H), 1.60 (s, 9H).

3.48 tert-Butyl [{2-[2-(aminooxy)ethoxy]pyridin-4-yl}(imino)methyl]carbamate

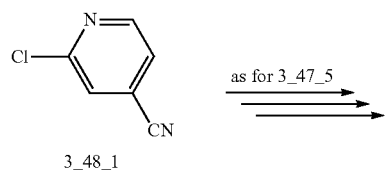

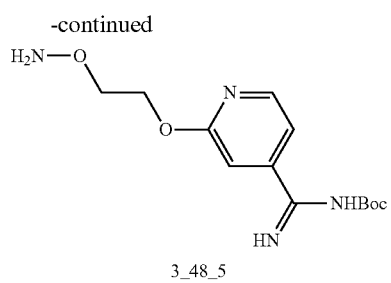

Following the procedure as described under 3.47 but using 2-chloro-4-cyano-pyridine 3_48_1 as the starting material instead of 4-chloro-2-cyano-pyridine 3_47_1 compound 3_48_5 was prepared.

3.49 tert-Butyl [{5-[2-(aminooxy)ethoxy]-3-hydroxy-pyridin-2-yl}(imino)methyl]carbamate

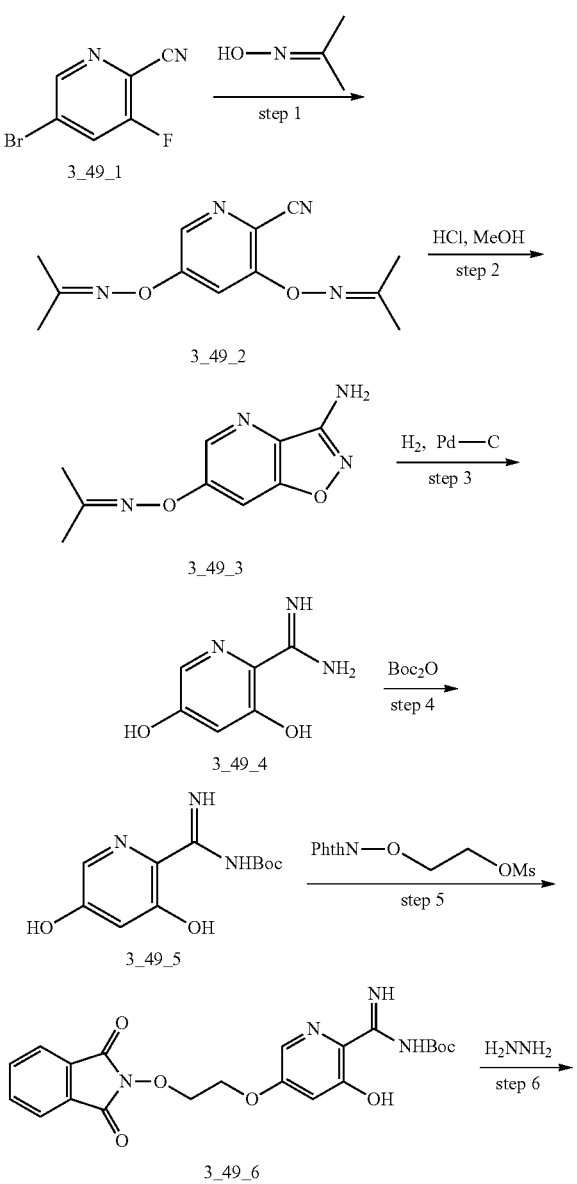

-continued

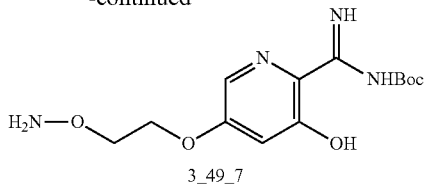

3_49_7

Step 1: 3,5-Bis-isopropylideneaminooxy-pyridine-2-carbonitrile (3_49_2)

Sodium hydride (0.875 g, 21.89 mmol, 60% in mineral oil) was added to a solution of acetone oxime (1.60 g, 9.95 mmol) in N,N-dimethylformamide (30 mL) at 0° C. and the resulting mixture was stirred at room temperature for 1 hour. A solution of 5-bromo-3-fluoro-pyridine-2-carbonitrile 3_49_1 (2.0 g, 9.95 mmol) in N,N-dimethylformamide (10 mL) was added at 0° C. and the reaction mixture was stirred at room temperature overnight. After the removal of most of the N,N-dimethylformamide, the mixture was cooled to 0° C. and water (40 mL) was added and the mixture was stirred for 0.5 hour. The white precipitate was collected, washed with cold water and dried to give the desired product (2.55 g, 100% yield) as a white solid.

$^1$H NMR (400 MHz, DMSO-$d_6$): δ=2.05 (s, 3H), 2.06 (s, 3H), 2.09 (s, 3H), 2.13 (s, 3H), 7.69 (d, J=2.3 Hz, 1H), 8.21 (d, J=2.3 Hz, 1H).

MS (ES$^+$) m/z: [M+H]$^+$ calcd for $C_{12}H_{15}N_4O_2$: 247.27. Found: 247.12.

Step 2: Propan-2-one O-(3-amino-isoxazolo[4,5-b]pyridin-6-yl)-oxime (3_49_3)

Conc. hydrochloric acid (1:1, 32 mL) was added to a mixture of 3,5-bis-isopropylideneaminooxy-pyridine-2-carbonitrile 3_49_2 (4.8 g, 19.49 mmol) in methanol (80 mL) and the resulting mixture was stirred at 60° C. for 4 hours. After cooling to room temperature, the white precipitate was collected, washed with water, and dried to give the desired product (3.50 g, 87% yield) as a white solid.

$^1$H NMR (400 MHz, CDCl$_3$): δ=2.01-2.04 (m, 3H), 2.06-2.09 (m, 3H), 6.42 (s, 2H), 7.63 (d, J=2.0 Hz, 1H), 8.40 (d, J=2.0 Hz, 1H).

MS (ES$^+$) m/z: [M+H]$^+$ calcd for $C_9H_{11}N_4O_2$: 207.21. Found: 207.11.

Step 3: 3,5-Dihydroxy-pyridine-2-carboxamidine (3_49_4)

Palladium on carbon (2.0 g, 10 wt. %, wet) was added to a solution of propan-2-one O-(3-amino-isoxazolo[4,5-b]pyridin-6-yl)-oxime 3_49_3 (3.67 g, 17.80 mmol) in anhydrous tetrahydrofuran (30 mL), methanol (30 mL) and N,N-dimethylformamide (150 mL) and the resulting mixture was hydrogenated under 1 atmosphere at room temperature for 3 hours. The reaction mixture was filtered and the filtrate was concentrated to dryness to afford the crude compound 3_49_4 (4.08 g, >100% yield) as a white solid, which was used in the next step without purification.

$^1$H NMR (400 MHz, DMSO-$d_6$): δ=6 6.08 (d, J=2.3 Hz, 1H), 7.23 (d, J=2.3 Hz, 1H), 7.53 (br s, 2H).

MS (ES$^+$) m/z: [M+H]$^+$ calcd for $C_6H_8N_3O_2$: 154.14. Found: 154.15.

Step 4: [(3,5-Dihydroxy-pyridin-2-yl)-imino-methyl]-carbamic acid tert-butyl ester (3_49_5)

Di-tert-butyl dicarbonate (Boc$_2$O, 5.826 g, 26.70 mmol) was added to a suspension of 3,5-dihydroxy-pyridine-2-carboxamidine 3_49_4 (4.08 g, crude, 17.8 mmol), in methanol (40 mL) and tetrahydrofuran (60 mL) followed by sodium carbonate (3.77 g, 35.61 mmol) in water (20 mL) at room temperature. After stirring at room temperature overnight, the resulting mixture was filtered and the filtrate was concentrated, diluted with ethyl acetate, washed with a saturated aqueous ammonium chloride solution and brine, dried and concentrated to give the desired product (2.90 g, 64% yield) as a white solid.

$^1$H NMR (400 MHz, DMSO-$d_6$): δ=1.48 (s, 9H), 6.55 (d, J=2.3 Hz, 1H), 7.40 (d, J=2.3 Hz, 1H), 7.85 (br s, 2H).

MS (ES$^+$) m/z: [M+H]$^+$ calcd for $C_{11}H_{14}N_3O_4$: 252.26. Found: 252.19.

Step 5: ({5-[2-(1,3-Dioxo-1,3-dihydro-isoindol-2-yloxy)-ethoxy]-3-hydroxy-pyridin-2-yl}-imino-methyl)-carbamic acid tert-butyl ester (3_49_6)

Triethylamine (1.465 g, 14.47 mmol) was added to a solution of N-(2-hydroxyethoxy)phthalimide (2.0 g, 9.65 mmol) in dichloromethane (20 mL) at 0° C. Methanesulfonyl chloride (1.657 g, 14.47 mmol) was slowly added to the reaction mixture at 0° C. After stirring at room temperature for 3 hours, the reaction mixture was washed with brine, dried over sodium sulfate and concentrated to dryness to give methanesulfonic acid 2-(1,3-dioxo-1,3-dihydro-isoindol-2-yloxy)-ethyl ester (2.46 g, 89% yield) as a white solid.

Potassium carbonate (0.994 g, 7.19 mmol) was added to a solution of [(3,5-dihydroxy-pyridin-2-yl)-imino-methyl]-carbamic acid tert-butyl ester 3_49_5 (0.911 g, 3.60 mmol) in N,N-dimethylformamide (20 mL). After stirring at 60° C. for 15 minutes, a solution of methanesulfonic acid 2-(1,3-dioxo-1,3-dihydro-isoindol-2-yloxy)-ethyl ester (1.026 g, 3.60 mmol) in N,N-dimethylformamide (30 mL) was slowly added at 60° C. and the mixture was stirred at 60° C. for 4 hours before it was neutralized to pH 7 using dilute hydrochloric acid and diluted with cold water. The precipitate was collected and purified by column chromatography to give the desired product (0.243 g, 15% yield) as a white solid.

$^1$H NMR (400 MHz, DMSO-$d_6$): δ=1.49 (s, 9H), 4.39 (br s, 2H), 4.44-4.57 (m, 2H), 6.76 (br s, 1H), 7.67 (br s, 1H), 7.87 (s, 4H), 9.03 (br s, 2H).

MS (ES$^+$) m/z: [M+H]$^+$ calcd for $C_{21}H_{23}N_4O_7$: 443.43. Found: 443.11.

Step 6: tert-Butyl [{5-[2-(aminooxy)ethoxy]-3-hydroxypyridin-2-yl}(imino)methyl]carbamate (3_49_7)

Hydrazine monohydrate (0.0445 g, 0.890 mmol) was slowly added to a solution of ({5-[2-(1,3-dioxo-1,3-dihydro-isoindol-2-yloxy)-ethoxy]-3-hydroxy-pyridin-2-yl}-imino-methyl)-carbamic acid tert-butyl ester 3_49_6 (0.358 g, 0.809 mmol) in tetrahydrofuran (3 mL) and ethanol (5 mL). The resulting mixture was stirred at room temperature for 1 hour and concentrated. The resulting solid was stirred with dichloromethane (25 mL) for 15 minutes and filtered. The filtrate was concentrated to give the desired product (0.320 g, >100% yield) as a white solid, which was used for the next step without further purification.

$^1$H NMR (400 MHz, DMSO-d$_6$): δ=1.49 (s, 9H), 3.77-3.91 (m, 2H), 4.10-4.26 (m, 2H), 6.12 (s, 2H), 6.79 (br s, 1H), 7.80 (br s, 1H).

MS (ES$^+$) m/z: [M+H]$^+$ calcd for C$_{13}$H$_{21}$N$_4$O$_5$: 313.33. Found: 313.13.

3.50 2-{4-[2-(Aminooxy)ethoxy]phenyl}-4,5-dihydro-1H-imidazole

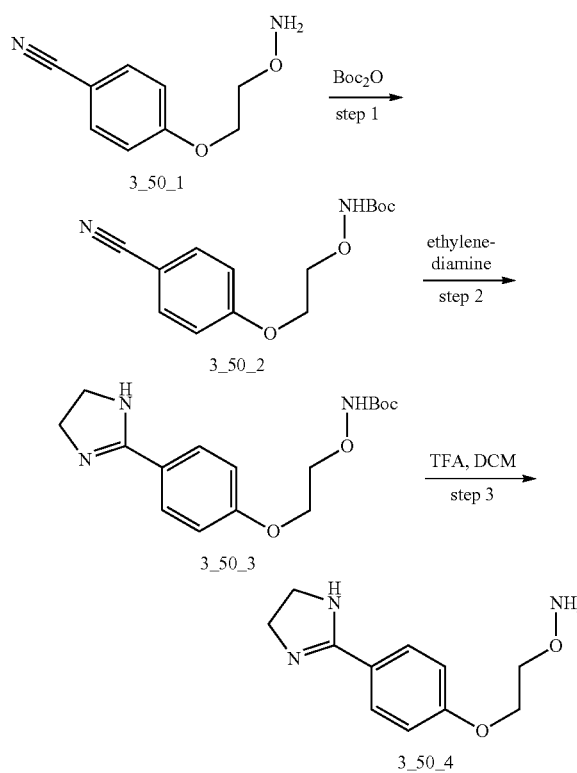

Step 1: tert-Butyl [2-(4-cyanophenoxyl)ethoxy]carbamate (3_50_2)

A mixture of 4-[2-(aminooxy)ethoxy]benzonitrile 3_50_1 (5.0 g, 28.0 mmol), di-tert-butyl dicarbonate (Boc$_2$O, 6.1 g, 28.0 mmol) and triethyl amine (2.8 g, 28.0 mmol) in dichloromethane (300 mL) was stirred overnight at room temperature. The mixture was evaporated and the residue suspended in ether (200 mL). The resulting white precipitate was collected to obtain compound 3_50_2 (7.1 g, 91% yield).

$^1$H NMR (400 MHz, DMSO-d$_6$): δ=1.36 (s, 9H), 4.02 (dd, J=5.2, 3.0 Hz, 2H), 4.21 (dd, J=5.2, 3.3 Hz, 2H), 7.10 (d, J=8.9 Hz, 2H), 7.75 (d, J=8.9 Hz, 2H), 10.08 (br s, 1H)

MS (ES$^+$) m/z: [M+H]$^+$ calcd for C$_{14}$H$_{19}$N$_2$O$_4$: 279.13. found: 279.12.

Step 2: tert-Butyl {2-[4-(4,5-dihydro-1H-imidazol-2-yl)phenoxy]ethoxy}carbamate (3_50_3)

Sodium hydrogen sulfide (0.16 g, 2.16 mmol) was added to a suspension of tert-butyl [2-(4-cyanophenoxyl)ethoxy]carbamate 3_50_2 (6.0 g, 21.6 mmol) and ethylenediamine (20 mL). The resulting mixture was heated at 120° C. for 2 hours, cooled to room temperature and poured into crushed ice to form a white solid. The solid was collected and dried under vacuum to obtain compound 3_50_3 (3.8 g, 55%) as a white solid.

$^1$H NMR (400 MHz, DMSO-d$_6$): δ=1.14-1.67 (m, 9H), 3.55 (s, 4H), 3.91-4.10 (m, 2H), 4.08-4.29 (m, 2H), 6.79-7.09 (m, 3H), 7.54-7.87 (m, 3H)

MS (ES$^+$) m/z: [M+H]$^+$ calcd for C$_{16}$H$_{24}$N$_3$O$_4$: 322.18. found: 322.15.

Step 3: 2-{4-[2-(Aminooxy)ethoxy]phenyl}-4,5-dihydro-1H-imidazole (3_50_4)

A solution of tert-butyl {2-[4-(4,5-dihydro-1H-imidazol-2-yl)phenoxy]ethoxy}carbamate 3_50_3 (3.8 g, 12.0 mmol) in dichloromethane (50 mL) was treated with trifluoroacetic acid (TFA, 3.8 mL). The resulting solution was stirred overnight at room temperature, evaporated to remove excess trifluoroacetic acid and diluted with dichloromethane (200 mL). The solution was washed with an aqueous sodium bicarbonate solution (10 ml), dried and evaporated to obtain compound 3_50_4 (2.17 g, 81% yield) as a gum.

$^1$H NMR (400 MHz, DMSO-d6): δ=3.69 (s, 4H), 3.77-3.94 (m, 2H), 4.10-4.30 (m, 2H), 6.11 (br s, 2H), 6.90-7.17 (m, 2H), 7.59-7.96 (m, 3H).

MS (ES$^+$) m/z: [M+H]$^+$ calcd for C$_{11}$H$_{16}$N$_3$O$_2$: 222.12. found: 222.14.

3.51 tert-Butyl 4-{[{4-[2-(aminooxy)ethoxy]phenyl}(imino)methyl](tert-butoxycarbonyl)amino}piperidine-1-carboxylate

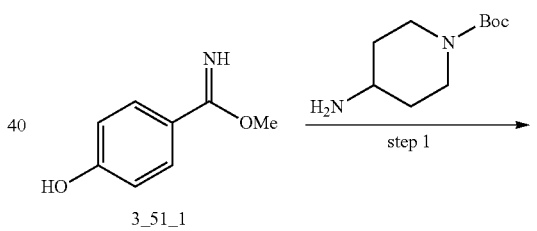

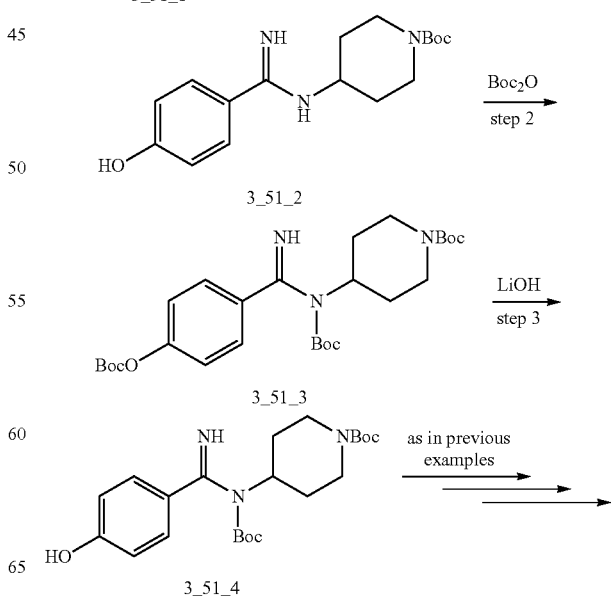

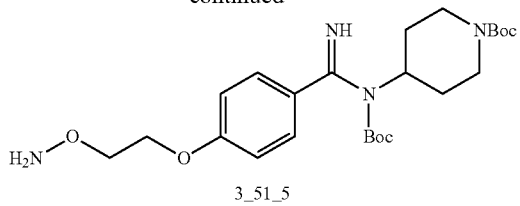

3_51_5

Step 1: tert-Butyl 4-{[(4-hydroxyphenyl)(imino)methyl]amino}piperidine-1-carboxylate (3_51_2)

A suspension of compound 3_51_1 (1.0 g, 4.46 mmol) in methanol (10.0 mL) was treated with triethylamine (1.20 mL, 0.86 mmol) at 0° C. to give a clear yellow solution. The solution was treated with tert-butyl 4-aminopiperidine-1-carboxylate (0.90 g, 4.46 mmol) in methanol (2.0 mL) and stirred at room temperature overnight. The mixture was concentrated in vacuo to a yellow foam. The foam was purified by column chromatography to afford compound 3_51_2 (1.20 g, 85% yield) as an off-white solid.

$^1$H NMR (400 MHz, DMSO-$d_6$): δ=1.22 (t, J=7.03 Hz, 2H), 1.42 (s, 9H), 1.46-1.55 (m, 2H), 1.88-1.93 (m, 2H), 3.05-3.10 (m, 1H), 3.80-4.11 (m, 2H), 6.95 (d, J=8.99 Hz, 2H), 7.61 (d, J=8.99 Hz, 2H), 9.02 (br s, 1H), 10.53 (br s, 1H).

MS (ES$^+$) m/z: [M+H]$^+$ calcd for $C_{17}H_{26}N_3O_3$: 320.20. Found: 320.21.

Step 2: tert-Butyl 4-{(tert-butoxycarbonyl)[{4-[(tert-butoxycarbonyl)oxy]phenyl}-(imino)methyl]amino}piperidine-1-carboxylate (3_51_3)

A solution of compound 3_51_2 (2.40 g, 7.51 mmol) in 1,4-dioxane (100 mL) was treated with a saturated sodium carbonate solution (100 mL) followed by di-tert-butyl dicarbonate (Boc$_2$O, 8.20 g, 37.57 mmol) at 0° C. The mixture was stirred at room temperature overnight and then extracted with ethyl acetate. The organic extracts were filtered through a short plug of silica gel and the pad was rinsed with ethyl acetate. The filtrate was concentrated to afford compound 3_51_3 (2.40 g, 62% yield) as a white solid.

$^1$H NMR (400 MHz, DMSO-$d_6$): δ=1.18 (s, 9H), 1.24-1.40 (m, 2H), 1.40 (s, 9H), 1.49 (s, 9H), 1.84-1.89 (m, 2H), 2.67-2.90 (m, 2H), 3.81-3.90 (m, 3H), 7.26 (d, J=8.60 Hz, 2H), 7.38 (d, J=8.60 Hz, 2H), 7.75 (d, J=6.25 Hz, 1H).

MS (ES$^+$) m/z: [M+H]$^+$ calcd for $C_{27}H_{42}N_3O_7$: 520.30. Found: 520.30.

Step 3: tert-Butyl 4-{(tert-butoxycarbonyl)[(4-hydroxyphenyl)(imino)methyl]amino}-piperidine-1-carboxylate (3_51_4)

A colorless solution of compound 3_51_3 (2.40 g, 4.62 mmol) in tetrahydrofuran (50 mL) and methanol (50 mL) was treated with lithium hydroxide monohydrate (0.58 g, 13.86 mmol) in water (5.0 mL) at 0° C. The mixture was stirred at room temperature for 2 hours and concentrated in vacuo to remove organic solvents. The residue was diluted with water and extracted with ethyl acetate. The extracts were dried over sodium sulfate, filtered and concentrated in vacuo to provide a white solid which was purified by column chromatography to give compound 3_51_4 (1.70 g, 88% yield) as a white solid.

$^1$H NMR (400 MHz, DMSO-$d_6$): δ=1.19 (s, 9H), 1.21-1.31 (m, 2H), 1.38 (s, 9H), 1.78-1.84 (m, 2H), 2.70-2.80 (m, 2H), 3.80-3.95 (m, 3H), 6.74 (d, J=8.60 Hz, 2H), 7.17 (d, J=8.60 Hz, 2H), 7.40-7.50 (m, 1H).

MS (ES$^+$) m/z: [M+H]$^+$ calcd for $C_{22}H_{34}N_3O_5$: 420.25. Found: 420.25.

Using the intermediate 3_51_4, compound 3_51_5 was prepared using the conditions as described in the previously cited examples.

3.52 tert-Butyl 4-{[{4-[(3S)-3-(aminooxy)ethoxy]phenyl}(imino)methyl](tert-butoxycarbonyl)amino}pyrrolidine-1-carboxylate

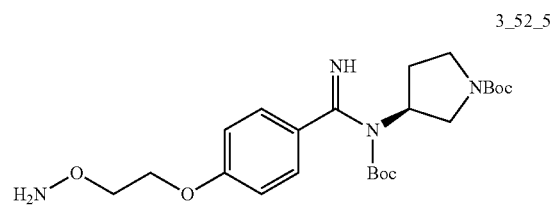 [SMILES: CC(C)(C)OC(=O)N1CC[C@H](N(C(=N)c2ccc(OCCON)cc2)C(=O)OC(C)(C)C)C1]

3_52_5

Using conditions as described under 3.51 but using tert-butyl (3S)-3-aminopyrrolidine-1-carboxylate instead of tert-butyl 4-aminopiperidine-1-carboxylate, compound 3_52_5 was prepared.

3.53 tert-Butyl (2S,4S)-4-{[{4-[2-(Aminooxy)ethoxy]phenyl}(imino)methyl](tert-butoxycarbonyl)amino}-N,N-dimethyl-prolinamide-1-carboxylate

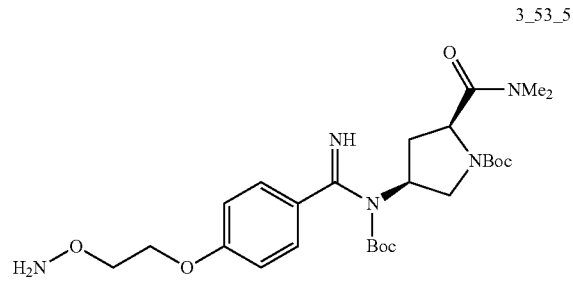 [SMILES: CN(C)C(=O)[C@@H]1C[C@H](N(C(=N)c2ccc(OCCON)cc2)C(=O)OC(C)(C)C)CN1C(=O)OC(C)(C)C]

3_53_5

Using conditions as described under 3.51 but using tert-butyl (2S,4S)-4-amino-2-(dimethylcarbamoyl)pyrrolidine-1-carboxylate instead of tert-butyl 4-aminopiperidine-1-carboxylate, compound 3_53_5 was prepared.

3.54 1-(2-{[{4-[2-(Aminooxy)ethoxy]phenyl}(imino)methyl]amino}ethyl)-1-methyl-pyrrolidinium trifluoroacetate

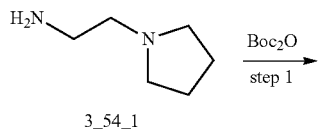

3_54_1

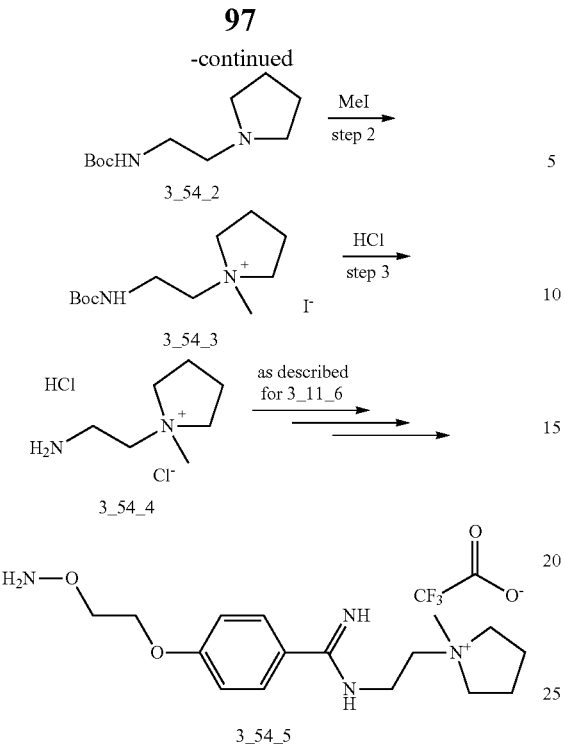

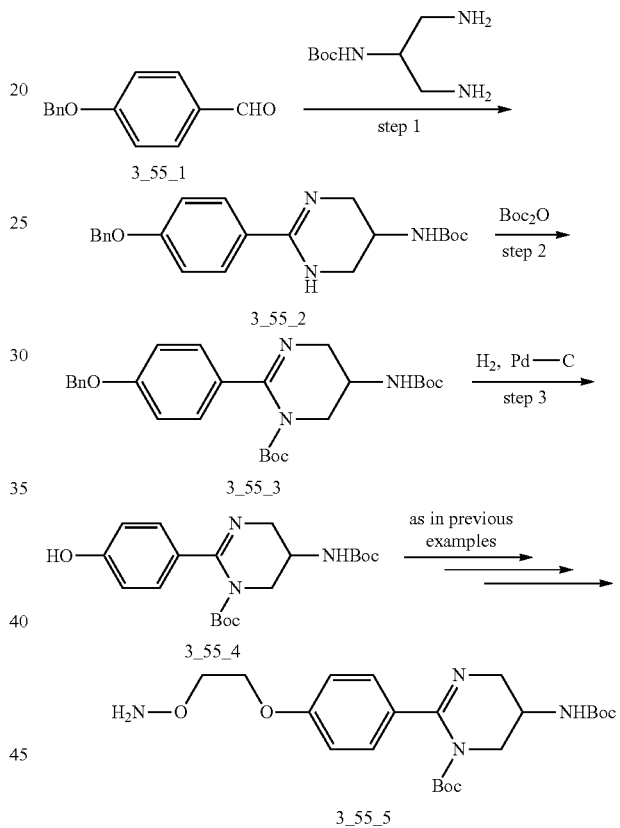

Step 1: (2-Pyrrolidin-1-yl-ethyl)-carbamic acid tert-butyl ester (3_54_2)

A solution of di-tert-butyldicarbonate (Boc$_2$O, 10.512 g, 48.2 mol) in tetrahydrofuran (20 mL) was added to a solution of 2-pyrrolidin-1-yl-ethylamine 3_54_1 (5.0 g, 43.8 mol) in tetrahydrofuran (40 mL) at 0° C. After stirring at room temperature overnight, the resulting mixture was concentrated to give the desired product (9.45 g, 100% yield) as a colorless oil, which was used in the next step without purification.

$^1$H NMR (400 MHz, CDCl$_3$): δ=1.45 (s, 9H), 1.74-78 (m, 4H), 2.48-2.58 (m, 6H), 3.22-3.26 (3, 2H), 5.08 (br s, 1H).

Step 2: 1-(2-tert-Butoxycarbonylamino-ethyl)-1-methyl-pyrrolidinium iodide (3_54_3)

Iodomethane (20 mL) was added to a solution of compound 3_54_2 (9.45 g, crude, 43.8 mmol) in dichloromethane (30 mL) at −10° C. The resulting solution was sealed, stirred at 60° C. overnight and concentrated to give the desired product (16.79 g, >100% yield) as a light yellow sticky solid, which was used in the next step without purification.

$^1$H NMR (400 MHz, DMSO-d$_6$): δ=1.38 (s, 9H), 2.06 (br s, 4H), 2.98 (s, 3H), 3.34-3.37 (m, 4H), 3.42-3.46 (m, 2H), 3.47-3.54 (m, 2H), 7.18 (br s, 1H).

Step 3: 1-(2-Amino-ethyl)-1-methyl-pyrrolidinium chloride hydrochloride salt (3_54_4)

Hydrogen chloride gas was introduced into a solution of compound 3_54_3 (16.79 g, crude, 47.1 mmol) in dichloromethane (100 mL) at 0° C. for 10 minutes. After stirring at room temperature for 1 hour, the resulting solid was filtered off, washed with dichloromethane and then dissolved in methanol (10 mL). Ether (30 mL) was added to the solution and the precipitate was collected and dried to give the desired product (10.1 g, 100% yield) as an off-white solid.

$^1$H NMR (400 MHz, DMSO-d$_6$): δ=2.06-2.11 (m, 4H), 3.05 (s, 3H), 3.27-3.33 (m, 2H), 3.48-3.56 (m, 2H), 3.57-3.65 (m, 4H), 8.60 (br s, 2H).

Using the intermediate 3_54_4 and following the procedure as described under 3.11 compound 3_54_5 was prepared.

3.55 tert-Butyl 2-{4-[2-(aminooxy)ethoxy]phenyl}-1-tert-butoxycarbonyl-1,4,5,6-tetrahydropyrimidin-5-carbamate

Step 1: tert-Butyl {2-[4-(benzyloxy)phenyl]-1,4,5,6-tetrahydropyrimidin-5-yl}carbamate (3_55_2)

4-(Benzyloxy)benzaldehyde 3_55_1 (1.00 g, 4.71 mmol) was treated with tert-butyl (1,3-diaminopropan-2-yl)carbamate (0.94 g, 4.97 mmol) in dichloromethane (47.0 mL). The mixture was stirred at room temperature for 7 h, cooled to 0° C., and treated with N-bromosuccinimide (0.88 g, 4.94 mmol). The suspension was stirred at 0° C. to room temperature overnight, and quenched with a saturated sodium metabisulfite solution and a 1N sodium hydroxide solution. The organic layer was dried over sodium sulfate, filtered and concentrated in vacuo to give a yellow oil. The oil was purified by column chromatography to afford compound 3_55_2 (1.05 g, 59% yield) as a light yellow solid.

$^1$H NMR (400 MHz, CD$_3$OD): δ=1.45 (s, 9H), 3.42 (dd, J=13.3, 5.1 Hz, 2H), 3.65 (dd, J=12.9, 3.9 Hz, 2H), 4.05-

4.09 (m, 1H), 5.18 (s, 2H), 7.15 (d, J=8.6 Hz, 2H), 7.30-7.75 (m, 5H), 7.66 (d, J=9.0 Hz, 2H).

Step 2: tert-Butyl 2-[4-(benzyloxy)phenyl]-5-[(tert-butoxycarbonyl)amino]-5,6-dihydro-pyrimidine-1(4H)-carboxylate (3_55_3)

A solution of compound 3_55_2 (1.05 g, 2.75 mmol) in a mixture of dioxane/methanol/tetrahydrofuran (1.0 mL/2.0 mL/53.0 mL) and a saturated sodium carbonate solution (50.0 mL) was cooled to 0° C., and treated with di-tert-butyl dicarbonate (Boc$_2$O, 2.86 g, 13.1 mmol) in portions. The suspension was stirred at room temperature overnight, concentrated in vacuo to remove the organic solvents, and diluted with ethyl acetate. The extracts were dried over sodium sulfate, filtered and concentrated to give a yellow oil. The oil was purified by column chromatography to afford compound 3_55_3 (1.10 g, 87% yield) as a yellow solid.

$^1$H NMR (400 MHz, CD$_3$OD): δ=1.08 (s, 9H), 1.43 (s, 9H), 3.37 (dd, J=16.0, 5.9 Hz, 1H), 3.68-3.81 (m, 3H), 3.84-3.37 (m, 1H), 5.15 (s, 2H), 7.00 (d, J=9.0 Hz, 2H), 7.25-7.45 (m, 7H).

Step 3: tert-Butyl 5-[(tert-butoxycarbonyl)amino]-2-(4-hydroxyphenyl)-5,6-dihydro-pyrimidine-1(4H)-carboxylate (3_55_4)

A solution of compound 3_55_3 (2.50 g, 5.19 mmol) in methanol was treated with palladium on carbon (10% wet, 0.25 g), and hydrogenated at 15 psi of hydrogen gas for 3 hours. The mixture was filtered through a pad of Celite and the filtrate was concentrated in vacuo to give a yellow oil. The oil was purified by column chromatography to afford compound 3_55_4 (1.50 g, 74% yield) as a white solid.

$^1$H NMR (400 MHz, DMSO-d$_6$): δ=1.09 (s, 9H), 1.39 (s, 9H), 3.25-3.39 (m, 2H), 3.64-3.73 (m, 3H), 6.73 (d, J=9.0 Hz, 2H), 7.00-7.04 (m, 1H), 7.27 (d, J=9.0 Hz, 2H), 9.67 (br s, 1H).

The above intermediate 3_55_4 was used to prepare compound 3_55_5 by following the conditions as described before.

3.56 tert-Butyl 1-(2-{4-[2-(Aminooxy)ethoxy]phenyl}-1-tert-butoxycarbonyl-4,5-dihydro-1H-imidazol-5-yl)methancarbamate

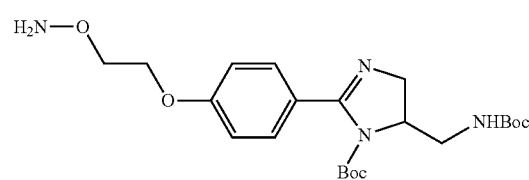

3_56_5

Using the conditions as described under 3.55 but using tert-butyl (2,3-diaminopropan-1-yl)carbamate in place of tert-butyl (1,3-diaminopropan-2-yl)carbamate, compound 3_56_5 was prepared.

3.57 Di-tert-butyl 4-{[{4-[2-(aminooxy)ethoxy]phenyl}(imino)methyl]amino}-pyrazolidine-1,2-dicarboxylate

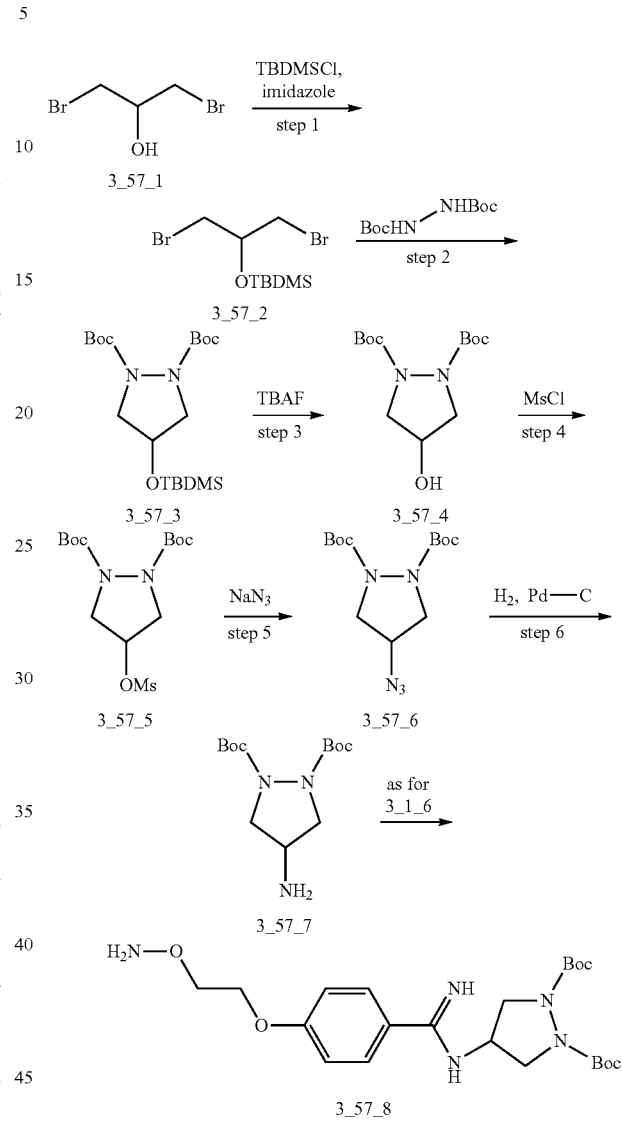

Step 1: tert-Butyl[(1,3-dibromopropan-2-yl)oxy]dimethylsilane (3_57_2)

Imidazole (19.69 g, 289 mmol) was added in portions to an ice-cold solution of 1,3-dibromopropan-2-ol 3_57_1 (25.2 g, 115 mmol) and tert-butyldimethylsilyl chloride (TBDMSCl, 20.92 g, 138 mmol) in N,N-dimethylformamide (116 mL) and the resulting solution was stirred at room temperature for 18 hours. The mixture was diluted with ethyl acetate, and washed with water and brine. The organic phase was dried and concentrated under reduced pressure. Vacuum distillation afforded compound 3_57_2 (27.6 g, 72% yield).

Step 2: Di-tert-butyl 4-{[tert-butyl(dimethyl)silyl]oxy}pyrazolidine-1,2-dicarboxylate (3_57_3)

A solution of di-tert-butyl hydrazine-1,2-dicarboxylate (BocNH—NHBoc, 1.51 g, 6.492 mmol) in N,N-dimethylformamide (32 mL) was treated with sodium hydride (60% in mineral oil, 0.262 g, 6.446 mmol) to give a yellow slurry. The mixture was stirred for 1.75 hours, treated with compound 3_57_2 (2.135 g, 6.428 mmol) and stirred for another 1.75 hours. Another portion of sodium hydride (60% in mineral oil, 0.270 g, 8.484 mmol) was added and the mixture was heated at 90° C. for 2 hours. The mixture was cooled to room temperature, another portion of sodium hydride was added (60%, in mineral oil, 0.103 g, 2.57 mmol) and the mixture was heated at 90° C. for 1 hour. The solvent was removed under reduced pressure, and the mixture was quenched with methanol and extracted with ethyl acetate. The organic extract was washed with water and brine, dried and concentrated under vacuum to afford crude compound 3_57_3 (2.1 g, 80% yield) as an oil.

Step 3: Di-tert-butyl 4-hydroxypyrazolidine-1,2-dicarboxylate (3_57_4)

A solution of compound 3_57_3 (9.05 g, 22.48 mmol) in tetrahydrofuran (225 mL) was cooled to 0° C., then treated with glacial acetic acid (3.87 mL, 67.46 mmol) followed by the addition of tetra-n-butylammonium fluoride (TBAF, 1N in tetrahydrofuran, 47.6 mL, 47.6 mmol). The mixture was heated at 50° C. for 4.5 hours, cooled to room temperature and extracted with ethyl acetate. The extract was washed with a saturated sodium bicarbonate solution, dried and concentrated in vacuo to afford the crude compound 3_57_4 (6.48 g, 100% yield), which was used without purification.

Step 4: Di-tert-butyl 4-[(methylsulfonyl)oxy]pyrazolidine-1,2-dicarboxylate (3_57_5)

A solution of compound 3_57_4 (6.48 g, 22.48 mmol) in dichloromethane (112 mL) at 0° C. was treated with triethylamine (TEA, 6.27 mL, 44.96 mmol) followed by methanesulfonyl chloride (MsCl, 2.62 mL, 11.24 mmol). The resulting mixture was stirred for 1.5 hours, washed with a saturated sodium bicarbonate solution, water and brine. The extract was dried and concentrated in vacuo to afford the crude compound 3_57_5 (8.24 g, 100% yield).

Step 5: Di-tert-butyl 4-azidopyrazolidine-1,2-dicarboxylate (3_57_6)

A solution of compound 3_57_5 (8.24 g, 22.48 mmol) in N,N-dimethylformamide was treated with sodium azide (4.38 g, 67.44 mmol). The resulting mixture was heated at 50° C. for 20 hours, then extracted with ethyl acetate (225 mL) and washed with water and brine. The extract was dried and concentrated in vacuo to afford the crude compound 3_57_6 (7.02 g, 100% yield).

Step 6: Di-tert-butyl 4-aminopyrazolidine-1,2-dicarboxylate (3_57_7)

A solution of compound 3_57_6 (0.125 g, 0.40 mmol) and palladium on charcoal (5%, 0.10 g) in methanol (6 mL) was hydrogenated at 42 psi of hydrogen for 4.5 hours. The mixture was filtered through a bed of Celite and the filtrate was concentrated in vacuo to afford crude compound 3_57_7 (0.103 g, 90% yield).
Treating the intermediate 3_1_5 with the above compound 3_57_7 instead of ammonia as described under 3.1 gave the desired compound 3_57_8.

3.58 tert-Butyl [(4-{[2-(aminooxy)-4-hydroxybutan-1-yl]oxy}phenyl)(imino)-methyl]carbamate

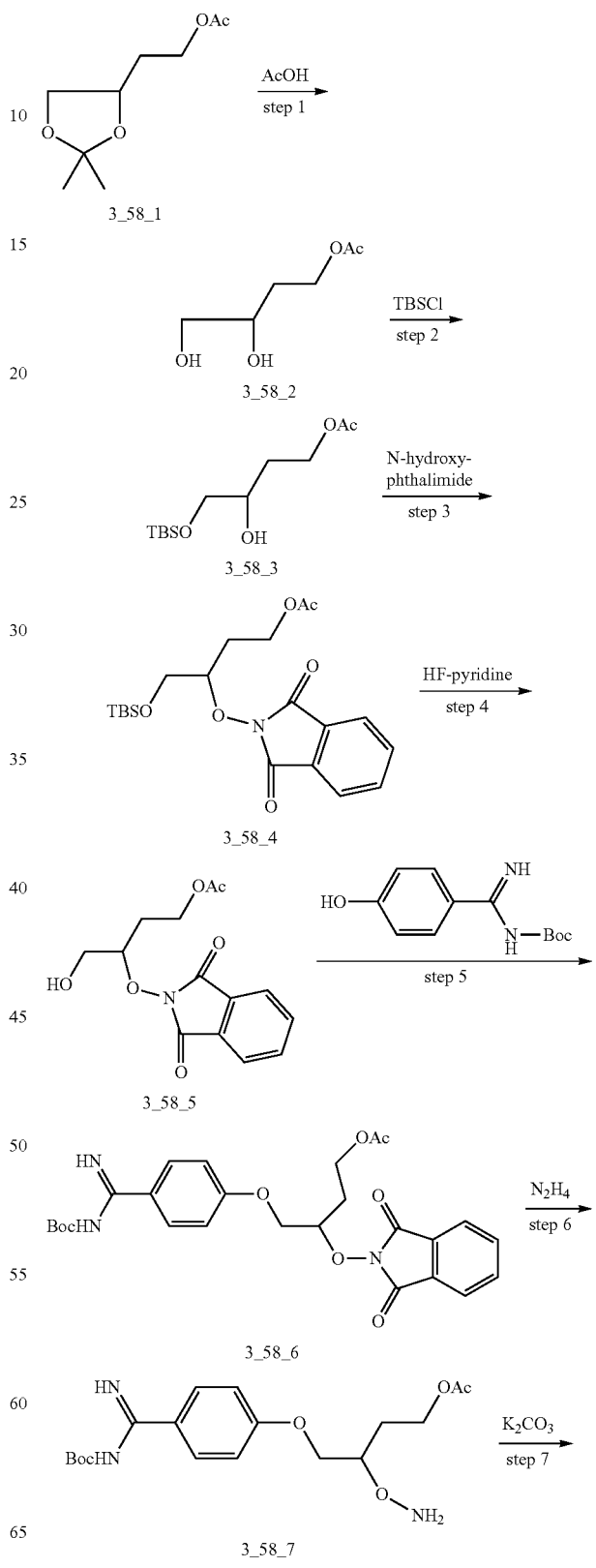

-continued

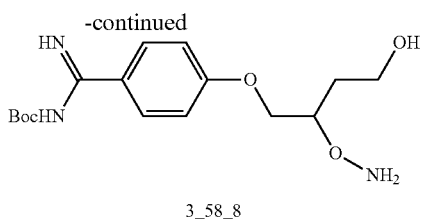

3_58_8

Step 1: 3,4-Dihydroxybutyl acetate (3_58_2)

A mixture of compound 3_58_1 (WO2005/70874, 30 g, 159.6 mmol) in acetic acid (150 mL) and water (100 mL) was heated at 60° C. for 2.5 hours and concentrated to dryness to give crude compound 3_58_2 (25 g, >100% yield) as an oil, which was used in the next step without further purification.

$^1$H NMR (400 MHz, CDCl$_3$): δ=1.78 (m, 2H), 1.97-2.18 (m, 5H), 3.45 (m, 1H), 3.67 (dd, J=11.3, 3.1 Hz, 1H), 3.80 (tt, J=8.0, 3.7 Hz, 1H), 4.03-4.25 (m, 1H), 4.38 (m, 1H).

Step 2: 4-{[tert-Butyl(dimethyl)silyl]oxy}-3-hydroxybutyl acetate (3_58_3)

Tert-butyldimethylchlorosilane (TBSCl, 24 g, 152.0 mmol) was added portionwise to a solution of compound 3_58_2 (crude 25 g), triethylamine (32.7 g, 235.2 mmol) and 4-dimethylaminopyridine (1.2 g, 9.8 mmol) in dichloromethane (250 mL). The reaction mixture was stirred at room temperature overnight, filtered and the filtrate was concentrated. The residue was dissolved in ethyl acetate, filtered again to remove the solid and the filtrate was concentrated to give a residue, which was purified by column chromatography to give compound 3_58_3 (13 g, 30% yield) as an oil.

$^1$H NMR (400 MHz, CDCl$_3$): δ=0.01 (s, 6H), 0.82 (s, 9H), 1.70 (m, 2H), 1.98 (s, 3H), 2.41 (d, J=3.6 Hz, 1H), 3.38 (m, 1H), 3.54 (m, 1H), 3.63 (m, 1H), 4.16 (m, 1H).

Step 3: 4-{[tert-Butyl(dimethyl)silyl]oxy}-3-[(1,3-dioxo-1,3-dihydro-2H-isoindol-2-yl)oxy]butyl acetate (3_58_4)

Triphenylphosphine (16.4 g, 62.8 mmol) was added to a solution of compound 3_58_3 (13 g, 48.3 mmol) and N-hydroxyphthalimide (11 g, 67.6 mmol) in tetrahydrofuran (200 mL), and diisopropyl azodicarboxylate (14.6 mL, 72.5 mmol) at 0° C., and the mixture was stirred at room temperature for 3 hours and concentrated to give a residue, which was purified by column chromatography to give compound 3_58_4 (20 g, 99% yield) as a yellow solid.

$^1$H NMR (400 MHz, CDCl$_3$): δ=0.02 (s, 6H), 0.80 (s, 9H), 2.10 (m, 5H), 3.81 (m, 1H), 3.96 (m, 1H), 4.42 (m, 3H), 7.78 (m, 2H), 7.82 (m, 2H).

Step 4: 3-[(1,3-Dioxo-1,3-dihydro-2H-isoindol-2-yl)oxy]-4-hydroxybutyl acetate (3_58_5)

Hydrogen fluoride-pyridine complex (HF-pyridine, 5 ml) was added to a solution of compound 3_58_4 (10 g, 24.1 mmol) in tetrahydrofuran (100 mL) under cooling, and the mixture was stirred at room temperature for 16 hours, and concentrated to give a residue, which was purified by column chromatography to give compound 3_58_5 (6.4 g, 91% yield) as a yellow solid.

$^1$H NMR (400 MHz, CDCl$_3$): δ=1.96 (m, 1H), 2.04 (s, 3H), 2.30 (m, 1H), 3.51 (m, 1H), 3.60 (m, 1H), 3.80 (m, 1H), 4.31 (m, 2H), 4.45 (m, 1H), 7.79 (m, 2H), 7.86 (m, 2H).

Step 5: 4-{4-[N-(tert-Butoxycarbonyl)carbamimidoyl]phenoxy}-3-[(1,3-dioxo-1,3-dihydro-2H-isoindol-2-yl)oxy]butyl acetate (3_58_6)

Diisopropyl azodicarboxylate (5.93 mL, 29.4 mmol) was added to a solution of compound 3_58_5 (5.74 g, 19.58 mmol), tert-butyl-N-[(4-hydroxyphenyl)iminomethyl]-carbamate (4.64 g, 19.58 mmol) and triphenylphosphine (6.1 g, 23.49 mmol) in tetrahydrofuran (100 mL) at 0° C. and the mixture was stirred at room temperature for 16 hours and concentrated to give a residue, which was purified by column chromatography to give compound 3_58_6 (8.76 g, 78% yield) as a gum.

$^1$H NMR (400 MHz, CDCl$_3$): 1.54 (s, 9H), 2.21 (s, 3H), 2.27 (m, 2H), 4.25 (m, 1H), 4.38 (m, 2H), 4.52 (m, 1H), 4.70 (m, 1H), 6.78 (d, J=6.4 Hz, 2H), 7.81 (m, 6H).

Step 6: 3-(Aminooxy)-4-{4-[N-(tert-butoxycarbonyl)carbamimidoyl]phenoxy}butyl acetate (3_58_7)

Hydrazine monohydrate (0.13 g, 2.6 mmol) was added to a solution of compound 3_58_6 (1.4 g, 2.73 mmol) in anhydrous ethanol (15 mL) under cooling. The resulting mixture was stirred at room temperature for 16 hours, filtered and the filtrate was concentrated to afford crude compound 3_58_7 (1 g, 96% yield) as a white solid.

$^1$H NMR (400 MHz, CDCl$_3$): δ=1.54 (s, 9H), 1.98 (m, 2H), 2.28 (s, 3H), 4.00 (m, 1H), 4.15 (m, 2H), 4.23 (m, 2H), 5.42 (br s, 2H), 6.85 (d, J=6.4 Hz, 2H), 7.81 (d, J=6.4 Hz, 2H).

Step 7: tert-Butyl [{4-[2-(aminooxy)-4-hydroxybutoxy]phenyl}(imino)methyl]carbamate (3_58_8)

Potassium carbonate (0.13 g, 2.6 mmol) was added to a solution of compound 3_58_7 (1 g, 2.62 mmol) in anhydrous methanol (30 mL) under cooling, and the mixture was stirred at room temperature for 1 hour. The resulting mixture was concentrated, extracted with ethyl acetate, washed with brine, dried over anhydrous sodium sulfate, filtered and concentrated. The residue was purified by column chromatography to give compound 3_58_8 (0.18 g, 20% yield) as a gum.

$^1$H NMR (400 MHz, DMSO-d$_6$): δ=1.42 (s, 9H), 1.43 (m, 1H), 1.78 (m, 1H), 3.50 (m, 1H), 3.80 (m, 1H), 4.16 (m, 2H), 4.42 (m, 1H), 5.95 (s, 2H), 7.22 (d, J=6.4 Hz, 2H), 7.96 (d, J=6.4 Hz, 2H).

3.59 Diphenylmethyl 2-(aminooxy)-3-{4-[N-(tert-butoxycarbonyl)-N-{2-[(tert-butoxycarbonyl)amino]ethyl}carbamimidoyl]phenoxy}propanoate

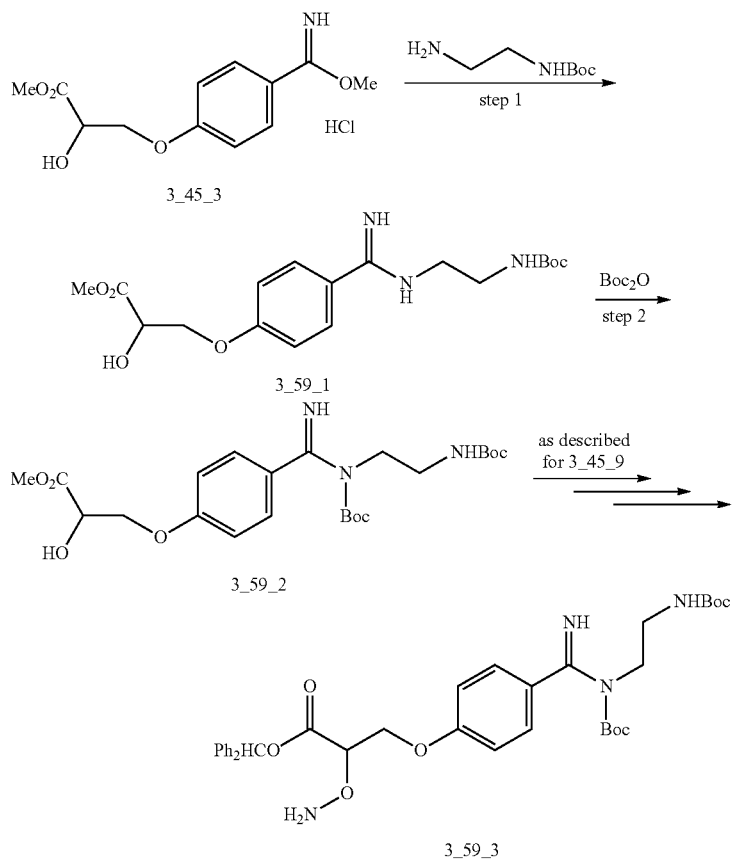

Step 1: 3-{4-[N-(2-tert-Butoxycarbonylamino-ethyl)-carbamimidoyl]-phenoxy}-2-hydroxy-propionic acid methyl ester (3_59_1)

Triethylamine (1.295 g, 12.8 mmol) and (2-amino-ethyl)-carbamic acid tert-butyl ester (1.76 g, 11.0 mmol) were added to a mixture of compound 3_45_3 (3.09 g, 10.7 mmol) in anhydrous methanol (50 mL) at 0° C. and the resulting mixture was stirred at room temperature overnight. The reaction mixture was concentrated to dryness and the residue was purified by column chromatography to give the desired product (3.09 g, 76% yield) as a white solid.

$^1$H NMR (400 MHz, DMSO-$d_6$): δ=1.35 (s, 9H), 3.18-3.27 (m, 2H), 3.38-3.47 (m, 2H), 3.65 (s, 3H), 4.23-4.28 (m, 2H), 4.44-4.50 (m, 1H), 5.95 (d, J=6.2 Hz, 1H), 7.12 (d, J=9.1 Hz, 2H), 7.72 (d, J=8.8 Hz, 2H), 8.96 (br. s., 1H), 9.36 (br s, 1H), 9.55 (br s, 1H).

Step 2: 3-(4-{[tert-Butoxycarbonyl-(2-tert-butoxycarbonylamino-ethyl)-amino]-imino-methyl}-phenoxy)-2-hydroxy-propionic acid methyl ester (3_59_2)

A saturated solution of sodium carbonate (20 mL) and di-tert-butyldicarbonate (Boc$_2$O, 3.519 g, 16.1 mmol) in 1,4-dioxane (25 mL) were added to a solution of compound 3_59_1 (2.05 g, 5.37 mmol) in water (30 mL) at 0° C. After stirring at room temperature for 4.5 hours, the resulting mixture was extracted with ethyl acetate and the extract was washed with brine, dried and concentrated. The residue was purified by column chromatography to give the desired product (0.66 g, 26% yield) as a white solid.

$^1$H NMR (400 MHz, DMSO-$d_6$): δ=1.21 (s, 9H), 1.37 (s, 9H), 3.05-3.14 (m, 2H), 3.17-3.25 (m, 2H), 3.64 (s, 3H), 4.13-4.19 (m, 2H), 4.44 (m, 1H), 5.87 (s, 1H), 6.95 (d, J=8.8 Hz, 2H), 7.31 (d, J=8.8 Hz, 2H).

Using compound 3_59_1 and following the procedure as described under 3.45 compound 3_59_3 was prepared.

3.60 Diphenylmethyl 2-(aminooxy)-3-[(6-{tert-butoxycarbonyl-carbamimidoyl}-pyridin-3-yl)oxy]propanoate

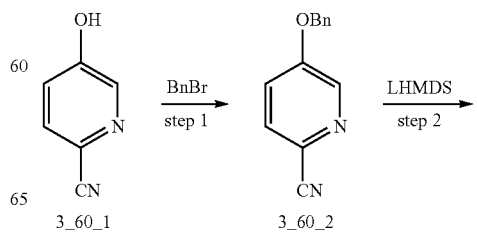

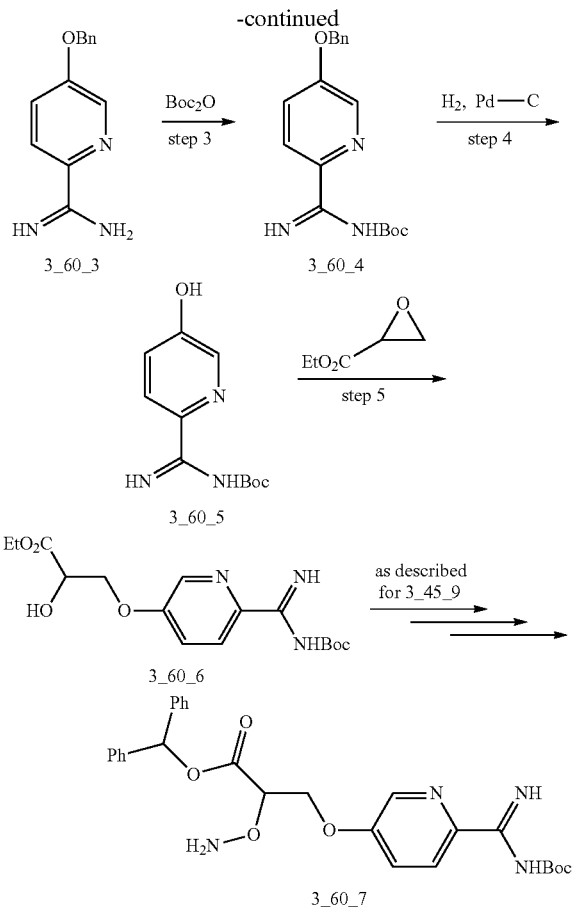

Step 1: 5-Benzyloxy-pyridine-2-carbonitrile (3_60_2)

A mixture of 5-hydroxy-pyridine-2-carbonitrile 3_60_1 (14 g, 116 mmol) and potassium carbonate (32.2 g, 233 mmol) in N,N-dimethylformamide (140 mL) was heated at 60° C. for 0.5 hours. Benzylbromide (13.9 g, 116 mmol) was added and the mixture was stirred at 66° C. for 1 hour, and filtered and the filtrate was concentrated, extracted with ethyl acetate, washed with brine, dried over sodium sulfate and concentrated. The residue was triturated with diethyl ether and hexanes to give a precipitate, which was collected to give compound 3_60_2 (21 g, 85% yield) as a solid.

$^1$H NMR (400 MHz, DMSO-d$_6$): δ=5.27 (s, 2H), 7.33-7.50 (m, 5H), 7.65 (dd, J=8.8, 2.9 Hz, 1H), 8.00 (d, J=8.6 Hz, 1H), 8.50 (d, J=3.2 Hz, 1H).

Step 2: 5-Benzyloxy-pyridine-2-carboxamidine (3_60_3)

Butyllithium (1.6N in hexane, 168 mL, 269 mmol) was added to a solution of hexamethyldisilazane (56.5 mL, 269 mmol) in tetrahydrofuran (250 mL) at 0° C., and stirred at 0° C. for 1 hour to form lithium hexamethyldisilazide (LHMDS). A solution of compound 3_60_2 (22.6 g, 107.6 mmol) in tetrahydrofuran (250 mL) was added slowly at 0° C., and the mixture was warmed to room temperature slowly and stirred for 16 hours at room temperature. A 1N hydrochloric acid solution (300 mL) was added to the reaction mixture to give a precipitate which was collected to give pure compound 3_60_3 (17 g, 70% yield). From the mother liquor an additional amount of crude compound 3_60_3 (10 g) was obtained as a gum.

$^1$H NMR (400 MHz, DMSO-d$_6$): δ=5.32 (s, 2H), 7.32-7.52 (m, 5H), 7.78 (dd, J=8.8, 2.9 Hz, 1H), 8.25 (d, J=8.6 Hz, 1H), 8.54 (d, J=2.7 Hz, 1H), 9.18 (s, 2H), 9.32 (s, 2H).

Step 3: Amino-(5-benzyloxy-pyridin-2-yl)-methylene]carbamic acid tert-butyl ester (3_60_4)

Sodium bicarbonate (7.78 g, 92.5 mmol) was added to a suspension of compound 3_60_3 (14 g, 61.67 mmol) in a mixture of dioxane (200 mL) and water (200 mL) at room temperature, and the mixture was stirred at room temperature for 20 minutes. Di-tert-butyl dicarbonate (Boc$_2$O, 13.4 g, 61.44 mmol) was added, and the mixture was stirred for 16 hours at room temperature to give a precipitate. The precipitate was collected, dissolved in ethyl acetate and washed with brine, dried over sodium sulfate and concentrated to give pure compound 3_60_4 (5 g, 25% yield). The filtrate was concentrated to remove dioxane, extracted with ethyl acetate, washed with brine, dried over sodium sulfate and concentrated to give a solid, which was triturated with diethyl ether to give further compound 3_60_4 (6.2 g, 31% yield) as a yellow solid.

$^1$H NMR (400 MHz, CDCl$_3$): δ=1.56 (d, J=5.1 Hz, 9H), 7.31 (dd, J=8.8, 2.9 Hz, 1H), 7.34-7.46 (m, 5H), 8.32 (d, J=2.7 Hz, 1H), 8.40 (d, J=9.0 Hz, 1H), 9.33 (br s, 1H).

Step 4: Amino-(5-hydroxy-pyridin-2-yl)-methylene]-carbamic acid tert-butyl ester (3_60_5)

A mixture of compound 3_60_4 (5 g, 15.3 mmol) and palladium on charcoal (10%, wet, 1 g) in a mixture of methanol (80 mL) and ethyl acetate (10 mL) was hydrogenated at room temperature under 35 psi for 3 hours. The reaction mixture was filtered and concentrated to give compound 3_60_5 (3.4 g, 97% yield) as a brown solid.

$^1$H NMR (400 MHz, CDCl$_3$): δ=1.57 (s, 9H), 5.15 (s, 2H), 7.51 (dd, J=8.8, 2.5 Hz, 1H), 8.27 (d, J=2.7 Hz, 1H), 8.73 (d, J=9.0 Hz, 1H).

Step 5: 3-[6-(tert-Butoxycarbonylamino-iminomethyl)-pyridin-3-yloxy]-2-hydroxy-propionic acid ethyl ester (3_60_6)

Potassium carbonate (5.46 g, 39.6 mmol) was added to a solution of compound 3_60_5 (3 g, 13.2 mmol) in acetonitrile (50 mL) and the mixture was heated at 93° C. for 0.5 hours. Ethyl 2,3-epoxypropanoate (4.6 g, 39.6 mmol) was added to the reaction mixture. After refluxing for 48 hours, the resulting mixture was cooled and filtered and the filtrate was concentrated to give a residue which was purified by column chromatography to give compound 3_60_6 (2 g, 21% yield) as a brown solid.

$^1$H NMR (400 MHz, DMSO-d$_6$): δ=1.18 (t, J=7.0 Hz, 3H), 1.45 (m, 9H), 4.15 (dd, J=7.0, 1.5 Hz, 2H), 4.29-4.37 (m, 2H), 4.48 (q, J=4.7 Hz, 1H), 5.92 (d, J=5.9 Hz, 1H), 7.55 (dd, J=8.8, 2.9 Hz, 1H), 8.19 (d, J=9.0 Hz, 1H), 8.35 (d, J=2.7 Hz, 1H), 8.75 (br. s., 1H), 9.02 (br. s, 1H).

Using the above alcohol 3_60_6 and following the procedure as described under 3.45 compound 3_60_7 was prepared.

3.61 tert-Butyl (1-{4-[2-(aminooxy)-3-(tert-butyl-dimethyl-silanyloxy)-propoxy]-phenyl}-iminomethyl)-carbamate

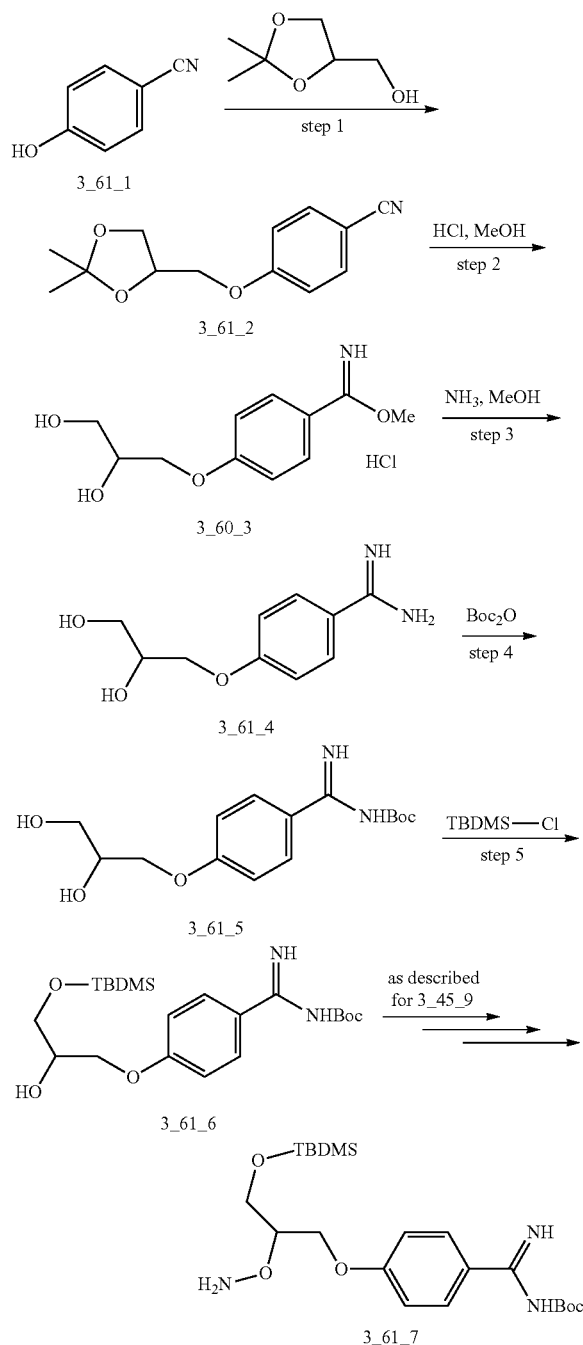

Step 1: 4-(2,2-Dimethyl-[1,3]dioxolan-4-yl-methoxy)-benzonitrile (3_61_2)

2,2-Dimethyl-1,3-dioxolane-4-methanol (3.66 g, 27.7 mmol) and triphenylphosphine (7.93 g, 30.2 mmol) were added to a solution of 4-hydroxybenzonitrile 3_61_1 (3.0 g, 25.2 mmol) in anhydrous tetrahydrofuran (80 mL) at room temperature. Diethyl azodicarboxylate (5.26 g, 30.2 mmol) was added dropwise to the resulting solution at 20° C. and the resulting mixture was stirred at room temperature overnight. After evaporation of the tetrahydrofuran, the crude product was purified by column chromatography to give the desired product (5.65 g, 96% yield) as a white solid.

$^1$H NMR (400 MHz, DMSO-d$_6$): δ=1.28 (s, 3H), 1.33 (s, 3H), 3.69-3.79 (m, 1H), 3.99-4.18 (m, 3H), 4.33-4.47 (m, 1H), 7.11 (d, J=8.8 Hz, 2H), 7.75 (d, J=8.8 Hz, 2H).

Step 2: 4-(2,3-Dihydroxy-propoxy)-benzimidic acid methyl ester hydrochloric acid salt (3_61_3)

Hydrogen chloride gas was introduced into a solution of compound 3_61_2 (3.02 g, 12.9 mmol) in anhydrous methanol (80 mL) at 0° C. for 10 minutes and the resulting mixture was stirred at room temperature overnight. After concentration, the residue was stirred with diethyl ether (60 mL) for 0.5 hours and the precipitate was collected and dried to give the desired product (3.26 g, 97% yield) as a white solid.

$^1$H NMR (400 MHz, DMSO-d$_6$): δ=3.37-3.48 (m, 2H), 3.75-3.84 (m, H), 4.00 (dd, J=10.1, 6.3 Hz, 1H), 4.13 (dd, J=10.3, 3.8 Hz, 1H), 4.23 (s, 3H), 7.14-7.19 (m, 2H), 8.06 (d, J=8.8 Hz, 2H).

Step 3: 4-(2,3-Dihydroxy-propoxy)-benzamidine (3_61_4)

Ammonia (27 mL, 7N in methanol, 0.187 mol) was added to a solution of compound 3_61_3 (3.26 g, 12.5 mmol) in anhydrous methanol (20 mL) at 0° C. and the resulting mixture was stirred at 40° C. for 3 hours. The reaction mixture was concentrated to dryness to give the crude desired product (2.92 g, >100% yield) as a white solid, which was used without purification.

$^1$H NMR (400 MHz, DMSO-d$_6$): δ=3.45 (br s, 2H), 3.81 (br. s, 1H), 3.99 (dd, J=10.3, 6.2 Hz, 1H), 4.12 (dd, J=10.1, 4.0 Hz, 1H), 4.74 (br. s, 1H), 5.04 (d, J=4.7 Hz, 1H), 7.12-7.19 (m, 2H), 7.79-7.86 (m, 2H), 8.90 (s, 2H), 9.19 (s, 2H).

Step 4: {[4-(2,3-Dihydroxy-propoxy)-phenyl]-imino-methyl}-carbamic acid tert-butyl ester (3_61_5)

A saturated sodium carbonate solution (8 mL) and di-tert-butyldicarbonate (Boc$_2$O, 6.52 g, 30 mmol) were added to a solution of compound 3_61_4 (3.70 g, crude, 12.5 mmol) in methanol (30 mL) and tetrahydrofuran (20 mL) at 0° C. After stirring at room temperature overnight, the resulting mixture was extracted with ethyl acetate and the extract was washed with brine, dried and concentrated. The residue was washed with a small volume of cold ethyl acetate to give the desired product (3.10 g, 80% yield) as a white solid.

$^1$H NMR (400 MHz, DMSO-d$_6$): δ=1.44 (s, 9H), 3.41-3.48 (m, 2H), 3.80 (d, J=5.0 Hz, 1H), 3.93 (dd, J=9.8, 6.3 Hz, 1H), 3.99-4.11 (m, 1H), 4.70 (t, J=5.7 Hz, 1H), 4.99 (d, J=5.0 Hz, 1H), 7.00 (d, J=9.1 Hz, 2H), 7.94 (d, J=9.1 Hz, 2H).

Step 5: ({4-[3-(tert-Butyl-dimethyl-silanyloxy)-2-hydroxy-propoxy]-phenyl}-imino-methyl)-carbamic acid tert-butyl ester (3_61_6)

Imidazole (1.44 g, 21.1 mmol) and tert-butyldimethylsilyl chloride (TBDMS-Cl, 1.592 g, 10.6 mmol) were added to a solution of compound 3_61_5 (2.98 g, 9.60 mmol) in N,N-dimethylformamide (15 mL) at 0° C. After stirring at room temperature overnight, the reaction mixture was quenched by adding ice-water (30 mL) and extracted with ethyl acetate. The extract was washed with brine, dried over sodium sulfate and concentrated to dryness to afford the crude desired product (4.81 g, >100% yield) as an off-white sticky solid, which was used without purification.

$^1$H NMR (400 MHz, DMSO-$d_6$): δ=0.05-0.14 (m, 6H), 0.87-0.92 (m, 9H), 1.48 (s, 9H), 3.68 (d, J=5.9 Hz, 2H), 3.82-3.91 (m, 1H), 3.95-4.04 (m, 1H), 4.05-4.14 (m, 1H), 5.11 (d, J=5.0 Hz, 1H), 6.99-7.07 (m, 2H), 7.94-8.01 (m, 2H).

Using the above alcohol 3_61_6 and following the procedure as described under 3.45 compound 3_61_7 was prepared.

3.62 tert-Butyl 4-{[(4-{[(2S)-2-(aminooxy)-3-(diphenylmethoxy)-3-oxopropyl]oxy}-phenyl)(imino)methyl]amino}piperidine-1-carboxylate

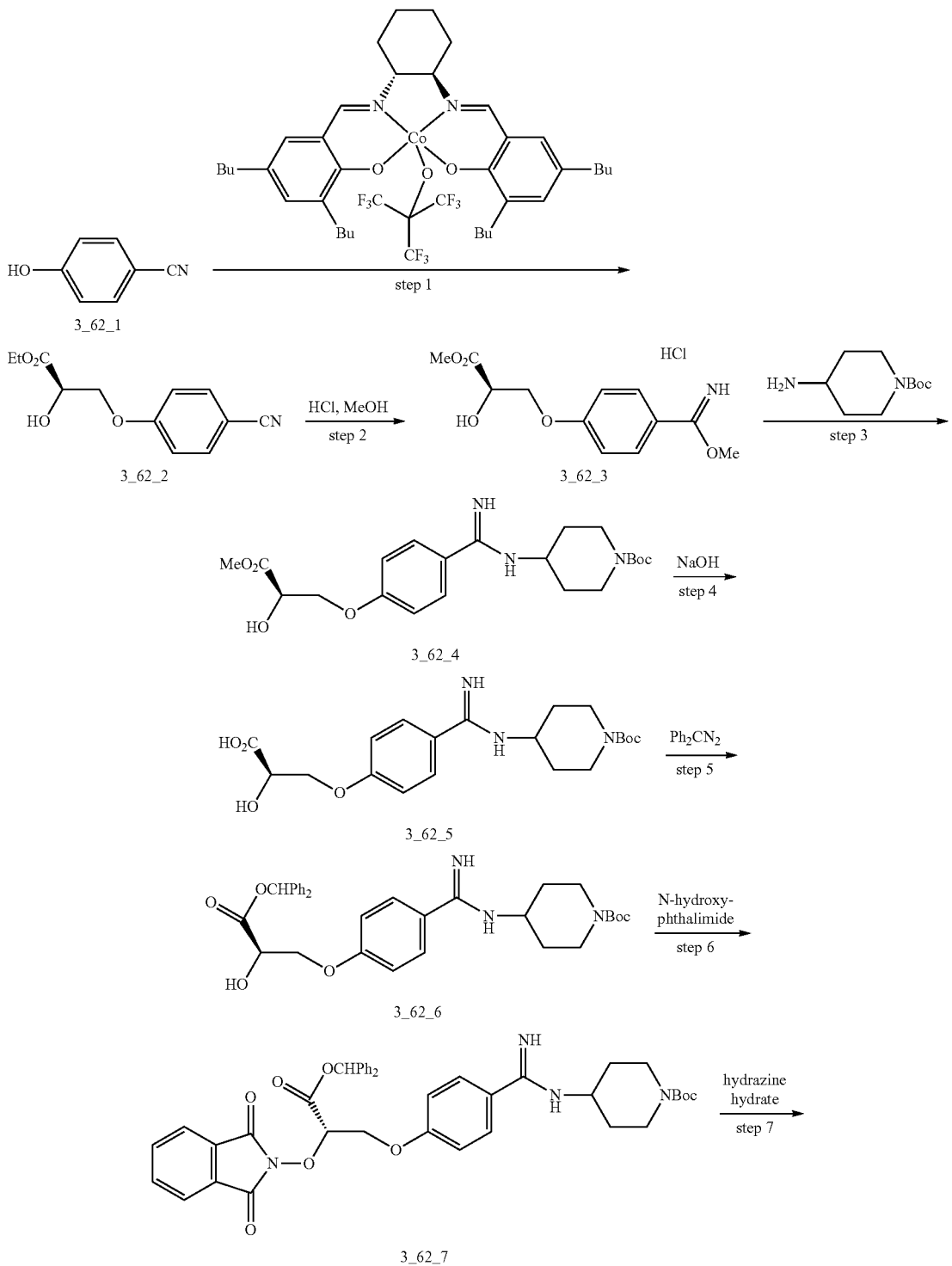

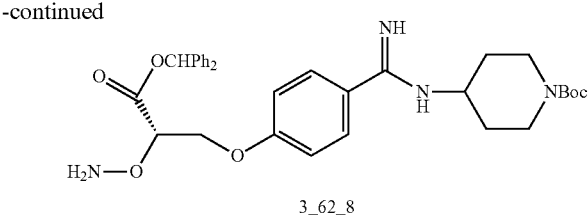

3_62_8

Step 1: (R)-3-(4-Cyano-phenoxy)-2-hydroxy-propionic acid ethyl ester (3_62_2)

A mixture of a Co(III)-catalyst (0.26 g, 0.31 mmol, ref: *J. Am. Chem. Soc.* 1999, 121, 6086-6087), and 4 Å molecular sieves (2 g) was treated with 4-hydroxybenzonitrile 3_62_1 (1.0 g, 8.4 mmol) and ethyl oxirane-2-carboxylate (2.0 g, 17 mmol) followed by tert-butyl methyl ether (3.0 mL) under a stream of nitrogen. The suspension was stirred at room temperature overnight and filtered through a pad of Celite. The filtrate was concentrated to give a dark brown liquid. The liquid was purified by column chromatography to afford compound 3_62_2 (1.9 g, 96% yield) as a brown oil.

$^1$H NMR (400 MHz, DMSO-d$_6$): δ=1.18 (t, J=1.7 Hz, 3H), 4.03-4.19 (m, 2H), 4.25 (d, J=4.4 Hz, 2H), 4.38-4.51 (m, 1H), 5.89 (d, J=5.9 Hz, 1H), 7.11 (d, J=8.8 Hz, 2H), 7.77 (d, J=8.8 Hz, 2H).

Step 2: (R)-2-Hydroxy-3-(4-methoxycarbonimidoyl-phenoxy)-propionic acid methyl ester hydrochloric acid salt (3_62_3)

A mixture of compound 3_62_2 (1.1 g, 4.7 mmol) in methanol (50 mL) was cooled to 0° C. in a sealed vessel. Anhydrous hydrogen chloride gas was bubbled through the solution until the mixture was saturated. The flask was sealed and stirred at 0° C. to room temperature overnight. The mixture was concentrated in vacuo and diluted with diethyl ether to give a suspension. The suspension was stirred for 15 minutes and compound 3_62_3 (1.1 g, 81% yield) as a white solid was collected after drying under high vacuum.

$^1$H NMR (400 MHz, DMSO-d$_6$): δ=3.66 (s, 3H), 4.24 (s, 3H), 4.27-4.30 (m, 2H), 4.48 (t, J=4.4 Hz, 1H), 7.16 (d, J=9.1 Hz, 2H), 8.09 (d, J=9.1 Hz, 2H).

Step 3: (R)-tert-Butyl 4-(4-(2-hydroxy-3-methoxy-3-oxopropoxy)benzimidamido)piperidine-1-carboxylate (3_62_4)

Triethylamine (1.537 g, 15.2 mmol) and tert-butyl 4-aminopiperidine-1-carboxylate (2.765 g, 13.8 mmol) were added to a mixture of compound 3_62_3 (4.0 g, 13.8 mmol) in anhydrous methanol (50 mL) at 0° C. and the resulting mixture was stirred at room temperature overnight. The reaction mixture was concentrated to dryness to give the crude desired product (7.81 g, >100% yield) as a white foam, which was used without purification.

$^1$H NMR (400 MHz, DMSO-d$_6$): δ=1.38 (s, 9H), 1.54-1.43 (m, 2H), 1.82-1.93 (m, 2H), 2.60-2.90 (m, 2H), 3.64 (s, 3H), 3.90-4.00 (m, 3H), 4.12-4.28 (m, 2H), 4.44-4.50 (m, 1H), 5.98 (s, 1H), 7.22 (d, J=8.8 Hz, 2H), 7.69 (d, J=8.8 Hz, 2H).

Step 4: (R)-3-(4-(N-(1-(tert-Butoxycarbonyl)piperidin-4-yl)carbamimidoyl)phenoxy)-2-hydroxypropanoic acid (3_62_5)

A solution of sodium hydroxide (0.552 g, 13.8 mmol) in water (20 mL) was added to a solution of compound 3_62_4 (3.905 g, crude, 6.90 mmol) in tetrahydrofuran (50 mL) at 0° C. After stirring at this temperature for 90 minutes, the reaction mixture was neutralized to pH 7 using 4N hydrogen chloride in dioxane. The mixture was concentrated and dried to afford the crude desired product (5.20 g, >100% yield) as a white solid, which was used in the next step without purification.

Step 5: (R)-tert-Butyl 4-(4-(3-(benzhydryloxy)-2-hydroxy-3-oxopropoxy)benzimidamido)-piperidine-1-carboxylate (3_62_6)

A solution of diazo(diphenyl)methane (Ph$_2$CN$_2$, 2.00 g, 10.35 mmol) in methanol (15 mL) was slowly added to a solution of compound 3_62_5 (5.20 g, crude, 6.90 mmol) in methanol (100 mL). The resulting mixture was stirred at room temperature overnight and concentrated to dryness. The residue was purified by column chromatography to give the desired product (1.8 g, 46% yield) as a white solid.

$^1$H NMR (400 MHz, DMSO-d$_6$): δ=1.39 (s, 9H), 1.42-1.52 (m, 2H), 1.87-1.92 (m, 2H), 2.82 (br. s, 2H), 3.90-4.00 (m, 3H), 4.30-4.42 (m, 2H), 4.62-4.65 (m, 1H), 6.48 (d, J=7.6 Hz, 1H), 6.84 (s, 1H), 7.09 (d, J=8.8 Hz, 2H), 7.22-7.41 (m, 10H), 7.69 (d, J=8.8 Hz, 2H), 9.10 (br. s, 1H), 9.38 (br. s, 1H).

MS: 574.14 (M+1).

Step 6: (S)-tert-Butyl 4-(4-(3-(benzhydryloxy)-2-((1,3-dioxoisoindolin-2-yl)oxy)-3-oxoprop-oxy)benzimidamido)piperidine-1-carboxylate (3_62_7)

N-Hydroxyphthalimide (0.573 g, 3.51 mmol) and triphenylphosphine (1.005 g, 3.83 mmol) were added to a solution of compound 3_62_6 (1.831 g, 3.19 mmol) in anhydrous tetrahydrofuran (60 mL) at room temperature. A solution of diethyl azodicarboxylate (0.667 g, 3.83 mmol) in tetrahydrofuran (5 mL) was added dropwise to the resulting solution at 20° C. The resulting mixture was stirred at room temperature for 2.5 hours. After evaporation of the tetrahydrofuran, the crude product was purified by column chromatography to give the desired product (1.5 g, 65% yield) as a white solid.

$^1$H NMR (400 MHz, DMSO-d$_6$): δ=1.42 (s, 9H), 1.44-1.53 (m, 2H), 1.92-1.96 (m, 2H), 2.82 (br. s, 2H), 3.92-4.16 (m, 3H), 4.68 (br. s, 1H), 5.48 (br m., 1H), 6.98 (s, 1H), 7.11 (d, J=8.6 Hz, 2H), 7.26-7.48 (m, 10H), 7.75 (d, J=8.6 Hz, 2H), 7.86 (s, 4H), 9.24 (br. s, 1H), 9.40 (b. s, 1H).

MS: 719.18 (M+1).

Step 7: 2-Aminooxy-3-(4-{[tert-butoxycarbonyl-(2-tert-butoxycarbonylamino-ethyl)-amino]-iminomethyl}-phenoxy)-propionic acid benzhydryl ester (3_62_8)

Hydrazine monohydrate (0.114 g, 2.28 mmol) was added to a solution of compound 3_62_7 (1.49 g, 2.07 mmol) in anhydrous ethanol (35 mL) and tetrahydrofuran (20 mL) at 0° C. and the resulting mixture was stirred at room temperature for 2 hours. The mixture was concentrated to dryness and the residue was stirred with dichloromethane (10 mL) at room temperature for 15 minutes and filtered. The filtrate was concentrated to afford the crude desired product (1.4 g, >100% yield) as an off-white foam, which was used in the next step without purification.

$^1$H NMR (400 MHz, DMSO-$d_6$): δ=1.42 (s, 9H), 1.44-1.53 (m, 2H), 1.89-1.94 (m, 2H), 2.85 (br. s, 2H), 3.92-4.02 (m, 3H), 4.36-4.47 (m, 2H), 4.62-4.66 (m, 1H), 6.45 (s, 2H), 6.91 (s, 1H), 7.09 (d, J=8.8 Hz, 2H), 7.26-7.45 (m, 10H), 7.72 (d, J=8.8 Hz, 2H), 9.25 (br. s, 2H).

Following the procedure detailed above under 3.62 but using the amines R—NH$_2$ shown in the table below instead of tert-butyl 4-aminopiperidine-1-carboxylate in step 3 of the synthesis, compounds 3_63_8 to 3_79_8 were prepared.

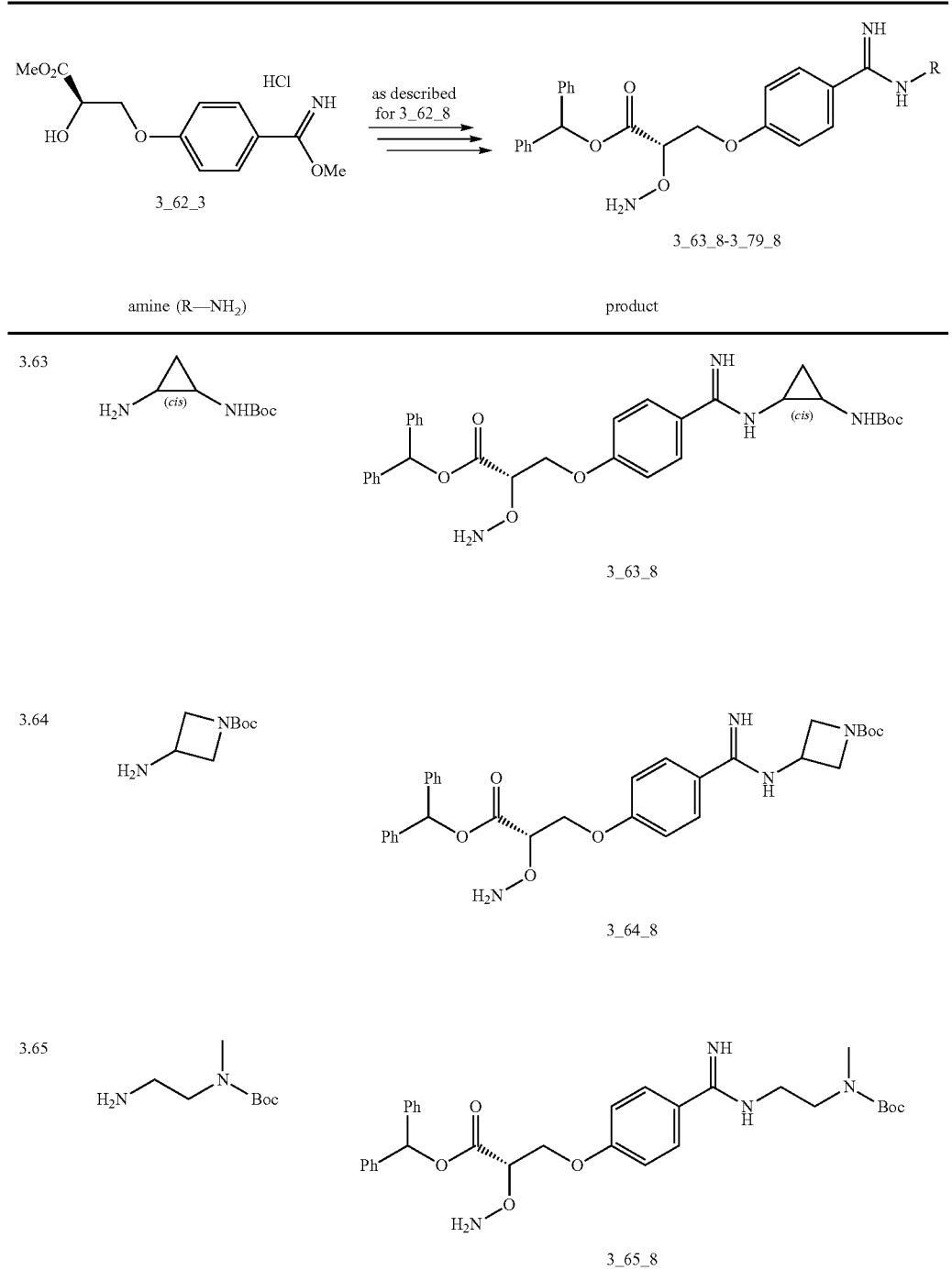

-continued
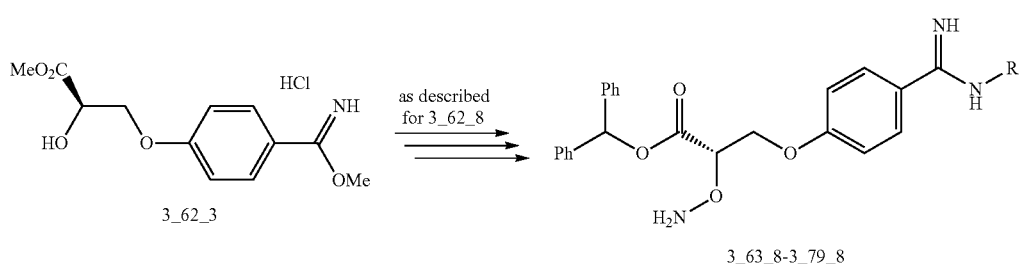
| amine (R—NH$_2$) | product |
|---|---|
| 3.66 | 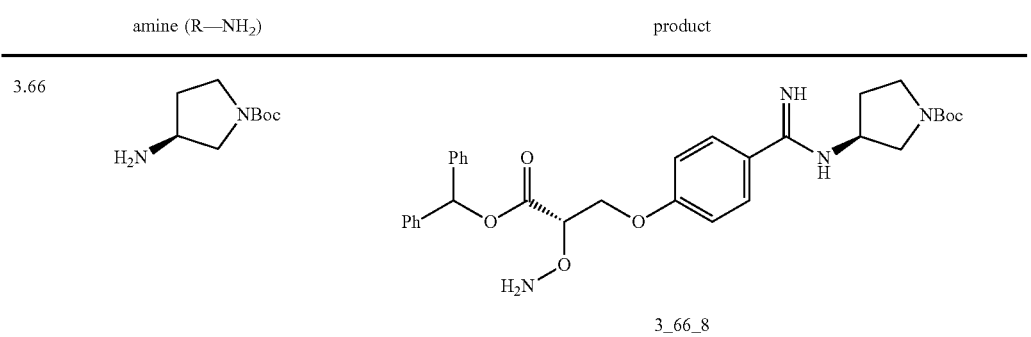 |
| 3.67 | 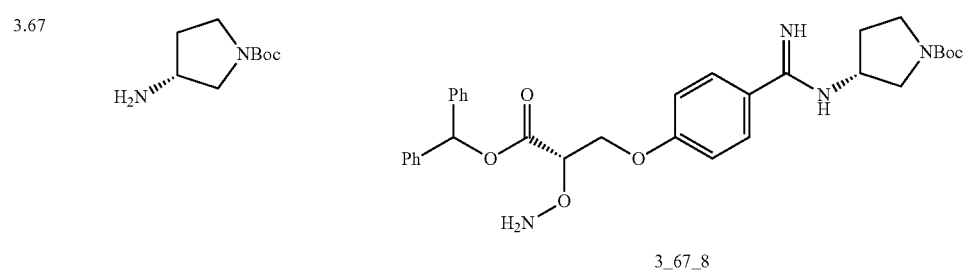 |
| 3.68 | 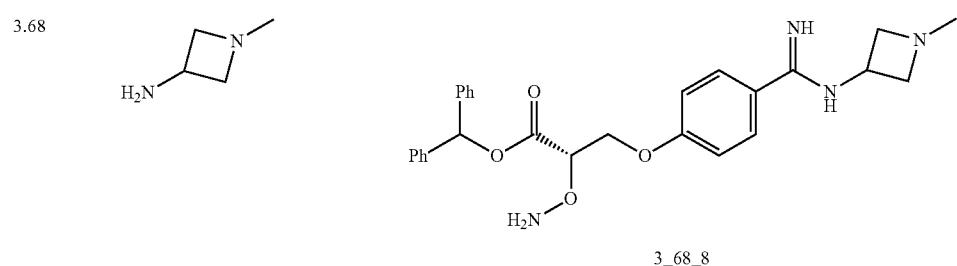 |
| 3.69 | 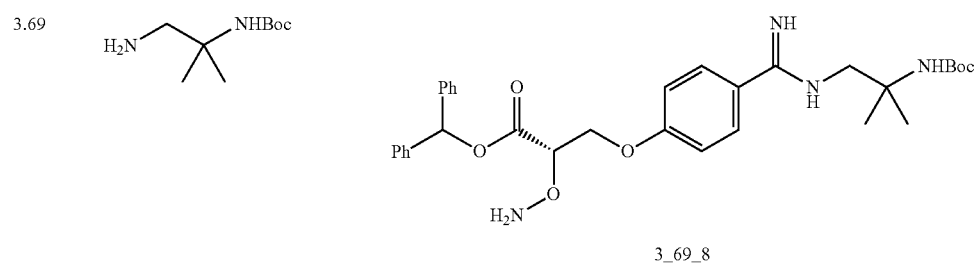 |

-continued
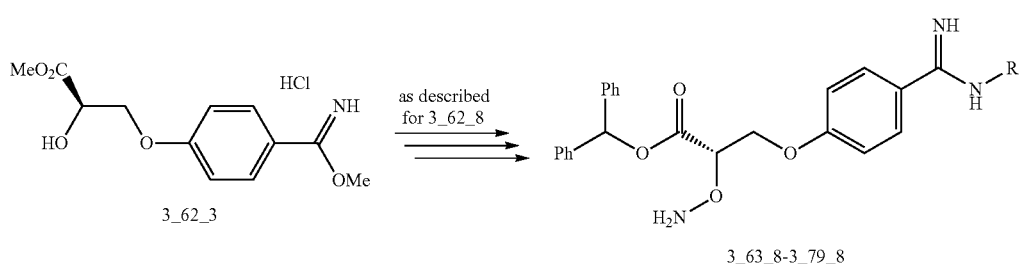
| amine (R—NH$_2$) | product |
|---|---|
| 3.70 | 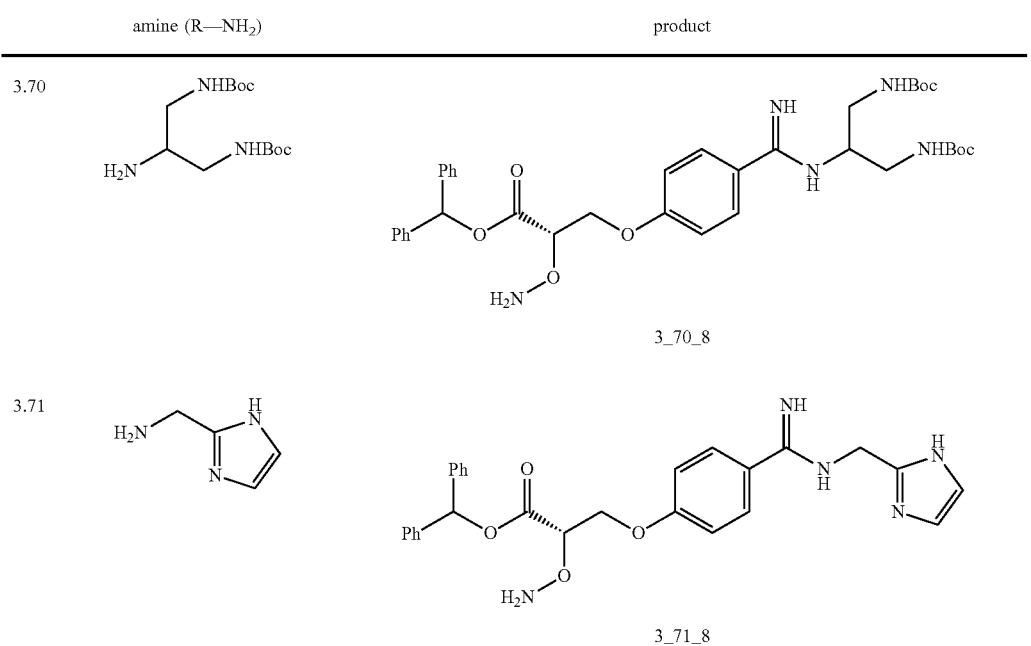 |
| 3.71 | |
| 3.72 | |
| 3.73 | 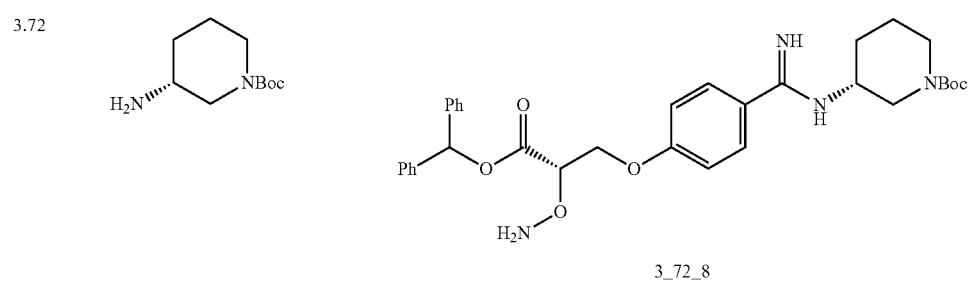 |
| | 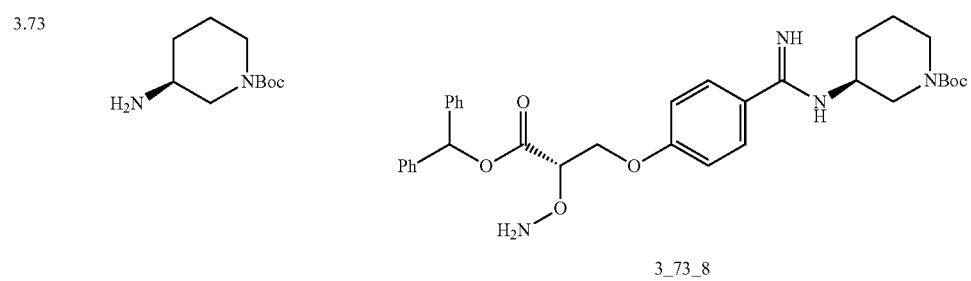 |

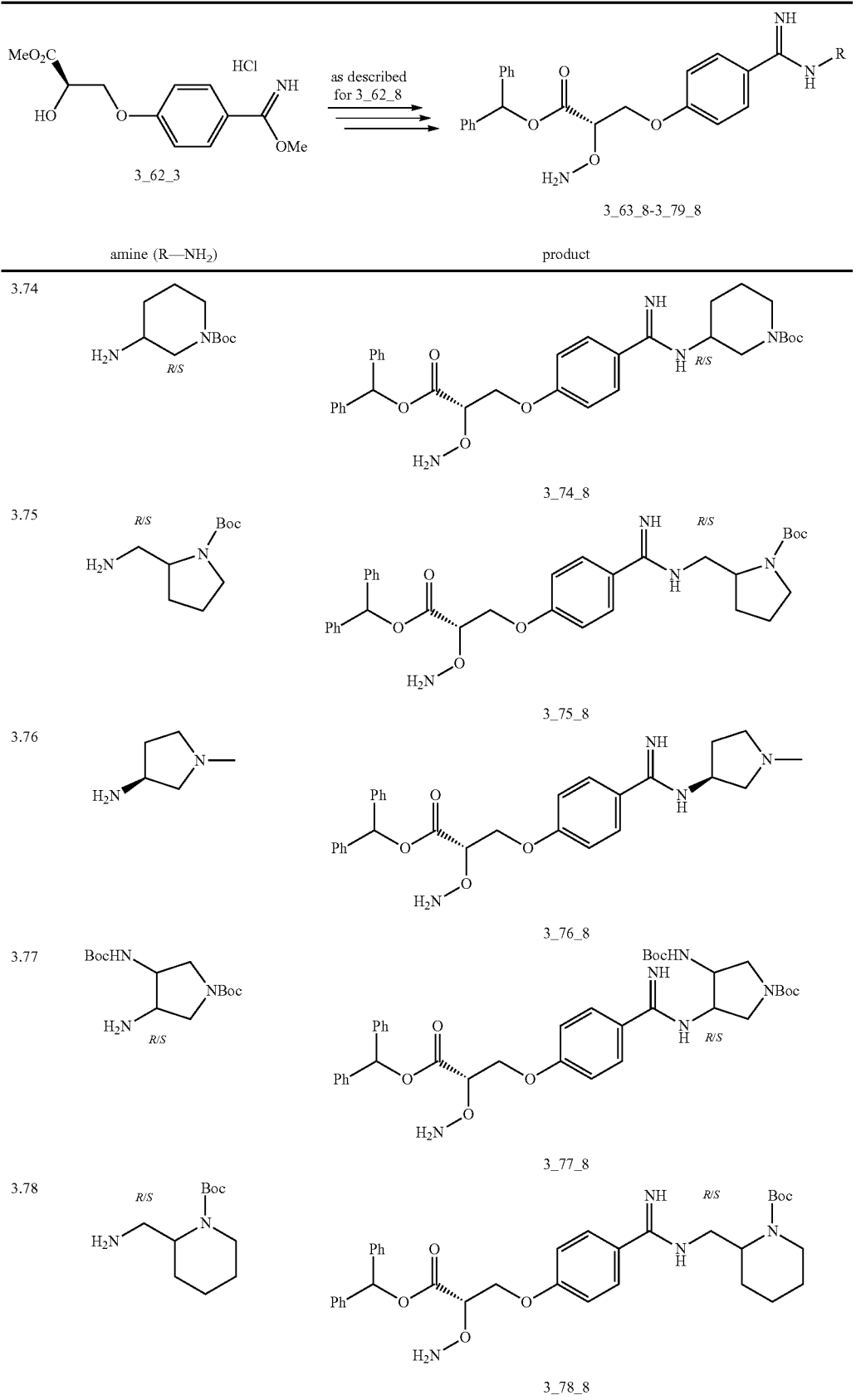

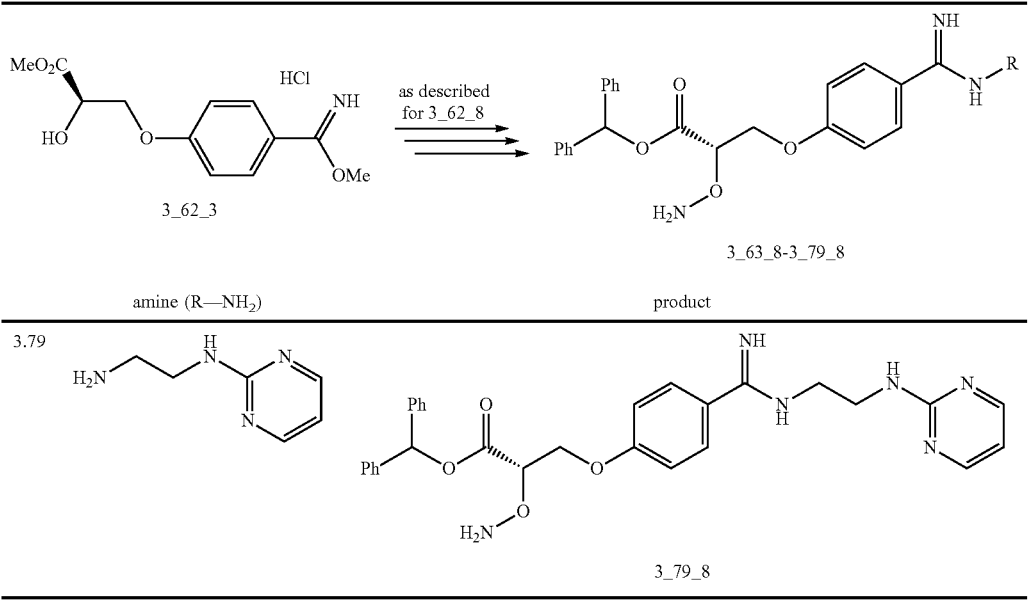
Following the procedure detailed above under 3.62 but using the enantio-mer of 3_62_3 and amines R—NH₂ shown in the table below instead of tert-butyl 4-aminopiperidine-1-carboxylate in step 3 of the synthesis, compounds 3_80_8 to 3_82_8 were prepared.
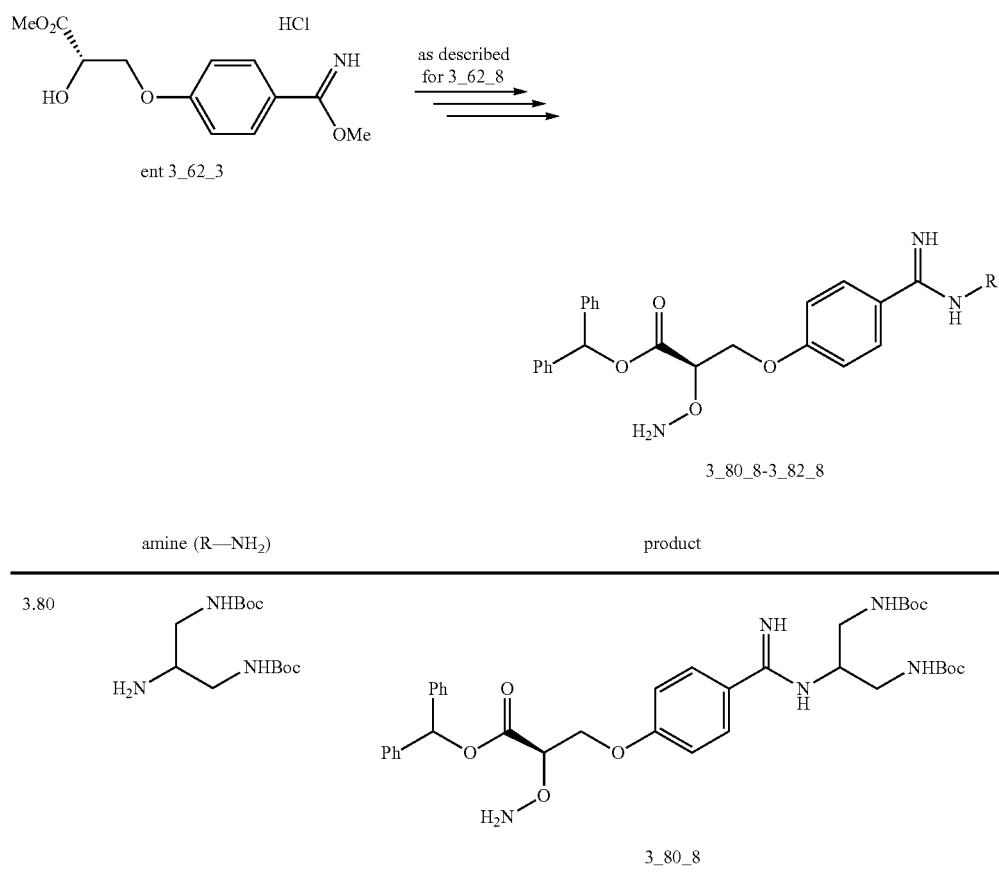

-continued
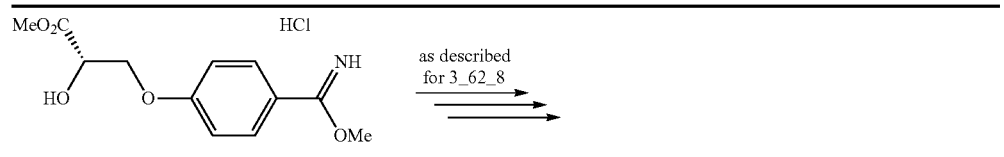
ent 3_62_3
as described for 3_62_8
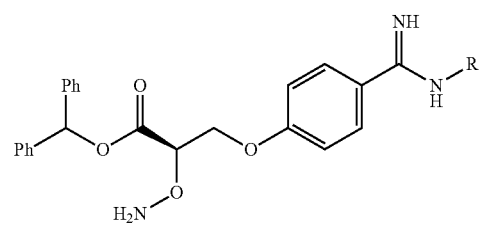
3_80_8-3_82_8
| amine (R—NH$_2$) | product |
|---|---|
| 3.81 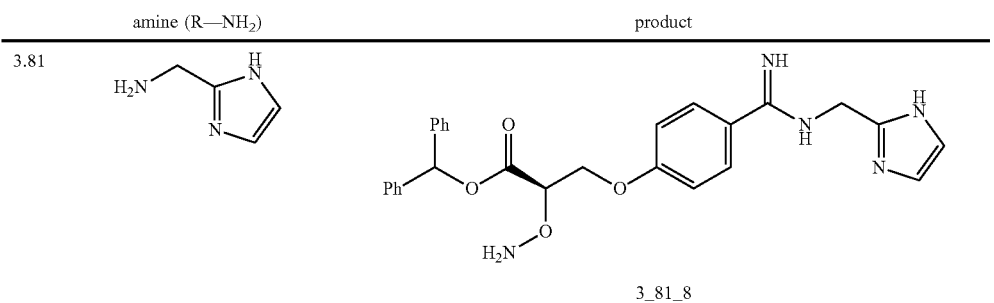 | |
| 3.82 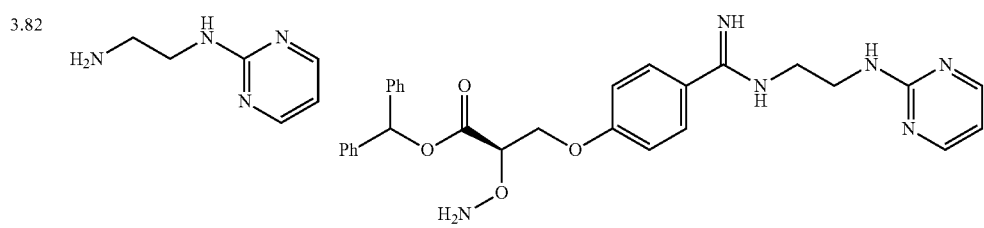 | |
3.83 tert-Butyl [{4-[3-amino-2-(aminooxy)-3-oxo-propoxy]phenyl}(imino)-methyl]carbamate
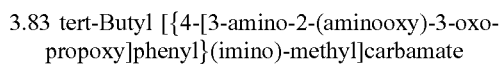
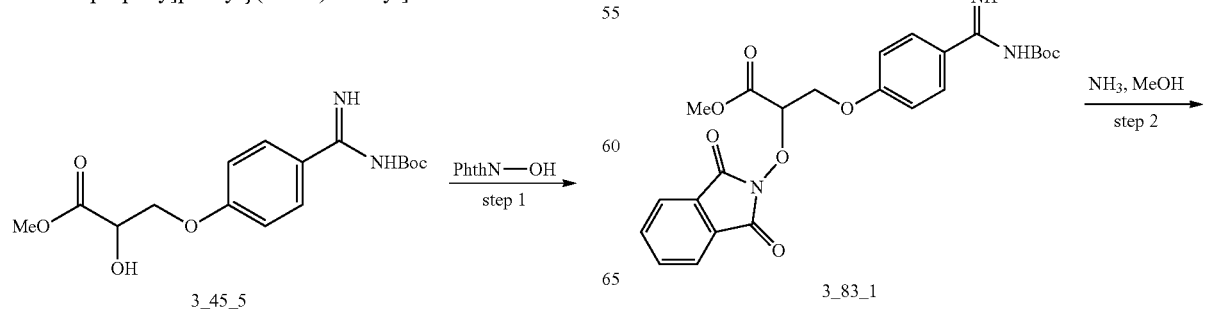
-continued
NH$_3$, MeOH
step 2

-continued

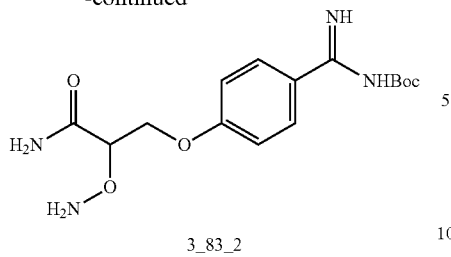

3_83_2

Step 1: Methyl 3-{4-[N-(tert-butoxycarbonyl)carbamimidoyl]phenoxy}-2-[(1,3-dioxo-1,3-dihydro-2H-isoindol-2-yl)oxy]propanoate (3_83_1)

Diisopropyl azodicarboxylate (0.39 g, 2.41 mmol) was added dropwise to a mixture of methyl 3-{4-[N-(tert-butoxycarbonyl)carbamimidoyl]phenoxy}-2-hydroxypropanoate 3_45_5 (0.68 g, 2.01 mmol), N-hydroxy-phthalimide (PhthN-OH, 0.68 g, 2.01 mmol) and triphenylphosphine (0.63 g, 2.41 mmol) in tetrahydrofuran. After the addition was complete, the mixture was stirred at room temperature for 16 hours and concentrated. The residue was purified by column chromatography to give compound 3_83_1 (1.0 g, 100% yield) as yellow foam.

$^1$H NMR (400 MHz, DMSO-$d_6$): δ=1.42 (s, 9H), 3.77 (s, 3H), 4.45 (m, 1H), 4.58 (m, 1H), 5.22 (m, 1H), 6.97 (d, J=8.2 Hz, 2H), 7.85 9 s, 4H), 7.92 (d, J=8.2 Hz, 2H).

MS (m/z, ES$^+$): 484.17

Step 2: tert-Butyl [{4-[3-amino-2-(aminooxy)-3-oxopropoxy]phenyl}(imino)methyl]carbamate (3_83_2)

Compound 3_83_1 (1.0 g, 4.29 mmol) was dissolved in a methanolic solution of 7N ammonia (10 mL), stirred at room temperature for 24 hours and filtered. The filtrate was concentrated to give compound 3_83_2 (0.7 g, 100% yield), which was used in the next step without further purification.

$^1$H NMR (400 MHz, DMSO-$d_6$): δ=1.42 (s, 9H), 4.20-4.50 (m, 3H), 6.40 (br. s, 2H), 6.97 (d, J=8.2 Hz, 2H), 7.85 (s, 4H), 7.92 (d, J=8.2 Hz, 2H).

MS (m/z, ES+): 339.11

3.84 tert-Butyl [(4-{[1-(aminooxy)-3-hydroxypropan-2-yl]oxy}phenyl)(imino)methyl]-carbamate

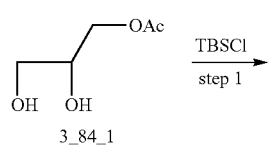

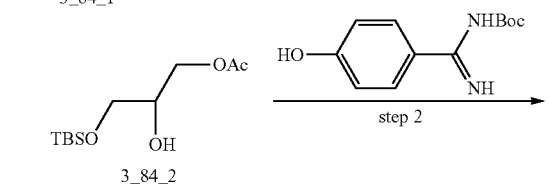

-continued

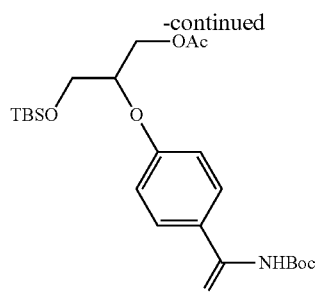

3_84_3

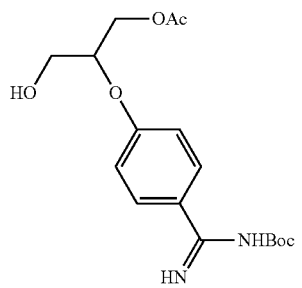

3_84_4

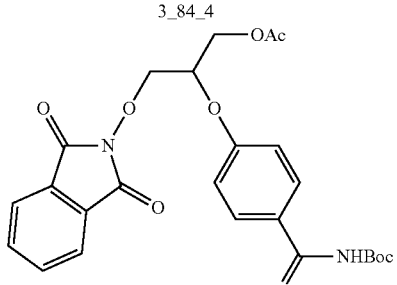

3_84_5

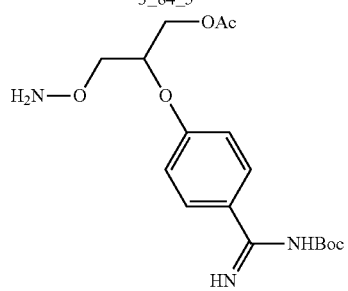

3_84_6

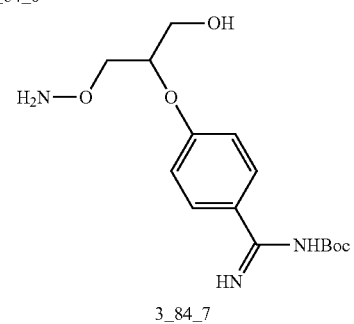

3_84_7

Step 1: 3-{[tert-Butyl(dimethyl)silyl]oxy}-2-hydroxypropyl acetate (3_84_2)

Tert-butyldimethylchlorosilane (TBSCl, 28.2 g, 180.1 mmol) was added portion wise to a mixture of compound 3_84_1 (27 g, 189.6 mmol; ref.: *J. Med. Chem.* 1989, 2104-2110), triethylamine (36.9 mL, 265.4 mmol) and 4-dimethylaminopyridine (1.38 g, 11.4 mmol) in dichloromethane (250 mL). The reaction mixture was stirred at room temperature overnight, filtered and the filtrate was concentrated. The residue was dissolved in EtOAc, filtered again to remove any solid, and the filtrate was concentrated to give a residue, which was purified by column chromatography eluting with 30% EtOAc in hexane to give compound 3_84_2 (22 g, 46% yield) as an oil.

$^1$H NMR (400 MHz, CDCl$_3$): δ=0.07 (s, 6H), 0.89 (s, 9H), 2.08 (s, 3H), 2.49 (d, J=5.5 Hz, 1H), 3.57-3.65 (m, 1H), 3.65-3.73 (m, 1H), 3.82-3.93 (m, 1H), 4.04-4.21 (m, 2H).

Step 2: 2-{4-[N-(tert-Butoxycarbonyl)carbamimidoyl]phenoxy}-3-{[tert-butyl(dimeth-yl)silyl]oxy}propyl acetate (3_84_3)

Triphenylphosphine (4.33 g, 16.53 mmol) was added to a mixture of compound 3_84_2 (3.5 g, 14.11 mmol) and tert-butyl [(4-hydroxyphenyl)(imino)methyl]-carbamate (3.26 g, 13.78 mmol) in tetrahydrofuran (100 mL), and diisopropyl azodicarboxylate (4.17 mL, 20.67 mmol) at 0° C., and the mixture was stirred at room temperature for 16 h. The mixture was concentrated to give a residue, which was purified by column chromatography eluting with 30% EtOAc in hexane to give compound 3_84_3 (6.5 g, 99% yield) as a yellow solid.

$^1$H NMR (400 MHz, CDCl$_3$): δ=0.09 (m, 6H), 0.87 (s, 9H), 1.55 (s, 9H), 2.04 (s, 3H), 3.75-3.86 (m, 2H), 4.25-4.41 (m, 2H), 4.51-4.64 (m, 1H), 6.98 (d, J=9.0 Hz, 2H), 7.83 (d, J=9.0 Hz, 2H).

Step 3: 2-{4-[N-(tert-Butoxycarbonyl)carbamimidoyl]phenoxy}-3-hydroxypropyl acetate (3_84_4)

Tetra-n-butylammonium fluoride (TBAF, 1N in tetrahydrofuran, 39.9 mL, 39.9 mmol) was added to a solution of compound 3_84_3 (9.3 g, 19.9 mmol) in tetrahydrofuran (100 mL) under cooling, and the mixture was stirred at room temperature for 2 h and concentrated to give a residue, which was purified by column chromatography to give compound 3_84_4 (3.6 g, 51% yield) as a gum.

$^1$H NMR (400 MHz, CDCl$_3$): δ=1.55 (s, 9H), 2.06 (s, 3H), 3.85 (dd, J=5.1, 2.3 Hz, 2H), 4.24-4.32 (m, 1H), 4.35-4.45 (m, 1H), 4.62 (t, J=5.1 Hz, 1H), 7.01 (d, J=9.0 Hz, 2H), 7.84 (d, J=9.0 Hz, 2H).

Step 4: 2-{4-[N-(tert-Butoxycarbonyl)carbamimidoyl]phenoxy}-3-[(1,3-dioxo-1,3-dihydro-2H-isoindol-2-yl)oxy]propyl acetate (3_84_5)

Diisopropyl azodicarboxylate (3.11 mL, 15.42 mmol) was added to a solution of compound 3_84_4 (3.62 g, 10.28 mmol), N-hydroxyphthalimide (PhthN-OH, 2.34 g, 14.39 mmol) and triphenylphosphine (3.50 g, 13.36 mmol) in tetrahydrofuran (100 mL) at 0° C., and the mixture was stirred at room temperature for 4 h. The mixture was concentrated, extracted with EtOAc, washed with a saturated sodium bicarbonate solution and brine, dried over sodium sulfate and concentrated to give a residue, which was purified by column chromatography to give compound 3_84_5 (3.4 g, 66% yield) as a white solid.

$^1$H NMR (400 MHz, CDCl$_3$): δ=1.54 (s, 9H), 2.08 (s, 3H), 4.41-4.50 (m, 4H), 4.91-5.00 (m, 1H), 6.98 (d, J=9.0 Hz, 2H), 7.70-7.86 (m, 6H).

Step 5: 3-(Aminooxy)-2-{4-[N-(tert-butoxycarbonyl)carbamimidoyl]phenoxy}propyl acetate (3_84_6)

Hydrazine monohydrate (0.34 g, 6.84 mmol) was added to a solution of 3_84_5 (3.4 g, 6.84 mmol) in anhydrous ethanol (40 mL) under cooling and the resulting mixture was stirred at room temperature for 5 h and filtered and the filtrate was concentrated to afford crude compound 3_84_6 (2.4 g, 96% yield) as a solid, which was used without purification.

$^1$H NMR (400 MHz, CDCl$_3$): δ=1.55 (s, 9H), 2.05 (s, 3H), 3.81-3.94 (m, 2H), 4.26-4.37 (m, 2H), 4.82-4.87 (m, 1H), 7.04 (d, J=9.0 Hz, 2H), 7.83 (d, J=9.0 Hz, 2H).

Step 6: tert-Butyl [(4-{[1-(aminooxy)-3-hydroxypropan-2-yl]oxy}phenyl)(imino)methyl]carbamate (3_84_7)

Potassium carbonate (0.9 g, 6.53 mmol) was added to a solution of compound 3_84_6 (2.4 g, 6.53 mmol) in anhydrous methanol (40 mL) under cooling and the resulting mixture was stirred for 1 h, concentrated, extracted with EtOAc, washed with brine, dried over anhydrous sodium sulfate, and filtered and the filtrate was concentrated to give compound 3_84_7 (1.57 g, 74% yield) as a gum, which was used without further purification.

$^1$H NMR (400 MHz, DMSO-d$_6$): ε=1.42 (s, 9H), 3.56 (m, 2H), 3.72 (m, 2H), 4.62 (t, J=5.2 Hz, 1H), 4.90 (s, 1H), 6.10 (s, 2H), 7.02 (d, J=8.4 Hz, 2H), 7.90 (d, J=8.4 Hz, 2H).

3.85 Diphenylmethyl 2-(aminooxy)-3-{3-hydroxy-4-[N-(tert-butoxycarbonyl)-carbamimidoyl]-phenoxy}-propanoate

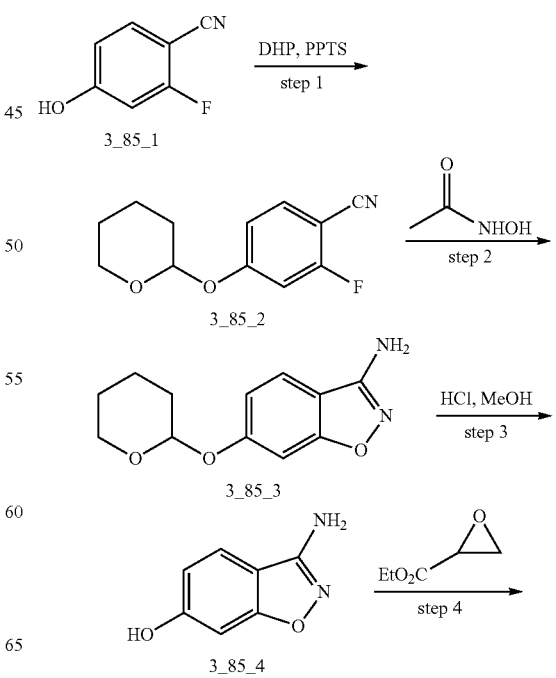

-continued

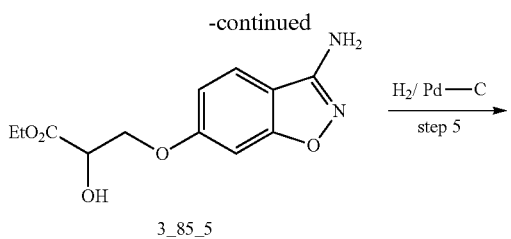

3_85_5

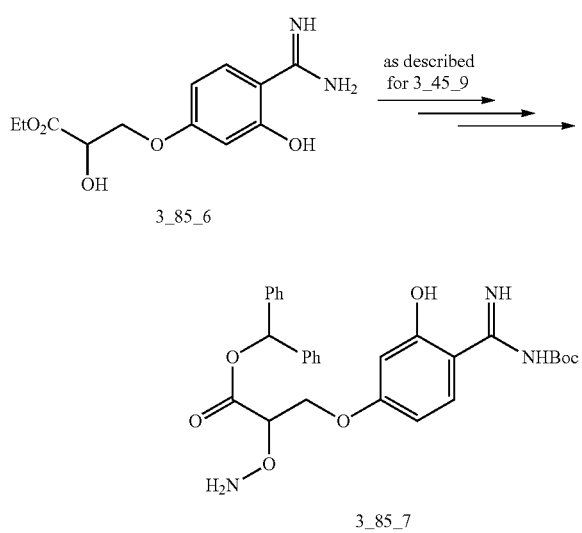

Step 1: 2-Fluoro-4-(tetrahydro-2H-pyran-2-yloxy) benzonitrile (3_85_2)

3,4-Dihydro-2H-pyran (DHP, 7.20 mL, 79.12 mmol) was added to a mixture of 2-fluoro-4-hydroxy-benzonitrile (5.42 g, 39.56 mmol) and pyridium p-toluenesulfonate (PPTS, 170 mg, 0.68 mmol) in dry dichloromethane (100 mL) and the mixture was stirred at room temperature for 16 hours and concentrated. The residue was purified by column chromatography to give compound 3_85_2 (8.9 g, 100% yield) as a clear oil.

Step 2: 6-(Tetrahydro-pyran-2-yloxy)-benzo[d]isoxazol-3-ylamine (3_85_3)

Potassium tert-butoxide (8.96 g, 80 mmol) was added in portions to a solution of N-hydroxy acetamide (6.00 g, 80 mmol) in N,N-dimethylformamide (40 mL). After the addition was complete, the resulting mixture was stirred at room temperature for 1 hour. A solution of 2-fluoro-4-(tetrahydro-2H-pyran-2-yloxy)benzonitrile 3_85_2 (8.90 g, 40 mmol) in N,N-dimethylformamide (20 mL) was added and the resulting mixture was stirred at room temperature for 24 hours and concentrated. The residue was diluted with ethyl acetate (200 mL), washed with water (20 mL) and brine (20 mL), dried and concentrated. The residue was purified by column chromatography to give compound 3_85_3 (6.5 g, 69% yield).

Step 3: 3-Amino-1,2-benzoxazol-6-ol (3_85_4)

1N hydrochloric acid solution (10 mL) was added to a solution of 6-(tetrahydro-pyran-2-yloxy)-benzo[d]isoxazol-3-ylamine 3_85_3 (6.5 g, 27.77 mmol) in methanol (30 mL) and the mixture was stirred at room temperature for 1 hour and concentrated. The residue was purified by column chromatography to give compound 3_85_4 (4.10 g, 100% yield) as a white solid.

$^1$H NMR (400 MHz, DMSO-d$_6$): δ=6.20 (br. s, 2H), 6.70 (m, 2H), 7.59 (d, J=9.4 Hz, 1H), 10.05 (br. s, 1H).

Step 4: 3-[(3-Amino-1,2-benzoxazol-6-yl)oxy]-2-hydroxypropanoate (3_85_5)

A mixture of 3_85_4 (7.31 g, 63 mmol) and potassium carbonate (11.60 g, 84 mmol) in dry acetonitrile (40 mL) was refluxed for 5 hours and filtered. The filtrate was concentrated and purified by column chromatography to give compound 3_85_5 (1.43 g, 26% yield) as a sticky gum.

$^1$H NMR (400 MHz, CDCl$_3$): δ=1.27 (t, J=9.5 Hz, 3H), 3.20 (d, J=2 Hz, 1H), 4.20-4.40 (m, 4H), 4.59 (m, 1H), 6.83 (d, J=8.6 Hz, 1H), 7.28 (s, 1H), 7.40 (d, J=8.6 Hz, 1H).

Step 5: 3-(4-Carbamimidoyl-3-hydroxyphenoxy)-2-hydroxypropanoate (3_85_6)

5% palladium on charcoal (140 mg) was added to a degassed solution of 3_85_5 (330 mg, 1.24 mmol) in methanol (30 mL). The mixture was stirred under hydrogen with a balloon for 2 hours and filtered through a pad of Celite. The filtrate was concentrated to give compound 3_85_6 (310 mg, 93% yield).

$^1$H NMR (400 MHz, CD$_3$OD): δ=1.23 (t, J=8.8 Hz, 3H), 4.20-4.30 (m, 4H), 4.50 (m, 1H), 6.15 (d, J=9.2 Hz, 1H), 6.20 (s, 1H), 7.43 (d, J=9.2 Hz, 1H).

MS (ES$^+$): 269.10 (Calcd: 268.11)

Following the same procedure as described above under 3.45 but using intermediate 3_85_6 instead of 3_45_4 compound 3_85_7 was obtained.

4. Oxime Formation, Coupling Reaction and De-Protection

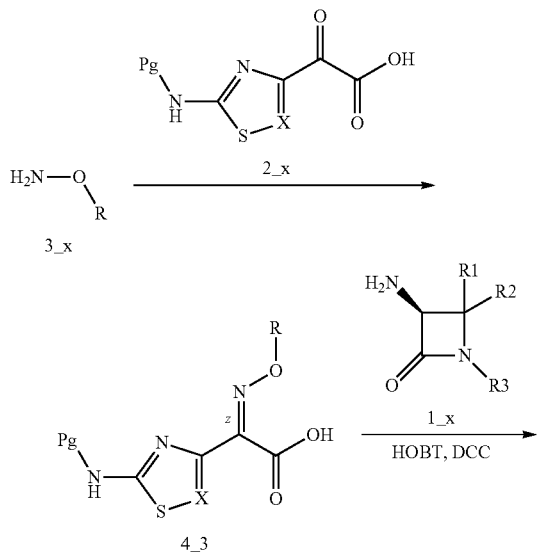

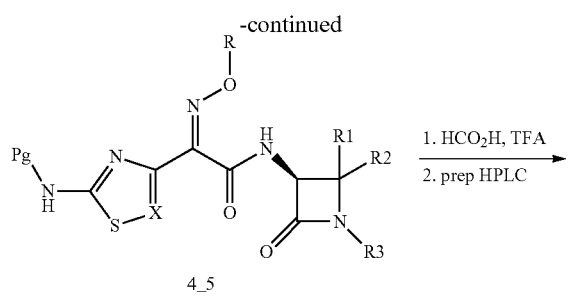

Ketoacid 2_x (1.7 mmol) was added to a solution of compound 3_x (1.7 mmol) in anhydrous ethanol (30 mL) and chloroform (10 mL) and the resulting mixture was stirred at room temperature overnight and concentrated under reduced pressure. The residue was re-crystallized from ethanol or purified by column chromatography to afford compound 4_3 (24%-91% yield) as a yellow solid.

Dicyclohexylcarbodiimide (DCC, 0.29 g, 1.41 mmol) and 1-hydroxybenzotriazole (HOBT, 0.14 g, 1.41 mmol) were added to a solution of compound 4_3 (0.706 mmol) in N,N-dimethylformamide (15 mL) at room temperature. After stirring at room temperature for 30 minutes, 3-amino-azetidin-2-one 1_x (1.06 mmol) was added followed by sodium bicarbonate (0.23 g, 2.8 mmol). The resulting mixture was stirred at room temperature overnight and concentrated under reduced pressure at 40° C. The residue was purified by column chromatography eluting with 5-10% methanol in dichloromethane to give compound 4_5 (8%-90% yield) as a yellow solid.

A solution of compound 4_5 (0.42 mmol) in 90% formic acid (15 mL) or trifluoroacetic acid/dichloromethane (1:1, 10 mL) was stirred at 40° C. for 40 min. After concentrating to dryness under reduced pressure, the residue was stirred with water (20 mL) for 20 min. After filtration, the filtrate was lyophilized to give the crude product which was purified by prep-HPLC to afford compound 4_6 (5%-78% yield) as formate or TFA salt as a colorless solid.

The compounds 4_6 of Examples 1-111 were prepared according to the procedures detailed above. The compound of Example 38 was prepared by treating the compound of Example 24 with isopropyl formimidate hydrochloride in the presence of potassium carbonate (conditions see e.g. US 2009/0012054). The compound of Example 43 was prepared by treating the compound of Example 39 with ethanimidoate hydrochloride in the presence of potassium carbonate (conditions see e.g. US 2009/0012054). The compound of Example 46 was prepared by oxidizing the compound of Example 81 with Jones reagent (conditions see e.g. Kenneth Bowden, I. M. Heilbron, E. R. H. Jones and B. C. L. Weedon, J. Chem. Soc., 1946, 39-45). The compounds of Example 87 were prepared by oxidizing the compound of Example 112 with Jones reagent (conditions see e.g. Kenneth Bowden, I. M. Heilbron, E. R. H. Jones and B. C. L. Weedon, J. Chem. Soc., 1946, 39-45) followed by a standard de-protection and HPLC separation.

The compound of Example 78 was prepared by treating the compound of Example 24 with diisopropylethylamine followed by di-tert-butyl [(Z)-1H-pyrazol-1-ylmethyl-ylidene]biscarbamate at room temperature for 15 hours (conditions see e.g. WO 2009/49028 A1). The compound of Example 60 was prepared by treating the compound of Example 59 with formic acid as formylating agent. The compound of Example 63 was prepared by treating the compound of Example 64 with formic acid as formylating agent.

For the convenience of the reader the structures of the final compounds as well as used building blocks (1_x, 2_x and 3_x) are provided in table 3, which is followed by analytical data for all examples.

TABLE 3

Structures of final compounds and used building blocks

| Example | Structure | BB 1 (1_x) | BB 2 (2_x) | BB 3 (3_x) |
|---|---|---|---|---|
| 1 | 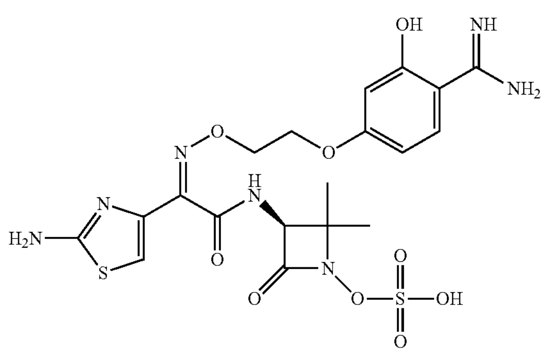 [SMILES: CC1(C)[C@H](NC(=O)/C(=N\OCCOc2ccc(C(=N)N)c(O)c2)c2csc(N)n2)C(=O)N1OS(=O)(=O)O] | 1_5_11 | 2_1_1 | 3_44_6 |

TABLE 3-continued

Structures of final compounds and used building blocks

| Example | Structure | BB 1 (1_x) | BB 2 (2_x) | BB 3 (3_x) |
|---|---|---|---|---|
| 2 | 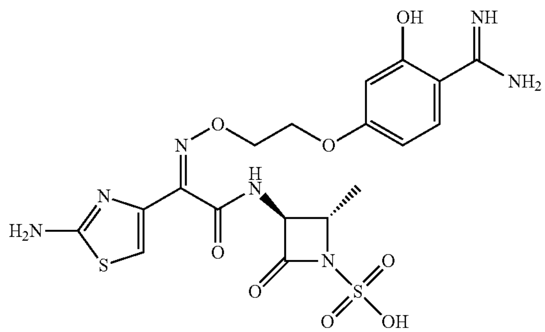 [SMILES: C[C@H]1[C@H](NC(=O)/C(=N\OCCOc2ccc(C(=N)N)c(O)c2)c2csc(N)n2)C(=O)N1S(=O)(=O)O] | 1_1_1 | 2_1_1 | 3_44_6 |
| 3 | 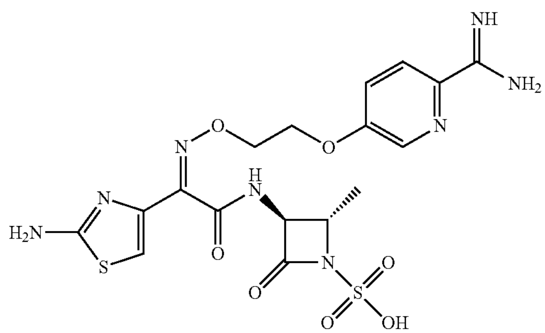 [SMILES: C[C@H]1[C@H](NC(=O)/C(=N\OCCOc2ccc(C(=N)N)nc2)c2csc(N)n2)C(=O)N1S(=O)(=O)O] | 1_1_1 | 2_1_1 | 3_32_5 |
| 4 | 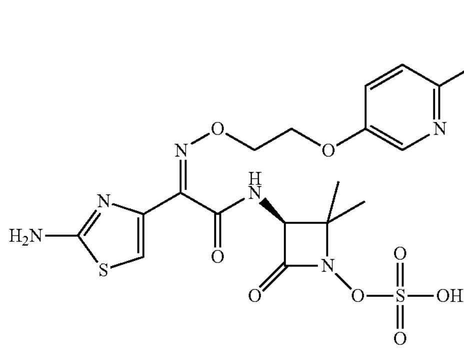 | 1_5_11 | 2_1_1 | 3_32_5 |
| 5 | 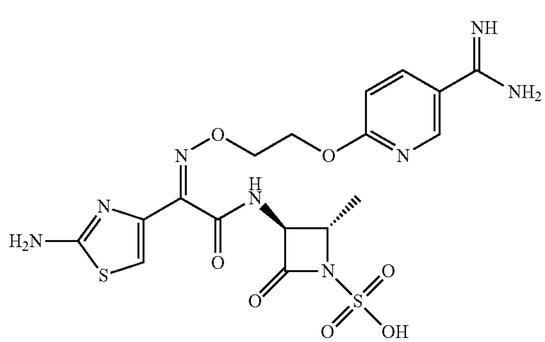 [SMILES: C[C@H]1[C@H](NC(=O)/C(=N\OCCOc2ccc(C(=N)N)cn2)c2csc(N)n2)C(=O)N1S(=O)(=O)O] | 1_1_1 | 2_1_1 | 3_34_5 |

TABLE 3-continued

Structures of final compounds and used building blocks

| Example | Structure | BB 1 (1_x) | BB 2 (2_x) | BB 3 (3_x) |
|---|---|---|---|---|
| 6 | 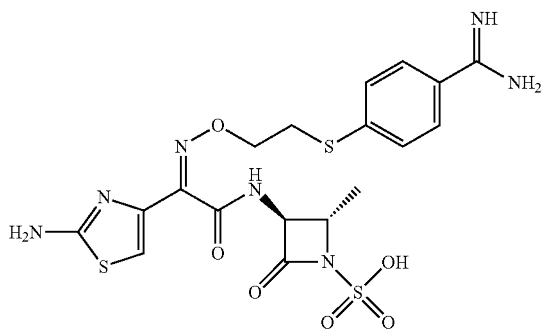 [SMILES: C[C@H]1[C@H](NC(=O)/C(=N\OCCSc2ccc(C(=N)N)cc2)c2csc(N)n2)C(=O)N1S(=O)(=O)O] | 1_1_1 | 2_1_1 | 3_10_6 |
| 7 | 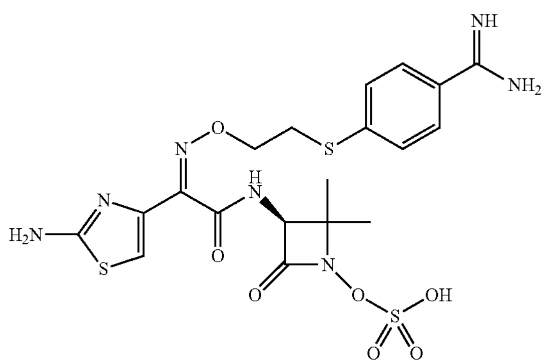 [SMILES: CC1(C)[C@H](NC(=O)/C(=N\OCCSc2ccc(C(=N)N)cc2)c2csc(N)n2)C(=O)N1OS(=O)(=O)O] | 1_5_11 | 2_1_1 | 3_10_6 |
| 8 | 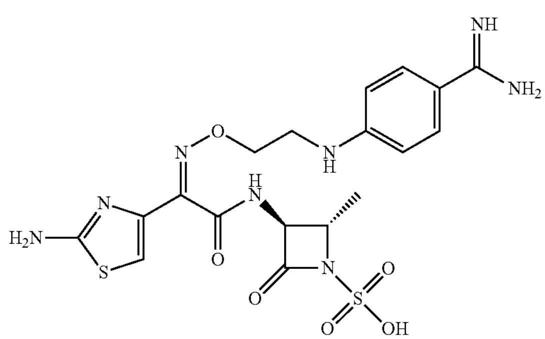 [SMILES: C[C@H]1[C@H](NC(=O)/C(=N\OCCNc2ccc(C(=N)N)cc2)c2csc(N)n2)C(=O)N1S(=O)(=O)O] | 1_1_1 | 2_1_1 | 3_25_6 |
| 9 | 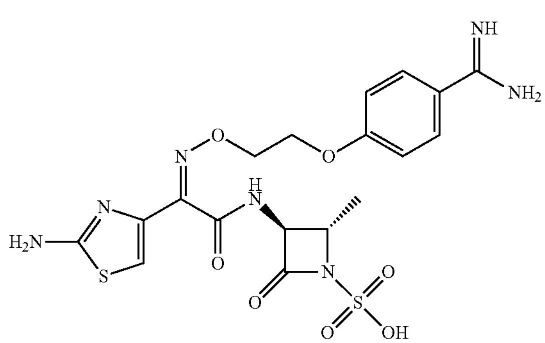 [SMILES: C[C@H]1[C@H](NC(=O)/C(=N\OCCOc2ccc(C(=N)N)cc2)c2csc(N)n2)C(=O)N1S(=O)(=O)O] | 1_1_1 | 2_1_1 | 3_01_6 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 10 | 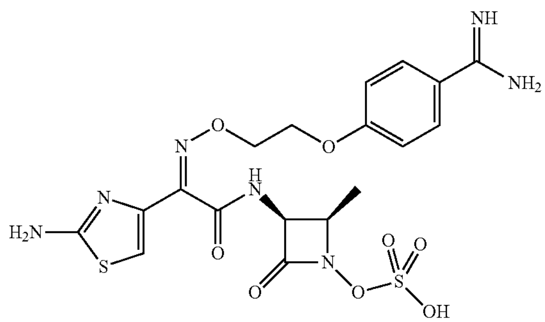 [SMILES: C[C@@H]1[C@H](NC(=O)/C(=N\OCCOc2ccc(C(=N)N)cc2)c2csc(N)n2)C(=O)N1OS(=O)(=O)O] | 1_4_7 | 2_1_1 | 3_01_6 |
| 11 | 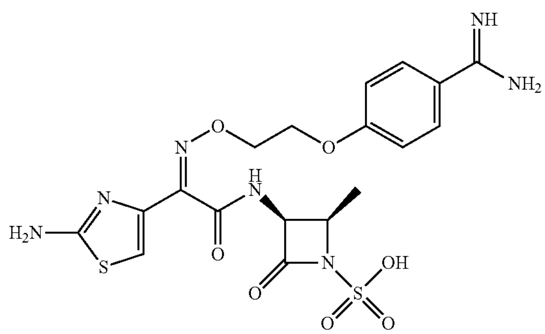 [SMILES: C[C@@H]1[C@H](NC(=O)/C(=N\OCCOc2ccc(C(=N)N)cc2)c2csc(N)n2)C(=O)N1S(=O)(=O)O] | 1_3_1 | 2_1_1 | 3_01_6 |
| 12 | 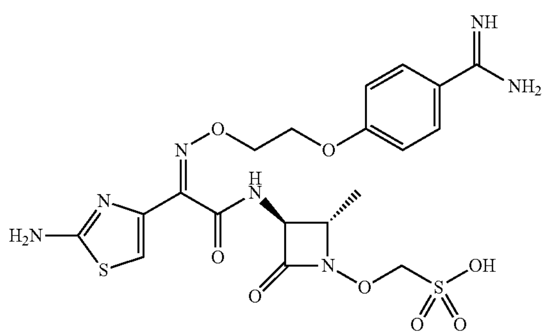 [SMILES: C[C@H]1[C@H](NC(=O)/C(=N\OCCOc2ccc(C(=N)N)cc2)c2csc(N)n2)C(=O)N1OCS(=O)(=O)O] | 1_6_9 | 2_1_1 | 3_01_6 |
| 13 | 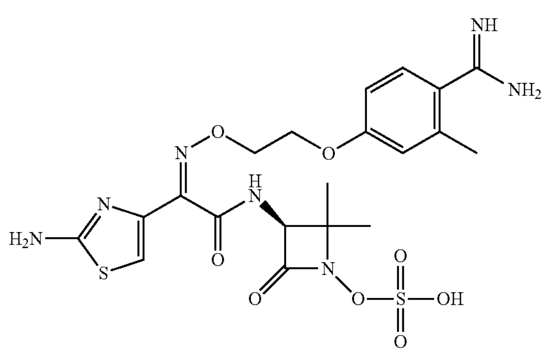 [SMILES: Cc1cc(OCCO/N=C(\C(=O)N[C@@H]2C(=O)N(OS(=O)(=O)O)C2(C)C)c2csc(N)n2)ccc1C(=N)N] | 1_5_11 | 2_1_1 | 3_46_3 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 14 | 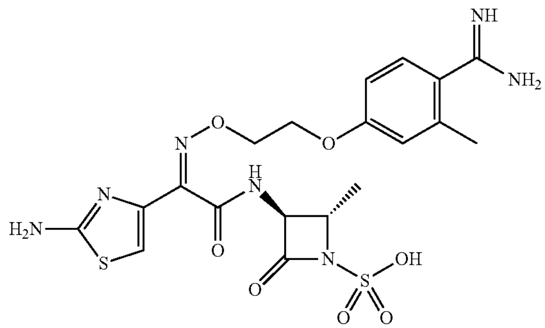 [SMILES: Cc1cc(OCCO/N=C(\C(=O)N[C@@H]2C(=O)N(S(=O)(=O)O)[C@H]2C)c2csc(N)n2)ccc1C(=N)N] | 1_1_1 | 2_1_1 | 3_46_3 |
| 15 | 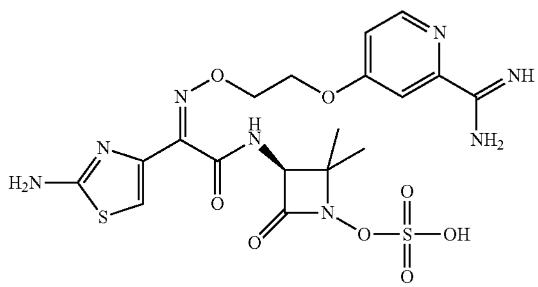 [SMILES: CC1(C)[C@H](NC(=O)/C(=N\OCCOc2ccnc(C(=N)N)c2)c2csc(N)n2)C(=O)N1OS(=O)(=O)O] | 1_5_11 | 2_1_1 | 3_47_5 |
| 16 | 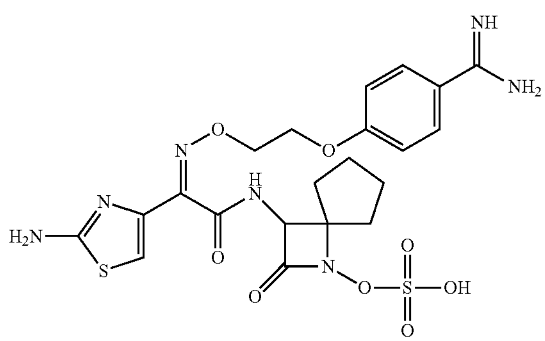 [SMILES: N=C(N)c1ccc(OCCO/N=C(\C(=O)NC2C(=O)N(OS(=O)(=O)O)C23CCCC3)c2csc(N)n2)cc1] | 1_8_8 | 2_1_1 | 3_01_6 |
| 17 | 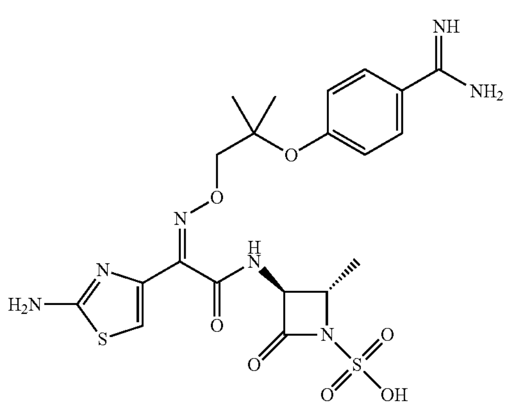 [SMILES: C[C@H]1[C@H](NC(=O)/C(=N\OCC(C)(C)Oc2ccc(C(=N)N)cc2)c2csc(N)n2)C(=O)N1S(=O)(=O)O] | 1_1_1 | 2_1_1 | 3_37_7 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 18 | 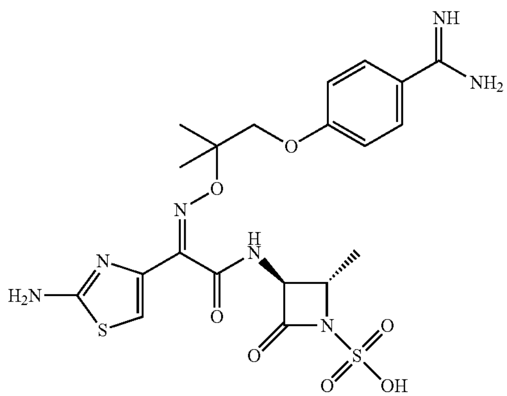 [SMILES: C[C@H]1[C@H](NC(=O)/C(=N\OC(C)(C)COc2ccc(C(=N)N)cc2)c2csc(N)n2)C(=O)N1S(=O)(=O)O] | 1_1_1 | 2_1_1 | 3_36_8 |
| 19 | 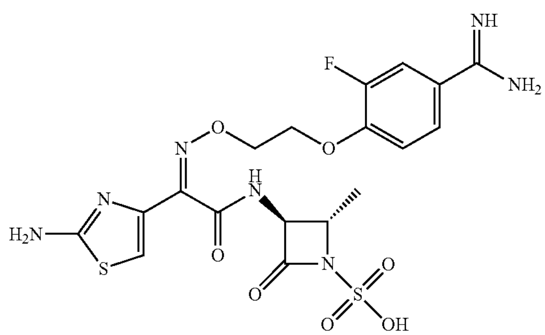 [SMILES: C[C@H]1[C@H](NC(=O)/C(=N\OCCOc2ccc(C(=N)N)cc2F)c2csc(N)n2)C(=O)N1S(=O)(=O)O] | 1_1_1 | 2_1_1 | 3_06_6 |
| 20 | 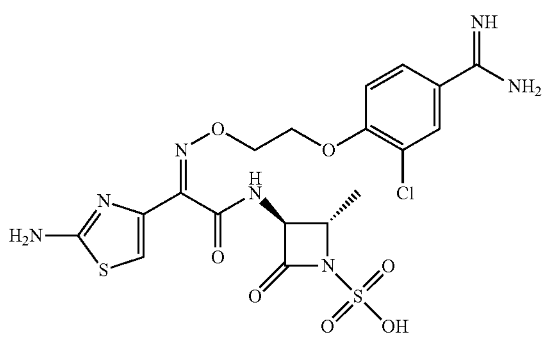 [SMILES: C[C@H]1[C@H](NC(=O)/C(=N\OCCOc2ccc(C(=N)N)cc2Cl)c2csc(N)n2)C(=O)N1S(=O)(=O)O] | 1_1_1 | 2_1_1 | 3_04_6 |
| 21 | 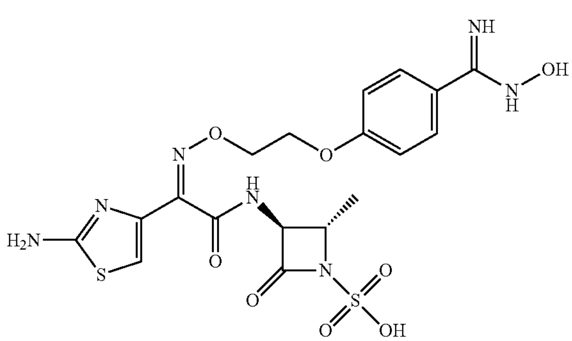 [SMILES: C[C@H]1[C@H](NC(=O)/C(=N\OCCOc2ccc(C(=N)NO)cc2)c2csc(N)n2)C(=O)N1S(=O)(=O)O] | 1_1_1 | 2_1_1 | 3_23_5 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 22 | 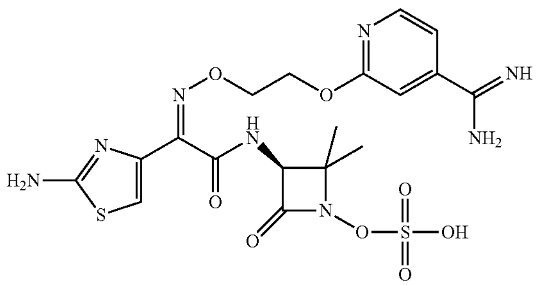 [SMILES: CC1(C)[C@H](NC(=O)/C(=N\OCCOc2cc(C(=N)N)ccn2)c2csc(N)n2)C(=O)N1OS(=O)(=O)O] | 1_5_11 | 2_1_1 | 3_48_5 |
| 23 | 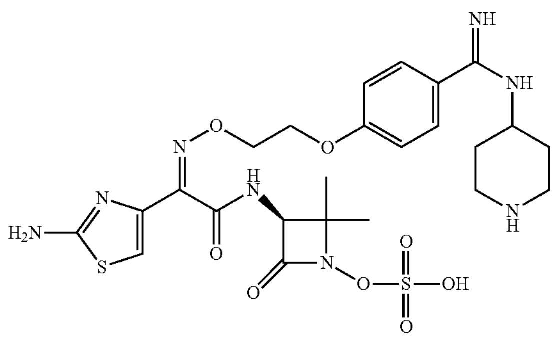 [SMILES: CC1(C)[C@H](NC(=O)/C(=N\OCCOc2ccc(C(=N)NC3CCNCC3)cc2)c2csc(N)n2)C(=O)N1OS(=O)(=O)O] | 1_5_11 | 2_1_1 | 3_51_5 |
| 24 | 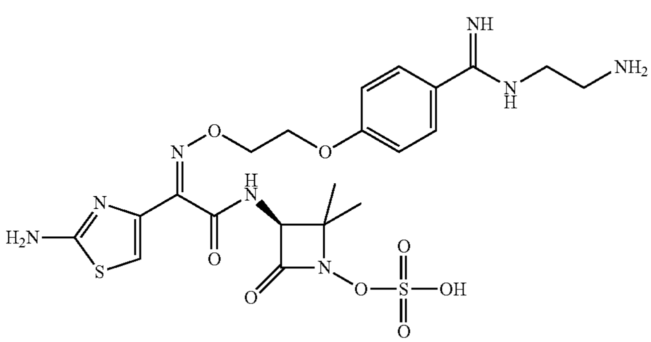 [SMILES: CC1(C)[C@H](NC(=O)/C(=N\OCCOc2ccc(C(=N)NCCN)cc2)c2csc(N)n2)C(=O)N1OS(=O)(=O)O] | 1_5_11 | 2_1_1 | 3_15_6 |
| 25 | 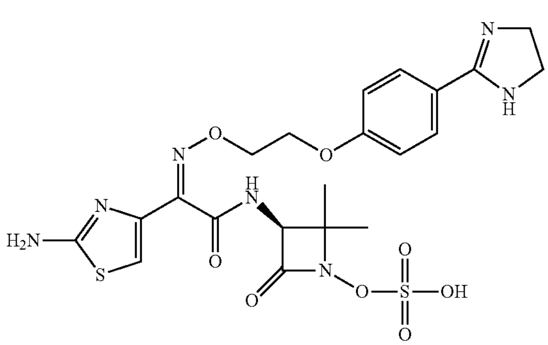 [SMILES: CC1(C)[C@H](NC(=O)/C(=N\OCCOc2ccc(C3=NCCN3)cc2)c2csc(N)n2)C(=O)N1OS(=O)(=O)O] | 1_5_11 | 2_1_1 | 3_50_4 |

US 9,556,165 B2
TABLE 3-continued
Structures of final compounds and used building blocks
| Example | Structure | BB 1 (1_x) | BB 2 (2_x) | BB 3 (3_x) |
|---|---|---|---|---|
| 26A | 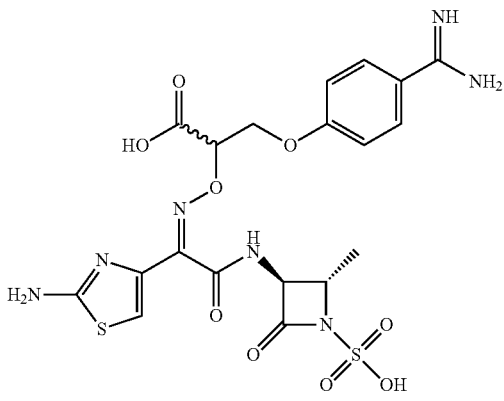<br>Epimer A | 1_1_1 | 2_1_1 | 3_45_9 |
| 26B | 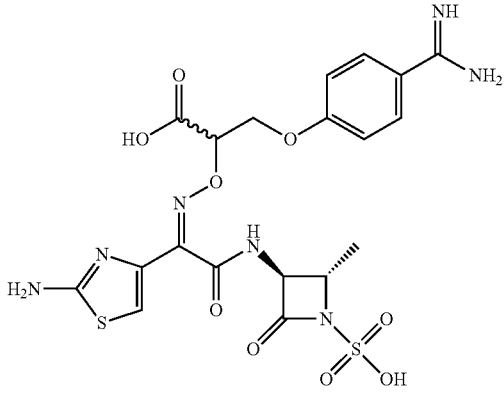<br>Epimer B | 1_1_1 | 2_1_1 | 3_45_9 |
| 27A | 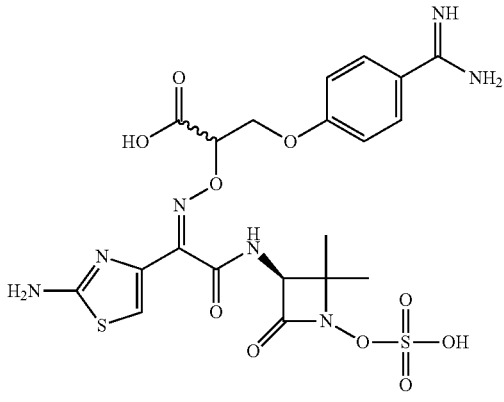<br>Epimer A | 1_5_11 | 2_1_1 | 3_45_9 |

TABLE 3-continued

Structures of final compounds and used building blocks

| Example | Structure | BB 1 (1_x) | BB 2 (2_x) | BB 3 (3_x) |
|---|---|---|---|---|
| 27B | Epimer B | 1_5_11 | 2_1_1 | 3_45_9 |
| 28 | 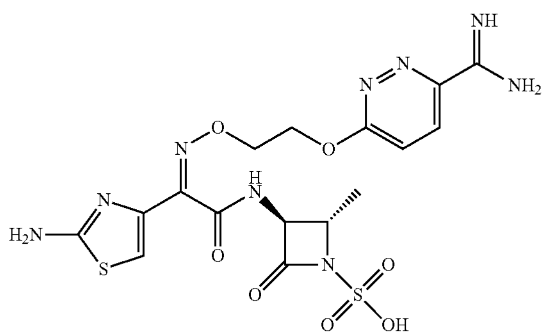 | 1_1_1 | 2_1_1 | 3_30_6 |
| 29 | 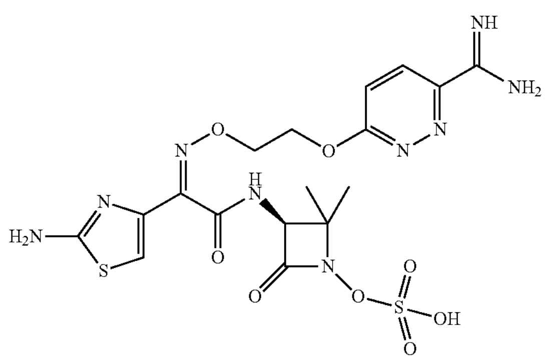 [SMILES: CC1(C)[C@H](NC(=O)/C(=N\OCCOc2ccc(C(=N)N)nn2)c2csc(N)n2)C(=O)N1OS(=O)(=O)O] | 1_5_11 | 2_1_1 | 3_30_6 |
| 30 | 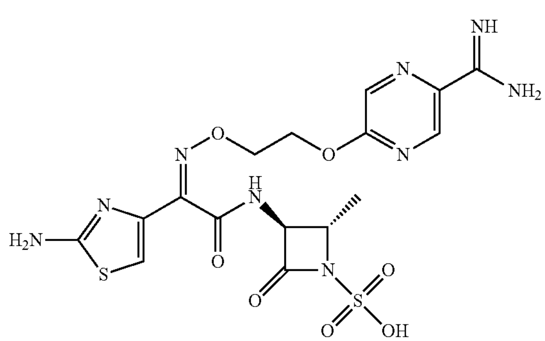 [SMILES: C[C@H]1[C@H](NC(=O)/C(=N\OCCOc2cnc(C(=N)N)cn2)c2csc(N)n2)C(=O)N1S(=O)(=O)O] | 1_1_1 | 2_1_1 | 3_31_6 |

TABLE 3-continued

Structures of final compounds and used building blocks

| Example | Structure | BB 1 (1_x) | BB 2 (2_x) | BB 3 (3_x) |
|---|---|---|---|---|
| 31 | 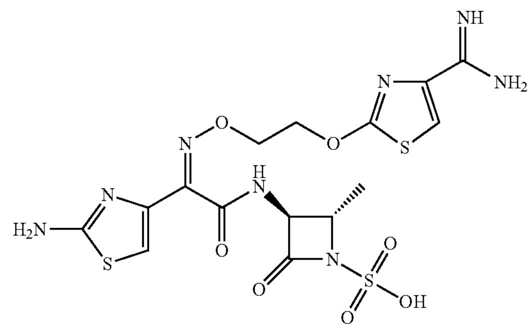 [SMILES: C[C@H]1[C@H](NC(=O)/C(=N\OCCOc2nc(C(=N)N)cs2)c2csc(N)n2)C(=O)N1S(=O)(=O)O] | 1_1_1 | 2_1_1 | 3_38_11 |
| 32 | 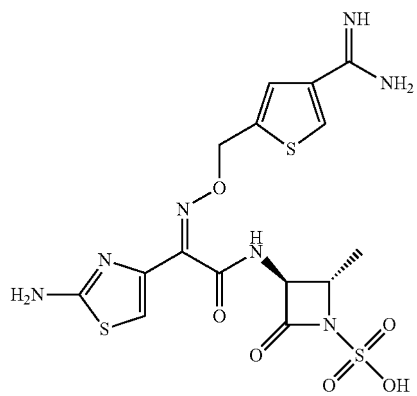 [SMILES: C[C@H]1[C@H](NC(=O)/C(=N\OCc2cc(C(=N)N)cs2)c2csc(N)n2)C(=O)N1S(=O)(=O)O] | 1_1_1 | 2_1_1 | 3_27_6 |
| 33 | 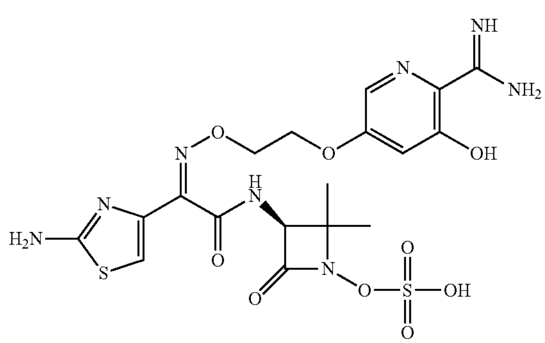 [SMILES: CC1(C)[C@H](NC(=O)/C(=N\OCCOc2cnc(C(=N)N)c(O)c2)c2csc(N)n2)C(=O)N1OS(=O)(=O)O] | 1_5_11 | 2_1_1 | 3_49_7 |
| 34A | Epimer A | 1_5_11 | 2_1_1 | 3_85_7 |

TABLE 3-continued
Structures of final compounds and used building blocks
| Example | Structure | BB 1 (1_x) | BB 2 (2_x) | BB 3 (3_x) |
|---|---|---|---|---|
| 34B | 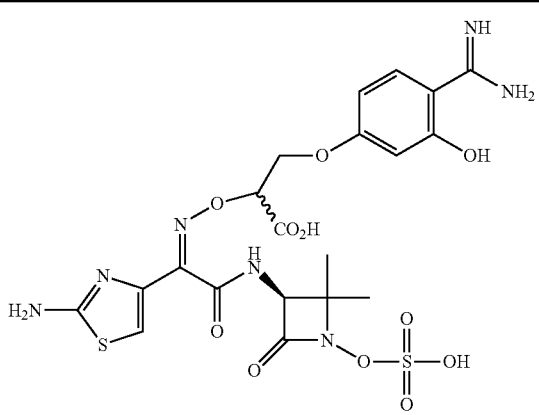<br>Epimer B | 1_5_1 | 2_1_1 | 3_85_7 |
| 35 | 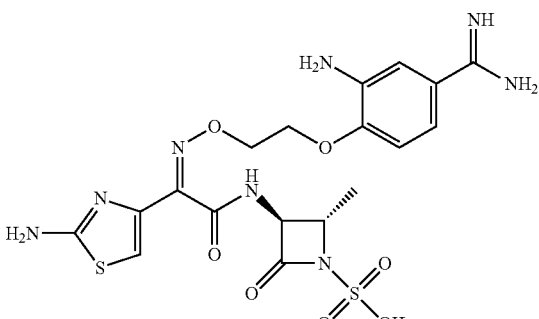 | 1_1_1 | 2_1_1 | 3_28_7 |
| 36A | 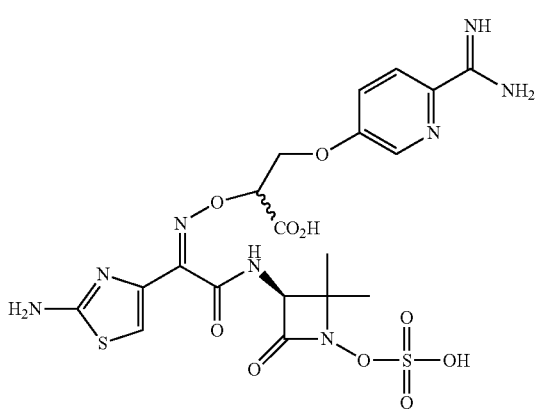<br>Epimer A | 1_5_11 | 2_1_1 | 3_60_7 |

TABLE 3-continued

Structures of final compounds and used building blocks

| Example | Structure | BB 1 (1_x) | BB 2 (2_x) | BB 3 (3_x) |
|---|---|---|---|---|
| 36B | Epimer B | 1_5_11 | 2_1_1 | 3_60_7 |
| 37 | 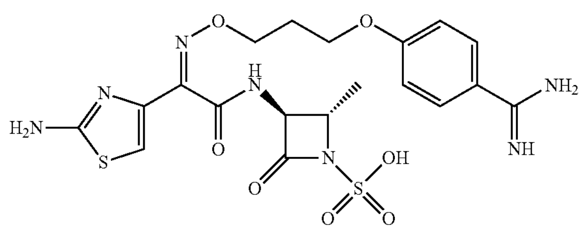 [SMILES: C[C@H]1[C@H](NC(=O)/C(=N\OCCCOc2ccc(C(=N)N)cc2)c2csc(N)n2)C(=O)N1S(=O)(=O)O] | 1_1_1 | 2_1_1 | 3_07_6 |
| 38 | 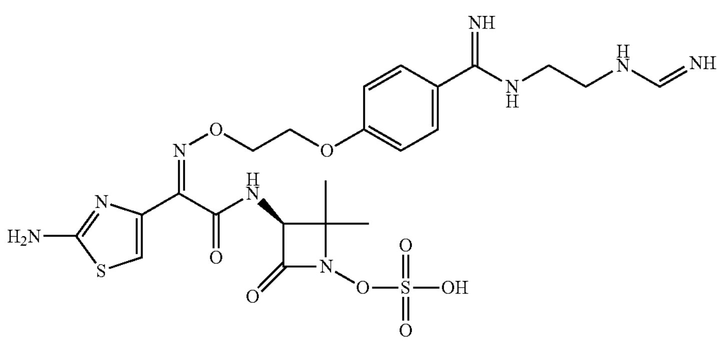 [SMILES: CC1(C)[C@H](NC(=O)/C(=N\OCCOc2ccc(C(=N)NCCNC=N)cc2)c2csc(N)n2)C(=O)N1OS(=O)(=O)O] | | | from example 24 |
| 39 | 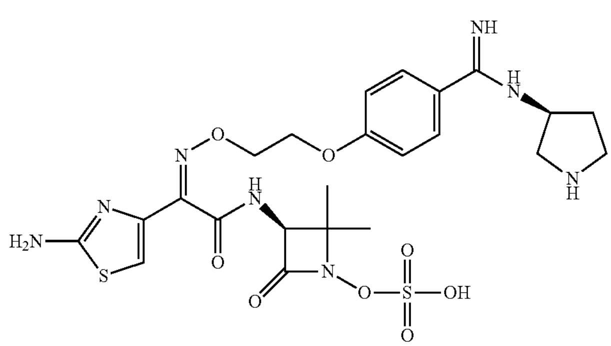 [SMILES: CC1(C)[C@H](NC(=O)/C(=N\OCCOc2ccc(C(=N)N[C@H]3CCNC3)cc2)c2csc(N)n2)C(=O)N1OS(=O)(=O)O] | 1_5_11 | 2_1_1 | 3_52_5 |

TABLE 3-continued

Structures of final compounds and used building blocks

| Example | Structure | BB 1 (1_x) | BB 2 (2_x) | BB 3 (3_x) |
|---|---|---|---|---|
| 40 | 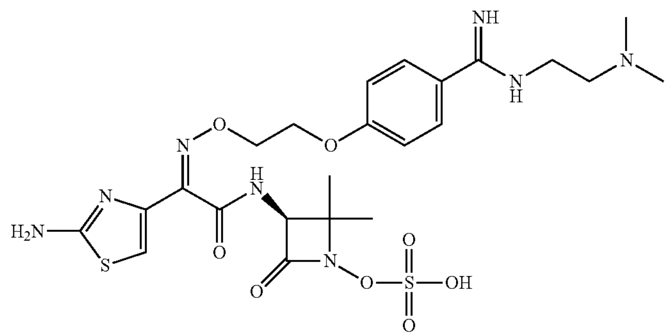 [SMILES: CN(C)CCNC(=N)c1ccc(OCCO/N=C(\C(=O)N[C@@H]2C(=O)N(OS(=O)(=O)O)C2(C)C)c2csc(N)n2)cc1] | 1_5_11 | 2_1_1 | 3_19_6 |
| 41 | 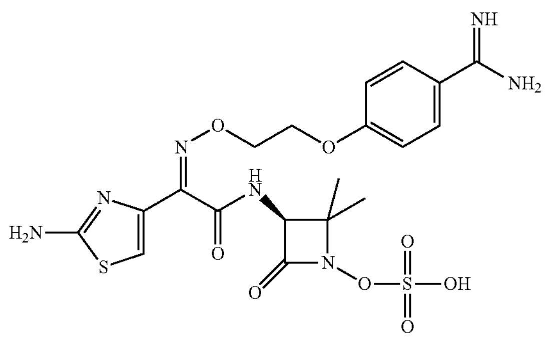 [SMILES: CC1(C)[C@H](NC(=O)/C(=N\OCCOc2ccc(C(=N)N)cc2)c2csc(N)n2)C(=O)N1OS(=O)(=O)O] | 1_5_11 | 2_1_1 | 3_01_6 |
| 42 | 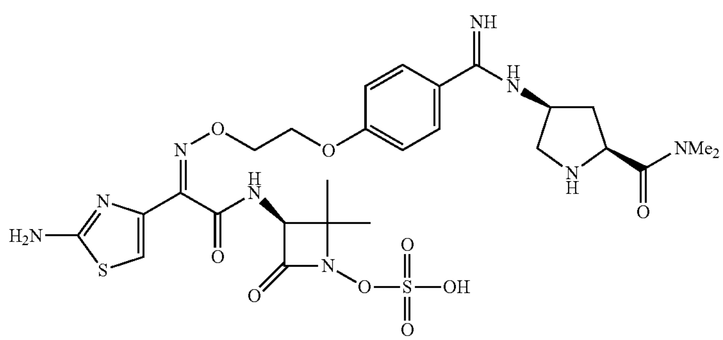 [SMILES: CN(C)C(=O)[C@@H]1C[C@H](NC(=N)c2ccc(OCCO/N=C(\C(=O)N[C@@H]3C(=O)N(OS(=O)(=O)O)C3(C)C)c3csc(N)n3)cc2)CN1] | 1_5_11 | 2_1_1 | 3_53_5 |
| 43 | 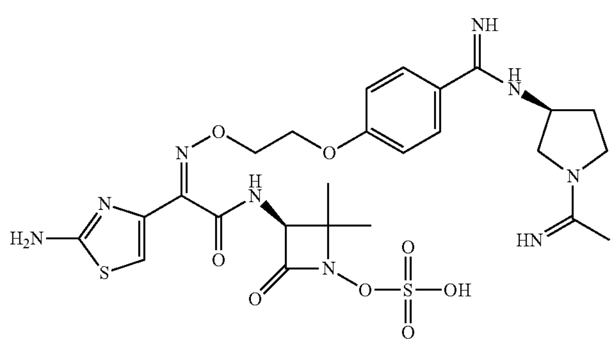 [SMILES: CC(=N)N1CC[C@H](NC(=N)c2ccc(OCCO/N=C(\C(=O)N[C@@H]3C(=O)N(OS(=O)(=O)O)C3(C)C)c3csc(N)n3)cc2)C1] | from example 39 | | |

TABLE 3-continued
Structures of final compounds and used building blocks
| Example | Structure | BB 1 (1_x) | BB 2 (2_x) | BB 3 (3_x) |
|---|---|---|---|---|
| 44A | 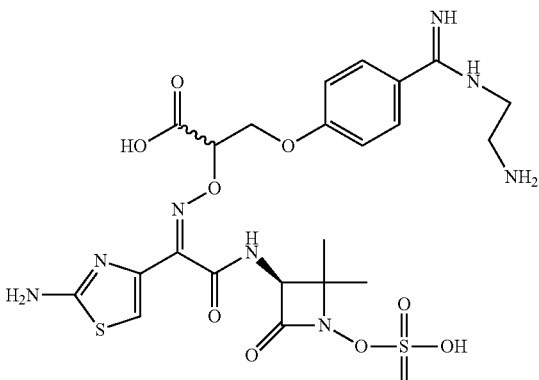 Epimer A | 1_5_11 | 2_1_1 | 3_59_3 |
| 44B | 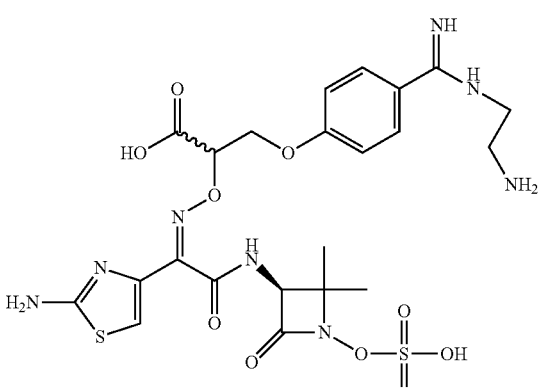 Epimer B | 1_5_11 | 2_1_1 | 3_59_3 |
| 45A | 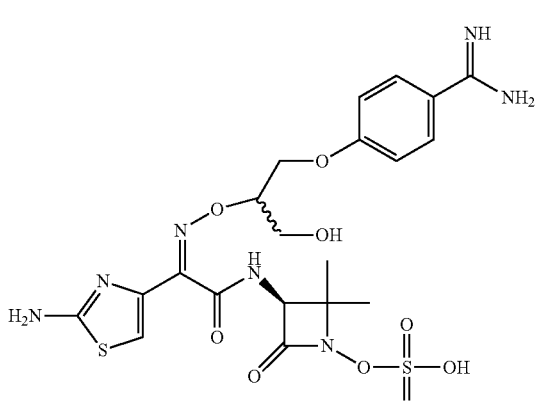 Epimer A | 1_5_11 | 2_1_1 | 3_61_7 |

TABLE 3-continued
Structures of final compounds and used building blocks
| Example | Structure | BB 1 (1_x) | BB 2 (2_x) | BB 3 (3_x) |
|---|---|---|---|---|
| 45B | 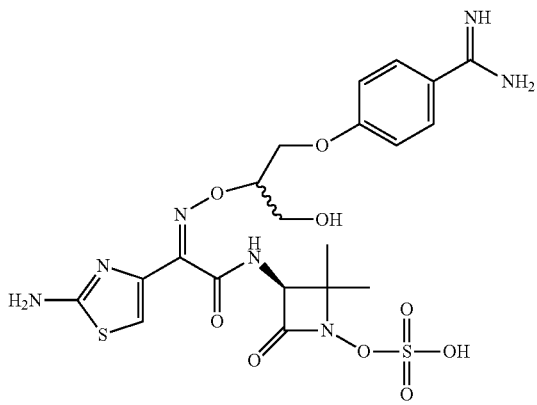 Epimer B | 1_5_11 | 2_1_1 | 3_61_7 |
| 46 | 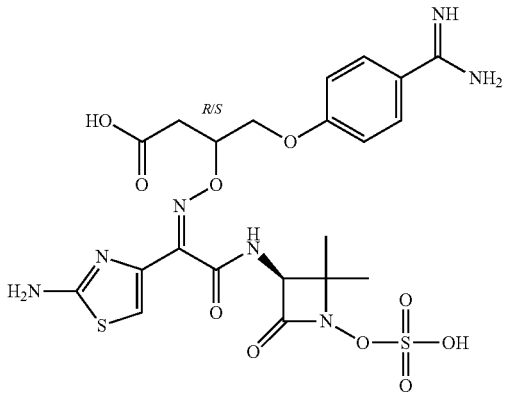 [SMILES: CC1(C)[C@H](NC(=O)/C(=N\OC(COc2ccc(C(=N)N)cc2)CC(=O)O)c2csc(N)n2)C(=O)N1OS(=O)(=O)O] | from example 81 (mixture of epimers) | | |
| 47 | 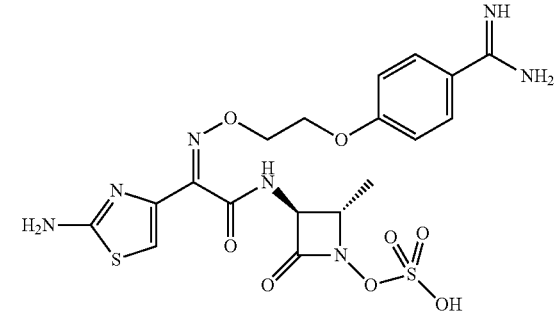 [SMILES: C[C@H]1[C@H](NC(=O)/C(=N\OCCOc2ccc(C(=N)N)cc2)c2csc(N)n2)C(=O)N1OS(=O)(=O)O] | 1_2_1 | 2_1_1 | 3_01_6 |
| 48 | 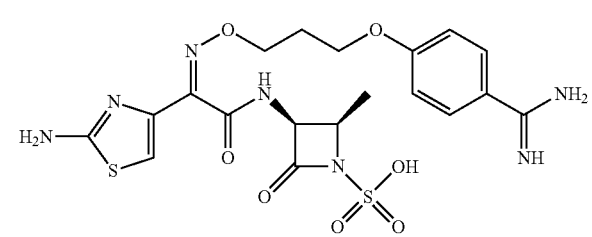 [SMILES: C[C@@H]1[C@H](NC(=O)/C(=N\OCCCOc2ccc(C(=N)N)cc2)c2csc(N)n2)C(=O)N1S(=O)(=O)O] | 1_3_1 | 2_1_1 | 3_07_6 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 49 | 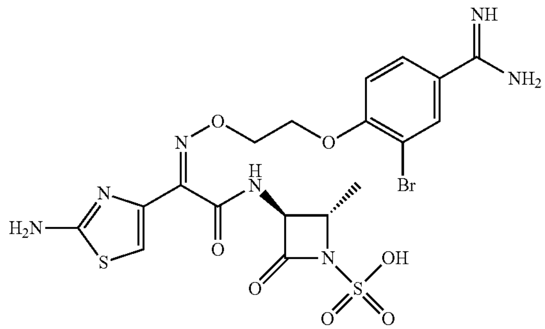 [SMILES: C[C@H]1[C@H](NC(=O)/C(=N\OCCOc2ccc(C(=N)N)cc2Br)c2csc(N)n2)C(=O)N1S(=O)(=O)O] | 1_1_1 | 2_1_1 | 3_02_6 |
| 50 | 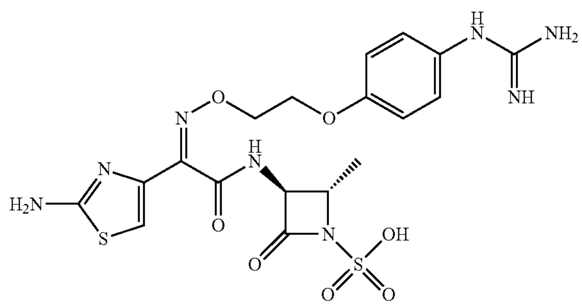 [SMILES: C[C@H]1[C@H](NC(=O)/C(=N\OCCOc2ccc(NC(=N)N)cc2)c2csc(N)n2)C(=O)N1S(=O)(=O)O] | 1_1_1 | 2_1_1 | 3_08_6 |
| 51 | 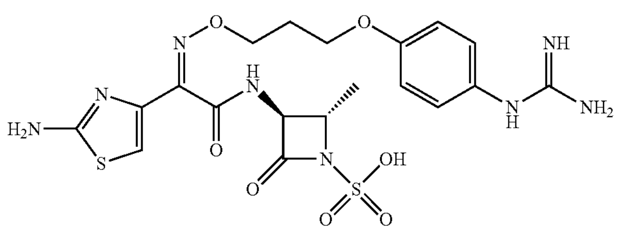 [SMILES: C[C@H]1[C@H](NC(=O)/C(=N\OCCCOc2ccc(NC(=N)N)cc2)c2csc(N)n2)C(=O)N1S(=O)(=O)O] | 1_1_1 | 2_1_1 | 3_09_6 |
| 52 | 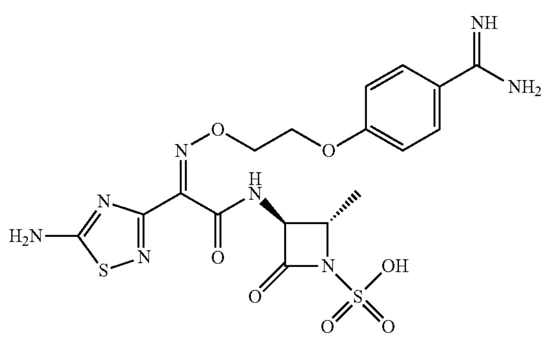 | 1_1_1 | 2_2_1 | 3_01_6 |
| 53 | 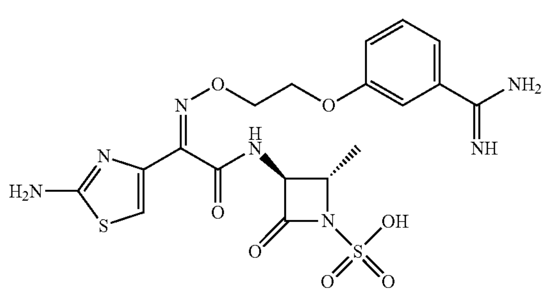 [SMILES: C[C@H]1[C@H](NC(=O)/C(=N\OCCOc2cccc(C(=N)N)c2)c2csc(N)n2)C(=O)N1S(=O)(=O)O] | 1_1_1 | 2_1_1 | 3_03_6 |

TABLE 3-continued

Structures of final compounds and used building blocks

| Example | Structure | BB 1 (1_x) | BB 2 (2_x) | BB 3 (3_x) |
|---|---|---|---|---|
| 54 | 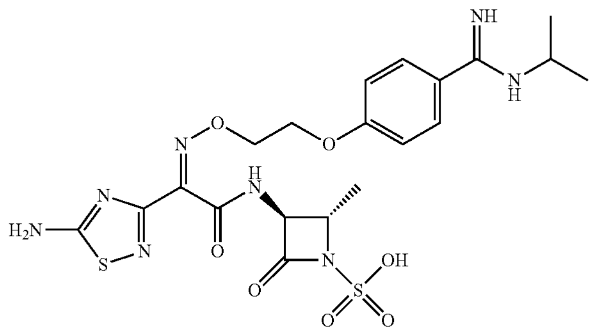 [SMILES: CC(C)NC(=N)c1ccc(OCCO/N=C(\C(=O)N[C@@H]2C(=O)N(S(=O)(=O)O)[C@H]2C)c2nsc(N)n2)cc1] | 1_1_1 | 2_1_1 | 3_11_6 |
| 55 | 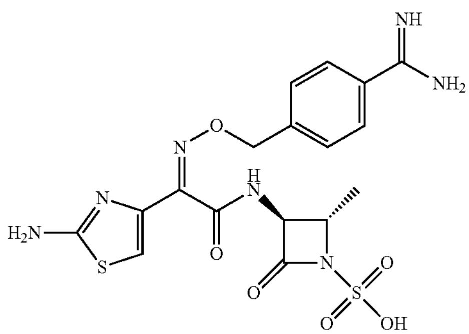 [SMILES: C[C@H]1[C@H](NC(=O)/C(=N\OCc2ccc(C(=N)N)cc2)c2csc(N)n2)C(=O)N1S(=O)(=O)O] | 1_1_1 | 2_1_1 | 3_24_5 |
| 56 | 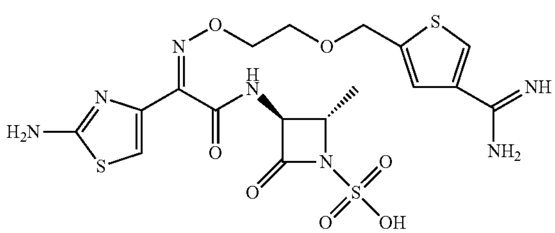 [SMILES: C[C@H]1[C@H](NC(=O)/C(=N\OCCOCc2cc(C(=N)N)cs2)c2csc(N)n2)C(=O)N1S(=O)(=O)O] | 1_1_1 | 2_1_1 | 3_26_5 |
| 57 | 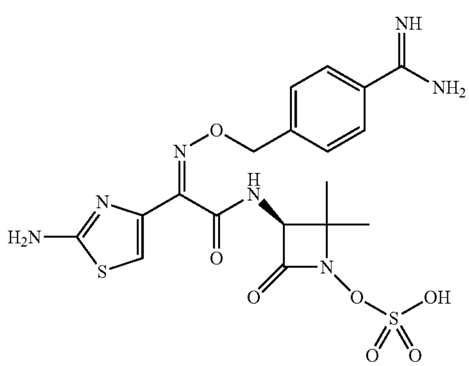 [SMILES: CC1(C)[C@H](NC(=O)/C(=N\OCc2ccc(C(=N)N)cc2)c2csc(N)n2)C(=O)N1OS(=O)(=O)O] | 1_5_11 | 2_1_1 | 3_24_5 |
| 58 | 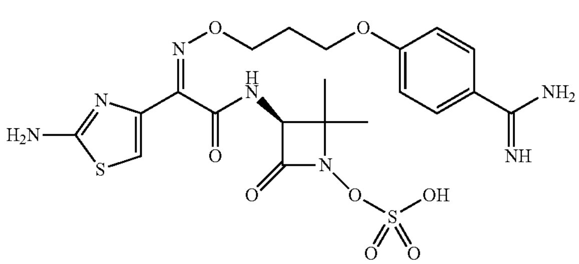 [SMILES: CC1(C)[C@H](NC(=O)/C(=N\OCCCOc2ccc(C(=N)N)cc2)c2csc(N)n2)C(=O)N1OS(=O)(=O)O] | 1_5_11 | 2_1_1 | 3_07_6 |

TABLE 3-continued

Structures of final compounds and used building blocks

| Example | Structure | BB 1 (1_x) | BB 2 (2_x) | BB 3 (3_x) |
|---|---|---|---|---|
| 59 | 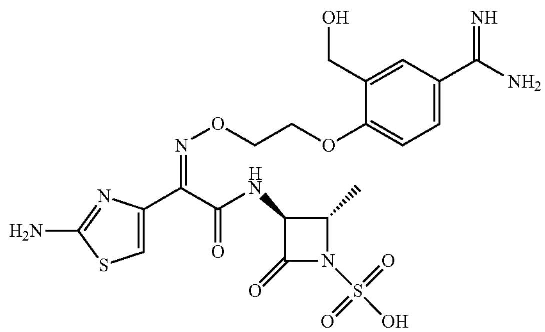 [SMILES: C[C@H]1[C@H](NC(=O)/C(=N\OCCOc2ccc(C(=N)N)cc2CO)c2csc(N)n2)C(=O)N1S(=O)(=O)O] | 1_1_1 | 2_1_1 | 3_29_5 |
| 60 | 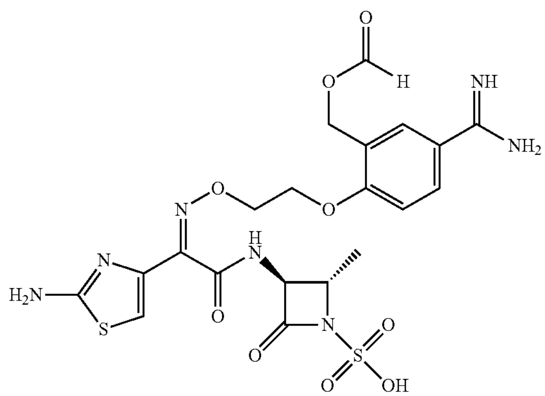 [SMILES: C[C@H]1[C@H](NC(=O)/C(=N\OCCOc2ccc(C(=N)N)cc2COC=O)c2csc(N)n2)C(=O)N1S(=O)(=O)O] | from example 59 | | |
| 61 | 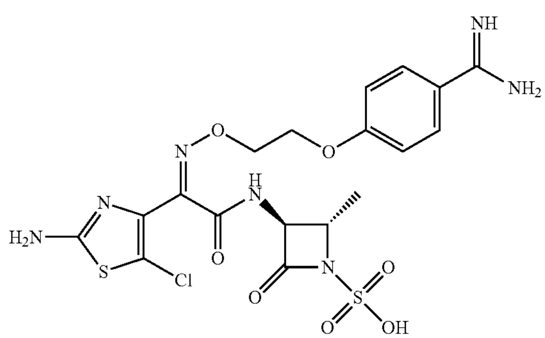 [SMILES: C[C@H]1[C@H](NC(=O)/C(=N\OCCOc2ccc(C(=N)N)cc2)c2nc(N)sc2Cl)C(=O)N1S(=O)(=O)O] | 1_1_1 | 2_3_1 | 3_01_6 |
| 62 | 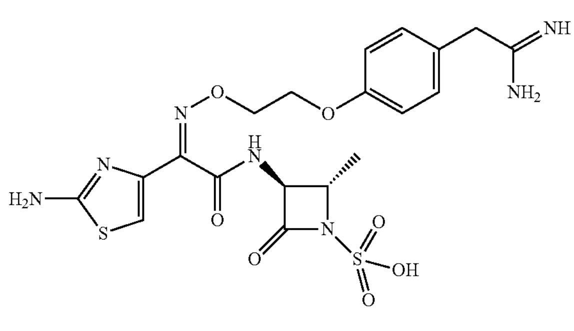 [SMILES: C[C@H]1[C@H](NC(=O)/C(=N\OCCOc2ccc(CC(=N)N)cc2)c2csc(N)n2)C(=O)N1S(=O)(=O)O] | 1_1_1 | 2_1_1 | 3_05_6 |

TABLE 3-continued

Structures of final compounds and used building blocks

| Example | Structure | BB 1 (1_x) | BB 2 (2_x) | BB 3 (3_x) |
|---|---|---|---|---|
| 63 | 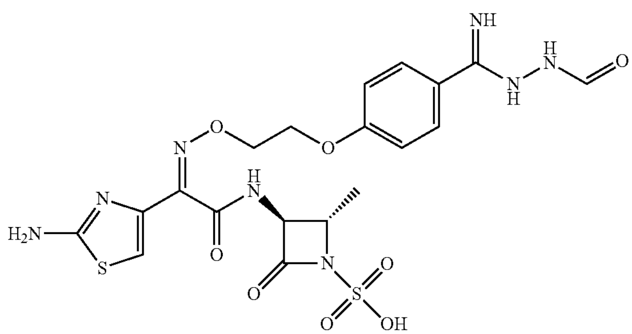 [SMILES: C[C@H]1[C@H](NC(=O)/C(=N\OCCOc2ccc(C(=N)NNC=O)cc2)c2csc(N)n2)C(=O)N1S(=O)(=O)O] | | from example 64 | |
| 64 | 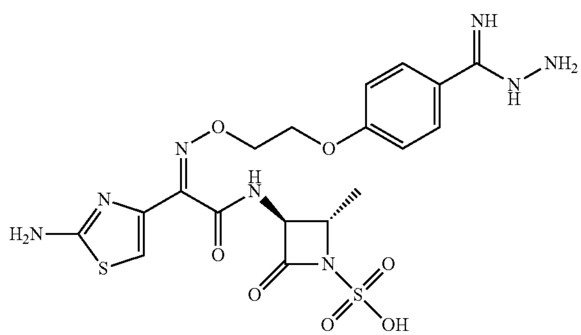 [SMILES: C[C@H]1[C@H](NC(=O)/C(=N\OCCOc2ccc(C(=N)NN)cc2)c2csc(N)n2)C(=O)N1S(=O)(=O)O] | 1_1_1 | 2_1_1 | 3_35_5 |
| 65 | 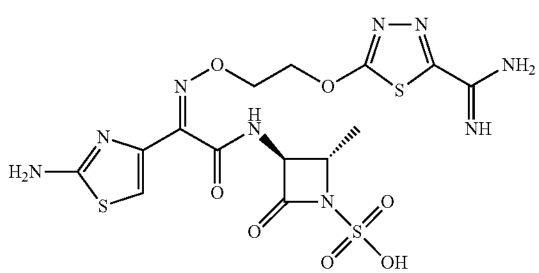 [SMILES: C[C@H]1[C@H](NC(=O)/C(=N\OCCOc2nnc(C(=N)N)s2)c2csc(N)n2)C(=O)N1S(=O)(=O)O] | 1_1_1 | 2_1_1 | 3_39_10 |
| 66 | 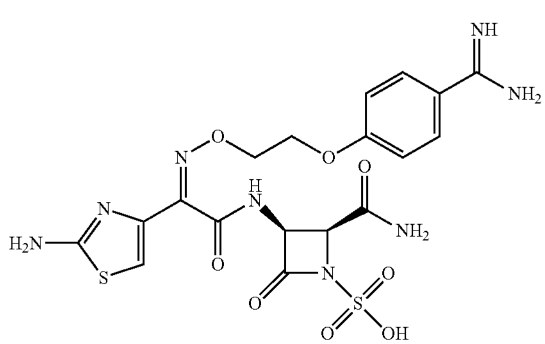 [SMILES: N=C(N)c1ccc(OCCO/N=C(\C(=O)N[C@@H]2C(=O)N(S(=O)(=O)O)[C@@H]2C(N)=O)c2csc(N)n2)cc1] | 1_9_1 | 2_1_1 | 3_01_6 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 67 | 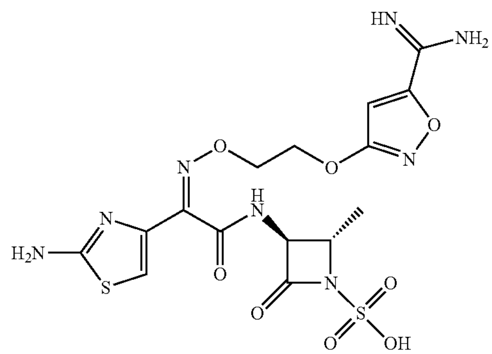 [SMILES: C[C@H]1[C@H](NC(=O)/C(=N\OCCOc2cc(C(=N)N)on2)c2csc(N)n2)C(=O)N1S(=O)(=O)O] | 1_1_1 | 2_1_1 | 3_40_10 |
| 68 | 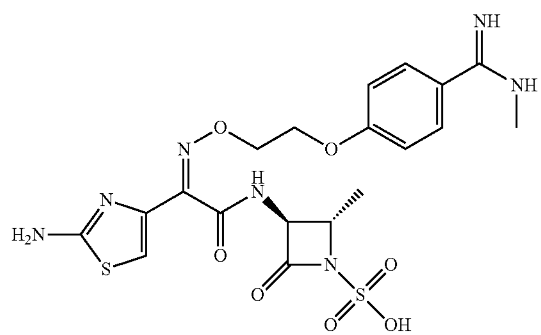 [SMILES: CNC(=N)c1ccc(OCCO/N=C(\C(=O)N[C@@H]2C(=O)N(S(=O)(=O)O)[C@H]2C)c2csc(N)n2)cc1] | 1_1_1 | 2_1_1 | 3_12_6 |
| 69 | 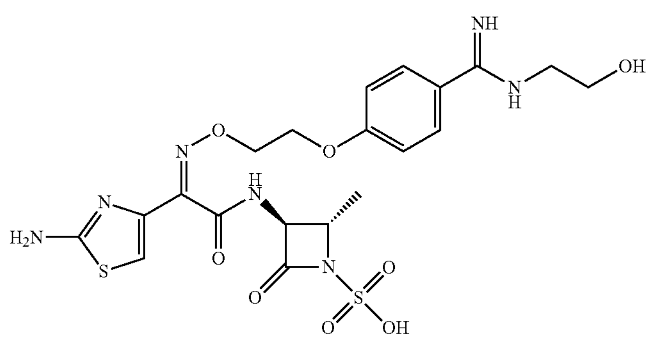 [SMILES: C[C@H]1[C@H](NC(=O)/C(=N\OCCOc2ccc(C(=N)NCCO)cc2)c2csc(N)n2)C(=O)N1S(=O)(=O)O] | 1_1_1 | 2_1_1 | 3_13_6 |
| 70 | 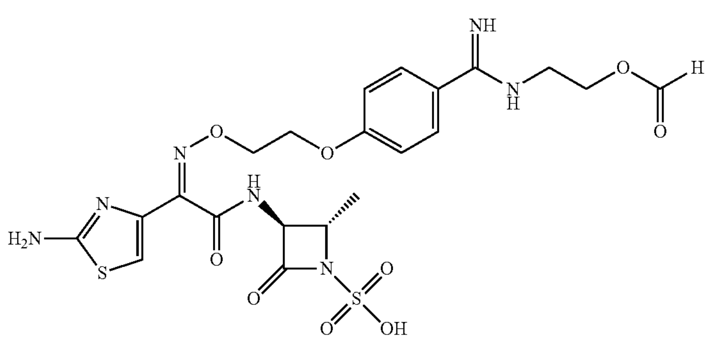 [SMILES: C[C@H]1[C@H](NC(=O)/C(=N\OCCOc2ccc(C(=N)NCCOC=O)cc2)c2csc(N)n2)C(=O)N1S(=O)(=O)O] | 1_1_1 | 2_1_1 | 3_14_7 |

TABLE 3-continued

Structures of final compounds and used building blocks

| Example | Structure | BB 1 (1_x) | BB 2 (2_x) | BB 3 (3_x) |
|---|---|---|---|---|
| 71 | 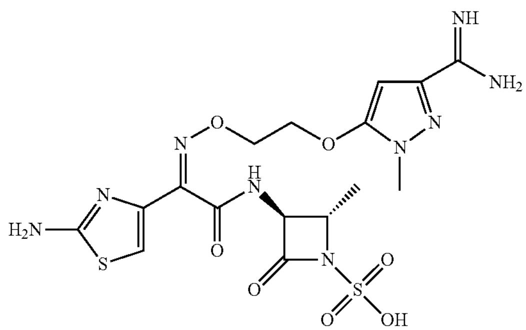 [SMILES: C[C@H]1[C@H](NC(=O)/C(=N\OCCOc2cc(C(=N)N)nn2C)c2csc(N)n2)C(=O)N1S(=O)(=O)O] | 1_1_1 | 2_1_1 | 3_42_10 |
| 72 | 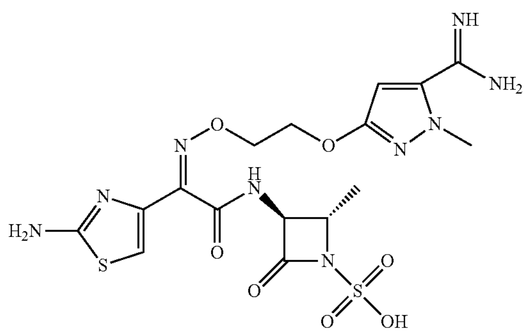 [SMILES: C[C@H]1[C@H](NC(=O)/C(=N\OCCOc2cc(C(=N)N)n(C)n2)c2csc(N)n2)C(=O)N1S(=O)(=O)O] | 1_1_1 | 2_1_1 | 3_41_10 |
| 73 | 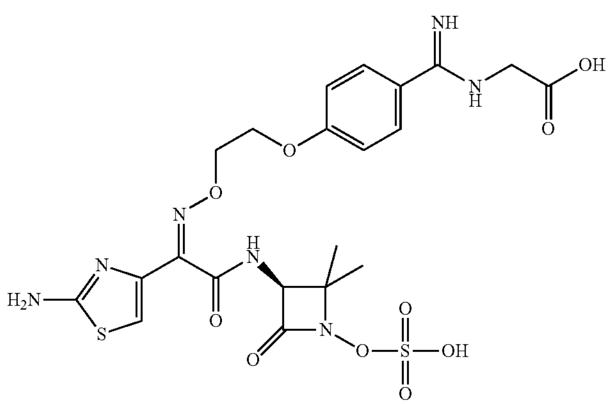 [SMILES: CC1(C)[C@H](NC(=O)/C(=N\OCCOc2ccc(C(=N)NCC(=O)O)cc2)c2csc(N)n2)C(=O)N1OS(=O)(=O)O] | 1_5_11 | 2_1_1 | 3_20_6 |
| 74 | 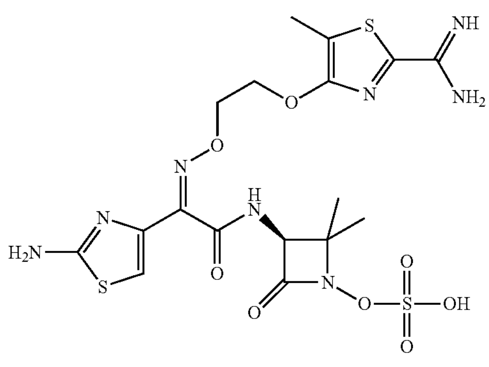 [SMILES: Cc1sc(C(=N)N)nc1OCCO/N=C(\C(=O)N[C@@H]1C(=O)N(OS(=O)(=O)O)C1(C)C)c1csc(N)n1] | 1_5_11 | 2_1_1 | 3_43_10 |

TABLE 3-continued
Structures of final compounds and used building blocks
| Example | Structure | BB 1 (1_x) | BB 2 (2_x) | BB 3 (3_x) |
|---|---|---|---|---|
| 75 | 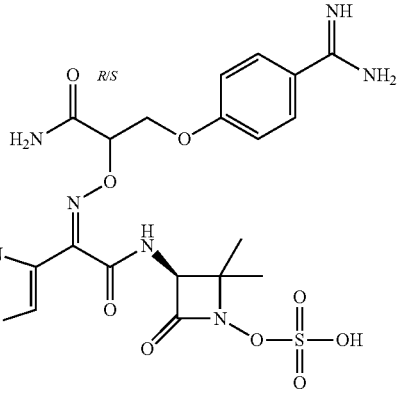 | 1_5_1 | 2_1_1 | 3_83_2 |
| 76 | 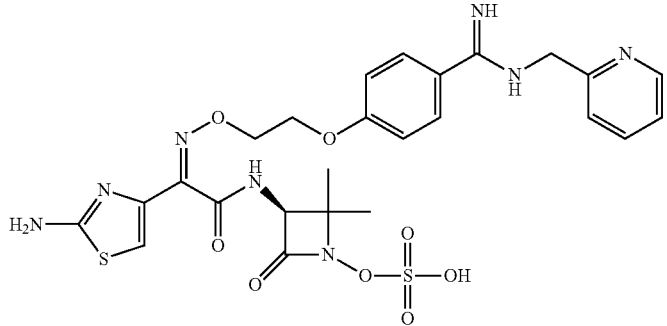 [SMILES: CC1(C)[C@H](NC(=O)/C(=N\OCCOc2ccc(C(=N)NCc3ccccn3)cc2)c2csc(N)n2)C(=O)N1OS(=O)(=O)O] | 1_5_11 | 2_1_1 | 3_17_6 |
| 77 | 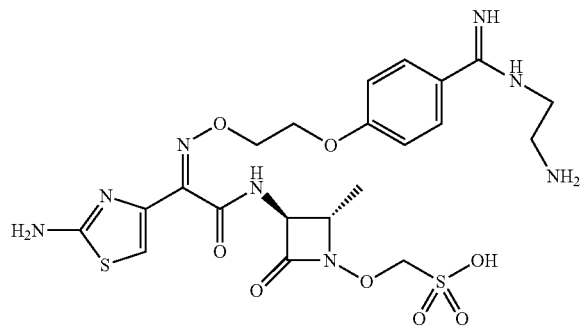 [SMILES: C[C@H]1[C@H](NC(=O)/C(=N\OCCOc2ccc(C(=N)NCCN)cc2)c2csc(N)n2)C(=O)N1OCS(=O)(=O)O] | 1_6_9 | 2_1_1 | 3_15_6 |
| 78 | 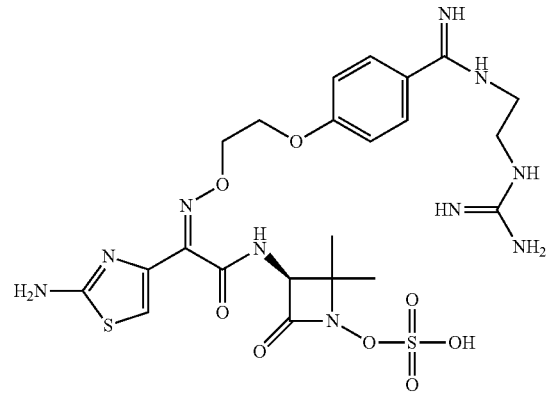 [SMILES: CC1(C)[C@H](NC(=O)/C(=N\OCCOc2ccc(C(=N)NCCNC(=N)N)cc2)c2csc(N)n2)C(=O)N1OS(=O)(=O)O] | | | from example 24 |

TABLE 3-continued
Structures of final compounds and used building blocks
| Example | Structure | BB 1 (1_x) | BB 2 (2_x) | BB 3 (3_x) |
|---|---|---|---|---|
| 79 | 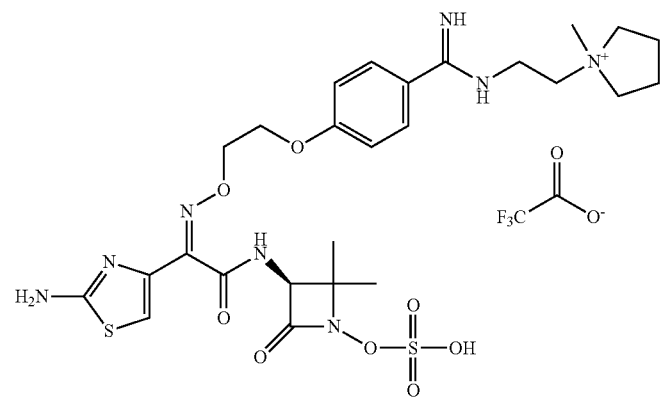 [SMILES: CC1(C)[C@H](NC(=O)/C(=N\OCCOc2ccc(C(=N)NCC[N+]3(C)CCCC3)cc2)c2csc(N)n2)C(=O)N1OS(=O)(=O)O ; O=C([O-])C(F)(F)F] | 1_5_11 | 2_1_1 | 3_54_5 |
| 80 | 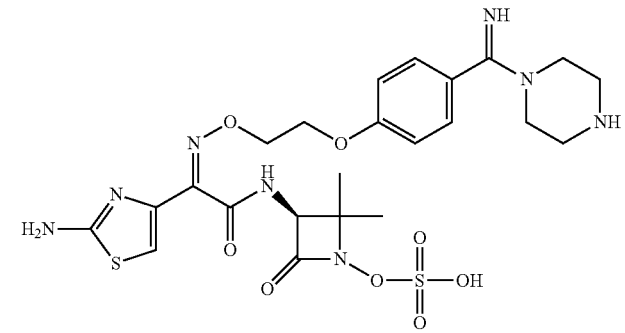 [SMILES: CC1(C)[C@H](NC(=O)/C(=N\OCCOc2ccc(C(=N)N3CCNCC3)cc2)c2csc(N)n2)C(=O)N1OS(=O)(=O)O] | 1_5_11 | 2_1_1 | 3_18_6 |
| 81A | 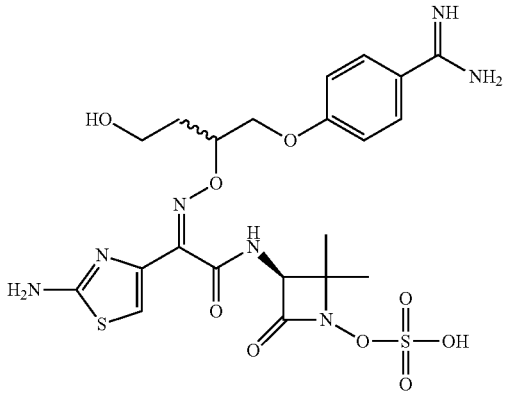
Epimer A | 1_5_11 | 2_1_1 | 3_58_8 |

TABLE 3-continued
Structures of final compounds and used building blocks
| Example | Structure | BB 1 (1_x) | BB 2 (2_x) | BB 3 (3_x) |
|---|---|---|---|---|
| 81B | 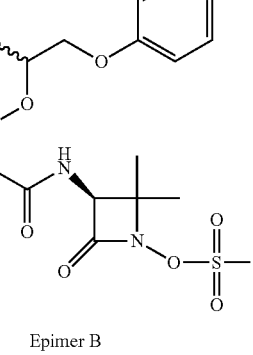 Epimer B | 1_5_11 | 2_1_1 | 3_58_8 |
| 82 | 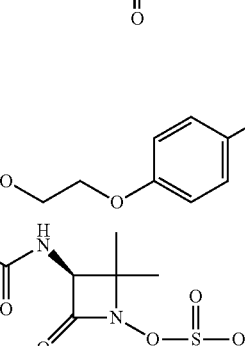 | 1_5_11 | 2_1_1 | 3_33_5 |
| 83 | 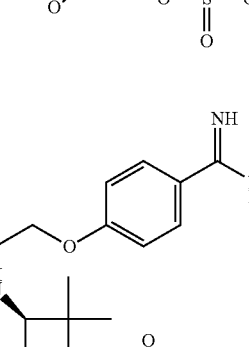 | 1_5_11 | 2_1_1 | 3_16_6 |
| 84 | 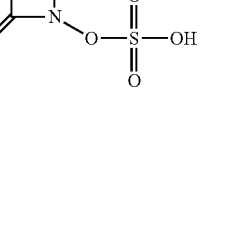 | 1_5_11 | 2_1_1 | 3_21_6 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 85 | 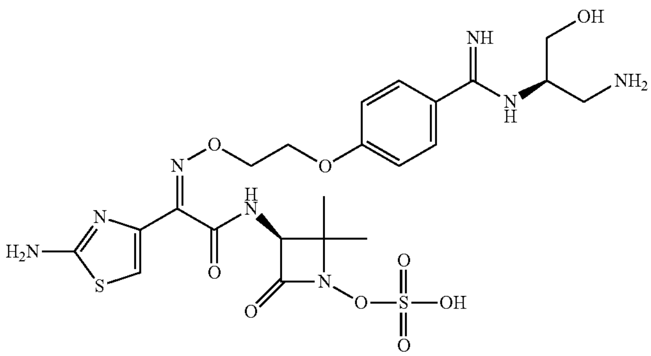 [SMILES: CC1(C)[C@H](NC(=O)/C(=N\OCCOc2ccc(C(=N)N[C@H](CN)CO)cc2)c2csc(N)n2)C(=O)N1OS(=O)(=O)O] | 1_5_11 | 2_1_1 | 3_22_6 |
| 86 | 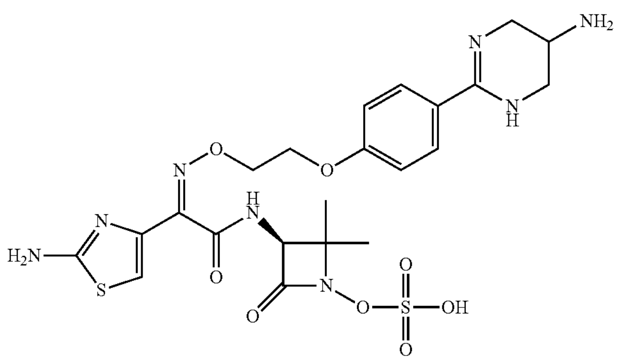 [SMILES: CC1(C)[C@H](NC(=O)/C(=N\OCCOc2ccc(C3=NCC(N)CN3)cc2)c2csc(N)n2)C(=O)N1OS(=O)(=O)O] | 1_5_11 | 2_1_1 | 3_55_5 |
| 87A | Epimer A | from example 112 | | |
| 87B | Epimer B | from example 112 | | |

TABLE 3-continued

Structures of final compounds and used building blocks

| Example | Structure | BB 1 (1_x) | BB 2 (2_x) | BB 3 (3_x) |
|---|---|---|---|---|
| 88 | 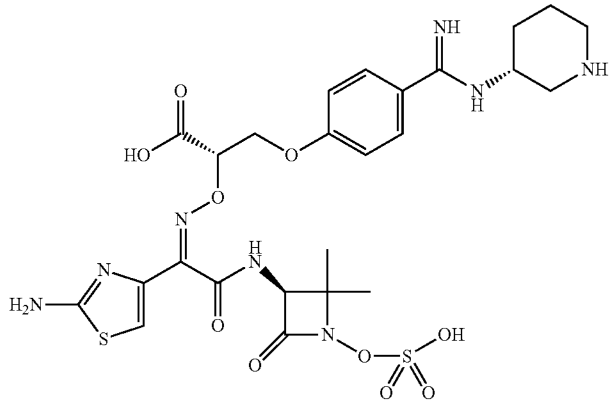 [SMILES: CC1(C)[C@H](NC(=O)/C(=N\O[C@@H](COc2ccc(C(=N)N[C@@H]3CCCNC3)cc2)C(=O)O)c2csc(N)n2)C(=O)N1OS(=O)(=O)O] | 1_5_11 | 2_1_1 | 3_72_8 |
| 89 | 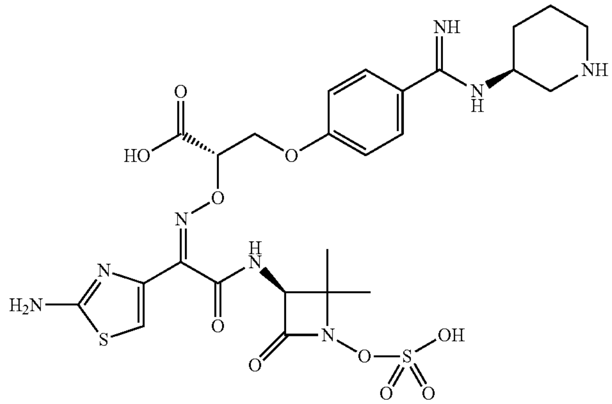 [SMILES: CC1(C)[C@H](NC(=O)/C(=N\O[C@@H](COc2ccc(C(=N)N[C@H]3CCCNC3)cc2)C(=O)O)c2csc(N)n2)C(=O)N1OS(=O)(=O)O] | 1_5_11 | 2_1_1 | 3_73_8 |
| 90 | 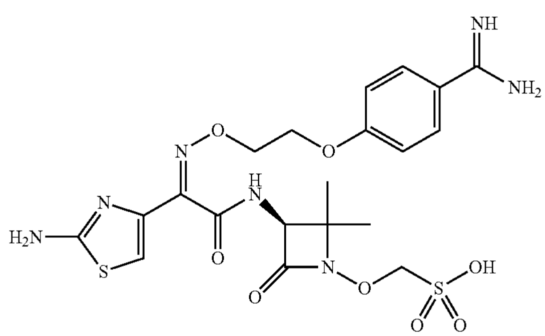 [SMILES: CC1(C)[C@H](NC(=O)/C(=N\OCCOc2ccc(C(=N)N)cc2)c2csc(N)n2)C(=O)N1OCS(=O)(=O)O] | 1_7_5 | 2_1_1 | 3_01_6 |
| 91 | 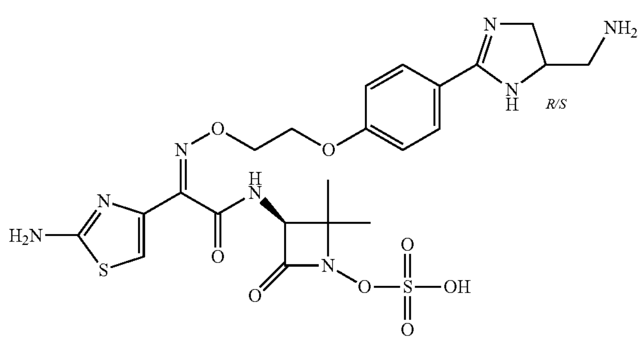 [SMILES: CC1(C)[C@H](NC(=O)/C(=N\OCCOc2ccc(C3=NCC(CN)N3)cc2)c2csc(N)n2)C(=O)N1OS(=O)(=O)O] | 1_5_11 | 2_1_1 | 3_56_5 |

TABLE 3-continued

Structures of final compounds and used building blocks

| Example | Structure | BB 1 (1_x) | BB 2 (2_x) | BB 3 (3_x) |
|---------|-----------|------------|------------|------------|
| 92 | 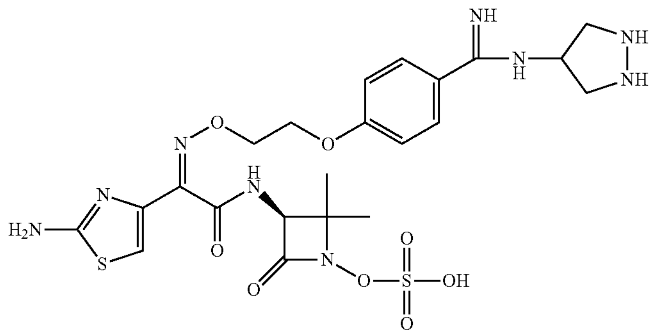 [SMILES: CC1(C)[C@H](NC(=O)/C(=N\OCCOc2ccc(C(=N)NC3CNNC3)cc2)c2csc(N)n2)C(=O)N1OS(=O)(=O)O] | 1_5_11 | 2_1_1 | 3_57_8 |
| 93 | 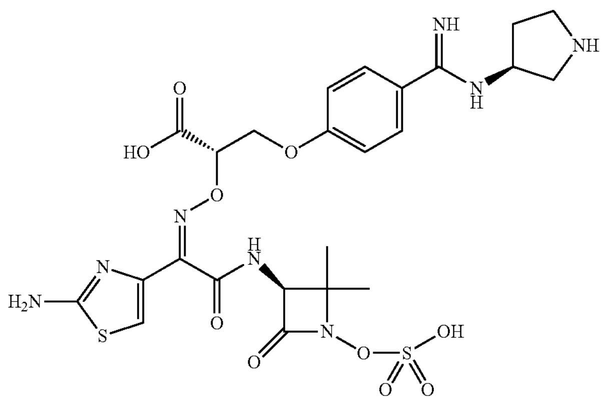 [SMILES: CC1(C)[C@H](NC(=O)/C(=N\O[C@@H](COc2ccc(C(=N)N[C@H]3CCNC3)cc2)C(=O)O)c2csc(N)n2)C(=O)N1OS(=O)(=O)O] | 1_5_11 | 2_1_1 | 3_66_8 |
| 94 | 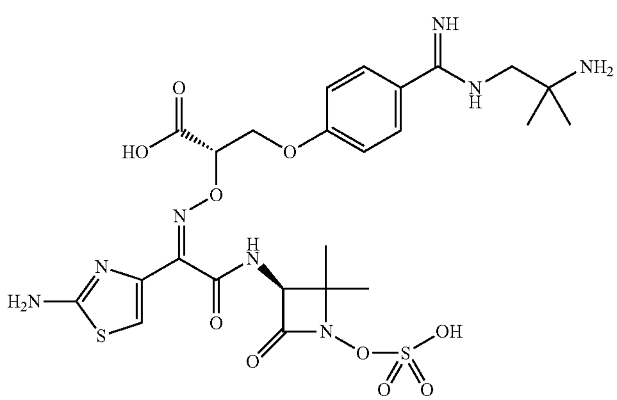 [SMILES: CC(C)(N)CNC(=N)c1ccc(OC[C@H](O/N=C(\C(=O)N[C@@H]2C(=O)N(OS(=O)(=O)O)C2(C)C)c2csc(N)n2)C(=O)O)cc1] | 1_5_11 | 2_1_1 | 3_69_8 |
| 95 | 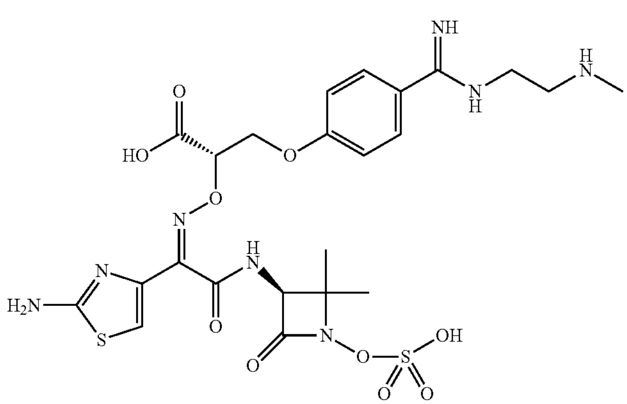 [SMILES: CNCCNC(=N)c1ccc(OC[C@H](O/N=C(\C(=O)N[C@@H]2C(=O)N(OS(=O)(=O)O)C2(C)C)c2csc(N)n2)C(=O)O)cc1] | 1_5_11 | 2_1_1 | 3_65_8 |

TABLE 3-continued

Structures of final compounds and used building blocks

| Example | Structure | BB 1 (1_x) | BB 2 (2_x) | BB 3 (3_x) |
|---|---|---|---|---|
| 96 | 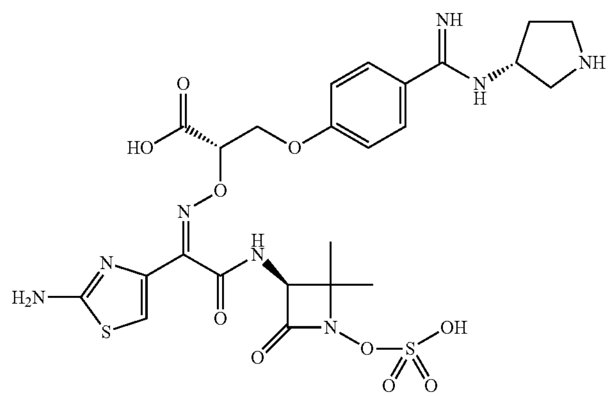 [SMILES: CC1(C)[C@H](NC(=O)/C(=N\O[C@@H](COc2ccc(C(=N)N[C@@H]3CCNC3)cc2)C(=O)O)c2csc(N)n2)C(=O)N1OS(=O)(=O)O] | 1_5_11 | 2_1_1 | 3_67_8 |
| 97 | 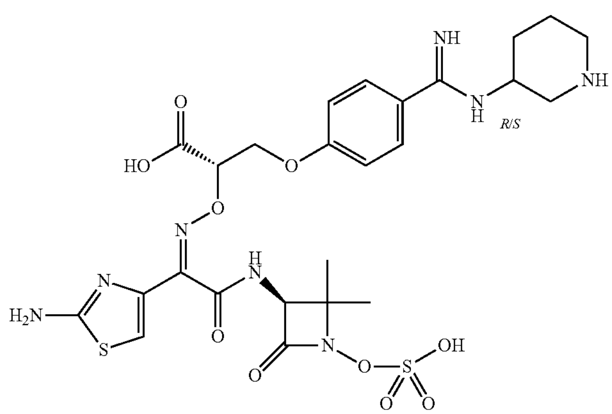 [SMILES: CC1(C)[C@H](NC(=O)/C(=N\O[C@@H](COc2ccc(C(=N)NC3CCCNC3)cc2)C(=O)O)c2csc(N)n2)C(=O)N1OS(=O)(=O)O] | 1_5_11 | 2_1_1 | 3_74_8 |
| 98 | 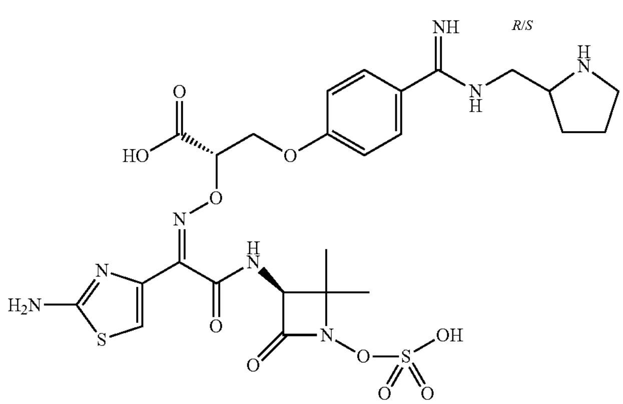 [SMILES: CC1(C)[C@H](NC(=O)/C(=N\O[C@@H](COc2ccc(C(=N)NCC3CCCN3)cc2)C(=O)O)c2csc(N)n2)C(=O)N1OS(=O)(=O)O] | 1_5_11 | 2_1_1 | 3_75_8 |

TABLE 3-continued
Structures of final compounds and used building blocks
| Example | Structure | BB 1 (1_x) | BB 2 (2_x) | BB 3 (3_x) |
|---|---|---|---|---|
| 99 | 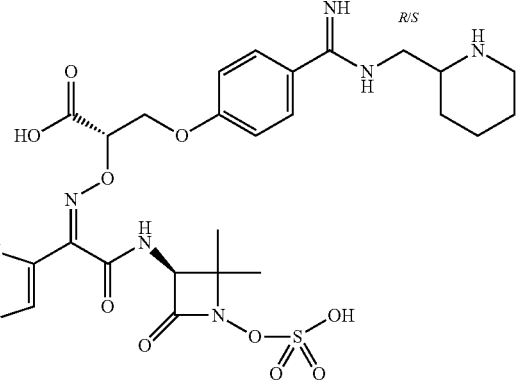 | 1_5_11 | 2_1_1 | 3_78_8 |
| 100A | 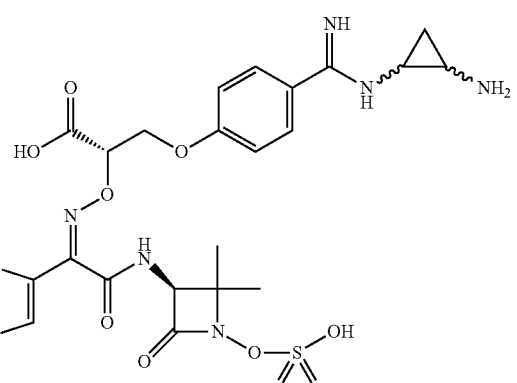  Anti Epimer A | 1_5_11 | 2_1_1 | 3_63_8 |
| 100B | 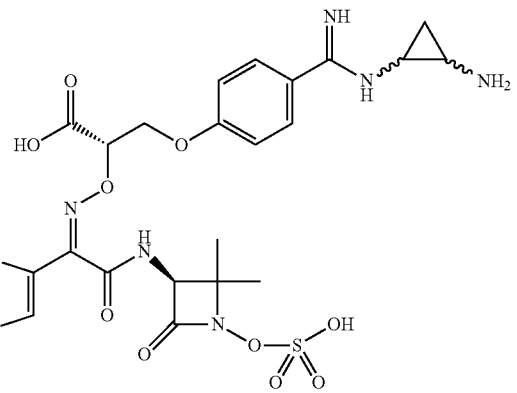  Anti Epimer B | 1_5_11 | 2_1_1 | 3_63_8 |

TABLE 3-continued
Structures of final compounds and used building blocks
| Example | Structure | BB 1 (1_x) | BB 2 (2_x) | BB 3 (3_x) |
|---|---|---|---|---|
| 101 | 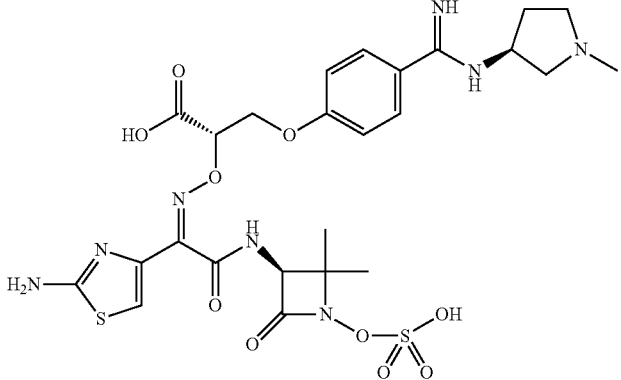 [SMILES: CN1CC[C@H](NC(=N)c2ccc(OC[C@H](O/N=C(\C(=O)N[C@@H]3C(=O)N(OS(=O)(=O)O)C3(C)C)c3csc(N)n3)C(=O)O)cc2)C1] | 1_5_11 | 2_1_1 | 3_76_8 |
| 102 | 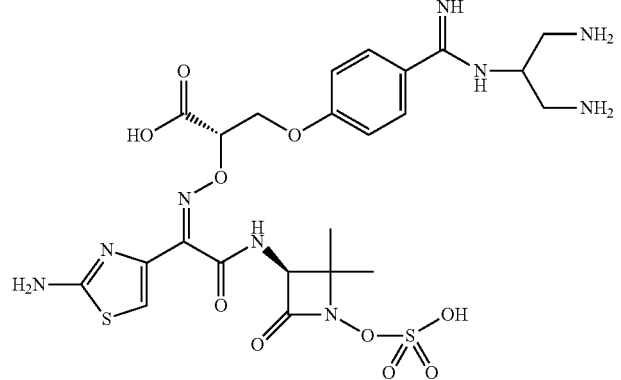 [SMILES: CC1(C)[C@H](NC(=O)/C(=N\O[C@@H](COc2ccc(C(=N)NC(CN)CN)cc2)C(=O)O)c2csc(N)n2)C(=O)N1OS(=O)(=O)O] | 1_5_11 | 2_1_1 | 3_70_8 |
| 103 | 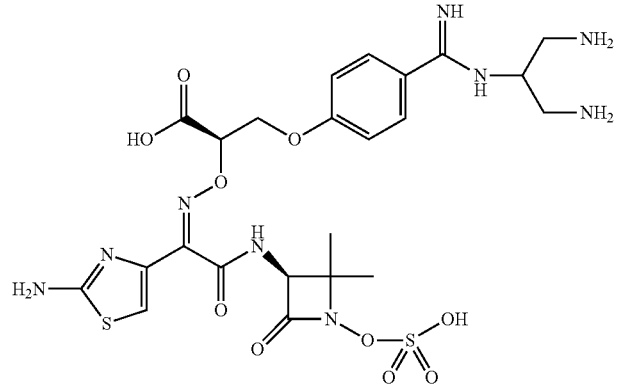 [SMILES: CC1(C)[C@H](NC(=O)/C(=N\O[C@H](COc2ccc(C(=N)NC(CN)CN)cc2)C(=O)O)c2csc(N)n2)C(=O)N1OS(=O)(=O)O] | 1_5_11 | 2_1_1 | 3_80_8 |

TABLE 3-continued
Structures of final compounds and used building blocks
| Example | Structure | BB 1 (1_x) | BB 2 (2_x) | BB 3 (3_x) |
|---|---|---|---|---|
| 104 | 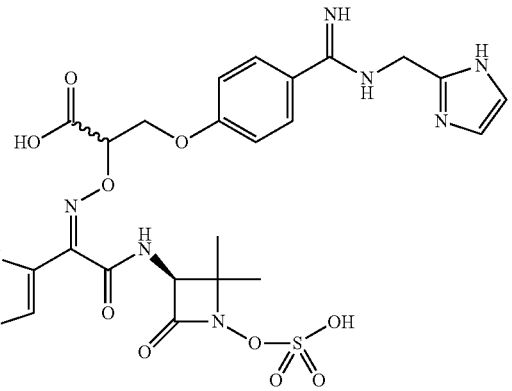<br>epimer A | 1_5_11 | 2_1_1 | 3_71_8 |
| 105 | 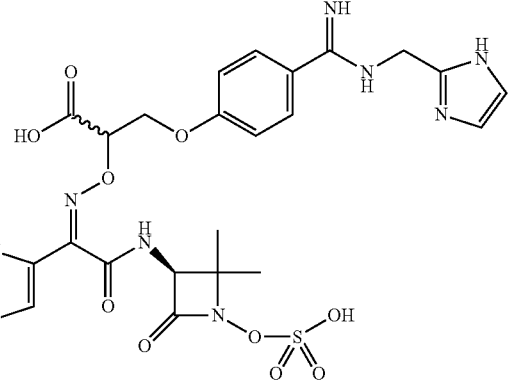<br>epimer B | 1_5_11 | 2_1_1 | 3_81_8 |
| 106 | 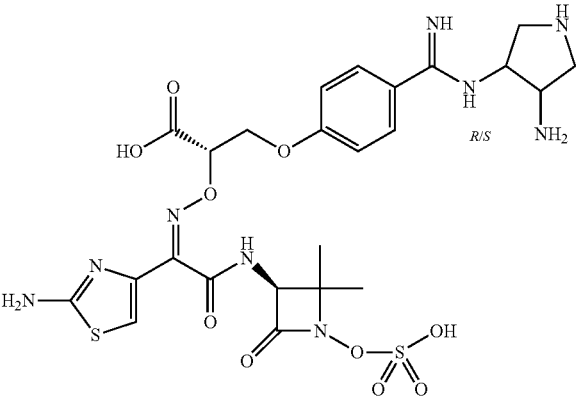 [SMILES: CC1(C)[C@H](NC(=O)/C(=N\O[C@@H](COc2ccc(C(=N)NC3CNCC3N)cc2)C(=O)O)c2csc(N)n2)C(=O)N1OS(=O)(=O)O] | 1_5_11 | 2_1_1 | 3_77_8 |

TABLE 3-continued

Structures of final compounds and used building blocks

| Example | Structure | BB 1 (1_x) | BB 2 (2_x) | BB 3 (3_x) |
|---|---|---|---|---|
| 107 | 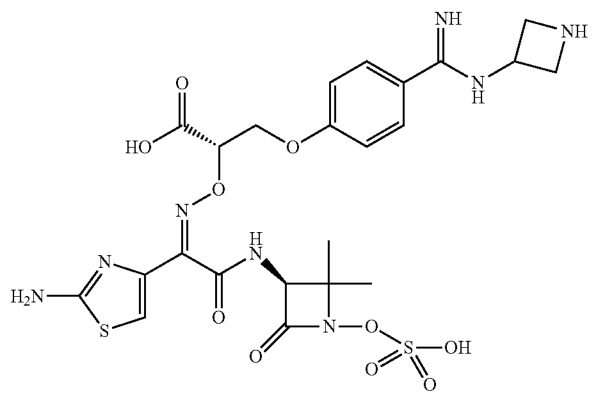 [SMILES: CC1(C)[C@H](NC(=O)/C(=N\O[C@@H](COc2ccc(C(=N)NC3CNC3)cc2)C(=O)O)c2csc(N)n2)C(=O)N1OS(=O)(=O)O] | 1_5_11 | 2_1_1 | 3_64_8 |
| 108 | 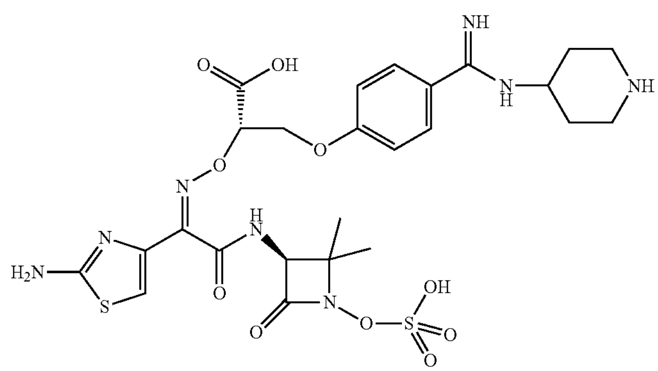 [SMILES: CC1(C)[C@H](NC(=O)/C(=N\O[C@@H](COc2ccc(C(=N)NC3CCNCC3)cc2)C(=O)O)c2csc(N)n2)C(=O)N1OS(=O)(=O)O] | 1_5_11 | 2_1_1 | 3_62_8 |
| 109 | 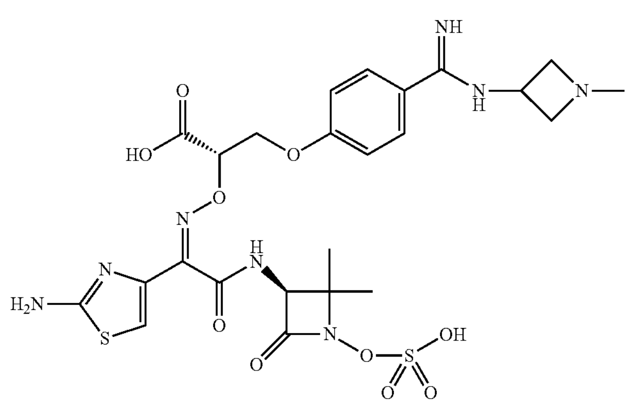 [SMILES: CN1CC(NC(=N)c2ccc(OC[C@H](O/N=C(\C(=O)N[C@@H]3C(=O)N(OS(=O)(=O)O)C3(C)C)c3csc(N)n3)C(=O)O)cc2)C1] | 1_5_11 | 2_1_1 | 3_68_8 |

TABLE 3-continued

Structures of final compounds and used building blocks

| Example | Structure | BB 1 (1_x) | BB 2 (2_x) | BB 3 (3_x) |
|---|---|---|---|---|
| 110 | 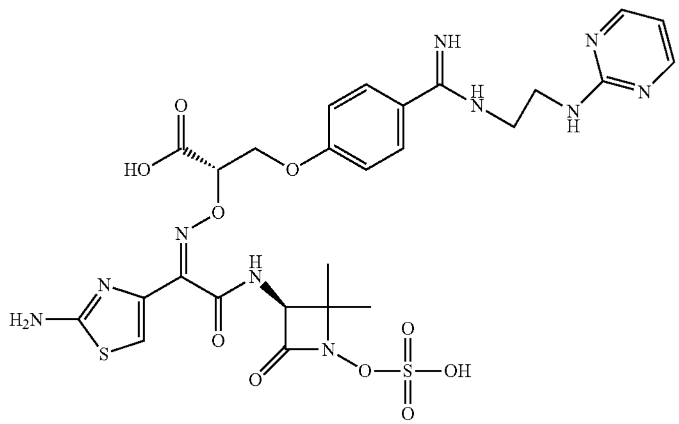 [SMILES: CC1(C)[C@H](NC(=O)/C(=N\O[C@@H](COc2ccc(C(=N)NCCNc3ncccn3)cc2)C(=O)O)c2csc(N)n2)C(=O)N1OS(=O)(=O)O] | 1_5_11 | 2_1_1 | 3_79_8 |
| 111 | 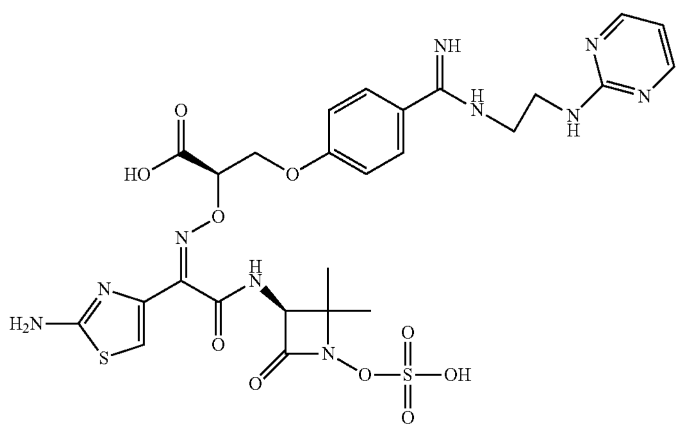 [SMILES: CC1(C)[C@H](NC(=O)/C(=N\O[C@H](COc2ccc(C(=N)NCCNc3ncccn3)cc2)C(=O)O)c2csc(N)n2)C(=O)N1OS(=O)(=O)O] | 1_5_11 | 2_1_1 | 3_82_8 |
| 112 | 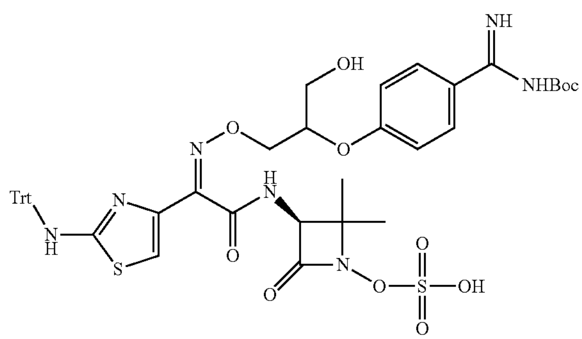 | 1_5_11 | 2_1_1 | 3_84_7 |

Analytical data for examples 1-112 (structures shown above):

Example 1

(2Z)-2-(2-Amino-1,3-thiazol-4-yl)-2-{[2-(4-carbamimidoyl-3-hydroxyphenoxy)ethoxy]imino}-N-[(3S)-2,2-dimethyl-4-oxo-1-(sulfooxy)azetidin-3-yl]ethanamide $^1$H NMR (400 MHz, DMSO-d$_6$): 1.23 (s, 3H), 1.40 (s, 3H), 4.19 (m, 2H), 4.38 (m, 2H), 4.59 (d, J=8.0 Hz, 1H), 6.49 (s, 1H), 6.57 (d, J=8.8 Hz, 1H,), 6.76 (s, 1H), 7.21 (br s, 2H), 7.57 (d, J=8.8 Hz, 1H), 9.49 (d, J=8.0 Hz, 1H).

MS (ES$^+$) m/z: [M+H]$^+$ calcd for C$_{19}$H$_{24}$N$_7$O$_9$S$_2$: 558.11. Found: 558.14.

HPLC: 98.63%

Example 2

(2S,3S)-3-{[(2Z)-2-(2-Amino-1,3-thiazol-4-yl)-2-{[2-(4-carbamimidoyl-3-hydroxyphenoxy)ethoxy]imino}acetyl]amino}-2-methyl-4-oxoazetidine-1-sulfonic acid $^1$H NMR (400 MHz, DMSO-d$_6$): 1.33 (d, J=6.2 Hz, 3H), 3.67 (m., 1H), 4.22 (m, 2H), 4.35 (m, 2H), 4.41 (m, 1H), 6.45 (br. s, 1H,), 6.52 (m, 1H), 6.79 (s, 1H), 7.22 (m, 2H), 7.56 (d, J=8.8 Hz, 1H), 9.32 (m, 1H).

MS (ES⁻) m/z: [M–H]⁻ calcd for $C_{18}H_{20}N_7O_8S_2$: 526.08. Found: 526.13.

HPLC: 91.43%

Example 3

(2S,3S)-3-{[(2Z)-2-(2-Amino-1,3-thiazol-4-yl)-2-({2-[(6-carbamimidoylpyridin-3-yl)oxy]ethoxy}imino)acetyl]amino}-2-methyl-4-oxoazetidine-1-sulfonic acid ¹H NMR (400 MHz, DMSO-d₆): 1.35 (d, J=6.2 Hz, 3H), 3.66 (dd, J=6.0 and 2.5 Hz, 1H), 4.26-4.57 (m, 5H), 6.78 (s, 1H), 7.76 (dd, J=8.9 and 2.7 Hz, 1H), 8.26 (d, J=8.9 Hz, 1H), 8.52 (d, J=2.3 Hz, 1H), 8.95 (s, 2H), 9.21-9.49 (m, 3H).

MS (ES⁻) m/z: [M–H]⁻ calcd for $C_{17}H_{20}N_8O_7S_2$: 512.09. Found: 512.53.

HPLC: 96.60%

Example 4

(2Z)-2-(2-Amino-1,3-thiazol-4-yl)-2-({2-[(6-carbamimidoylpyridin-3-yl)oxy]ethoxy}imino)-N-[(3)-2,2-dimethyl-4-oxo-1-(sulfooxy)azetidin-3-yl]ethanamide ¹H NMR (400 MHz, DMSO-d₆): 1.23 (s, 3H), 1.40 (s, 3H), 3.77 (d, J=3.9 Hz, 1H), 4.42 (d, J=4.6 Hz, 3H), 4.59 (d, J=7.8 Hz, 1H), 7.21 (s, 2H), 7.74 (dd, J=8.7 and 2.9 Hz, 1H), 8.12-8.40 (m, 2H), 8.49 (d, J=2.7 Hz, 1H), 9.44 (d, J=8.2 Hz, 3H).

MS (ES⁻) m/z: [M–H]⁻ calcd for $C_{18}H_{21}N_8O_7S_2$: 541.09. Found: 541.23.

HPLC: 88.45%

Example 5

(2S,3S)-3-{[(2Z)-2-(2-Amino-1,3-thiazol-4-yl)-2-({2-[(5-carbamimidoylpyridin-2-yl)oxy]-ethoxy}imino)acetyl]amino}-2-methyl-4-oxoazetidine-1-sulfonic acid ¹H NMR (400 MHz, DMSO-d₆): 1.33 (d, J=6.2 Hz, 3H), 3.61 (dd, J=6.0 and 2.5 Hz, 1H), 4.35-4.49 (m, 3H), 4.49-4.71 (m, 2H), 6.79 (s, 1H), 7.12 (d, J=8.9 Hz, 1H), 8.10 (dd, J=8.7 and 2.5 Hz, 1H), 8.64 (d, J=1.9 Hz, 1H), 8.86 (s, 4H), 9.12-9.43 (m, 2H).

MS (ES⁻) m/z: [M–H]⁻ calcd for $C_{17}H_{19}N_8O_7S_2$: 511.08. Found: 511.13.

HPLC: 96.6%

Example 6

(2S,3S)-3-{[(2Z)-2-(2-Amino-1,3-thiazol-4-yl)-2-({2-[(4-carbamimidoylphenyl)sulfanyl]ethoxy}imino)acetyl]amino}-2-methyl-4-oxoazetidine-1-sulfonic acid ¹H NMR (400 MHz, DMSO-d₆): 1.40 (d, J=5.8 Hz, 3H), 3.28-3.40 (m, 2H), 3.73 (dd, J=6.0 and 2.5 Hz, 1H), 4.25 (t, J=6.2 Hz, 2H), 4.44 (dd, J=7.8 and 2.3 Hz, 1H), 6.78 and 8.16 (2 s, 1H), 7.22 (br. s, 2H), 7.57 (m, 2H), 7.76 (m, 2H), 8.85 (br. s, 2H), 9.26 (s, 2H), 9.21 (s, 1H).

MS (ES⁺) m/z: [M+H]⁺ calcd for $C_{18}H_{22}N_7O_6S_3$: 528.08. Found: 527.97.

HPLC: 98.3%

Example 7

(2Z)-2-(2-Amino-1,3-thiazol-4-yl)-2-({2-[(4-carbamimidoylphenyl)sulfanyl]ethoxy}imino)-N-[(3S)-2,2-dimethyl-4-oxo-1-(sulfooxy)azetidin-3-yl]ethanamide ¹H NMR (400 MHz, DMSO-d₆): 1.29 (s, 3H), 1.43 (s, 3H), 3.38 (t, J=6.6 Hz, 2H), 4.25 (t, J=6.6 Hz, 2H), 4.61 (d, J=7.8 Hz, 1H), 6.82 (s, 1H), 7.5 (br. s, 2H), 7.55 (d, J=8.6 Hz, 2H), 7.75 (d, J=8.6 Hz, 2H), 8.82 (s, 2H), 9.23 (s, 2H), 9.46 (d, J=7.8 Hz, 1H).

MS (ES⁺) m/z: [M+H]⁺ calcd for $C_{19}H_{24}N_7O_7S_3$: 558.09. Found: 558.09.

HPLC: 92.85%

Example 8

(2S,3S)-3-{[(2Z)-2-(2-Amino-1,3-thiazol-4-yl)-2-({2-[(4-carbamimidoylphenyl)amino]ethoxy}imino)acetyl]amino}-2-methyl-4-oxoazetidine-1-sulfonic acid ¹H NMR (400 MHz, DMSO-d₆): =1.36 (d, J=6.2 Hz, 3H), 3.45 (t, J=4.8 Hz, 2H), 3.66 (dd, J=6.2 and 2.3 Hz, 1H), 4.20 (t, J=5.0 Hz, 2H), 4.45 (dd, J=8.0 and 2.5 Hz, 1H), 6.66-6.86 (m, 3H), 7.65 (d, J=8.9 Hz, 2H), 8.28 (br. s, 2H), 8.77 (s, 2H), 9.27 (d, J=7.8 Hz, 1H).

MS (ES⁺) m/z: [M+H]⁺ calcd for $C_{18}H_{23}N_8O_6S_2$: 511.12. Found: 510.96.

HPLC: 95.40%

Example 9

(2S,3S)-3-{[(2Z)-2-(2-Amino-1,3-thiazol-4-yl)-2-{[2-(4-carbamimidoylphenoxy)ethoxy]imino}acetyl]amino}-2-methyl-4-oxoazetidine-1-sulfonic acid ¹H NMR (400 MHz, DMSO-d₆): 1.33 (d, J=6.3 Hz, 3H), 3.64 (dd, J=6.1 and 2.7 Hz, 2H), 4.34 (d, J=5.3 Hz, 2H), 4.36-4.49 (m, 3H), 6.78 (s, 1H), 7.21 (d, J=8.8 Hz, 2H), 7.80 (d, J=8.8 Hz, 2H), 8.67 (s, 2H), 9.13 (s, 2H), 9.31 (d, J=9.2 Hz, 1H).

MS (ES⁺) m/z: [M+H]⁺ calcd for $C_{18}H_{21}N_7O_7S_2$: 512.09. Found: 512.13.

HPLC: 99.00%

Example 10

(2Z)-2-(2-Amino-1,3-thiazol-4-yl)-2-{[2-(4-carbamimidoylphenoxy)ethoxy]imino}-N-[(2R,3S)-2-methyl-4-oxo-1-(sulfooxy)azetidin-3-yl]ethanamide ¹H NMR (400 MHz, DMSO-d₆): 1.11 (d, J=6.2 Hz, 3H), 4.20-4.44 (m, 5H), 4.85-5.04 (m, 1H), 6.79 (s, 1H), 7.18 (d, J=8.2 Hz, 3H), 7.80 (d, J=8.9 Hz, 2H), 8.67 (s, 2H), 9.15 (s, 2H), 9.34 (d, J=8.6 Hz, 1H).

MS (ES⁺) m/z: [M+H]⁺ calcd for $C_{18}H_{22}N_7O_8S_2$: 528.10. Found: 527.90.

HPLC: 92.10%

Example 11

(2R,3S)-3-{[(2Z)-2-(2-Amino-1,3-thiazol-4-yl)-2-{[2-(4-carbamimidoylphenoxy)ethoxy]imino}acetyl]amino}-2-methyl-4-oxoazetidine-1-sulfonic acid $^1$H NMR (400 MHz, DMSO-d$_6$): 1.33 (d, J=6.2 Hz, 3H), 3.64 (dd, J=6.0 and 2.1 Hz, 1H), 4.33 (br. s, 2H), 4.35-4.47 (m, 3H), 6.76 (s, 1H), 7.15-7.27 (m, 4H), 7.80 (d, J=8.5 Hz, 2H), 8.65 (br. s, 2H), 9.12 (br. s, 2H), 9.29 (d, J=8.2 Hz, 1H).
MS (ES$^-$) m/z: [M−H]$^-$ calcd for C$_{18}$H$_{20}$N$_7$O$_7$S$_2$: 510.09. Found: 510.02.
HPLC: 95.60%

Example 12

{[(2S,3S)-3-{[(2Z)-2-(2-Amino-1,3-thiazol-4-yl)-2-{[2-(4-carbamimidoylphenoxy)ethoxy]imino}acetyl]amino}-2-methyl-4-oxoazetidin-1-yl]oxy}methanesulfonic acid $^1$H NMR (400 MHz, DMSO-d$_6$): 1.30 (d, J=7.8, 1 H), 3.96 (dd, J=6.2 and 1.9 Hz, 1H), 4.25-4.35 (m, 2H), 4.35-4.47 (m, 4H), 6.76 (s, 1H), 7.11-7.29 (m, 4H), 7.82 (d, J=8.9 Hz, 2H), 9.03 (br. s, 4H), 9.25 (d, J=7.8 Hz, 1H).
MS (ES$^-$) m/z: [M−H]$^-$ calcd for C$_{19}$H$_{22}$N$_7$O$_8$S$_2$: 540.10. Found: 540.10.
HPLC: 98.51%

Example 13

(2Z)-2-(2-Amino-1,3-thiazol-4-yl)-2-{[2-(4-carbamimidoyl-3-methylphenoxy)ethoxy]imino}-N-[(3S)-2,2-dimethyl-4-oxo-1-(sulfooxy)azetidin-3-yl]ethanamide $^1$H NMR (400 MHz, DMSO-d$_6$): 1.23 (s, 3H), 1.41 (s, 3H), 2.37 (s, 3H), 4.20-4.31 (m, 2H), 4.40 (t, J=4.3 Hz, 2H), 4.59 (d, J=7.8 Hz, 1H), 6.79 (s, 1H), 6.89-7.06 (m, 1H), 7.40 (d, J=8.6 Hz, 1H), 8.85 (s, 2H), 9.11 (s, 2H), 9.48 (d, J=7.8 Hz, 1H).
MS (ES$^-$) m/z: [M−H]$^-$ calcd for C$_{20}$H$_{24}$N$_7$O$_8$S$_2$: 554.11. Found: 554.14.
HPLC: 97.18%

Example 14

(2S,3S)-3-{[(2Z)-2-(2-Amino-1,3-thiazol-4-yl)-2-{[2-(4-carbamimidoyl-3-methylphenoxy)ethoxy]imino}acetyl]amino}-2-methyl-4-oxoazetidine-1-sulfonic acid $^1$H NMR (400 MHz, DMSO-d$_6$): 1.34 (d, J=6.2 Hz, 3H), 2.36 (s, 3H) 3.60 (dd, J=6.0 and 2.5 Hz, 1H), 4.24-4.31 (m, 2H), 4.35-4.40 (m, 2H), 4.43 (dd, J=8.2 and 2.7 Hz, 1H), 6.75 (s, 1H), 6.92-7.05 (m, 2H), 7.21 (s, 2H), 7.39 (d, J=8.6 Hz, 1H), 8.90 (br. s, 2H), 9.09 (br. s, 2H), 9.27 (d, J=8.2 Hz, 1H).
MS (ES$^-$) m/z: [M−H]$^-$ calcd for C$_{19}$H$_{22}$N$_7$O$_7$S$_2$: 524.10. Found: 524.06.
HPLC: 96.56%

Example 15

(2Z)-2-(2-Amino-1,3-thiazol-4-yl)-2-({2-[(2-carbamimidoylpyridin-4-yl)oxy]ethoxy}imino)-N-[(3S)-2,2-dimethyl-4-oxo-1-(sulfooxy)azetidin-3-yl]ethanamide $^1$H NMR (400 MHz, DMSO-d$_6$): 1.22 (s, 3H), 1.40 (s, 3H), 4.36-4.44 (m, 4H), 4.57 (d, J=2.3 Hz, 1H), 6.76 (s, 1H), 7.19 (s, 2H), 7.36 (m, 1H), 7.86 (s, 1H), 8.61 (m, 1H), 9.20-9.40 (br. s, 2H), 9.45 (m, J=8.2 Hz, 1H).
MS (ES$^+$) m/z: [M+H]$^+$ calcd for C$_{18}$H$_{23}$N$_8$O$_8$S$_2$: 543.11. Found: 543.08.
HPLC: 98.52%

Example 16

(2Z)-2-(2-Amino-1,3-thiazol-4-yl)-2-{[2-(4-carbamimidoylphenoxy)ethoxy]imino}-N-[2-oxo-1-(sulfooxy)-1-azaspiro[3.4]oct-3-yl]ethanamide $^1$H NMR (400 MHz, DMSO-d$_6$): 1.20-1.60 (m, 4H), 1.70-1.90 (m, 3H), 2.10-2.20 (m, 1H), 4.30 (br. s, 2H), 4.40 (br. s, 2H), 4.65 (d, J=8.3 Hz, 1H), 6.96 (s, 1H), 7.20 (m, 4H), 7.80 (d, J=9.2 Hz, 2H), 8.80 (br. s, 2H), 9.10 (br. s, 2H), 9.48 (d, J=8.3 Hz, 1H).
MS (ES$^+$) m/z: [M+H]$^+$ calcd for C$_{21}$H$_{26}$N$_7$O$_8$S$_2$: 568.13. Found: 568.17.
HPLC: 97.04%

Example 17

(2S,3S)-3-{[(2Z)-2-(2-Amino-1,3-thiazol-4-yl)-2-{[2-(4-carbamimidoylphenoxy)-2-methyl-propoxy]imino}acetyl]amino}-2-methyl-4-oxoazetidine-1-sulfonic acid $^1$H NMR (400 MHz, DMSO-d$_6$): 1.24-1.47 (d, 3H), 3.71 (br. s, 1H), 4.15 (s, 2H), 4.44 (br. s, 1H), 6.74 (s, 1H), 7.25 (d, J=8.5 Hz, 2H), 7.22 (br. s, 2H), 7.77 (d, J=8.5 Hz, 2H) 8.96 (br. s, 1H), 9.36 (br. s, 1H).
MS (ES$^+$) m/z: [M+H]$^+$ calcd for C$_{20}$H$_{26}$N$_7$O$_7$S$_2$: 540.13. Found: 540.17.
HPLC: 92.38%

Example 18

(2S,3S)-3-{[(2Z)-2-(2-Amino-1,3-thiazol-4-yl)-2-({[1-(4-carbamimidoylphenoxy)-2-methylpropan-2-yl]oxy}imino)acetyl]amino}-2-methyl-4-oxoazetidine-1-sulfonic acid $^1$H NMR (400 MHz, DMSO-d$_6$): 1.28-1.46 (m, 9H), 3.66 (dd, J=6.1 and 2.3 Hz, 1H), 4.10 (d, J=1.9 Hz, 2H), 4.44 (dd, J=7.9 and 2.5 Hz, 1H), 6.72 (s, 1H), 7.09-7.31 (m, 4H), 7.80 (d, J=8.8 Hz, 2H), 8.65 (br. s, 2H), 8.98-9.20 (m, 3H).
MS (ES$^+$) m/z: [M+H]$^+$ calcd for C$_{20}$H$_{26}$N$_7$O$_7$S$_2$: 540.13. Found: 540.08.
HPLC: 97.8%

Example 19

(2S,3S)-3-{[(2Z)-2-(2-Amino-1,3-thiazol-4-yl)-2-{[2-(4-carbamimidoyl-2-fluorophenoxy)ethoxy]imino}acetyl]amino}-2-methyl-4-oxoazetidine-1-sulfonic acid $^1$H NMR (400 MHz, DMSO-d$_6$): 1.34 (d, J=6.0 Hz, 3H), 4.27-4.52 (m, 4H), 6.77 (s, 1H), 7.40-7.54 (m, 1H), 7.78 (d, J=2.5 Hz, 1H), 7.75 (s, 1H), 8.80 (br. s, 2H), 9.19 (br. s, 2H), 9.31 (s, 1H).
MS (ES$^-$) m/z: [M−H]$^-$ calcd for C$_{18}$H$_{19}$N$_7$O$_7$S$_2$: 528.08. Found: 528.06.
HPLC: 97.7%

Example 20

(2S,3S)-3-{[(2Z)-2-(2-Amino-1,3-thiazol-4-yl)-2-{[2-(4-carbamimidoyl-2-chlorophenoxy)ethoxy]imino}acetyl]amino}-2-methyl-4-oxoazetidine-1-sulfonic acid $^1$H NMR (400 MHz, DMSO-$d_6$): 1.35 (d, J=5.8 Hz, 3H), 3.66 (dd, J=6.0 and 2.5 Hz, 1H), 4.44 (s, 4H), 6.76 (s, 1H), 7.22 (s, 2H), 7.41 (d, J=8.6 Hz, 1H), 7.69-7.89 (m, 1H), 7.96 (d, J=1.9 Hz, 1H), 9.28 (d, J=7.4 Hz, 4H).

MS (ES$^+$) m/z: [M+H]$^+$ calcd for $C_{18}H_{21}ClN_7O_7S_2$: 546.06. Found: 546.15.

HPLC: 99.0%

Example 21

(2S,3S)-3-{[(2Z)-2-(2-Amino-1,3-thiazol-4-yl)-2-({2-[4-(N-hydroxycarbamimidoyl)phenoxy]ethoxy}imino)acetyl]amino}-2-methyl-4-oxoazetidine-1-sulfonic acid $^1$H NMR (400 MHz, DMSO-$d_6$): 1.33 (d, J=6.0 Hz, 3H), 3.64 (m, 1H), 4.25 (m, 2H), 4.40-4.42 (m, 3H), 6.78 (s, 1H), 7.20 (d, J=8.8 Hz, 2H), 7.40 (br. s, 2H), 7.68 (d, J=9.2 Hz, 2H), 8.85 (br. s, 1H), 9.20 (br. s, 1H) 9.31 (d, J=7.6 Hz, 2H), 10.97 (s, 1H).

MS (ES$^+$) m/z: [M+H]$^+$ calcd for $C_{18}H_{22}N_7O_8S_2$: 528.10. Found: 528.15.

HPLC: 95.6%

Example 22

(2Z)-2-(2-Amino-1,3-thiazol-4-yl)-2-({2-[(4-carbamimidoylpyridin-2-yl)oxy]ethoxy}imino)-N-[(3S)-2,2-dimethyl-4-oxo-1-(sulfooxy)azetidin-3-yl]ethanamide $^1$H NMR (400 MHz, DMSO-$d_6$): 1.23 (s, 3H), 1.40 (s, 3H), 4.38-4.41 (m, 2H), 4.50-4.54 (m, 2H), 4.58 (d, J=7.8 Hz, 1H), 6.75 (s, 1H), 7.20 (s, 2H), 7.22 (s, 1H), 7.32 (d, J=5.0 Hz, 1H), 8.40 (d, J=5.4 Hz, 1H), 9.30 (br. s, 1H), 9.45 (d, J=8.2 Hz, 1H).

MS (ES$^+$) m/z: [M+H]$^+$ calcd for $C_{18}H_{23}N_8O_8S_2$: 543.11. Found: 542.98.

HPLC: 91.72%

Example 23

(2Z)-2-(2-Amino-1,3-thiazol-4-yl)-N-[(3S)-2,2-dimethyl-4-oxo-1-(sulfooxy)azetidin-3-yl]-2-[(2-{4-[N-(piperidin-4-yl)carbamimidoyl]phenoxy}ethoxy)imino]ethanamide $^1$H NMR (400 MHz, DMSO-$d_6$): 1.21 (s, 3H), 1.39 (s, 3H), 1.51-1.57 (m, 2H), 1.82-1.90 (m, 2H), 2.52-2.68 (m, 2H), 3.04-3.13 (m, 2H), 3.66-3.79 (m, 1H), 4.26-4.32 (m, 2H), 4.40-4.43 (m, 2H), 4.58 (d, J=7.8 Hz, 1H), 6.77 (s, 1H), 7.16 (d, J=8.9 Hz, 2H), 7.21 (s, 2H), 7.70 (d, J=8.6 Hz, 2H), 9.44 (d, J=8.2 Hz, 1H).

MS (ES$^-$) m/z: [M–H]$^-$ calcd for $C_{24}H_{31}N_8O_8S_2$: 623.17. Found: 622.94.

HPLC: 96.71%

Example 24

(2Z)-2-[(2-{4-[N-(2-Aminoethyl)carbamimidoyl]phenoxy}ethoxy)imino]-2-(2-amino-1,3-thiazol-4-yl)-N-[(3S)-2,2-dimethyl-4-oxo-1-(sulfooxy)azetidin-3-yl]ethanamide $^1$H NMR (400 MHz, DMSO-$d_6$+TFA): 1.18 (s, 3H), 1.38 (s, 3H), 2.48 (t, J=1.7 Hz, 2H), 3.95 (s, 4H), 4.29-4.45 (m, 2H), 4.44-4.58 (m, 2H), 4.59 (d, J=7.8 Hz, 1H), 6.96 (s, 1H), 6.97 (s, 1H), 7.08 (s, 1H), 7.14-7.27 (m, 4H), 7.89 (d, J=8.9 Hz, 2H), 9.68 (d, J=7.8 Hz, 1H), 10.27 (s, 1H).

MS (ES$^-$) m/z: [M–H]$^-$ calcd for $C_{21}H_{27}N_8O_8S_2$: 583.14. Found: 583.14.

HPLC: 98.64%

Example 25

(2Z)-2-(2-Amino-1,3-thiazol-4-yl)-2-({2-[4-(4,5-dihydro-1H-imidazol-2-yl)phenoxy]ethoxy}imino)-N-[(3S)-2,2-dimethyl-4-oxo-1-(sulfooxy)azetidin-3-yl]ethanamide $^1$H NMR (400 MHz, DMSO-$d_6$+TFA): 1.19 (s, 3H), 1.38 (s, 3H), 3.94 (s, 4H), 4.33-4.43 (m, 2H), 4.47-4.56 (m, 2H), 4.60 (d, J=7.8 Hz, 1H), 6.98 (s, 1H), 7.18 (d, J=8.6 Hz, 2H), 7.89 (d, J=8.6 Hz, 2H), 9.69 (d, J=7.4 Hz, 1H), 10.26 (s, 1H), 12.05-12.49 (m, 3H).

MS (ES$^-$) m/z: [M-1-1]$^-$ calcd for $C_{21}H_{24}N_7O_8S_2$: 566.11. Found: 566.16.

HPLC: 98.64%

Example 26

(2S and 2R)-2-({[(1Z)-1-(2-Amino-1,3-thiazol-4-yl)-2-{[(2S,3S)-2-methyl-4-oxo-1-sulfoazetidin-3-yl]amino}-2-oxoethylidene]amino}oxy)-3-(4-carbamidinoyl-phenoxy)propanoic acid Epimer A $^1$H NMR (400 MHz, DMSO-$d_6$): 1.29 (d, J=6.2 Hz, 3H), 3.61 (dd, J=5.7 and 2.8 Hz, 1H), 4.31-4.55 (m, 3H), 4.82 (br. s., 1H), 6.53 (s, 1H), 6.79 (s, 1H), 7.11-7.30 (m, 4H), 7.78 (d, J=9.1 Hz, 2H), 8.85 (br. s., 2H), 9.08 (br. s., 2H).

MS (ES$^-$) m/z: [M–H]$^-$ calcd for $C_{19}H_{20}N_7O_9S_2$: 554.08. Found: 554.20.

HPLC: 99.59% (RT: 11.050 min).

Epimer B $^1$H NMR (400 MHz, DMSO-$d_6$): 1.33 (d, J=6.2 Hz, 3H), 3.75 (br. s., 1H), 4.33-4.58 (m, 3H), 4.85 (br. s., 1H), 6.51 (s, 1H), 6.82 (s, 1H), 7.15-7.29 (m, 4H), 7.78 (d, J=9.1 Hz, 2H), 8.75-8.91 (m, 2H), 9.09 (s, 2H).

MS (ES$^-$) m/z: [M–H]$^-$ calcd for $C_{19}H_{20}N_7O_9S_2$: 554.08. Found: 554.20.

HPLC: 98.82% (RT: 11.168 min).

Example 27

(2S and 2R)-2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)-3-(4-carbamimidoylphenoxy)-propanoic acid Epimer A
$^1$H NMR (400 MHz, DMSO-d$_6$): 1.10 (s, 3H) 1.40 (s, 3H), 4.40 (m, 2H), 4.60 (d, J=6.6 Hz, 1H), 5.0 (m, 1H), 6.80 (s, 1H), 7.17 (d, J=8.8 Hz, 2H), 7.24 (br. s, 2H), 7.80 (d, J=8.8 Hz, 2H), 8.60 (s, 2H), 9.27 (s, 2H), 9.40 (d, J=6.6 Hz, 1H). $^{19}$F NMR: −74.
MS (ES$^-$) m/z: [M−H]$^-$ calcd for C$_{20}$H$_{22}$N$_7$O$_{10}$S$_2$: 584.09. Found: 584.08.
HPLC: 97.15%.

Epimer B
$^1$H NMR (400 MHz, DMSO-d$_6$): 1.24 (s, 3H) 1.420 (s, 3H), 4.45 (m, 2H), 4.60 (d, J=6.6 Hz, 1H), 5.0 (m, 1H), 6.80 (s, 1H), 7.20 (d, J=8.8 Hz, 2H), 7.24 (br. s, 2H), 7.80 (d, J=8.8 Hz, 2H), 8.64 (s, 2H), 9.18 (s, 2H), 9.40 (d, J=6.6 Hz, 1H). $^{19}$F NMR: −74.
MS (ES$^-$) m/z: [M−H]$^-$ calcd for C$_{20}$H$_{22}$N$_7$O$_{10}$S$_2$: 584.09. Found: 584.08.
HPLC: 97.08%.

Example 28

(2S,3S)-3-{[(2Z)-2-(2-Amino-1,3-thiazol-4-yl)-2-({2-[(6-carbamimidoylpyridazin-3-yl)oxy]ethoxy}imino)acetyl]amino}-2-methyl-4-oxoazetidine-1-sulfonic acid $^1$H NMR (400 MHz, DMSO-d$_6$): 1.35 (d, J=6.2 Hz, 3H), 3.62 (dd, J=6.3 and 2.8 Hz, 1H), 4.42 (dd, J=7.9 and 2.6 Hz, 1H), 4.48 (t, J=4.4 Hz, 2H), 4.69-4.85 (m, 2H), 6.76 (s, 1H), 7.22 (s, 2H), 7.64 (d, J=9.4 Hz, 1H), 8.31 (d, J=9.4 Hz, 1H), 9.26 (d, J=7.9 Hz, 1H).
MS (ES$^-$) m/z: [M−H]$^-$ calcd for C$_{16}$H$_{18}$N$_9$O$_7$S$_2$: 512.51. Found: 512.08.
HPLC: 92.31%.

Example 29

(2Z)-2-(2-Amino-1,3-thiazol-4-yl)-2-({2-[(6-carbamimidoylpyridazin-3-yl)oxy]-ethoxy}imino)-N-[(3S)-2,2-dimethyl-4-oxo-1-(sulfooxy)azetidin-3-yl]ethanamide $^1$H NMR (400 MHz, DMSO-d$_6$): 1.24 (s, 3H), 1.40 (s, 3H), 4.45-4.52 (m, 2H), 4.56 (d, J=7.6 Hz, 1H), 4.68-4.84 (m, 2H), 6.79 (s, 1H), 7.62 (d, J=9.4 Hz, 1H), 8.31 (d, J=9.4 Hz, 1H), 9.23 (br. s., 2H), 9.46 (br. s, 1H), 9.69 (br. s, 2H).
MS (ES$^-$) m/z: [M−H]$^-$ calcd for C$_{17}$H$_{20}$N$_9$O$_8$S$_2$: 542.54. Found: 542.13.
HPLC: 91.40%.

Example 30

(2S,3S)-3-{[(2Z)-2-(2-Amino-1,3-thiazol-4-yl)-2-({2-[(5-carbamimidoylpyrazin-2-yl)oxy]-ethoxy}imino)acetyl]amino}-2-methyl-4-oxoazetidine-1-sulfonic acid $^1$H NMR (400 MHz, DMSO-d$_6$): =1.36 (d, J=6.2 Hz, 3H), 3.64 (dd, J=6.3 and 2.5 Hz, 1H), 4.32-4.54 (m, 3H), 4.60-4.77 (m, 2H), 6.80 (s, 1H), 8.58 (d, J=1.2 Hz, 1H), 9.01 (d, J=1.2 Hz, 1H), 9.11 (s, 2H), 9.31 (d, J=7.9 Hz, 1H), 9.47 (s, 2H).
MS (ES$^-$) m/z: [M−H]$^-$ calcd for C$_{16}$H$_{18}$N$_9$O$_7$S$_2$: 512.51. Found: 512.20.
HPLC: 95.45%.

Example 31

(2S,3S)-3-{[(2Z)-2-(2-Amino-1,3-thiazol-4-yl)-2-({2-[(4-carbamimidoyl-1,3-thiazol-2-yl)oxy]ethoxy}imino)acetyl]amino}-2-methyl-4-oxoazetidine-1-sulfonic acid $^1$H NMR (400 MHz, DMSO-d$_6$): 1.37 (d, J=6.2 Hz, 3H), 3.58-3.72 (m, 1H), 4.36-4.55 (m, 3H), 4.64-4.76 (m, 2H), 6.79 (s, 1H), 8.26 (s, 1H), 8.91 (s, 2H), 9.14 (s, 2H), 9.33 (d, J=7.9 Hz, 1H).
MS (ES$^-$) m/z: [M−H]$^-$ calcd for C$_{15}$H$_{17}$N$_8$O$_7$S$_3$: 517.55. Found: 517.23.
HPLC: 98.78%.

Example 32

(2S,3S)-3-{[(2Z)-2-(2-Amino-1,3-thiazol-4-yl)-2-(2-[(4-carbamimidoylthiophen-2-yl)methoxy]imino)acetyl]amino}-2-methyl-4-oxoazetidine-1-sulfonic acid $^1$H NMR (400 MHz, DMSO-d$_6$): 1.38 (d, J=6.2 Hz, 3H), 3.68 (dd, J=6.2 and 2.6 Hz, 1H), 4.42 (dd, J=7.9 and 2.6 Hz, 1H), 5.29 (s, 2H), 6.79 (s, 1H), 7.23 (s, 2H), 7.61 (s, 1H), 8.49 (d, J=1.5 Hz, 1H), 8.66 (s, 2H), 9.17 (s, 2H), 9.34 (d, J=7.6 Hz, 1H).
MS (ES$^+$) m/z: [M+H]$^+$ calcd for C$_{15}$H$_{18}$N$_7$O$_6$S$_3$: 488.54. Found: 488.00.
HPLC: 95.07%.

Example 33

(2Z)-2-(2-Amino-1,3-thiazol-4-yl)-2-({2-[(6-carbamimidoyl-5-hydroxypyridin-3-yl)oxy]ethoxy}imino)-N-[(3S)-2,2-dimethyl-4-oxo-1-(sulfooxy)azetidin-3-yl]ethanamide $^1$H NMR (400 MHz, DMSO-d$_6$): 1.23 (s, 3H), 1.40 (s, 3H), 4.34 (t, J=4.4 Hz, 2H), 4.44 (t, J=4.1 Hz, 2H), 4.60 (d, J=8.2 Hz, 1H), 6.79 (s, 1H), 6.97 (d, J=2.6 Hz, 1H), 8.04 (d, J=2.3 Hz, 1H), 8.61 (s, 2H), 8.84 (s, 2H), 9.45 (d, J=7.9 Hz, 1H).
MS (ES$^-$) m/z: [M−H]$^-$ calcd for C$_{18}$H$_{21}$N$_8$O$_9$S$_2$: 557.55. Found: 557.08.
HPLC: 94.21%.

Example 34

(2S and 2R)-2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)-3-(4-carbamimidoyl-3-hydroxyphenoxy)propanoic acid Epimer A
$^1$H NMR (400 MHz, DMSO-d$_6$): 1.19 (s, 3H), 1.41 (s, 3H), 4.30-4.40 (m, 2H), 4.60 (d, J=8.4 Hz, 1H), 4.95 (m, 1H), 6.51 (s, 1H), 6.60 (m, 1H), 6.80 (s, 1H), 7.25 (br s, 2H), 7.57 (d, J=9.2 Hz, 1H), 8.48 (s, 2H), 8.82 (s, 2H), 9.40 (d, J=8.4 Hz, 1H), 11.29 (s, 1H). $^{19}$F NMR: −74 ppm.

MS (ES⁻) m/z: [M–H]⁻ calcd for $C_{20}H_{22}N_7O_{11}S_2$: 600.08. Found: 600.06.
HPLC: 91.6%.
Epimer B
¹H NMR (400 MHz, DMSO-d₆): 1.24 (s, 3H) 1.420 (s, 3H), 4.45 (m, 2H), 4.60 (d, J=6.6 Hz, 1H), 5.0 (m, 1H), 6.80 (s, 1H), 7.20 (d, J=8.8 Hz, 2H), 7.24 (br s, 2H), 7.80 (d, J=8.8 Hz, 2H), 8.64 (s, 2H), 9.18 (s, 2H), 9.40 (d, J=6.6 Hz, 1H). ¹⁹F NMR: –74 ppm.
MS (ES⁻) m/z: [M–H]⁻ calcd for $C_{20}H_{22}N_7O_{11}S_2$: 600.08. Found: 600.06.
HPLC: 95.4%.

Example 35

(2S,3S)-3-{[(2Z)-2-{[2-(2-Amino-4-carbamimidoyl-phenoxy)ethoxy]imino}-2-(2-amino-1,3-thiazol-4-yl)acetyl]amino}-2-methyl-4-oxoazetidine-1-sulfonic acid ¹H NMR (400 MHz, DMSO-d₆): 1.32 (d, J=6.4 Hz, 3H), 3.52-3.69 (m, 1H), 4.25-4.35 (m, 2H), 4.37-4.50 (m, 3H), 6.79 (s, 1H), 6.92-7.12 (m, 3H), 8.56 (s, 2H), 8.99 (s, 2H), 9.32 (d, J=7.3 Hz, 1H).
MS (ES⁻) m/z: [M–H]⁻ calcd for $C_{18}H_{21}N_8O_7S_2$: 525.55. Found: 525.16.
HPLC: 98.17%.

Example 36

(2S and 2R)-2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)-3-[(6-carbamimidoylpyridin-3-yl)oxy]propanoic acid Epimer A
¹H NMR (400 MHz, DMSO-d₆): 1.21 (s, 3H), 1.42 (s, 3H), 4.56 (m, 2H), 4.66 (d, J=8.6 Hz, 1H), 4.76-4.98 (br, 1H), 6.54 (s, 1H) s, 6.81 (s, 1H), 7.19 (s, 1H), 7.78 (dd, J=8.8 and 2.9 Hz, 2H), 8.25 (d, J=8.6 Hz, 1H), 8.53 (s, J=2.3 Hz, 1H), 9.09 (br. s, 2H), 9.34 (br. s, 2H).
MS (ES⁻) m/z: [M–H]⁻ calcd for $C_{19}H_{22}N_8O_{10}S_2$: 585.10. Found: 585.15.
HPLC: 92.9%.
Epimer B
¹H NMR (400 MHz, DMSO-d₆): 1.28 (s, 3H), 1.42 (s, 3H), 4.35-4.49 (m, 1H), 4.59 (d, J=8.2 Hz, 2H), 4.72-4.91 (m, 1H), 6.54 (s, 1H), 6.84 (s, 1H), 7.19 (s, 2H), 7.80 (d, J=2.7 Hz, 1H), 8.25 (d, J=9.0 Hz, 1H), 8.51 (d, J=2.3 Hz, 1H), 9.13 (br. s, 2H), 9.33 (br. s, 2H).
MS (ES⁻) m/z: [M–H]⁻ calcd for $C_{19}H_{22}N_8O_{10}S_2$: 585.10. Found: 585.15.
HPLC: 91.5%.

Example 37

(2S,3S)-3-{[(2Z)-2-(2-Amino-1,3-thiazol-4-yl)-2-[{3-(4-carbamimidoylphenoxy)propoxy]imino}acetyl]amino}-2-methyl-4-oxoazetidine-1-sulfonic acid ¹H NMR (400 MHz, DMSO-d₆): 1.27 (d, J=8.20 Hz, 3H), 2.01-2.11 (m, 2H), 3.58-3.68 (m, 1H), 4.10-4.17 (m, 2H), 4.22 (t, J=5.66 Hz, 2H), 4.43 (dd, J=8.20, 2.73 Hz, 1H), 6.75 (s, 1H), 7.14 (d, J=8.98 Hz, 2H), 7.78 (d, J=8.59 Hz, 2H), 8.66 (br. s., 2H), 9.07 (br. s, 2H), 9.33 (d, J=8.20 Hz, 1H).

MS (ES⁺) m/z: [M+H]⁺ calcd for $C_{19}H_{23}N_7O_7S_2$: 525.57. Found: 526.27.
HPLC: 98.74%

Example 38

(2Z)-2-(2-Amino-1,3-thiazol-4-yl)-N-[(3S)-1-hydroxy-2,2-dimethyl-4-oxoazetidin-3-yl]-2-({2-[4-(N-{2-[(iminomethyl)amino]ethyl}carbamimidoyl)phenoxy]ethoxy}imino)ethanamide ¹H NMR (400 MHz, DMSO-d₆+TFA): 1.18 (s, 3H), 1.38 (s, 3H), 3.56 (br s, 4H), 4.340-4.37 (m, 2H), 4.50-4.52 (m, 2H), 4.60 (d, J=7.6 Hz, 1H), 6.98 (s, 1H), 7.15-7.18 (m, 2H), 7.71-7.73 (m, 2H), 7.96-7.98 (m, 1H), 8.11 (s, 1H), 9.00-9.10 (m, 2H), 9.32-9.53 (m, 2H), 9.61-9.69 (m, 2H).
MS (ES⁺) m/z: [M+H]⁺ calcd for $C_{22}H_{30}N_9O_8S_2$: 612.17. Found: 612.01.
HPLC: 90.08%

Example 39

(2Z)-2-(2-Amino-1,3-thiazol-4-yl)-N-[(3S)-2,2-dimethyl-4-oxo-1-(sulfooxy)azetidin-3-yl]-2-{[2-(4-{N-[(3S)-pyrrolidin-3-yl]carbamimidoyl}phenoxy)ethoxy]imino}ethanamide ¹H NMR (400 MHz, DMSO-d₆): =1.21 (s, 3H), 1.39 (s, 3H), 1.79-1.97 (m, 1H), 2.12-2.20 (m, 1H), 2.80-2.97 (m, 1H), 3.00-3.15 (m, 3H), 4.14-4.20 (m, 1H), 4.26-4.30 (m, 2H), 4.38-4.42 (m, 2H), 4.58 (d, J=7.82 Hz, 1H), 6.77 (s, 1H), 7.14 (d, J=9.0 Hz, 2H), 7.21 (s, 1H), 7.71 (d, J=9.0 Hz, 2H), 9.44 (d, J=7.8 Hz, 1H).
MS (ES⁺) m/z: [M–H]⁻ calcd for $C_{23}H_{29}N_8O_8S_2$: 609.16. Found: 609.00.
HPLC: 91.82%

Example 40

(2Z)-2-(2-Amino-1,3-thiazol-4-yl)-2-{[2-(4-{N-[2-(dimethylamino)ethyl]carbamimidoyl}phenoxy)ethoxy]imino}-N-[(3S)-2,2-dimethyl-4-oxo-1-(sulfooxy)azetidin-3-yl]ethanamide ¹H NMR (400 MHz, DMSO-d₆): 1.19 (s, 3H), 1.39 (s, 3H), 2.50 (s, 6H), 3.34-3.53 (m, 2H), 3.68-3.84 (m, 2H), 4.21-4.37 (m, 2H), 4.37-4.50 (m, 2H), 4.59 (d, J=7.8 Hz, 1H), 6.81 (s, 1H), 7.19 (d, J=8.99 Hz, 2H), 7.53 (br. s, 1H), 7.79 (d, J=8.9 Hz, 2H), 9.10 (s, 1H), 9.48 (d, J=7.8 Hz, 1H), 9.57 (br. s, 2H), 9.84 (br. s, 1H).
MS (ES⁻) m/z: [M–H]⁻ calcd for $C_{23}H_{31}N_8O_8S_2$: 611.17. Found: 611.01.
HPLC: 97.87%

Example 41

(2Z)-2-(2-Amino-1,3-thiazol-4-yl)-2-{[2-(4-carbamimidoylphenoxy)ethoxy]imino}-N-[(3S)-2,2-dimethyl-4-oxo-1-(sulfooxy)azetidin-3-yl]ethanamide ¹H NMR (400 MHz, DMSO-d₆): 1.21 (s, 3H) 1.39 (s, 3H) 4.19-4.50 (m, 4H) 4.59 (d, J=7.8 Hz, 1H) 6.79 (s, 1H) 7.06-7.31 (m, 2H) 7.81 (d, J=8.9 Hz, 2H) 8.67 (s, 2H) 9.14 (s, 1H) 9.47 (d, J=7.8 Hz, 1H).
MS (ES⁺) m/z: [M+H]⁺ calcd for $C_{19}H_{23}N_7O_8S_2$: 542.10. Found: 542.01.
HPLC: 92.4%.

Example 42

(4S)-4-{[{4-[2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)ethoxy]phenyl}(imino)methyl]amino}-N,N-dimethyl-L-prolinamide ¹H NMR (400 MHz, DMSO-d₆): 1.19 (s, 3H), 1.38 (s, 3H), 2.03-2.10 (m, 1H), 2.40-2.50 (m, 1H), 2.80-3.10 (m, 2H), 2.94 (s, 3H), 3.00 (s, 3H), 4.27-4.32 (m, 2H), 4.40-4.43 (m, 2H), 4.44-4.53 (m, 1H), 4.57 (d, J=8.2 Hz, 1H), 4.65-4.75 (m, 1H), 6.78 (s, 1H), 7.20 (d, J=8.2 Hz, 2H), 7.20-7.39 (m, 1H), 7.73 (d, J=8.2 Hz, 2H), 8.71-8.85 (m, 1H), 9.18 (br. s, 1H), 9.35-9.47 (m, 2H), 9.59 (br. s, 1H), 9.89-10.01 (m, 1H).

MS (ES⁻) m/z: [M−H]⁻ calcd for $C_{26}H_{34}N_9O_9S_2$: 680.19. Found: 680.05.

HPLC: 91.92%

Example 43

(2Z)-2-(2-Amino-1,3-thiazol-4-yl)-N-[(3S)-2,2-dimethyl-4-oxo-1-(sulfooxy)azetidin-3-yl]-2-{[2-(4-{N-[(3S)-1-ethanimidoylpyrrolidin-3-yl]carbamimidoyl}phenoxy)ethoxy]-imino}ethanamide ¹H NMR (400 MHz, DMSO-d₆): 1.19 (s, 3H), 1.39 (s, 3H), 2.25 (d, J=5.4 Hz, 3H), 3.49-3.65 (m, 2H), 3.69-3.83 (m, 3H), 3.85-3.98 (m, 1H), 4.28-1.30 (m, 2H), 4.40-4.42 (m, 2H), 4.47-4.49 (m, 1H), 4.57 (d, J=8.2 Hz, 1H), 6.78 (s, 1H), 7.18 (d, J=9.0 Hz, 2H), 7.24-7.40 (m, 1H), 7.72 (d, J=8.2 Hz, 2H), 8.45 (s, 1H), 9.15-9.35 (m, 2H), 9.44 (d, J=7.4 Hz, 1H), 9.45-9.55 (m, 1H), 9.61-9.70 (m, 1H).

MS (ES⁺) m/z: [M+H]⁺ calcd for $C_{25}H_{34}N_9O_8S_2$: 652.20. Found: 651.92.

HPLC: 86.7%

Example 44

(2R and 2S)-3-{4-[N-(2-Aminoethyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid Epimer A ¹H NMR (400 MHz, DMSO-d₆): 1.26 (s, 3H), 1.35 (s, 3H), 3.14-3.21 (m, 2H), 3.57-3.62 (m, 2H), 4.37-4.46 (m, 2H), 4.57 (d, J=8.0 Hz, 1H), 4.95-4.96 (m, 1H), 6.51 (br. s, 1H), 6.78 (s, 1H), 7.18 (d, J=8.8 Hz, 2H), 7.23 (br. s, 2H), 7.80 (d, J=8.8 Hz, 2H), 7.87 (br. s, 3H), 8.98 (br. s, 1H), 9.38 (d, J=7.3 Hz, 1H), 9.48 (br. s, 2H).

MS (ES⁻) m/z: [M−H]⁻ calcd for $C_{22}H_{27}N_8O_{10}S_2$: 627.13. Found: 626.99.

HPLC: 97.08% (RT: 8.435 min).

Epimer B

¹H NMR (400 MHz, DMSO-d₆): 1.22 (s, 3H), 1.37 (s, 3H), 3.15-3.22 (m, 2H), 3.57-3.62 (m, 2H), 4.42-4.44 (m, 2H), 4.56 (d, J=7.6 Hz, 1H), 4.95-4.99 (m, 1H), 6.50 (br. s, 1H), 6.80 (s, 1H), 7.18-7.22 (m, 4H), 7.80 (d, J=8.8 Hz, 2H), 7.84 (br. s, 3H), 8.98 (br. s, 1H), 9.35 (d, J=7.3 Hz, 1H), 9.43-9.47 (br. s, 2H).

MS (ES⁻) m/z: [M−H]⁻ calcd for $C_{22}H_{27}N_8O_{10}S_2$: 627.13. Found: 626.99.

HPLC: 97.02% (RT: 8.793 min).

Example 45

(2Z)-2-(2-Amino-1,3-thiazol-4-yl)-2-({[(2R and 2S)-1-(4-carbamimidoylphenoxy)-3-hydroxypropan-2-yl]oxy}imino)-N-[(3S)-2,2-dimethyl-4-oxo-1-(sulfooxy)azetidin-3-yl]ethanamide Epimer A ¹H NMR (400 MHz, DMSO-d₆): 1.20 (s, 3H), 1.40 (s, 3H), 3.59-3.77 (m, 2H), 4.21-4.29 (m, 2H), 4.38-4.44 (m, 1H), 4.56 (d, J=7.6 Hz, 1H), 6.78 (s, 1H), 7.18 (d, J=8.8 Hz, 2H), 7.81 (d, J=9.1 Hz, 2H), 8.66 (s, 2H), 9.14 (s, 2H), 9.37 (d, J=7.6 Hz, 1H).

MS (ES⁻) m/z: [M−H]⁻ calcd for $C_{20}H_{24}N_7O_9S_2$: 570.11. Found: 570.08.

HPLC: 87.39% (RT: 2.210 min).

Epimer B

¹H NMR (400 MHz, DMSO-d₆): 1.21 (s, 3H), 1.36 (s, 3H), 3.65-3.72 (m, 2H), 4.15-4.22 (m, 1H), 4.24-4.30 (m, 1H), 4.38-4.44 (m, 1H), 4.56 (d, J=7.6 Hz, 1H), 6.78 (s, 1H), 7.16 (d, J=9.1 Hz, 2H), 7.79 (d, J=9.1 Hz, 2H), 8.64 (s, 2H), 9.12 (s, 2H), 9.34 (d, J=7.6 Hz, 1H).

MS (ES⁻) m/z: [M−H]⁻ calcd for $C_{20}H_{24}N_7O_9S_2$: 570.11. Found: 570.08.

HPLC: 92.48% (RT: 2.317 min).

Example 46

3-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-4-(4-carbamimidoylphenoxy)butanoic acid ¹H NMR (400 MHz, DMSO-d₆): =1.24 (d, 3H), 1.40 (s, 3H), 2.65-2.76 (m, 2H), 4.26 (d, J=5.5 Hz, 2H), 4.57 (dd, J=7.6 and 3.7 Hz, 1H) 4.77 (br. s, 1H), 6.79 (s, 1H), 7.18 (dd, J=9.0 and 3.1 Hz, 2H), 7.23-7.32 (br. s, 2H), 7.81 (d, J=7.4 Hz, 2H), 8.70 (br. s, 2H), 9.13 (s, 2H), 9.36 (m, 1H).

MS (ES⁺) m/z: [M+H]⁺ calcd for $C_{21}H_{25}N_7O_{10}S_2$: 600.11. Found: 599.98.

HPLC: 95.2%.

Example 47

(2Z)-2-(2-Amino-1,3-thiazol-4-yl)-2-{[2-(4-carbamimidoylphenoxy)ethoxy]imino}-N-[(2S,3S)-2-methyl-4-oxo-1-(sulfooxy)azetidin-3-yl]ethanamide ¹H NMR (400 MHz, DMSO-d₆): 1.32 (d, J=6.2 Hz, 3H), 3.90 (m, 1H), 4.28-4.48 (m, 2H), 4.40-4.48 (m, 3H), 6.78 (s, 1H), 7.28-7.32 (m, 3H), 7.80 (d, J=8.9 Hz, 2H), 8.67 (s, 2H), 9.15 (s, 2H), 9.44 (d, J=8.6 Hz, 1H).

MS (ES⁺) m/z: [M+H]⁺ calcd for $C_{18}H_{22}N_7O_8S_2$: 528.10. Found: 528.10.

HPLC: 92.75%.

Example 48

(2R,3S)-3-{[(2Z)-2-(2-Amino-1,3-thiazol-4-yl)-2-{[3-(4-carbamimidoylphenoxy)propoxy]imino}acetyl]amino}-2-methyl-4-oxoazetidine-1-sulfonic acid ¹H NMR (400 MHz, DMSO-d₆): 1.30 (d, J=6.2 Hz, 3H), 2.08 (m, 2H), 3.17-4.25 (m, 5H), 4.44 (dd, J=2.4 and 7.8 Hz, 1H), 6.77 (s, 1H), 7.11 (d, J=9.0 Hz, 2H), 7.80 (d, J=9.0 Hz, 2H), 8.68 (s, 2H), 9.09 (s, 2H), 9.35 (d, J=8.2 Hz, 1H).

MS (ES$^+$) m/z: [M+H]$^+$ calcd for $C_{19}H_{24}N_7O_7S_2$: 526.12. Found: 526.08.

HPLC: 94.79%.

Example 49

(2S,3S)-3-{[(2Z)-2-(2-Amino-1,3-thiazol-4-yl)-2-{[2-(2-bromo-4-carbamimidoyl-phenoxy)ethoxy]imino}acetyl]amino}-2-methyl-4-oxoazetidine-1-sulfonic acid $^1$H NMR (400 MHz, DMSO-d$_6$): 1.36 (d, J=6.2 Hz, 3H), 3.67 (dd, J=2.7 and 5.8 Hz, 1H), 4.36-4.52 (m, 5H), 6.79 (s, 1H), 7.37 (d, J=8.9 Hz, 1H), 7.86 (d, J=1.9 Hz, 1H), 8.10 (d, J=2.3 Hz, 1H), 8.80 (br. s., 2H), 9.20 (br. s, 2H), 9.30 (br. s, 1H).

MS (ES$^-$) m/z: [M–H]$^-$ calcd for $C_{18}H_{20}BrN_7O_7S_2$: 590.00. found: 589.88.

HPLC: 93.93%.

Example 50

(2S,3S)-3-{[(2Z)-2-(2-Amino-1,3-thiazol-4-yl)-2-{[2-(4-carbamimidamidophenoxy)ethoxy]imino}acetyl]amino}-2-methyl-4-oxoazetidine-1-sulfonic acid $^1$H NMR (400 MHz, DMSO-d$_6$): 1.35 (d, J=6.4 Hz, 2H), 3.64 (m, 1H), 4.24 (m, 2H), 4.42 (m, 2H), 4.44 (m, 1H), 6.80 (s, 1H), 7.03 (d, J=8.4 Hz, 2H), 7.17 (s, 6H), 9.34 (s, 1H), 9.36 (s, 1H).

MS (ES$^+$) m/z: [M+H]$^+$ calcd for $C_{18}H_{22}N_8O_7S_2$: 527.10. Found: 527.02.

HPLC: 93.93%.

Example 51

(2S,3S)-3-{[(2Z)-2-(2-Amino-1,3-thiazol-4-yl)-2-{[3-(4-carbamimidamidophenoxy)propoxy]imino}acetyl]amino}-2-methyl-4-oxoazetidine-1-sulfonic acid $^1$H NMR (400 MHz, DMSO-d$_6$): δ=1.35 (d, J=6.0 Hz, 2H), 2.07 (m, 2H), 3.65 (m, 1H), 4.06 (t, J=6.0 Hz, 2H), 4.23 (t, J=6.0 Hz, 2H), 4.50 (m, 1H), 6.78 (s, 1H), 7.01 (d, J=8.8 Hz, 2H), 7.16 (br. s, 6H), 9.33 (s, 1H), 9.36 (d, J=8.8 Hz, 1H).

MS (ES$^+$) m/z: [M+H]$^+$ calcd for $C_{19}H_{24}N_8O_7S_2$: 541.12. Found: 541.01.

HPLC: 95.00%.

Example 52

(2Z)-2-(5-Amino-1,2,4-thiadiazol-3-yl)-2-{[2-(4-carbamimidoylphenoxy)ethoxy]-imino}-N-[(2S,3S)-1-hydroxy-2-methyl-4-oxoazetidin-3-yl]ethanamide $^1$H NMR (400 MHz, DMSO-d$_6$): 1.32 (d, J=6.0 Hz, 3H), 3.57 (m, 2H), 4.34 (m, 2H), 4.40 (dd, J=2.4 and 7.6 Hz, 2H), 4.49 (m, 2H), 7.21 (d, J=8.8 Hz, 2H), 7.80 (d, J=8.8 Hz, 2H), 8.16 (s, 2H), 8.67 (s, 2H), 9.13 (s, 2H), 9.33 (s, 2H).

MS (ES$^+$) m/z: [M+H]$^+$ calcd for $C_{17}H_{20}N_8O_7S_2$: 512.09. Found: 512.85.

HPLC: 91.20%.

Example 53

(2S,3S)-3-{[(2Z)-2-(2-Amino-1,3-thiazol-4-yl)-2-{[2-(3-carbamimidoylphenoxy)ethoxy]imino}acetyl]amino}-2-methyl-4-oxoazetidine-1-sulfonic acid $^1$H NMR (400 MHz, DMSO-d$_6$): =1.33 (d, J=6.0 Hz, 3H), 3.66 (qd, J=2.5 and 6.0 Hz, 1H), 4.26-4.36 (m, 2H), 4.36-4.51 (m, 3H), 6.82 (s, 1H), 7.30-7.41 (m, 3H), 7.51 (t, J=8.0 Hz, 1H), 8.94 (br. s, 2H), 9.25 (br. s, 2H), 9.37 (d, J=7.9 Hz, 1H).

MS (ES$^-$) m/z: [M–H]$^-$ calcd for $C_{18}H_{21}N_7O_7S_2$: 512.09. Found: 511.97.

HPLC: 90.81%.

Example 54

(2S,3S)-3-({(2Z)-2-(2-Amino-1,3-thiazol-4-yl)-2-[(2-{4-[N-(propan-2-yl)carbamimidoyl]phenoxy}ethoxy)imino]acetyl}amino)-2-methyl-4-oxoazetidine-1-sulfonic acid $^1$H NMR (400 MHz, DMSO-d$_6$): 1.23 (d, J=6.4 Hz, 6H), 1.31 (d, J=6.4 Hz, 3H), 3.6 (m, 1H), 3.9 (m, 1H), 4.29 (d, J=4.0 Hz, 2H), 4.39 (m, 3H), 6.73 (s, 1H), 7.17 (m, 4H), 7.65 (d, J=8.8 Hz, 2H), 8.68 (s, 2H), 9.06 (br. s, 1H), 9.26 (d, J=8.0 Hz, 1H).

MS (ES$^-$) m/z: [M–H]$^-$ calcd for $C_{21}H_{26}N_7O_7S_2$: 552.13. Found: 551.90.

HPLC: 94.27%.

Example 55

(2S,3S)-3-{[(2Z)-2-(2-Amino-1,3-thiazol-4-yl)-2-{[(4-carbamimidoylbenzyl)oxy]imino}-acetyl]amino}-2-methyl-4-oxoazetidine-1-sulfonic acid $^1$H NMR (400 MHz, DMSO-d$_6$): 1.38 (d, J=6.4 Hz, 3H), 3.65 (dd, J=2.5 and 6.0 Hz, 1H), 4.45 (dd, J=2.9 and 7.9 Hz, 1H), 5.26 (s, 1H), 6.78 (s, 1H), 7.28 (br. s, 2H), 7.59 (d, J=8.5 Hz, 2H), 7.79 (d, J=8.5 Hz, 2H), 8.86 (s, 2H), 9.24 (s, 1H), 9.44 (d, J=7.9 Hz, 1H).

MS (ES$^+$) m/z: [M+H]$^+$ calcd for $C_{17}H_{20}N_7O_6S_2$: 482.09. Found: 481.93.

HPLC: 96.47%.

Example 56

(2S,3S)-3-{[(2Z)-2-(2-Amino-1,3-thiazol-4-yl)-2-({2-[(4-carbamimidoylthiophen-2-yl)methoxy]ethoxy}imino)acetyl]amino}-2-methyl-4-oxoazetidine-1-sulfonic acid $^1$H NMR (400 MHz, DMSO-d$_6$): 1.36 (d, 3H), 3.61-3.80 (m, 3H), 4.16-4.28 (m, 2H), 4.41 (dd, J=7.9, 2.6 Hz, 1H), 4.71 (s, 2H), 6.72 (s, 1H), 7.20 (s, 2H), 7.55 (s, 1H), 8.45 (d, J=1.5 Hz, 1H), 8.70 (br. s, 2H), 9.10 (br. s, 2H), 9.28 (d, J=7.6 Hz, 1H).

MS (ES$^-$) m/z: [M–H]$^-$ calcd for $C_{17}H_{20}N_7O_7S_3$: 530.59. Found: 530.07.

HPLC: 97.62%.

Example 57

(2Z)-2-(2-Amino-1,3-thiazol-4-yl)-2-{[(4-carbamimidoylbenzyl)oxy]imino}-N-[(3S)-2,2-dimethyl-4-oxo-1-(sulfooxy)azetidin-3-yl]ethanamide $^1$H NMR (400 MHz, DMSO-$d_6$): 1.22 (s, 3H), 1.43 (s, 3H), 4.60-4.66 (m, 1H), 5.25 (s, 2H), 6.75 (s, 1H), 7.20 (s, 2H), 7.59 (d, J=8.6 Hz, 2H), 7.78 (d, J=8.6 Hz, 2H), 8.22 (s, 1H), 9.07-9.17 (m, 2H), 9.19-9.27 (m, 1H), 9.59 (d, J=7.9 Hz, 1H).

MS (ES$^-$) m/z: [M−H]$^-$ calcd for $C_{18}H_{20}N_7O_7S_2$: 510.08. Found: 510.16.

HPLC: 99.75%.

Example 58

(2Z)-2-(2-Amino-1,3-thiazol-4-yl)-2-{[3-(4-carbamimidoylphenoxy)propoxy]imino}-N-[(3S)-2,2-dimethyl-4-oxo-1-(sulfooxy)azetidin-3-yl]ethanamide $^1$H NMR (400 MHz, DMSO-$d_6$): 1.23 (s, 3H), 1.39 (s, 3H), 2.03-2.13 (m, 2H), 4.17 (t, J=8.0 Hz, 2H), 4.23 (t, J=8.0 Hz, 2H), 4.60 (d, J=7.9 Hz, 1H), 6.76 (s, 1H), 7.16 (d, J=9.2 Hz, 2H), 7.81 (d, J=8.9 Hz, 2H), 8.67 (s, 2H), 9.12 (s, 2H), 9.49 (d, J=7.9 Hz, 1H).

MS (ES$^+$) m/z: [M+H]$^+$ calcd for $C_{20}H_{25}N_7O_8S_2$: 556.12. Found: 556.14.

HPLC: 98.10%.

Example 59

(2S,3S)-3-{[(2Z)-2-(2-Amino-1,3-thiazol-4-yl)-2-({2-[4-carbamimidoyl-2-(hydroxymethyl) phenoxy]ethoxy}imino)acetyl]amino}-2-methyl-4-oxoazetidine-1-sulfonic acid $^1$H NMR (400 MHz, METHANOL-$d_4$): 1.45 (d, J=8.0 Hz, 2H), 3.82 (dd, J=2.7 and 6.1 Hz, 1H), 4.39-4.49 (m, 1H), 4.50-4.62 (m, 2H), 4.66-4.81 (m, 2H), 6.85 (s, 1H), 7.19 (d, J=8.5 Hz, 1H), 7.74 (dd, J=2.3 and 8.7 Hz, 1H), 7.85 (d, J=1.9 Hz, 1H).

MS (ES$^-$) m/z: [M−H]$^-$ calcd for $C_{19}H_{23}N_7O_8S_2$: 540.1. Found: 540.1.

HPLC: 86.90%.

Example 60

(2S,3S)-3-({(2Z)-2-(2-Amino-1,3-thiazol-4-yl)-2-[(2-{4-carbamimidoyl-2-[(formyloxy)-methyl]phenoxy}ethoxy)imino]acetyl}amino)-2-methyl-4-oxoazetidine-1-sulfonic acid $^1$H NMR (400 MHz, DMSO-$d_6$): 1.33 (d, J=6.2 Hz, 3H), 3.62 (dd, J=2.5 and 6.0 Hz, 1H), 4.27-4.50 (m, 3H), 5.23 (s, 2H), 6.75 (s, 2H), 7.21 (s, OH), 7.31 (d, J=8.9 Hz, 1H), 7.65-7.93 (m, 3H), 8.27-8.43 (m, 2H), 9.11 (br. s, 1H), 9.28 (d, 2H).

MS (ES$^-$) m/z: [M−H]$^-$ calcd for $C_{20}H_{22}N_7O_9S_2$: 568.09. Found: 568.09.

HPLC: 86.60%.

Example 61

(2S,3S)-3-{[(2Z)-2-(2-Amino-5-chloro-1,3-thiazol-4-yl)-2-{[2-(4-carbamimidoylphenoxy)ethoxy]imino}acetyl]amino}-2-methyl-4-oxoazetidine-1-sulfonic acid $^1$H NMR (400 MHz, DMSO-$d_6$): =1.31 (d, J=6.3 Hz, 3H), 3.60 (m, 1H), 4.38 (m, 2H), 4.40 (m, 1H), 4.42 (m, 2H), 7.21 (d, J=8.9 Hz, 2H), 7.80 (d, J=9.2 Hz, 2H), 8.66 (s, 2H), 9.12 (s, 2H), 9.30 (d, J=8.4 Hz, 1H).

MS (ES$^-$) m/z: [M−H]$^-$ calcd for $C_{18}H_{20}ClN_7O_7S_2$: 544.05. Found: 544.14.

HPLC: 97.10%.

Example 62

(2S,3S)-3-{[(2Z)-2-({2-[4-(2-Amino-2-iminoethyl)phenoxy]ethoxy}imino)-2-(2-amino-1,3-thiazol-4-yl)acetyl]amino}-2-methyl-4-oxoazetidine-1-sulfonic acid $^1$H NMR (400 MHz, DMSO-$d_6$): 1.23-1.46 (m, 3H), 2.49 (br. s., 1H), 3.56-3.75 (m, 2H), 4.09-4.27 (m, 2H), 4.27-4.52 (m, 2H), 6.56-6.83 (m, 1H), 6.86-7.04 (m, 2H), 7.17-7.43 (m, 3H), 8.32-8.53 (m, 2H), 8.82-9.10 (m, 2H), 9.26 (s, 1H).

MS (ES$^+$) m/z: [M+H]$^+$ calcd for $C_{19}H_{24}N_7O_7S_2$: 526.12. Found: 526.13.

HPLC: 95.50%.

Example 63

(2S,3S)-3-({(2Z)-2-(2-Amino-1,3-thiazol-4-yl)-2-[(2-{4-[(2-formylhydrazinyl)(imino)methyl]phenoxy}ethoxy)imino]acetyl}amino)-2-methyl-4-oxoazetidine-1-sulfonic acid $^1$H NMR (400 MHz, DMSO-$d_6$): 1.34 (d, J=6.2 Hz, 3H), 3.44 (br. s., 2H), 3.61-3.73 (m, 1H), 4.30-4.38 (m, 2H), 4.38-4.48 (m, 3H), 6.78 (s, 1H), 7.25 (d, J=8.9 Hz, 2H), 7.78 (d, J=8.9 Hz, 2H), 8.23 (s, 1H), 9.32 (d, J=7.8 Hz, 1H), 9.41 (br. s, 1H), 9.80 (br. s, 1H), 10.73 (s, 1H).

MS (ES$^+$) m/z: [M+H]$^+$ calcd for $C_{19}H_{23}N_8O_8S_2$: 555.56. Found: 555.23.

HPLC: 92.05%.

Example 64

(2S,3S)-3-({(2Z)-2-(2-Amino-1,3-thiazol-4-yl)-2-[(2-{4-[hydrazinyl(imino)methyl]phenoxy}ethoxy)imino]acetyl}amino)-2-methyl-4-oxoazetidine-1-sulfonic acid $^1$H NMR (400 MHz, DMSO-$d_6$): 1.40 (d, J=6.2 Hz, 3H), 3.58-3.71 (m, 1H), 4.26-4.36 (m, 2H), 4.35-4.51 (m, 3H), 5.13-5.31 (m, 1H), 6.73 (s, 1H), 7.28 (br. s, 2H), 7.69 (d, 2H), 7.78 (d, J=8.9 Hz, 2H), 8.72 (br. s, 1H), 9.26 (br. s, 2H), 10.75 (br. s, 1H).

MS (ES⁻) m/z: [M−H]⁻ calcd for $C_{18}H_{21}N_8O_7S_2$: 525.54. Found: 525.31.

HPLC: 96.80%.

Example 65

(2S,3S)-3-{[(2Z)-2-(2-Amino-1,3-thiazol-4-yl)-2-({2-[(5-carbamimidoyl-1,3,4-thiadiazol-2-yl)oxy]ethoxy}imino)acetyl]amino}-2-methyl-4-oxoazetidine-1-sulfonic acid ¹H NMR (400 MHz, DMSO-d₆): 1.39 (d, J=6.25 Hz, 3H), 3.64 (dd, J=6.1 and 2.5 Hz, 1H), 4.38-4.52 (m, 3H), 4.81 (d, J=4.7 Hz, 2H), 6.78 (s, 1H), 9.29 (d, J=8.2 Hz, 1H), 9.42 (s, 2H), 9.78 (s, 2H).

MS (ES⁻) m/z: [M+H]⁻ calcd for $C_{14}H_{17}N_9O_7S_3$: 518.04. Found: 518.17.

HPLC: 94.0%.

Example 66

(2S,3S)-3-{[(2Z)-2-(2-Amino-1,3-thiazol-4-yl)-2-{[2-(4-carbamimidoylphenoxy)-ethoxy]imino}acetyl]amino}-2-carbamoyl-4-oxoazetidine-1-sulfonic acid ¹H NMR (400 MHz, DMSO-d₆): 4.35 (m, 4H), 5.26-5.43 (m, 1H), 6.97 (s, 1H), 7.19-7.24 (m, 2H), 7.85 (m, 2H), 8.55-8.82 (m, 2H), 9.05-9.33 (m, 2H).

MS (ES⁺) m/z: [M+H]⁺ calcd for $C_{18}H_{21}N_8O_8S_2$: 541.09. Found: 541.23.

HPLC: 91.2%.

Example 67

(2S,3S)-3-{[(2Z)-2-(2-Amino-1,3-thiazol-4-yl)-2-({2-[(3-carbamimidoyl-1,2-oxazol-5-yl)oxy]ethoxy}imino)acetyl]amino}-2-methyl-4-oxoazetidine-1-sulfonic acid ¹H NMR (400 MHz, DMSO-d₆): 1.38 (d, J=6.2 Hz, 3H), 3.67 (d, J=2.3 Hz, 1H), 4.32-4.51 (m, 5H), 6.76 (s, 1H), 6.87 (s, 1H), 7.23 (s, 3H), 8.32 (s, 2H), 9.31 (d, J=8.2 Hz, 1H).

MS (ES⁺) m/z: [M+H]⁺ calcd for $C_{15}H_{18}N_8O_8S_2$: 503.06. Found: 503.20.

HPLC: 91.9%.

Example 68

(2S,3S)-3-{[(2Z)-2-(2-Amino-1,3-thiazol-4-yl)-2-({2-[4-(N-methylcarbamimidoyl)-phenoxy]ethoxy}imino)acetyl]amino}-2-methyl-4-oxoazetidine-1-sulfonic acid ¹H NMR (400 MHz, DMSO-d₆): 1.33 (d, J=6.2 Hz, 3H), 2.97 (s, 3H), 3.61-3.67 (m, 1H), 4.29-4.35 (m, 2H), 4.38-4.42 (m, 2H), 4.43 (d, J=2.7 Hz, 1H), 6.75 (s, 1H), 7.20 (d, J=8.9 Hz, 2H), 7.21 (s, 2H), 7.72 (d, J=8.9 Hz, 2H), 8.41-8.47 (m, 1H), 9.28 (d, J=8.2 Hz, 1H).

MS (ES⁻) m/z: [M−H]⁻ calcd for $C_{19}H_{22}N_7O_7S_2$: 524.55. Found: 524.25.

HPLC: 97.51%.

Example 69

(2S,3S)-3-({(2Z)-2-(2-Amino-1,3-thiazol-4-yl)-2-[(2-{4-[N-(2-hydroxyethyl)carbamimidoyl]-phenoxy}ethoxy)imino]acetyl}amino)-2-methyl-4-oxoazetidine-1-sulfonic acid ¹H NMR (400 MHz, DMSO-d₆): 1.32 (d, J=6.2 Hz, 3H), 3.42-3.48 (m, 2H), 3.56-3.71 (m, 2H), 4.22-4.36 (m, 3H), 4.36-4.51 (m, 4H), 6.74 (s, 1H), 7.11-7.26 (m, 4H), 7.71 (d, J=8.6 Hz, 2H), 8.30 (s, 1H), 9.27 (d, J=7.8 Hz, 1H).

MS (ES⁻) m/z: [M−H]⁻ calcd for $C_{20}H_{24}N_7O_8S_2$: 554.58. Found: 554.26.

HPLC: 97.00%.

Example 70

(2S,3S)-3-{[(2Z)-2-(2-Amino-1,3-thiazol-4-yl)-2-{[2-(4-{N-[2-(formyloxy)ethyl]carbamimidoyl}phenoxy)ethoxy]imino}acetyl]amino}-2-methyl-4-oxoazetidine-1-sulfonic acid ¹H NMR (400 MHz, DMSO-d₆): 1.31 (d, J=6.2 Hz, 3H), 3.40-3.42 (m, 2H), 3.58-3.71 (m, 2H), 4.26-4.36 (m, 4H), 4.36-4.44 (m, 3H), 6.74 (s, 1H), 7.15-7.24 (m, 4H), 7.68 (d, J=8.9 Hz, 2H), 8.26 (s, 1H), 8.31 (s, 1H), 9.27 (d, J=7.8 Hz, 1H).

MS (ES⁻) m/z: [M−H]⁻ calcd for $C_{21}H_{24}N_7O_9S_2$: 582.59. Found: 582.27.

HPLC: 91.79%.

Example 71

(2S,3S)-3-{[(2Z)-2-(2-Amino-1,3-thiazol-4-yl)-2-({2-[(3-carbamimidoyl-1-methyl-1H-pyrazol-5-yl)oxy]ethoxy}imino)acetyl]amino}-2-methyl-4-oxoazetidine-1-sulfonic acid ¹H NMR (400 MHz, DMSO-d₆): 1.37 (d, J=5.8 Hz, 3H), 3.65-3.68 (m, 1H), 3.71 (s, 3H), 4.30-4.37 (m, 2H), 4.41 (m, 3H), 6.50 (s, 1H), 6.76 (s, 1H), 7.21 (s, 1H), 8.36 (br. s., 1H), 9.34 (d, J=8.0 Hz, 1H).

MS (ES⁺) m/z: [M+H]⁺ calcd for $C_{16}H_{21}N_9O_7S_2$: 516.10. Found: 516.10.

HPLC: 96.30%.

Example 72

(2S,3S)-3-{[(2Z)-2-(2-Amino-1,3-thiazol-4-yl)-2-({2-[(5-carbamimidoyl-1-methyl-1H-pyrazol-3-yl)oxy]ethoxy}imino)acetyl]amino}-2-methyl-4-oxoazetidine-1-sulfonic acid ¹H NMR (400 MHz, DMSO-d₆): 1.35 (d, J=6.2 Hz, 3H), 3.53-3.72 (m, 1H), 3.80 (s, 3H), 4.34 (d, J=5.5 Hz, 4H), 4.38-4.51 (m, 1H), 6.32 (s, 1H), 6.75 (s, 1H), 7.21 (br. s., 2H), 8.17 (s, 1H), 9.27 (d, J=8.0 Hz, 1H).

MS (ES⁻) m/z: [M−H]⁻ calcd for $C_{16}H_{21}N_9O_7S_2$: 514.10. Found: 514.16.
HPLC: 97.70%.

Example 73

N-[{4-[2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)ethoxy]phenyl}(imino)methyl]glycine ¹H NMR (400 MHz, DMSO-d₆): 1.22 (s, 3H), 1.38 (s, 3H), 2.31 (dt, J=1.9 and 3.6 Hz, 1H), 2.61-2.68 (m, 2H), 4.24-4.31 (m, 2H), 4.35-4.41 (m, 2H), 6.58 (s, 2H), 6.75 (s, 1H), 7.14 (d, J=8.9 Hz, 2H), 7.19 (s, 2H), 7.71 (d, J=8.9 Hz, 2H), 8.42 (br. s., 1H), 9.43 (d, J=8.2 Hz, 1H).
MS (ES⁻) m/z: [M−H]⁻ calcd for $C_{21}H_{24}N_7O_{10}S_2$: 598.59. Found: 598.12.
HPLC: 84.19%.

Example 74

(2Z)-2-(2-Amino-1,3-thiazol-4-yl)-2-({2-[(2-carbamimidoyl-5-methyl-1,3-thiazol-4-yl)oxy]ethoxy}imino)-N-[(3S)-2,2-dimethyl-4-oxo-1-(sulfooxy)azetidin-3-yl]ethanamide 1H NMR (400 MHz, DMSO-d₆): 1.22 (s, 3H), 1.40 (s, 3H), 2.34 (s, 3H), 4.38 (d, J=4.7 Hz, 2H), 4.54 (q, J=4.4 Hz, 2H), 4.57 (d, J=7.8 Hz, 1H), 6.74 (s, 1H), 7.19 (s, 2H), 8.17 (s, 1H), 9.45 (d, J=7.8 Hz, 1H).
MS (ES⁺) m/z: [M+H]⁺ calcd for $C_{17}H_{22}N_8O_8S_3$: 563.07. Found: 563.09.
HPLC: 98.60%.

Example 75

2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-carbamimidoylphenoxy)propanamide ¹H NMR (400 MHz, DMSO-d₆): 1.15 (s, 3H), 1.34 (s, 3H), 4.33-4.47 (m, 1H), 4.56-4.66 (m, 2H), 4.80-4.91 (m, 1H), 6.82 (s, 1H), 7.12-7.23 (m, 2H), 7.74-7.90 (m, 2H), 8.74 (s, 1H), 9.20 (s, 1H), 9.70 (s, 1H).
MS (ES⁻) m/z: [M−H]⁻ calcd for $C_{20}H_{23}N_8O_9S_2$: 583.10. Found: 582.90.
HPLC: 75.70%.

Example 76

(2Z)-2-(2-Amino-1,3-thiazol-4-yl)-N-[(3S)-2,2-dimethyl-4-oxo-1-(sulfooxy)azetidin-3-yl]-2-[(2-{4-[N-(pyridin-2-ylmethyl)carbamimidoyl]phenoxy}ethoxy)imino]ethanamide ¹H NMR (400 MHz, DMSO-d₆): 1.22 (s, 3H), 1.40 (s, 3H), 4.29 (br. s., 2H), 4.41 (d, J=4.6 Hz, 2H), 4.59 (d, J=8.2 Hz, 1H), 4.74 (s, 2H), 6.77 (s, 1H), 7.11-7.25 (m, 4H), 7.36 (d, J=4.6 Hz, 1H), 7.47 (d, J=7.8 Hz, 1H), 7.71-7.92 (m, 3H), 8.38 (s, 1H), 8.58 (d, J=3.9 Hz, 1H), 9.45 (d, J=7.8 Hz, 1H).
MS (ES⁻) m/z: [M−H]⁻ calcd for $C_{25}H_{27}N_8O_8S_2$: 631.66. Found: 631.06.
HPLC: 95.66%.

Example 77

{[(2S,3S)-3-{[(2Z)-2-[(2-{4-[N-(2-Aminoethyl)carbamimidoyl]phenoxy}ethoxy)imino]-2-(2-amino-1,3-thiazol-4-yl)acetyl]amino}-2-methyl-4-oxoazetidin-1-yl]oxy}methanesulfonic acid ¹H NMR (400 MHz, DMSO-d₆): 1.37 (d, J=5.8 Hz, 3H), 3.17-3.31 (m, 2H), 3.64-3.76 (m, 2H), 3.96-4.06 (m, 1H), 4.33-4.53 (m, 6H), 4.60 (d, J=4.6 Hz, 1H), 7.10 (s, 1H), 7.17 (s, 1H), 7.26 (d, J=8.6 Hz, 2H), 7.82-7.92 (m, 2H), 8.00 (br. s, 2H), 9.08 (br. s, 1H), 9.46-9.64 (m, 3H).
MS (ES⁻) m/z: [M−H]⁻ calcd for $C_{21}H_{27}N_8O_8S_2$: 583.14. Found: 582.75.
HPLC: 87.53%.

Example 78

(2Z)-2-(2-Amino-1,3-thiazol-4-yl)-2-[(2-{4-[N-(2-carbamimidamidoethyl)carbamimidoyl]phenoxy}ethoxy)imino]-N-[(3S)-2,2-dimethyl-4-oxo-1-(sulfooxy)azetidin-3-yl]ethanamide ¹H NMR (400 MHz, DMSO-d₆): 1.19 (s, 3H), 1.39 (s, 3H), 3.35-3.41 (m, 2H), 3.47-3.53 (m, 4H), 4.25-4.35 (m, 2H), 4.36-4.46 (m, 2H), 4.58 (d, J=7.8 Hz, 1H), 6.78 (s, 1H), 7.18 (d, J=8.9 Hz, 2H), 7.25 (br. s, 2H), 7.71-7.77 (m, 3H), 8.96 (s, 1H), 9.41 (br. s, 1H), 9.44 (d, J=7.8 Hz, 1H), 9.57 (t, J=5.0 Hz, 1H).
MS (ES⁺) m/z: [M+H]⁺ calcd for $C_{22}H_{31}N_{10}O_8S_2$: 627.18. Found: 626.92.
HPLC: 91.16%.

Example 79

1-(2-{[{4-[2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)ethoxy]phenyl}(imino)-methyl]amino}ethyl)-1-methylpyrrolidinium chloride ¹H NMR (400 MHz, DMSO-d₆): 1.17 (s, 3H), 1.38 (s, 3H), 2.13 (br. s, 4H), 3.49-3.56 (m, 2H), 3.59-3.63 (m, 2H), 3.67-3.71 (m, 2H), 3.87-3.89 (m, 2H), 4.31-4.33 (m, 2H), 4.41-4.43 (m, 2H), 4.57 (d, J=8.0 Hz, 1H), 6.78 (s, 1H), 7.21 (d, J=8.8 Hz, 2H), 7.26 (br.s, 2H), 7.73 (d, J=8.8 Hz, 2H), 9.14 (br. s, 1H), 9.43 (d, J=7.6 Hz, 1H), 9.60-9.63 (m, 2H).
MS (ES⁺) m/z: M⁺ calcd for $C_{26}H_{37}N_8O_8S_2$: 653.22. Found: 653.05.
HPLC: 96.65%.

Example 80

(2Z)-2-(2-Amino-1,3-thiazol-4-yl)-N-[(3S)-2,2-dimethyl-4-oxo-1-(sulfooxy)azetidin-3-yl]-2-[(2-{4-[imino(piperazin-1-yl)methyl]phenoxy}ethoxy)imino]ethanamide ¹H NMR (400 MHz, DMSO-d₆): =1.16 (s, 3H), 1.38 (s, 3H), 3.26 (br. s., 2H), 3.59 (br. s., 2H), 3.88 (br. s., 2H), 4.30 (br. s., 2H), 4.42 (d, J=4.6 Hz, 2H), 4.57 (d, J=7.8 Hz, 1H), 6.77 (s, 1H), 7.19 (d, J=8.9 Hz, 2H), 7.24 (s, 1H), 7.26-7.33 (m, 1H), 7.60 (d, J=8.5 Hz, 2H), 9.09 (br. s., 2H), 9.32 (br. s., 1H), 9.44 (d, J=7.8 Hz, 1H), 9.64 (s, 1H).

MS (ES⁻) m/z: [M−H]⁻ calcd for $C_{23}H_{29}N_8O_8S_2$: 609.15. Found: 609.13.

HPLC: 89.11%.

Example 81

(2Z)-2-(2-Amino-1,3-thiazol-4-yl)-2-({[1-(4-carbamimidoylphenoxy)-4-hydroxybutan-2-yl]oxy}imino)-N-[(3S)-2,2-dimethyl-4-oxo-1-(sulfooxy)azetidin-3-yl]ethanamide Epimer A ¹H NMR (400 MHz, DMSO-d₆): 1.27 (s, 3H), 1.41 (s, 3H), 1.84 (m, 1H), 1.91 (m, 1H), 3.54 (m, 2H), 4.21 (m, 2H), 4.55 (m, 1H), 4.58 (d, J=8.0 Hz, 1H), 6.74 (s, 1H), 7.14 (J=8.8 Hz, 2H), 7.21 (s, 2H), 7.79 (d, J=8.8 Hz, 2H), 8.46 (br. s, 4H), 9.42 (d, J=7.2 Hz, 1H).

MS (ES⁻) m/z: [M−H]⁻ calcd for $C_{21}H_{27}N_7O_9S_2$: 584.13. Found: 584.01.

HPLC: 95.20%.

Epimer B

¹H NMR (400 MHz, DMSO-d₆): 1.23 (s, 3H), 1.42 (s, 3H), 1.86 (m, 1H), 2.51 (m, 1H), 3.54 (m, 2H), 4.22 (m, 2H), 4.55 (m, 1H), 4.60 (d, J=8.8 Hz, 1H), 6.74 (s, 1H), 7.14 (J=8.8 Hz, 2H), 7.221 (s, 2H), 7.79 (d, J=8.8 Hz, 2H), 8.49 (br. s, 4H), 9.38 (d, J=7.2 Hz, 1H).

MS (ES⁻) m/z: [M−H]⁻ calcd for $C_{21}H_{27}N_7O_9S_2$: 584.13. Found: 584.01.

HPLC: 92.70%.

Example 82

(2Z)-2-{[2-({6-[N-(2-Aminoethyl)carbamimidoyl]pyridin-3-yl}oxy)ethoxy]imino}-2-(2-amino-1,3-thiazol-4-yl)-N-[(3S)-2,2-dimethyl-4-oxo-1-(sulfooxy)azetidin-3-yl]ethanamide ¹H NMR (400 MHz, DMSO-d₆): 3.15 (dd, J=4.1 and 10.4 Hz, 2H), 3.69 (dd, J=5.9 and 12.1 Hz, 2H), 4.41-4.45 (m, 4H), 4.58 (d, J=7.8 Hz, 1H), 6.78 (s, 1H), 7.20-7.26 (m, 2H), 7.76-7.86 (m, 4H), 8.25 (d, J=9.0 Hz, 1H), 8.51 (d, J=2.7 Hz, 1H), 9.25 (br. s, 1H), 9.43 (d, J=7.8 Hz, 1H), 9.72 (br. s, 1H), 9.80 (s, 1H).

MS (ES⁺) m/z: [M+H]⁺ calcd. for $C_{20}H_{28}N_9O_8S_2$: 586.15. Found: 586.14.

HPLC: 94.78%.

Example 83

(2Z)-2-[(2-{4-[N-(3-Aminopropyl)carbamimidoyl]phenoxy}ethoxy)imino]-2-(2-amino-1,3-thiazol-4-yl)-N-[(3S)-2,2-dimethyl-4-oxo-1-(sulfooxy)azetidin-3-yl]ethanamide ¹H NMR (400 MHz, DMSO-d₆): 1.20 (s, 3H), 1.39 (s, 3H), 1.81-1.98 (m, 2H), 2.80-3.00 (m, 2H), 3.41-3.48 (m, 2H), 4.24-4.36 (m, 2H), 4.37-4.47 (m, 2H), 4.58 (d, J=7.8 Hz, 1H), 6.78 (s, 1H), 7.02 (s, 1H), 7.18 (d, J=8.9 Hz, 2H), 7.27 (s, 1H), 7.73 (d, J=8.9 Hz, 2H), 7.76-7.89 (m, 2H), 8.92 (br. s., 1H), 9.37 (br. s., 1H), 9.46 (d, J=7.8 Hz, 1H), 9.59 (br. s., 1H).

MS (ES⁺) m/z: [M+H]⁺ calcd for $C_{22}H_{31}N_8O_8S_2$: 599.17. Found: 599.23.

HPLC: 90.78%.

Example 84

(2Z)-2-(2-Amino-1,3-thiazol-4-yl)-2-[(2-{4-[N-(1,3-diaminopropan-2-yl)carbamimidoyl]phenoxy}ethoxy)imino]-N-[(3S)-2,2-dimethyl-4-oxo-1-(sulfooxy)azetidin-3-yl]ethanamide ¹H NMR (400 MHz, DMSO-d₆): 1.17 (s, 3H), 1.39 (s, 3H), 3.10-3.32 (m, 4H), 3.57-3.64 (m, 4H), 4.25-4.37 (m, 2H), 4.37-4.47 (m, 2H), 4.58 (d, J=7.8 Hz, 1H), 6.79 (s, 1H), 7.22 (d, J=8.9 Hz, 2H), 7.23-7.33 (m, 1H), 7.89 (d, J=8.9 Hz, 2H), 8.09 (br. s, 2H), 9.03 (br. s, 1H), 9.32 (d, J=7.0 Hz, 1H), 9.44 (d, J=7.8 Hz, 1H), 9.76 (br. s, 1H).

MS (ES⁻) m/z: [M−H]⁻ calcd for $C_{22}H_{30}N_9O_8S_2$: 612.17. Found: 612.20.

HPLC: 90.51%.

Example 85

(2Z)-2-{[2-(4-{N-[(2R)-1-Amino-3-hydroxypropan-2-yl]carbamimidoyl}phenoxy)ethoxy]imino}-2-(2-amino-1,3-thiazol-4-yl)-N-[(3S)-2,2-dimethyl-4-oxo-1-(sulfooxy)azetidin-3-yl]ethanamide ¹H NMR (400 MHz, DMSO-d₆): 1.22 (s, 3H), 1.42 (s, 3H), 3.20 (m, 2H), 4.10 (m, 1H), 4.30 (m, 2H), 4.40 (m, 2H), 4.60 (d, J=8.8 Hz, 1H), 6.80 (s, 1H), 7.20 (d, J=8.8 Hz, 2H), 7.22 (s, 2H), 7.79 (d, J=8.8 Hz, 2H), 8.00 (br. s., 3H), 9.00 (s, 1H), 9.38 (d, J=7.2 Hz, 1H), 9.50 (m, 2H).

MS (ES⁻) m/z: [M−H]⁻ calcd for $C_{22}H_{29}N_8O_9S_2$: 613.15. Found: 613.10.

HPLC: 92.70%.

Example 86

(2Z)-2-({2-[4-(5-Amino-1,4,5,6-tetrahydropyrimidin-2-yl)phenoxy]ethoxy}imino)-2-(2-amino-1,3-thiazol-4-yl)-N-[(3S)-2,2-dimethyl-4-oxo-1-(sulfooxy)azetidin-3-yl]ethanamide ¹H NMR (400 MHz, DMSO-d₆): 1.16 (s, 3H), 1.38 (s, 3H), 3.50-3.57 (m, 2H), 3.72-3.79 (m, 2H), 3.98-4.04 (m, 1H), 4.28-4.32 (m, 2H), 4.41-4.45 (m, 2H), 4.57 (d, J=7.8 Hz, 1H), 6.79 (s, 1H), 7.22 (d, J=8.6 Hz, 2H), 7.22-7.44 (m, 1H), 7.70 (d, J=8.6 Hz, 2H), 8.22-8.42 (br. m, 3H), 9.44 (d, J=7.8 Hz, 1H), 10.00 (br. s, 1H).

MS (ES⁻) m/z: [M−H]⁻ calcd for $C_{22}H_{27}N_8O_8S_2$: 595.14. Found: 595.09.

HPLC: 93.67%.

Example 87

3-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-2-(4-carbamimidoylphenoxy)propanoic acid Epimer A ¹H NMR (400 MHz, DMSO-d₆): =0.20 (s, 3H), 1.37 (s, 3H), 4.4-4.5 (m, 2H), 4.57 (d, J=8.0 Hz, 1H), 5.02 (m, 1H), 6.76 (s, 1H), 7.05 (d, J=9.0 Hz, 2H), 7.2 (s, 2H), 7.8 (d, J=9.0 Hz, 2H), 8.9 (s, 2H), 9.1 (s, 2H), 9.43 (d, J=8.0 Hz, 1H).

MS (ES⁺) m/z: [M+H]⁺ calcd for $C_{20}H_{23}N_7O_{10}S_2$: 584.09. Found: 584.13.

HPLC: 87.90%.

Epimer B

¹H NMR (400 MHz, DMSO-d₆): 1.20 (s, 3H), 1.39 (s, 3H), 4.37-4.52 (m, 2H), 4.56 (d, J=8.2 Hz, 1H), 4.90-5.09 (m, 1H), 6.76 (s, 1H), 7.06 (d, J=9.0 Hz, 2H), 7.22 (s, 2H), 7.75 (d, J=9.0 Hz, 2H), 8.87 (s, 2H), 9.08 (s, 2H), 9.47 (d, J=7.2 Hz, 1H).

MS (ES⁻) m/z: [M−H]⁻ calcd for $C_{20}H_{23}N_7O_{10}S_2$: 584.09. Found: 584.13.

HPLC: 91.10%.

Example 88

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[(3R)-piperidin-3-yl]carbamimidoyl}phenoxy)propanoic acid ¹H NMR (400 MHz, DMSO-d₆): =1.24 (s, 3H), 1.44 (s, 3H), 1.64-1.76 (m, 2H), 1.90-2.04 (m, 2H), 2.84-2.98 (m, 2H), 3.06-3.16 (m, 1H), 3.86 (br. s, 1H), 4.19 (d, J=10.55 Hz, 1H), 4.35-4.46 (m, 1H), 4.69-4.77 (m, 2H), 6.84 (s, 1H), 7.08 (d, J=8.99 Hz, 2H), 7.19 (br. s, 2H), 7.61 (d, J=8.60 Hz, 2H), 8.17 (s, 2H), 8.97 (br. s, 1H), 9.24-9.82 (m, 3H), 10.59 (br. s, 1H).

MS (ES⁻) m/z: [M−H]⁻ calcd $C_{25}H_{32}N_8O_{10}S_2$: 668.17. Found: 667.05.

HPLC: 98.6%

Example 89

(2R)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-(4-{N-[(3R)-piperidin-3-yl]carbamimidoyl}phenoxy)propanoic acid ¹H NMR (400 MHz, DMSO-d₆): =1.22 (s, 3H), 1.40 (s, 3H), 1.52 (s, 3H), 1.69 (br. s, 2H), 1.71-1.83 (m, 2H), 1.83-2.00 (m, 2H), 2.74-2.88 (m, 2H), 2.87-3.03 (m, 2H), 3.81-3.95 (m, 2H), 3.95-4.08 (m, 1H) 4.18-4.36 (m, 1H), 4.67 (d, J=8.59 Hz, 2H), 6.82 (s, 1H), 7.09 (d, J=8.98 Hz, 2H), 7.16 (br. s, 1H), 7.71 (d, J=8.98 Hz, 2H), 8.14 (s, 1H).

MS (ES⁻) m/z: [M−H]⁻ calcd $C_{25}H_{32}N_8O_{10}S_2$: 668.17. Found: 667.05.

HPLC: 98.0%

Example 90

{[(3S)-3-{[(2Z)-2-(2-Amino-1,3-thiazol-4-yl)-2-{[(4-carbamimidoylbenzyl)oxy]-imino}acetyl]amino}-2,2-dimethyl-4-oxoazetidin-1-yl]oxy}methanesulfonic acid ¹H NMR (400 MHz, DMSO-d₆): 1.16 (s, 3H), 1.41 (s, 3H), 4.22-4.32 (m, 3H), 4.37-4.43 (m, 3H), 4.54 (d, J=7.6 Hz, 1H), 6.79 (s, 1H), 7.15 (d, J=8.0 Hz, 2H), 7.80 (d, J=8.0 Hz, 2H), 8.66 (br. s, 2H), 9.13 (br. s, 2H), 9.39 (d, J=7.6 Hz, 1H).

MS (ES⁺) m/z: [M+H]⁺ calcd for $C_{20}H_{26}N_7O_8S_2$: 556.13. Found: 556.06.

HPLC: 98.76%.

Example 91

(2Z)-2-[(2-{4-[5-(Aminomethyl)-4,5-dihydro-1H-imidazol-2-yl]phenoxy}ethoxy)imino]-2-(2-amino-1,3-thiazol-4-yl)-N-[(3S)-2,2-dimethyl-4-oxo-1-(sulfooxy)azetidin-3-yl]ethanamide ¹H NMR (400 MHz, DMSO-d₆): 1.16 (s, 3H), 1.37 (s, 3H), 3.16 (t, J=5.0 Hz, 2H), 3.44 (br. s, 2H), 3.87 (dd, J=7.2 and 11.5 Hz, 1H), 4.13 (t, J=11.7 Hz, 1H), 4.29-4.36 (m, 2H), 4.39-4.45 (m, 2H), 4.57 (d, J=7.8 Hz, 1H), 6.78 (s, 1H), 7.26 (d, J=8.9 Hz, 2H), 7.91 (d, J=9.3 Hz, 2H), 8.03 (br. s, 2H), 9.43 (d, J=8.2 Hz, 1H), 10.37 (br. s, 1H), 10.55 (br. s, 1H).

MS (ES⁻) m/z: [M−H]⁻ calcd for $C_{22}H_{27}N_8O_8S_2$: 595.14. Found: 595.22.

HPLC: 93.28%.

Example 92

(3S)-3-({(2Z)-2-(2-Amino-1,3-thiazol-4-yl)-2-[(2-{4-[N-(pyrazolidin-4-yl)carbamimidoyl]phenoxy}ethoxy)imino]acetyl}amino)-2,2-dimethyl-4-oxoazetidine-1-sulfonic acid ¹H NMR (400 MHz, DMSO-d₆): =1.17 (s, 3H), 1.36 (s, 3H), 3.00-3.80 (4H, masked by H₂O), 4.26-4.48 (m, 5H), 4.56 (d, J=7.4 Hz, 1H), 6.77 (s, 1H), 7.12 (d, J=8.0 Hz, 2H), 7.64 (d, J=8.0 Hz, 2H), 9.03 (d, J=2.3 Hz, 1H), 9.34-9.45 (m, 3H).

MS (ES⁻) m/z: [M−H]⁻ calcd for $C_{22}H_{29}N_9O_8S_2$: 610.16. Found: 610.19.

HPLC: 90.14%.

Example 93

(2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3S)-pyrrolidin-3-yl]carbamimidoyl}phenoxy)propanoic acid ¹H NMR (400 MHz, DMSO-d₆): =1.08 (s, 3H), 1.37 (s, 3H), 2.08-2.36 (m, 2H), 3.17-3.62 (m, 4H), 4.35-4.48 (m, 3H), 4.60 (d, J=7.8 Hz, 1H), 4.88-5.04 (m, 1H), 6.81 (s, 1H), 7.20 (d, J=8.9 Hz, 2H), 7.35 (br. s, 1H), 7.76 (d, J=8.9 Hz, 2H), 8.82-9.10 (m, 1H), 9.15 (br. s, 1H), 9.45 (d, J=8.2 Hz, 1H), 9.57 (br. s, 2H).

MS (ES⁻) m/z: [M−H]⁻ calcd. for $C_{24}H_{30}N_8O_{10}S_2$: 653.15. Found: 652.99.

HPLC: 94.26%.

Example 94

(2S)-3-{4-[N-(2-Amino-2-methylpropyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid ¹H NMR (400 MHz, DMSO-d₆): 1.09 (s, 3H), 1.33 (s, 6H), 1.37 (s, 3H), 3.58 (d, J=6.3 Hz, 2H), 4.37-4.42 (m, 1H), 4.44-4.50 (m, 1H), 4.60 (d, J=7.8 Hz, 1H), 4.95-5.01 (m, 1H), 6.82 (s, 1H), 7.21 (d, J=9.0 Hz, 2H), 7.39 (br. s, 1H), 7.85 (d, J=9.0 Hz, 2H), 8.00 (br. s, 2H), 9.09 (br. s, 1H), 9.46 (d, J=7.8 Hz, 1H), 9.55 (br. s, 1H), 9.61 (br. s, 1H).

MS (ES⁻) m/z: [M–H]⁻ calcd for $C_{24}H_{31}N_8O_{10}S_2$: 655.16. Found: 654.93.

HPLC: 94.85%.

Example 95

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[2-(methylamino)ethyl]carbamimidoyl}phenoxy)propanoic acid ¹H NMR (400 MHz, DMSO-d₆): 1.20 (s, 3H), 1.40 (s, 3H), 2.35 (s, 1H), 3.65-3.75 (m, 3H), 3.60-3.80 (m, 2H), 4.30-4.50 (m, 2H), 4.60 (d, J=7.8 Hz, 1H), 4.95-5.00 (m, 1H), 6.80 (s, 1H), 7.18 (d, J=8.9 Hz, 2H), 7.27 (br. s, 2H), 7.80 (d, J=8.9 Hz, 2H), 8.45 (br. s, 2H), 9.05 (br. s, 1H), 9.40-9.60 (m, 3H).

MS (ES⁺) m/z: [M+H]⁺ calcd for $C_{23}H_{31}N_8O_{10}S_2$: 643.16. Found: 643.02.

HPLC: 95.18%.

Example 96

(2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3R)-pyrrolidin-3-yl]carbamimidoyl}phenoxy)propanoic acid ¹H NMR (400 MHz, DMSO-d₆): 1.24 (s, 3H), 1.43 (s, 3H), 2.17 (m, 1H), 2.23-2.34 (m, 1H), 3.19-3.27 (m, 2H), 3.54 (d, J=1.6 Hz, 2H), 4.05 (d, J=11.6 Hz, 1H), 4.20-4.29 (m, 1H), 4.48 (br. s, 1H), 4.66 (d, J=7.8 Hz, 1H), 4.71 (dd, J=2.0 and 8.6 Hz, 1H), 6.84 (s, 1H), 7.07 (d, J=8.6 Hz, 2H), 7.19 (br. s, 2H), 7.76 (d, J=9.0 Hz, 2H), 10.51 (br. s, 1H).

MS (ES⁻) m/z: [M–H]⁻ calcd for $C_{24}H_{30}N_8O_{10}S_2$: 653.15. Found: 653.02.

HPLC: 97.20%.

Example 97

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(piperidin-3-yl)carbamimidoyl]phenoxy}propanoic acid ¹H NMR (400 MHz, DMSO-d₆): 1.08 (s, 3H), 1.36 (s, 3H), 1.53-2.11 (m, 4H), 2.77-3.54 (m, 4H), 3.94 (br. s, 1H), 4.41-4.57 (m, 2H), 4.62 (dd, J=1.5 and 7.8 Hz, 1H), 5.08 (d, J=1.9 Hz, 1H), 6.93-7.26 (m, 3H), 7.71 (br. s, 2H), 8.02 (d, J=16.7 Hz, 1H), 8.56 (br. s, 1H), 8.84 (br. s, 1H), 9.13 (br. s, 1H), 9.33-9.57 (m, 2H), 9.57-9.76 (m, 1H).

MS (ES⁻) m/z: [M–H]⁻ calcd for $C_{25}H_{31}N_8O_{10}S_2$: 667.16. Found: 667.02.

HPLC: 96.60%.

Example 98

(2S)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-{4-[N-(pyrrolidin-2-ylmethyl)carbamimidoyl]phenoxy}propanoic acid ¹H NMR (400 MHz, DMSO-d₆): 1.24 (d, 3H), 1.43 (s, 3H), 1.52-1.67 (m, 1H), 1.77-1.98 (m, 2H), 2.05-2.17 (m, 1H), 3.08-3.25 (m, 2H), 3.46-3.76 (m, 2H), 3.77-3.90 (m, 1H), 4.17 (m, 1H), 4.26-4.39 (m, 1H), 4.64-4.75 (m, 2H), 6.82-6.87 (m, 1H), 7.05 (d, J=8.7 Hz, 1H), 7.11 (d, J=8.4 Hz, 1H), 7.20 (br. s, 2H), 7.26-7.26 (m, 1H), 7.72-7.80 (m, 2H).

MS (ES⁻) m/z: [M–H]⁻ calcd for $C_{25}H_{31}N_8O_{10}S_2$: 667.16. Found: 667.02.

HPLC: 89.04%.

Example 99

(2S)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-{4-[N-(piperidin-2-ylmethyl)carbamimidoyl]phenoxy}propanoic acid ¹H NMR (400 MHz, DMSO-d₆): 1.08 (s, 3H), 1.37 (s, 3H), 1.36-1.62 (m, 3H), 1.62-1.81 (m, 2H), 1.90-2.00 (m, 1H), 2.85-3.00 (m, 1H), 3.30-3.42 (m, 2H), 3.42-3.61 (m, 2H), 4.38-4.49 (m, 2H), 4.60 (d, J=7.8 Hz, 1H), 4.96-5.00 (m, 1H), 6.81 (s, 1H), 7.21 (d, J=8.6 Hz, 2H), 7.21-7.40 (br. s, 2H), 7.83 (d, J=9.0 Hz, 2H), 8.40-8.60 (br. s, 2H), 9.05 (br. s, 1H), 9.41 (d, J=7.8 Hz, 1H), 9.56 (br. s, 2H).

MS (ES⁺) m/z: [M+H]⁺ calcd for $C_{26}H_{33}N_8O_{10}S_2$: 681.18. Found: 681.05.

HPLC: 96.45%.

Example 100

(2S)-3-{4-[N-(trans-2-Aminocyclopropyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid Anti Epimer A ¹H NMR (400 MHz, DMSO-d₆): 1.07 (s, 3H), 1.37 (s, 3H), 1.37-1.42 (m, 2H), 2.90-3.07 (m, 1H), 3.08-3.17 (m, 1H), 4.35-4.42 (m, 1H), 4.42-4.49 (m, 1H), 4.59 (d, J=7.8 Hz, 1H), 4.96-5.00 (m, 1H), 6.83 (s, 1H), 7.19 (d, J=8.9 Hz, 2H), 7.73 (d, J=9.0 Hz, 2H), 8.29 (br. s, 3H), 9.04 (br. s, 1H), 9.45 (d, J=7.8 Hz, 1H), 9.67 (br. s, 1H), 9.78 (br. s, 1H).

MS (ES⁺) m/z: [M+H]⁺ calcd for $C_{23}H_{27}N_8O_{10}S_2$: 639.13. Found: 639.08.

HPLC: 96.02%.

Anti Epimer B

¹H NMR (400 MHz, DMSO-d₆): 1.23 (s, 3H), 1.39 (s, 3H), 1.37-1.43 (m, 2H), 2.90-3.07 (m, 1H), 3.08-3.17 (m, 1H), 4.43-4.48 (m, 1H), 4.58 (d, J=7.4 Hz, 1H), 4.97-5.02 (m, 1H), 6.84 (s, 1H), 7.19 (d, J=8.9 Hz, 2H), 7.73 (d, J=9.0 Hz, 2H), 8.31 (br. s, 3H), 9.05 (br. s, 1H), 9.43 (d, J=7.8 Hz, 1H), 9.68 (br. s, 1H), 9.79 (br. s, 1H).

MS (ES⁺) m/z: [M+H]⁺ calcd for $C_{23}H_{27}N_8O_{10}S_2$: 639.13. Found: 639.01.

HPLC: 93.77%.

Example 101

(2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3S)-1-methylpyrrolidin-3-yl]carbamimidoyl}phenoxy)propanoic acid ¹H NMR (400 MHz, DMSO-d₆): 1.07 (s, 3H), 1.36 (s, 3H), 2.16-2.33 (m, 1H), 2.65 (br. s, 1H), 2.90 (br. s, 3H), 3.39 (br. s, 6H), 3.75 (br. s, 1H), 4.30-4.54 (m, 3H), 4.58 (d, J=7.8 Hz, 1H), 4.96 (t, J=3.7 Hz, 1H), 6.78 (s, 1H), 7.18 (d, J=8.6 Hz, 2H), 7.23 (br. s, 2H), 7.75 (d, J=7.8 Hz, 2H), 9.12 (br. s, 1H), 9.38 (d, J=7.4 Hz, 1H), 9.55 (br. s, 1H).

MS (ES$^-$) m/z: [M–H]$^-$ calcd C$_{25}$H$_{32}$N$_8$O$_{10}$S$_2$: 667.17. Found: 666.99.

HPLC: 97.10%.

Example 102

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1,3-diaminopropan-2-yl)carbamimidoyl]phenoxy}propanoic acid $^1$H NMR (400 MHz, DMSO-d$_6$): 1.04 (s, 3H), 1.37 (s, 3H), 2.29-2.36 (m, 1H), 2.64-2.71 (m, 1H), 3.08-3.29 (m, 4H), 4.22-4.35 (m, 1H), 4.35-4.54 (m, 2H), 4.60 (d, J=7.8 Hz, 1H), 4.93-5.02 (m, 1H), 6.55 (s, 1H), 6.81 (s, 1H), 7.24 (d, J=7.8 Hz, 2H), 7.28 (br. s, 1H), 7.90 (d, J=8.9 Hz, 2H), 8.01 (br. s, 2H), 8.86-9.10 (m, 1H), 9.32 (d, J=9.7 Hz, 1H), 9.42 (d, J=7.4 Hz, 1H), 9.71-9.82 (m, 1H).

MS (ES$^+$) m/z: [M+H]$^+$ calcd for C$_{23}$H$_{32}$N$_9$O$_{10}$S$_2$: 658.17. Found: 657.94.

HPLC: 81.08%.

Example 103

(2R)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-{4-[N-(1,3-diaminopropan-2-yl)carbamimidoyl]phenoxy}propanoic acid $^1$H NMR (400 MHz, DMSO-d$_6$): 1.23 (s, 3H), 1.39 (s, 3H), 2.25-2.39 (m, 3H), 2.64-2.73 (m, 2H), 3.56-3.79 (m, 2H), 4.47 (br. s, 3H), 4.59 (d, J=7.4 Hz, 1H), 4.98 (br. s, 1H), 6.58 (br. s, 2H), 6.82 (s, 1H), 7.24 (d, J=8.5 Hz, 1H), 7.28 (br. s, 1H), 7.80 (d, J=8.5 Hz, 1H), 7.97 (br. s, 2H), 8.20 (br. s, 1H), 8.93-9.18 (m, 1H), 9.42 (br. s, 1H), 9.69 (br. s, 1H).

MS (ES$^-$) m/z: [M–H]$^-$ calcd for C$_{23}$H$_{30}$N$_9$O$_{10}$S$_2$: 656.16. Found: 656.06.

HPLC: 83.70%.

Example 104

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1H-imidazol-2-ylmeth-yl)carbamimidoyl]phenoxy}propanoic acid $^1$H NMR (400 MHz, DMSO-d$_6$): 1.28 (s, 3H), 1.38 (s, 3H), 4.39-4.42 (m, 2H), 4.49-4.55 (m, 4H), 6.58 (s, 1H), 6.81 (s, 1H), 7.05 (s, 2H), 7.18 (s, 2H), 7.22 (d, J=8.8 Hz, 2H), 7.76 (d, J=8.8 Hz, 2H), 8.18 (br. s, 1H).

MS (ES$^-$) m/z: [M–H]$^-$ calcd for C$_{24}$H$_{26}$N$_9$O$_{10}$S$_2$: 664.12. Found: 663.95.

HPLC: 92.00%.

Example 105

(2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1H-imidazol-2-ylmeth-yl)carbamimidoyl]phenoxy}propanoic acid $^1$H NMR (400 MHz, DMSO-d$_6$): 1.25 (s, 3H), 1.36 (s, 3H), 4.18 (m, 1H), 4.45-4.65 (m, 5H), 6.62 (br. s, 1H), 6.85 (s, 1H), 7.05 (br. s, 2H), 7.18 (s, 2H), 7.22 (d, J=8.8 Hz, 2H), 7.78 (d, J=8.8 Hz, 2H), 8.18 (br. s, 1H).

MS (ES$^-$) m/z: [M–H]$^-$ calcd for C$_{24}$H$_{26}$N$_9$O$_{10}$S$_2$: 664.12. Found: 664.01.

HPLC: 80.60%.

Example 106

(2S)-3-{4-[N-(4-Aminopyrrolidin-3-yl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid $^1$H NMR (400 MHz, DMSO-d$_6$): 1.03 (s, 3H), 1.38 (s, 3H), 3.00 (m, 2H), 3.65-3.83 (m, 1H), 4.08-4.22 (m, 1H), 4.38-4.68 (m, 4H), 5.01 (m, 1H), 6.78 (s, 1H), 7.19-7.38 (m, 3H), 7.80 (m, 2H), 8.40 (m, 1H), 9.38-9.48 (m, 1H), 9.60 (m, 1H), 9.70 (m, 1H).

MS (ES$^-$) m/z: [M–H]$^-$ calcd for C$_{24}$H$_{30}$N$_9$O$_{10}$S$_2$: 668.16. Found: 668.05.

HPLC: 92.04%.

Example 107

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(azetidin-3-yl)carbamimidoyl]phenoxy}propanoic acid $^1$H NMR (400 MHz, DMSO-d$_6$): 1.06 (s, 3H), 1.35 (s, 3H), 4.14-4.33 (m, 4H), 4.35-4.51 (m, 2H), 4.57 (d, J=7.8 Hz, 1H), 4.63-4.80 (m, 1H), 4.97 (m, 1H), 6.79 (s, 1H), 7.20 (d, J=8.9 Hz, 2H), 7.25 (br. s, 2H), 7.76 (d, J=8.9 Hz, 2H), 8.85-9.03 (br. s, 2H), 9.02 (s, 1H), 9.39 (d, J=7.8 Hz, 1H), 9.61 (br. s, 1H), 10.11 (d, J=7.8 Hz, 1H).

MS (ES$^-$) m/z: [M–H]$^-$ calcd for C$_{23}$H$_{27}$N$_8$O$_{10}$S$_2$: 639.13. Found: 638.92.

HPLC: 95.07%.

Example 108

(2S)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-{4-[N-(piperidin-4-yl)carbamimidoyl]phenoxy}propanoic acid $^1$H NMR (400 MHz, DMSO-d$_6$): δ=1.27 (s, 3H), 1.44 (s, 3H), 1.71 (br. s, 2H), 1.98 (br. s, 2H), 2.78 (br. s, 2H), 3.23 (br. s, 2H), 3.83 (br. s, 1H), 4.43 (m, 2H), 4.65-4.75 (m, 2H), 6.84 (s, 1H), 7.15 (br. s, 2H), 7.20 (d, J=8.7 Hz, 2H), 7.70 (d, J=8.7 Hz, 2H).

MS (ES$^-$) m/z: [M–H]$^-$ calcd for C$_{25}$H$_{31}$N$_8$O$_{10}$S$_2$: 667.16. Found: 666.93.

HPLC: 95.80%.

Example 109

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(azetidin-3-yl)carbamimidoyl]phenoxy}propanoic acid $^1$H NMR (400 MHz, DMSO-d$_6$): 1.04 (s, 3H), 1.36 (s, 4H), 2.68 (t, J=4.6 Hz, 4H), 3.27 (d, J=11.7 Hz, 4H), 3.77-4.00 (m, 3H), 4.15 (t, J=11.7 Hz, 3H), 4.31-4.81 (m, 8H), 4.99 (br. s, 2H), 6.80 (s, 1H), 7.27 (d, J=8.6 Hz, 5H), 7.92 (d, J=8.9 Hz, 3H), 8.63 (br. s, 2H), 9.38 (d, J=7.8 Hz, 1H), 10.37 (br. s, 1H), 10.62 (br. s, 1H).

MS (ES$^-$) m/z: [M–H]$^-$ calcd for $C_{24}H_{30}N_8O_{10}S_2$: 653.15. Found: 652.96.

HPLC: 91.44%.

Example 110

(2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[2-(pyrimidin-2-ylami-no)ethyl]carbamimidoyl}phenoxy)propanoic acid $^1$H NMR (400 MHz, DMSO-d$_6$): 1.09 (s, 3H), 1.36 (s, 3H), 3.30-3.60 (m, 4H), 4.59-4.35 (m, 2H), 4.95 (d, J=11.2 Hz, 1H), 4.96 (br.s, 1H), 6.61 (t, J=4.8 Hz, 1H), 6.79 (s, 1H), 7.25 (d, J=9.2 Hz, 2H),), 7.36 (br. s, 2H), 7.68 (d, J=9.2 Hz, 2H), 8.28 (d, J=4.8 Hz, 2H), 8.91 (br. s, 2H), 9.32 (br. s, 1H), 9.42 (d, J=11.2 Hz, 1H), 9.60 (br. s, 1H).

MS (ES$^-$) m/z: [M–H]$^-$ calcd $C_{26}H_{30}N_{10}O_{10}S_2$: 706.72. Found: 705.14.

HPLC: 96.03%

Example 111

(2R)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-(4-{N-[2-(pyrimidin-2-ylamino)ethyl]carbamimidoyl}phenoxy)propanoic acid $^1$H NMR (400 MHz, DMSO-d$_6$): 1.39 (s, 3H), 2.50 (s, 3H), 3.57-3.51 (m, 4H), 4.45-4.43 (m, 2H), 4.60 (d, J=7.6 Hz, 1H), 5.00-4.97 (m, 1H), 6.64 (t, J=4.4 Hz, 1H), 6.82 (s, 1H), 7.18 (d, J=8.8 Hz, 2H), 7.40 (br. s, 2H), 7.70 (d, J=8.8 Hz, 2H), 8.30 (d, J=4.4 Hz, 2H), 8.95 (br. s, 2H), 9.35 (br. s, 1H), 9.43 (d, J=7.6 Hz, 1H), 9.62 (br. s, 1H).

MS (ES$^-$) m/z: [M–H]$^-$ calcd $C_{26}H_{30}N_{10}O_{10}S_2$: 706.72. Found: 705.14.

HPLC: 79.11%

Example 112 tert-Butyl {[4-({1-[({(1Z)-2-{[(3S)-2,2-dimethyl-4-oxo-1-(sulfooxy)azetidin-3-yl]amino}-2-oxo-1-[2-(tritylamino)-1,3-thiazol-4-yl]ethylidene}amino)oxy]-3-hydroxypropan-2-yl}oxy)phenyl](imino)methyl}carbamate $^1$H (400 MHz, DMSO-d$_6$): 1.16 (s, 1.5H), 1.17 (s, 1.5H), 1.27 (s, 3H), 1.5 (s, 9H), 3.6-3.7 (m, 2H), 4.2-4.3 (m, 2H), 4.5 (t, J=7.6 Hz, 1H), 4.7 (br. s., 1H), 5.0 (br. s., 1H), 6.7 (s, 1H), 7.1 (d, J=9.0 Hz, 2H), 7.2-7.4 (m, 16H), 7.8 (d, J=9.0 Hz, 2H), 9.35 (d, J=7.6, 0.5H), 9.38 (d, J=7.6, 0.5H).

MS (ES$^-$) m/z: [M–H]$^-$ calcd $C_{38}H_{43}N_7O_{11}S_2$: 837.93. Found: 836.44.

HPLC: 90.05%

Pharmacological Methods

ABBREVIATIONS

MIC: minimum inhibitory concentration
CFU: colony forming units
ED100: 100% protective dose The antimicrobial activity of the compounds of this invention against a selection of different bacteria may be evaluated by a number of assays, including the in-vitro determination of the minimum inhibitory concentration (MIC) or the determination of the in-vivo efficacy in mouse infection models.

Minimum Inhibitory Concentration (MIC) Determination

Compounds of this invention were tested for antimicrobial activity by determining minimum inhibitory concentrations (MICs, in µg/mL) using the broth microdilution method according to the guidelines of the Clinical Laboratories and Standards Institute ("Methods for Dilution Antimicrobial Susceptibility Tests for Bacteria that Grow Aerobically", Approved standard, 7th ed., Clinical and Laboratory Standards Institute (CLSI) Document M7-A8, Wayne, Pa., USA, 2009). Test compounds were dissolved in DMSO. The compounds were then diluted in microbial growth medium (Mueller Hinton Broth II, cation adjusted) resulting in a final concentration range of 0.063-32 µg/mL in serial two-fold dilution. In all cases the final DMSO concentration was less than 0.5%. Bacteria were added to 96-well microtitre plates containing the serial two-fold dilutions of the compounds; the final cell density was approximately 5×10$^5$ colony forming units/mL (CFU/mL). Plates were incubated at 37° C. for 18-24 hours and read visually. The MIC, i.e. the lowest concentration of the test compound that inhibited visible growth of the bacteria, was recorded. The same assay conditions were used when the compounds of this invention were tested in combination with -lactamase inhibitors. While the compounds of this invention were serially diluted as described above, a constant concentration of the -lactamase inhibitors of 4 µg/mL was used.

Bacterial strains that were used to evaluate the antimicrobial activity using the MIC determination included but were not limited to *E. coli* ATCC25922, *K. pneumoniae* 60, *E. cloacae* 34654, *C. freundii* K21/3034, *M. morganii* 126/3048, *P. aeruginosa* PAO1, *P. aeruginosa* 2297 (AmpC wt), *P. aeruginosa* 2297-con (AmpC derepressed), *A. baumannii* ATCC15308, *S. maltophilia* ICB7569, *S. aureus* 133, *M. catarrhalis* ICB489, *H. influenzae* ATCC 49247, *S. pneumoniae* 113, *B. fragilis* 6688, *C. perfringens* DSM756, *E. coli* J62, and *E. coli* J62-TEM-3.

TABLE 4

| | | | | | Biological data | | | | | | |
|---|---|---|---|---|---|---|---|---|---|---|---|
| compound example No. | strain 1 MIC [mg/L] | strain 2 MIC [mg/L] | strain 3 MIC [mg/L] | strain 4 MIC [mg/L] | strain 5 MIC [mg/L] | strain 6 MIC [mg/L] | strain 7 MIC [mg/L] | strain 8 MIC [mg/L] | strain 9 MIC [mg/L] | strain 10 MIC [mg/L] | strain 11 MIC [mg/L] |
| 1 | 0.25 | 0.25 | 0.5 | 0.5 | 0.125 | 4 | 8 | 4 | 8 | 8 | |
| 2 | 0.125 | 0.125 | 0.25 | 0.125 | ≤0.063 | 2 | | | 4 | 0.125 | 0.25 |
| 3 | 0.125 | ≤0.063 | 0.125 | ≤0.063 | 0.125 | 2 | 4 | 16 | 1 | | ≤0.063 |
| 4 | 0.125 | 0.25 | 0.5 | 0.125 | 0.25 | 4 | 16 | 8 | 1 | 4 | ≤0.063 |
| 5 | 0.25 | ≤0.063 | 0.125 | 0.25 | 0.125 | 4 | 4 | 32 | 1 | | 0.125 |

TABLE 4-continued

Biological data

| | | | | | | | | | | | |
|---|---|---|---|---|---|---|---|---|---|---|---|
| 6 | 0.125 | 0.25 | 0.125 | ≤0.125 | ≤0.125 | 4 | 8 | 16 | 1 | 32 | ≤0.063 |
| 7 | 0.5 | 1 | 1 | 0.5 | 0.5 | 8 | 16 | 8 | 2 | 4 | ≤0.063 |
| 8 | 1 | 0.5 | 2 | 0.5 | 0.25 | 8 | 32 | 32 | 4 | | 0.25 |
| 9 | 0.125 | 0.125 | 0.125 | 0.125 | 0.125 | 2 | 2 | 16 | 0.5 | 32 | ≤0.063 |
| 10 | 0.5 | 2 | 1 | 1 | 4 | 8 | 8 | | 8 | | |
| 11 | 0.125 | ≤0.125 | ≤0.063 | ≤0.125 | ≤0.063 | 1 | 2 | 16 | 0.5 | 32 | 0.125 |
| 12 | 0.5 | 0.25 | 0.5 | 0.25 | 0.25 | 4 | 8 | | 4 | 8 | 0.125 |
| 13 | 0.5 | 1 | 1 | 0.25 | 0.5 | 8 | 16 | 8 | 1 | | ≤0.063 |
| 14 | 0.5 | 1 | 0.5 | 0.25 | 0.5 | 4 | 8 | 32 | 2 | | ≤0.063 |
| 15 | 0.5 | 1 | 1 | 0.5 | 0.5 | 8 | 8 | 8 | 2 | 4 | ≤0.063 |
| 16 | 1 | 1 | 1 | 2 | 0.5 | 32 | 32 | 32 | 4 | 8 | ≤0.063 |
| 17 | 2 | 2 | 2 | 1 | ≤0.063 | 8 | 16 | 32 | 8 | | 2 |
| 18 | 1 | 1 | 2 | 1 | 1 | 4 | 4 | 16 | 16 | 16 | 0.25 |
| 19 | 0.5 | 0.125 | 0.5 | 0.5 | 0.25 | 8 | 16 | | 4 | | |
| 20 | 2 | 2 | 2 | 1 | 2 | 8 | 8 | 32 | 2 | | 0.125 |
| 21 | 1 | 0.25 | 1 | 0.25 | 0.5 | 16 | 16 | | 8 | | 0.5 |
| 22 | 1 | 1 | 1 | 0.5 | 1 | 16 | 32 | 16 | 4 | 4 | ≤0.063 |
| 23 | 0.125 | 0.25 | 0.5 | 0.125 | 0.5 | 2 | 2 | 2 | 0.5 | 16 | ≤0.063 |
| 24 | 0.125 | 0.25 | 0.25 | 0.125 | 0.125 | 2 | 4 | 2 | 1 | 8 | ≤0.063 |
| 25 | 0.125 | 0.25 | 0.25 | 0.125 | 0.125 | 2 | 4 | 4 | 2 | 8 | ≤0.063 |
| 26A | ≤0.063 | 0.031 | 0.125 | ≤0.063 | ≤0.063 | 1 | 2 | 8 | 8 | 16 | ≤0.063 |
| 26B | 2 | 0.5 | 1 | 2 | 0.5 | 4 | 8 | 32 | 16 | | |
| 27A | 0.25 | 0.125 | 0.25 | 0.25 | 0.125 | 4 | 4 | 4 | 4 | 4 | ≤0.063 |
| 27B | 2 | 1 | 4 | 1 | 1 | 16 | 32 | 16 | 16 | 8 | 0.125 |
| 28 | 0.125 | 0.125 | 0.125 | 0.125 | 0.125 | 4 | 8 | 32 | 0.5 | | 0.125 |
| 29 | 0.25 | 0.25 | 0.5 | 0.25 | 0.25 | 8 | 16 | 8 | 2 | 8 | |
| 30 | 0.125 | ≤0.063 | 0.25 | ≤0.063 | ≤0.063 | 4 | 4 | 32 | 1 | | 0.125 |
| 31 | 0.125 | ≤0.063 | 0.25 | ≤0.063 | 0.25 | 8 | 8 | 32 | 1 | | ≤0.063 |
| 32 | 1 | | 0.5 | 0.5 | 0.5 | 16 | 32 | | 2 | | ≤0.063 |
| 33 | 0.25 | 0.5 | 0.5 | 0.25 | 0.25 | 8 | 16 | 8 | 8 | 16 | ≤0.063 |
| 34A | 1 | 1 | 0.5 | 1 | 0.25 | 8 | 8 | 16 | 32 | 8 | ≤0.063 |
| 34B | 8 | 8 | 4 | 8 | 4 | 32 | 32 | 32 | 32 | 32 | 0.25 |
| 35 | 2 | 2 | 4 | 2 | 1 | 16 | 16 | 32 | 2 | | 0.25 |
| 36A | 0.125 | ≤0.063 | ≤0.063 | 0.125 | ≤0.063 | 4 | 4 | 4 | 4 | 2 | ≤0.063 |
| 36B | 2 | 1 | 2 | 0.5 | 2 | 16 | | 32 | 32 | 16 | 0.125 |
| 37 | 2 | 2 | 2 | 2 | 1 | 8 | 8 | | 4 | | 1 |
| 38 | 0.125 | 0.25 | 0.25 | 0.125 | 0.5 | 4 | 8 | 4 | 0.25 | 32 | ≤0.063 |
| 39 | 0.25 | 0.5 | 0.5 | 0.25 | 0.5 | 2 | 4 | 2 | 0.5 | 16 | ≤0.063 |
| 40 | 0.125 | 0.25 | 0.5 | 0.125 | 0.5 | 4 | 8 | 4 | 2 | 16 | ≤0.063 |
| 41 | 0.25 | 0.5 | 0.25 | 0.125 | 0.25 | 4 | 4 | 4 | 1 | 4 | ≤0.063 |
| 42 | 1 | 1 | 2 | 1 | 2 | 16 | 16 | 16 | 8 | 16 | ≤0.063 |
| 43 | 0.5 | 0.5 | 1 | 0.25 | 1 | 8 | 8 | 8 | 0.5 | 32 | |
| 44A | ≤0.063 | ≤0.063 | 0.125 | ≤0.063 | 0.125 | 1 | 2 | 1 | 2 | 2 | ≤0.063 |
| 44B | 2 | 1 | 4 | 2 | 4 | 8 | 16 | 8 | 8 | 16 | ≤0.063 |
| 45A | 0.5 | 0.5 | 1 | 0.25 | 0.5 | 8 | 16 | 8 | 2 | 8 | |
| 45B | 2 | 2 | 4 | 1 | 4 | 16 | 32 | 32 | 4 | 32 | ≤0.063 |
| 46 | 2 | 1 | 2 | 1 | 1 | 8 | 32 | 32 | 16 | 8 | |
| 47 | 0.25 | 0.5 | 1 | 0.5 | 2 | 4 | 2 | | 2 | | ≤0.063 |
| 48 | 2 | 4 | 4 | 2 | 1 | 8 | 16 | 32 | 8 | | 0.5 |
| 49 | 1 | 2 | 2 | 1 | 2 | 8 | 16 | 32 | 4 | | 0.125 |
| 50 | 0.5 | 0.5 | 1 | 1 | 0.5 | 8 | 16 | 32 | 2 | | 0.125 |
| 51 | 2 | 4 | 2 | 2 | 2 | 16 | 16 | 32 | 4 | | 0.5 |
| 52 | 1 | 0.5 | 1 | 0.25 | 1 | 4 | 4 | 16 | 1 | | 2 |
| 53 | 0.5 | | 0.5 | 0.5 | 2 | 16 | 16 | 32 | 4 | | |
| 54 | 0.5 | 0.5 | 0.5 | 0.25 | 1 | 4 | 8 | | 4 | | |
| 55 | 0.5 | 1 | 0.5 | 0.25 | 0.25 | 16 | | 32 | 4 | | 0.25 |
| 56 | 2 | 0.5 | 4 | 0.5 | 0.5 | 32 | 32 | | 4 | | 1 |
| 57 | 1 | 2 | 2 | 1 | 1 | 32 | 32 | 16 | 2 | 32 | ≤0.063 |
| 58 | 2 | 4 | 4 | 1 | 1 | 16 | 32 | 16 | 16 | | ≤0.063 |
| 59 | 1 | 1 | 1 | 0.5 | 1 | 16 | 16 | 32 | 1 | | 0.25 |
| 60 | 1 | 1 | 2 | 1 | 0.5 | 16 | 16 | 32 | 4 | | 0.25 |
| 61 | 2 | 2 | 2 | 1 | 0.5 | 2 | 2 | 16 | 2 | 16 | ≤0.063 |
| 62 | 1 | 0.5 | 1 | 0.5 | 0.125 | 4 | 8 | 32 | 2 | | 0.125 |
| 63 | 0.5 | 0.25 | 0.5 | 0.25 | 0.5 | 8 | 8 | | 16 | 16 | 0.5 |
| 64 | 0.5 | 0.25 | 0.5 | 0.5 | 0.5 | 8 | 16 | | 8 | 32 | 16 |
| 65 | 0.5 | 0.25 | 0.5 | 0.25 | 0.125 | 16 | 32 | | 8 | | 0.25 |
| 66 | 2 | 1 | 4 | 2 | 2 | 32 | 32 | | 4 | | 1 |
| 67 | 0.5 | 2 | 0.5 | 0.25 | 0.125 | 8 | 32 | | 4 | | 0.25 |
| 68 | 0.125 | 0.25 | 0.125 | 0.125 | 0.125 | 2 | 8 | 32 | 2 | | ≤0.063 |
| 69 | 0.125 | 0.25 | 0.25 | 0.125 | 0.125 | 4 | 8 | | 2 | | ≤0.063 |
| 70 | 0.125 | 0.25 | 0.25 | 0.125 | 0.125 | 4 | 4 | | 2 | | 0.125 |
| 71 | 2 | 1 | 4 | 1 | 1 | 16 | 32 | | 4 | 4 | 0.25 |
| 72 | 0.5 | 0.25 | 1 | 0.5 | 0.25 | 8 | 8 | | 4 | | 0.25 |
| 73 | 0.5 | 0.5 | 0.5 | 0.5 | 0.5 | 16 | 32 | 32 | 16 | 32 | ≤0.063 |
| 74 | 1 | 2 | 4 | 1 | 1 | 16 | 32 | 32 | 2 | 16 | ≤0.063 |
| 75 | 0.25 | 0.5 | 0.5 | 0.125 | 0.25 | 8 | 16 | 8 | 2 | 4 | |
| 76 | 0.5 | 0.5 | 1 | 0.5 | 1 | 16 | 16 | 32 | 4 | 16 | ≤0.063 |
| 77 | 0.5 | 2 | 2 | 0.5 | 2 | 8 | 16 | | 8 | | |

TABLE 4-continued

Biological data

| | | | | | | | | | | | |
|---|---|---|---|---|---|---|---|---|---|---|---|
| 78 | 0.25 | 0.25 | 0.5 | 0.25 | 0.5 | 4 | 4 | 2 | 0.25 | 8 | ≤0.063 |
| 79 | 0.5 | 0.5 | 0.5 | 0.25 | 1 | 8 | 8 | 4 | 0.5 | | ≤0.063 |
| 80 | 0.25 | 0.5 | 1 | 0.25 | | 16 | 16 | 8 | 2 | 32 | |
| 81A | 4 | 8 | 16 | 4 | 8 | | | | 8 | 16 | |
| 81B | 2 | 4 | 4 | 2 | 4 | | | | 8 | 16 | |
| 82 | 0.25 | 0.125 | 0.5 | 0.25 | 0.5 | 8 | 16 | 8 | 4 | 32 | ≤0.063 |
| 83 | 0.125 | 0.25 | 0.25 | 0.125 | 0.5 | 2 | 4 | 4 | 0.25 | 16 | ≤0.063 |
| 84 | ≤0.063 | 0.125 | 0.125 | ≤0.063 | 0.25 | 1 | 2 | 2 | 1 | 32 | ≤0.063 |
| 85 | 0.25 | 0.5 | 0.5 | 0.25 | 0.25 | 4 | 8 | 8 | 2 | 32 | ≤0.063 |
| 86 | 0.25 | 0.5 | 0.5 | 0.25 | 0.5 | 4 | 8 | 8 | 2 | 32 | ≤0.063 |
| 87A | 1 | 1 | 1 | 1 | 0.25 | 32 | | | 8 | | ≤0.063 |
| 87B | 0.5 | 0.5 | 1 | 0.5 | 0.25 | 16 | 32 | 32 | 16 | 16 | ≤0.063 |
| 88 | ≤0.063 | 0.125 | ≤0.063 | ≤0.063 | ≤0.063 | 1 | 1 | 1 | 2 | 4 | |
| 89 | 0.125 | 0.25 | 0.125 | 0.125 | ≤0.063 | 1 | 1 | 1 | 1 | 4 | |
| 90 | 0.5 | | 1 | 0.25 | 0.5 | 32 | 32 | 32 | | 4 | 0.5 |
| 91 | 0.125 | 0.125 | 0.25 | 0.125 | 0.25 | 2 | 4 | 2 | 1 | 16 | ≤0.063 |
| 92 | 0.5 | 0.5 | 1 | 0.5 | 0.5 | 8 | 8 | 8 | 4 | 32 | ≤0.063 |
| 93 | ≤0.063 | 0.125 | 0.125 | ≤0.063 | | 1 | 1 | 1 | 1 | 4 | |
| 94 | 0.125 | 0.125 | 0.125 | 0.125 | 0.125 | 2 | 2 | 2 | 2 | 4 | ≤0.063 |
| 95 | 0.125 | 0.125 | 0.125 | 0.125 | ≤0.063 | 1 | 2 | 2 | 2 | 4 | ≤0.063 |
| 96 | 0.125 | ≤0.063 | ≤0.063 | ≤0.063 | ≤0.063 | 1 | 1 | 1 | 1 | 4 | ≤0.063 |
| 97 | ≤0.063 | 0.125 | 0.125 | ≤0.063 | ≤0.063 | 1 | 1 | 1 | 1 | 4 | ≤0.063 |
| 98 | 0.125 | 0.125 | 0.125 | 0.125 | ≤0.063 | 1 | 2 | 2 | 1 | 4 | ≤0.063 |
| 99 | 0.125 | 0.25 | 0.25 | 0.125 | ≤0.063 | 2 | 2 | 2 | 2 | 4 | ≤0.063 |
| 100A | 0.125 | 0.25 | 0.125 | 0.125 | ≤0.063 | 2 | 4 | 4 | 8 | 8 | ≤0.063 |
| 100B | 2 | 2 | 4 | 2 | | 16 | 32 | 16 | 32 | 32 | |
| 101 | 0.125 | 0.125 | 0.125 | 0.125 | 0.125 | 2 | 4 | 2 | 4 | 8 | ≤0.063 |
| 102 | 0.125 | ≤0.063 | 0.25 | ≤0.063 | ≤0.063 | 1 | 2 | 2 | 4 | 4 | ≤0.063 |
| 103 | 2 | | | | 2 | 16 | | | 32 | | ≤0.063 |
| 104 | 1 | 1 | 1 | 1 | 0.5 | 16 | | | | 16 | ≤0.063 |
| 105 | 16 | | | | | | | | | | |
| 106 | 0.125 | 0.125 | 0.125 | 0.125 | ≤0.063 | 1 | 2 | 1 | 2 | 4 | ≤0.063 |
| 107 | ≤0.063 | 0.125 | 0.25 | ≤0.063 | ≤0.063 | 1 | 1 | 1 | 1 | 4 | ≤0.063 |
| 108 | 0.125 | 0.125 | 0.125 | ≤0.063 | ≤0.063 | 0.5 | 1 | 1 | 1 | 4 | ≤0.063 |
| 109 | 0.125 | 0.125 | 0.125 | 0.125 | 0.125 | 2 | 2 | 2 | 2 | 8 | ≤0.063 |
| 110 | 0.5 | 1 | 1 | 0.5 | 0.25 | 8 | 8 | 16 | 32 | 8 | ≤0.063 |
| 111 | 8 | 8 | 16 | 4 | 8 | 32 | 32 | 32 | 32 | | |

| compound example No. | strain 12 MIC [mg/L] | strain 13 MIC [mg/L] | strain 14 MIC [mg/L] | strain 15 MIC [mg/L] | strain 16 MIC [mg/L] | strain 17 MIC [mg/L] | strain 18 MIC [mg/L] | strain 19 MIC [mg/L] | strain 20 MIC [mg/L] | strain 21 MIC [mg/L] |
|---|---|---|---|---|---|---|---|---|---|---|
| 1 | | | 16 | | | 0.25 | 16 | 0.25 | 0.25 | 0.25 |
| 2 | ≤0.063 | 0.5 | 16 | 16 | | 0.25 | 32 | 0.125 | 0.125 | 0.25 |
| 3 | 0.125 | 0.5 | 8 | 8 | | 0.25 | 16 | 0.125 | 0.125 | 0.25 |
| 4 | ≤0.063 | ≤0.063 | 16 | 2 | 2 | 0.25 | 8 | 0.125 | 0.25 | 0.25 |
| 5 | 0.25 | 0.5 | 4 | 8 | | 0.5 | 16 | 0.25 | 0.25 | 0.25 |
| 6 | | | 4 | | | 0.25 | 16 | 0.25 | 0.25 | 0.25 |
| 7 | 0.25 | ≤0.063 | 2 | 1 | 2 | 1 | 8 | 0.5 | 1 | 1 |
| 8 | 0.5 | 1 | 8 | 16 | | 4 | | 2 | 4 | 4 |
| 9 | ≤0.063 | 0.25 | 4 | 8 | | 0.25 | 16 | 0.125 | 0.125 | 0.125 |
| 10 | | | 2 | | | 0.5 | | 0.5 | 0.5 | 0.5 |
| 11 | 0.125 | 0.5 | 4 | 8 | | 0.25 | 8 | 0.25 | 0.25 | 0.25 |
| 12 | 0.25 | ≤0.063 | 32 | 8 | 16 | 0.5 | 8 | 0.5 | 0.25 | 0.25 |
| 13 | 0.125 | ≤0.063 | 4 | 4 | 2 | 0.5 | 32 | 0.5 | 0.5 | 0.5 |
| 14 | 0.25 | 0.5 | 8 | 16 | | 1 | 32 | 0.5 | 0.5 | 0.5 |
| 15 | ≤0.063 | ≤0.063 | 2 | 2 | 0.5 | 1 | 8 | 0.5 | 0.5 | 0.5 |
| 16 | 1 | ≤0.063 | | 8 | 4 | 2 | 4 | 1 | 1 | 1 |
| 17 | 2 | 1 | 2 | 4 | | 2 | 32 | 1 | 2 | 2 |
| 18 | 0.5 | 0.5 | 4 | 4 | | 2 | 4 | 2 | 2 | 2 |
| 19 | | | 16 | | | 0.5 | 32 | 0.5 | 1 | 1 |
| 20 | 0.5 | 0.5 | 16 | 16 | | 2 | 32 | 2 | 2 | 1 |
| 21 | 0.25 | 1 | 32 | 32 | | 2 | 16 | 0.5 | 1 | 1 |
| 22 | 0.125 | ≤0.063 | 2 | 4 | 2 | 1 | 8 | 0.5 | 1 | 1 |
| 23 | ≤0.063 | ≤0.063 | 1 | 4 | 2 | 0.25 | 1 | 0.125 | 0.125 | 0.25 |
| 24 | ≤0.063 | ≤0.063 | 2 | 2 | 2 | 0.125 | 2 | 0.125 | 0.25 | 0.5 |
| 25 | ≤0.063 | ≤0.063 | 4 | 2 | 2 | 0.25 | 4 | 0.125 | 0.125 | 0.125 |
| 26A | ≤0.063 | 2 | 32 | 8 | | 0.125 | 32 | ≤0.063 | 0.125 | 0.125 |
| 26B | 2 | | | | | 2 | 32 | 1 | 2 | 2 |
| 27A | ≤0.063 | 0.5 | | 8 | 4 | 0.25 | 8 | 0.25 | 0.25 | 0.25 |
| 27B | 0.25 | 0.5 | | 32 | 32 | 2 | 8 | 1 | 2 | 2 |
| 28 | 0.25 | 0.5 | 2 | 8 | | 0.25 | 32 | 0.25 | 0.25 | 0.25 |
| 29 | | | 4 | | | 0.5 | 8 | 0.5 | 0.5 | 0.5 |
| 30 | 0.25 | 0.5 | 4 | 8 | | 0.25 | 16 | 0.25 | 0.25 | 0.25 |
| 31 | 0.25 | 0.25 | 8 | 4 | | 0.25 | 32 | 0.125 | 0.25 | 0.25 |
| 32 | 0.75 | 0.5 | 8 | 3 | | 2 | 32 | 1 | 2 | 1 |
| 33 | 0.125 | ≤0.063 | 32 | 4 | 2 | 0.5 | 32 | 0.25 | 0.25 | 0.5 |
| 34A | ≤0.063 | 0.5 | | 16 | 2 | 1 | 32 | 0.5 | 0.5 | 0.5 |

TABLE 4-continued

Biological data

```
34B    0.5      8                      32    16    32    4       4       8
35     1        1        32    16            4     32    2       8       4
36A    ≤0.063   0.5            8     2       0.125 8     0.125   ≤0.063  0.125
36B    0.5      4              32    32      4     32    2       2       2
37     0.5      1        4     16            4           2       2       2
38     ≤0.063   ≤0.063   2     4     2       0.25  4     0.125   0.25    0.25
39     0.25     0.25     2     16    8       0.25  4     0.125   0.25    0.25
40     ≤0.063   ≤0.063         4     2       0.25  8     0.125   0.25    0.25
41     ≤0.063   ≤0.063   4     2     1       0.25  8     0.25    0.25    0.25
42     0.25     0.125    16    8     4       1     16    1       1       1
43     0.125    ≤0.063   4     8     2       0.5   8     0.25    0.5     0.5
44A    ≤0.063   0.5      32    8     1       0.125 2     ≤0.063  ≤0.063  ≤0.063
44B    0.5      4                            2     4     2       2       4
45A                      8                   0.5   1     0.5     0.5     0.5
45B    0.5      0.125    16    4     2       4     16    2       4       4
46     0.25     1              32    4       2     16    1       1       1
47     0.125    0.125    1     16    1       0.5   32    0.5     0.5     0.5
48     0.5      1        4     16            2           2       2       2
49     0.5      0.5      16    16            2           2       2       2
50     0.25     1        8     16            1           1       1       1
51     0.5      1        8     16            4           4       4       4
52     8        16       8     32            2           2       2       2
53                       32                  1           1       1       1
54                       2                   0.5   16    0.5     0.25    0.5
55     1        0.125    8     8             1           1       0.5     0.5
56     2        4        8     32            2     32    1       4       4
57     0.125    ≤0.063   4     1     2       2     32    1       1       2
58     0.5      ≤0.063   4     4     4       4     32    2       2       2
59     1        0.5      32    16            2     32    2       2       2
60     1        1        16    16            2     32    2       2       2
61     0.25     ≤0.063   8     8     8       2     8     2       2       2
62     0.25     1        8     16            1     16    1       1       1
63     0.125    0.5      16    16            0.5   8     0.25    0.5     0.5
64     8        32       8                   1     32    1       1       2
65     0.5      1        8     16            1     32    0.5     1       2
66     2        1              16    16      2     4     2       2       2
67     0.5      0.5      4     8             0.5   32    0.5     1       1
68     0.125    0.5      2     8             0.25  16    0.125   0.25    0.25
69     ≤0.063   ≤0.063   4     1     1       0.25  16    0.25    0.25    0.25
70     0.125    0.5      8     16            0.25  16    0.25    0.25    0.25
71     1        0.5            8             8     32    2       4       4
72     0.5      2        16    16            1     32    1       1       1
73     0.25     ≤0.063   32    8     4       1     32    0.5     0.5     1
74     0.25     ≤0.063   32    2     2       4     16    1       1       2
75                       16                  0.5   1     0.25    0.5     0.5
76     0.25     ≤0.063   4     4     2       0.5   8     0.5     0.5     0.5
77                                           0.5   16    1       1       1
78     ≤0.063   ≤0.063   1     4     2       0.5   4     0.25    0.5     0.5
79     ≤0.063   ≤0.063   2     4     2       0.5   8     0.5     0.5     0.5
80                       4                   0.5   16    0.5     0.5     0.5
81A    2        0.25     32    16    8       8     32    8       8       8
81B    2        0.125    32    16    4       4     4     4       4       4
82     ≤0.063   ≤0.063   8     4     4       0.25  8     0.25    0.25    0.5
83     ≤0.063   ≤0.063   2     4     2       0.25  4     0.125   0.25    0.25
84     ≤0.063   ≤0.063   2     4     2       0.125 4     ≤0.063  0.125   0.125
85     ≤0.063   ≤0.063   8     4     4       0.5   8     0.25    0.25    0.5
86     ≤0.063   ≤0.063   4     4     2       0.25  16    0.25    0.25    0.5
87A    0.25     0.5            32    8       2     32    1       1       2
87B    0.125    1              16    16      1     32    0.5     1       2
88     ≤0.063   0.5      32    8     0.5     0.125 2     ≤0.063  ≤0.063  ≤0.063
89     ≤0.063   0.5      32    8     1       0.125 4     ≤0.063  ≤0.063  0.125
90     0.5      0.5            4     16      1     0.5   0.5     0.5     1
91     ≤0.063   ≤0.063   2     4     2       0.125 4     0.125   0.125   0.125
92     0.125    ≤0.063   8     8     2       1     32    0.5     0.5     0.5
93                       32                  0.125 4     0.125   0.125   0.125
94     ≤0.063   0.5      32    8     0.5     0.25  8     0.125   ≤0.063  0.125
95     ≤0.063   0.5            8     2       0.125 4     0.125   ≤0.063  0.125
96     ≤0.063   0.5      32    8     1       0.125 4     ≤0.063  ≤0.063  ≤0.063
97     ≤0.063   0.5      32    4     0.5     0.125 4     ≤0.063  ≤0.063  ≤0.063
98     ≤0.063   0.5      32    8     2       0.125 8     0.125   0.125   0.125
99     ≤0.063   0.5      32    8     0.5     0.25  4     0.125   0.125   0.25
100A   ≤0.063   0.5            8     2       0.25  32    0.125   0.125   0.25
100B                                         4     16    2       2       2
101    ≤0.063   0.5            8     2       0.125 8     ≤0.063  ≤0.063  0.125
102    ≤0.063   0.5            8     2       0.125 4     ≤0.063  ≤0.063  0.125
103    0.25     4              32
104    ≤0.063   1              8             1     32    1       1       1
105
```

TABLE 4-continued

Biological data

| 106 | ≤0.063 | 0.5  |    | 8  | 1     | 0.125 | 8  | 0.125  | ≤0.063 | 0.125  |
|-----|--------|------|----|----|-------|-------|----|--------|--------|--------|
| 107 | ≤0.063 | 0.5  | 32 | 8  | 0.125 | 0.125 | 4  | ≤0.063 | ≤0.063 | ≤0.063 |
| 108 | ≤0.063 | 0.5  | 32 | 8  | 1     | 0.125 | 4  | ≤0.063 | ≤0.063 | 0.125  |
| 109 | ≤0.063 | 0.5  |    | 16 | 4     | 0.125 | 2  | ≤0.063 | 0.25   | 0.125  |
| 110 | ≤0.063 | 0.25 |    | 16 | 8     | 1     | 32 | 0.5    | 0.5    | 0.5    |
| 111 | 0.25   | 2    |    |    |       | 16    | 32 | 8      | 8      | 8      | strain 1   E. coli ATCC25922
strain 2   K. pneumoniae 60
strain 3   E. cloacae 34654
strain 4   C. freundii K21/3034
strain 5   M. morganii I26/3048
strain 6   P. aeruginosa PAO1
strain 7   P. aeruginosa 2297 (AmpC wt)
strain 8   P. aeruginosa 2297-con (AmpC derepressed)
strain 9   A. baumannii ATCC15308
strain 10  S. maltophilia ICB7569
strain 11  M. catarrhalis ICB489
strain 12  H. influenzae ATCC 49247
strain 13  S. pneumoniae 113
strain 14  S. aureus 133
strain 15  B. fragilis 6688
strain 16  C. perfringens DSM756
strain 17  E. coli J62
strain 18  E. coli J62-TEM-3
strain 19  E. coli J62-TEM-3 + 4 µg/mL clavulanic acid
strain 20  E. coli J62-TEM-3 + 4 µg/mL sulbactam
strain 21  E. coli J62-TEM-3 + 4 µg/mL tazobactam Determination of the In-Vivo Activity in Mouse Infection Models Formulations Commercial 10% aqueous mannitol solution was diluted with Aquadest to a 3% aqueous mannitol solution. Compounds of this invention were dissolved at 20-45° C. to form clear application solutions of a concentration in the range from 0.02 mg/mL to 3 mg/mL.

Commercial 10% aqueous mannitol solution was diluted with Aquadest to a 3% aqueous mannitol solution. Solid sodium acetate was added to obtain 2-20 mM sodium acetate solutions in 3% aqueous mannitol. Compounds of this invention were dissolved at 20-45° C. to form clear application solutions of a concentration in the range from 0.02 mg/mL to 3 mg/mL.

Compounds of this invention were dissolved in DMSO at 20-25° C. to form clear stock solutions of a concentration in the range of 60 mg/mL. The stock solutions were diluted with 3% aqueous mannitol solution at 20-25° C. to form clear application solutions of a concentration in the range of 2.1 mg/mL.

Compounds of this invention were dissolved at 20-45° C. in commercial lac-tated Ringer's solution to form clear application solutions of a concentration in the range from 0.02 mg/mL to 3 mg/mL.

Compounds of this invention were dissolved at 20-45° C. in commercial Dulbecco's Phosphate Buffered Saline (DPBS) without calcium and magnesium to form clear application solutions of a concentration in the range from 0.02 mg/mL to 3 mg/mL.

D(+)-Glucose monohydrate was dissolved in Aquadest to a 5% aqueous glucose solution. Compounds of this invention were dissolved at 20-45° C. to form clear application solutions of a concentration in the range from 0.02 mg/mL to 3 mg/mL.

Compounds of this invention were dissolved at 20-45° C. in commercial 0.9% saline to form clear application solutions of a concentration in the range from 0.02 mg/mL to 3 mg/mL.

Peritonitis Models

Female CD-1 mice were infected intraperitoneally with a bacterial inoculum in 5% mucin that led to the death of the untreated group (n=5) within the first 24 hours of the experiment (~$1 \times 10^4$ CFU—$5 \times 10^7$ CFU per mouse depending on the virulence of the strain used). Strains that were used included but were not limited to wild-type E. coli Neu-mann, wild-type P. aeruginosa Walther, wild-type A. baumannii ATCC15308 and resistant K. pneumoniae CL5761 (KPC-3 producer). Mice were treated via intravenous injection 30, 60 and 120 minutes post infection with compounds of this invention (alone or in combination with a -lactamase inhibitor) as well as with control antibiotics including but not limited to meropenem. Lethalities were followed over 5 days and the 100% protective dose (ED100) was determined.

Lung Infection Model

Female BALB/c mice anesthetized with isoflurane and infected intranasally with 32 µL of the bacterial inoculum (e.g. ~$3.5 \times 10^7$ CFU per mouse for P. aeruginosa PAO1). Mice were treated via intravenous injection 30, 60 and 120 minutes post infection with compounds of this invention as well as with control antibiotics including but not limited to meropenem. Animals, including an untreated control group were sacrificed after 24 hours. Lungs were aseptically removed, homogenized, serially diluted and plated onto sheep-blood agar plates to determine CFU counts.

Urinary Tract Infection Model

Female CD-1 mice were given 5% glucose solution as the sole source of drinking water from 16 hours before the experiment to the end. Anesthetized mice were infected via the urethra with an uropathogenic E. coli strain (e.g. E. coli 70430001) in 0.9% NaCl with 0.25% agar-agar in a 25 µL volume (~$5 \times 10^6$ CFU per mouse). Mice were treated via intravenous injection 1, 5, 23, and 30 hours post infection with compounds of this invention as well as with control antibiotics including but not limited to meropenem. Mice, including an untreated control group were sacrificed at 48 hours post infection. Bladders were aseptically removed, homogenized, serially diluted and plated onto Mueller Hinton agar plates to determine CFU counts.

The invention claimed is:
1. A compound which is selected from the compounds of formula (I):

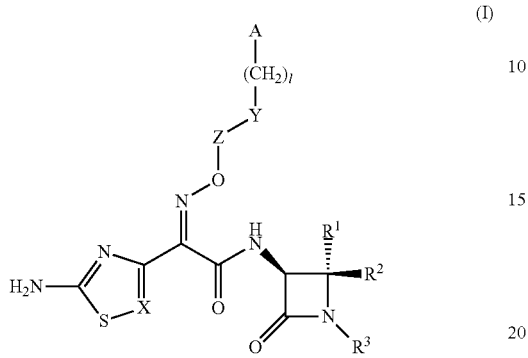

in which
$R^1$ and $R^2$ independently of one another represent hydrogen, aminocarbonyl or $(C_1-C_4)$-alkyl, or
$R^1$ and $R^2$ together with the carbon atom to which they are bonded form a $(C_3-C_8)$-cycloalkyl,
$R^3$ represents $-(CH_2)_m-(SO_2)OH$ or $-O-(CH_2)_o-(SO_2)OH$,
  wherein m and o independently of one another represent an integer 0, 1, 2 or 3, and
  wherein any $CH_2$-group contained in the residues which $R^3$ represents may be substituted with one or two $(C_1-C_4)$-alkyl-residues,
X represents $CR^4$ or N,
$R^4$ represents hydrogen or halogen,
Z represents a bond or an alkyl-chain having one, two, three or four carbon atoms,
  whereby the alkyl-chain may be substituted with one, two, three or four substituents, selected independently of one another from the group consisting of carboxy, aminocarbonyl and $(C_1-C_4)$-alkyl,
    whereby alkyl in turn may be substituted with a substituent selected from the group consisting of hydroxy, carboxy and aminocarbonyl,
Y represents a bond, O, NH or S,
A represents $(C_6-C_{10})$-aryl or 5- to 10-membered heteroaryl,
  whereby aryl and heteroaryl are substituted with a substituent of the following formula

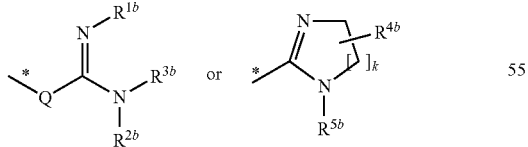

wherein
$R^{1b}$, $R^{2b}$ and $R^{3b}$ independently of one another represent hydrogen, amino, hydroxy, $(C_1-C_4)$-alkyl, $(C_1-C_4)$-alkoxy, $(C_3-C_6)$-cycloalkyl, 4-, 5-6- or 7-membered heterocyclyl or 5- or 6-membered heteroaryl,
  whereby amino and hydroxy may be substituted with one or two substituents selected independently of one another from the group consisting of carbonyl, $(C_1-C_4)$-alkylcarbonyl, mono- or di-$(C_1-C_4)$-alkylaminocarbonyl, and $(C_1-C_4)$-alkyl,
  whereby alkoxy, heterocyclyl and heteroaryl may be substituted with one, two or three substituents selected independently of one another from the group consisting of halogen, hydroxy, amino, carbonyl, carboxy, $(C_1-C_4)$-alkylcarbonyl, $(C_1-C_4)$-alkoxy, mono- or di-$(C_1-C_4)$-alkylamino, mono- or di-$(C_1-C_4)$-alkylaminocarbonyl, $-NH-CH(=NH)$, $-NH-C(=NH)(NH_2)$, $-C(=NH)CH_3$ and $(C_1-C_4)$-alkyl, and
  whereby alkyl and cycloalkyl may be substituted with one, two or three substituents selected independently of one another from the group consisting of halogen, hydroxy, amino, carbonyl, carboxy, carbonyloxy, aminocarbonyl, carbonylamino, $(C_1-C_4)$-alkylcarbonyl, $(C_1-C_4)$-alkoxy, mono- or di-$(C_1-C_4)$-alkylamino, mono- or di-$(C_1-C_4)$-alkylaminocarbonyl, $-NH-CH(=NH)$, $-NH-C(=NH)(NH_2)$, $-CH(=NH)CH_3$, $(C_6-C_{10})$-aryl, 5- or 6-membered heteroaryl and 5- or 6-membered heterocyclyl,
    whereby heteroaryl and heterocyclyl in turn may be substituted with $(C_1-C_4)$-alkyl, and
    whereby amino in turn may be substituted with 5- or 6-membered heteroaryl, or
$R^{2b}$ and $R^{3b}$ together with the nitrogen atom to which they are bonded form a 5- to 7-membered heterocycle including one, two or three further heteroatoms selected from the series N, O and S and $R^{1b}$ is as defined above,
$R^{4b}$ represents hydrogen, amino, hydroxy, $(C_1-C_4)$-alkyl or $(C_1-C_4)$-alkoxy,
  whereby amino and hydroxy may be substituted with one or two substituents selected independently of one another from the group consisting of $(C_1-C_4)$-alkylcarbonyl, mono- or di-$(C_1-C_4)$-alkylaminocarbonyl and $(C_1-C_4)$-alkyl,
  whereby alkoxy may be substituted with one, two or three substituents selected independently of one another from the group consisting of halogen, hydroxy, amino, carbonyl, carboxy, $(C_1-C_4)$-alkylcarbonyl, $(C_1-C_4)$-alkoxy, mono- or di-$(C_1-C_4)$-alkylamino, mono- or di-$(C_1-C_4)$-alkylaminocarbonyl, $-NH-CH(=NH)$, $-NH-C(=NH)(NH_2)$, $-CH(=NH)CH_3$ and $(C_1-C_4)$-alkyl, and
  whereby alkyl may be substituted with one, two or three substituents selected independently of one another from the group consisting of halogen, hydroxy, amino, carbonyl, carboxy, aminocarbonyl, $(C_1-C_4)$-alkylcarbonyl, $(C_1-C_4)$-alkoxy, mono- or di-$(C_1-C_4)$-alkylamino, mono- or di-$(C_1-C_4)$-alkylaminocarbonyl, $-NH-CH(=NH)$, $-NH-C(=NH)(NH_2)$, $-CH(=NH)CH_3$, $(C_1-C_4)$-alkyl, $(C_6-C_{10})$-aryl and 5- or 6-membered heteroaryl,
$R^{5b}$ represents hydrogen or $(C_1-C_4)$-alkyl,
Q represents a bond, $CH_2$ or NH,
k represents an integer 1 or 2, and
* is the linkage site to the residue represented by A, and
whereby aryl and heteroaryl further may be substituted with one or two substituents selected independently of one another from the group consisting of halogen, cyano, amino, hydroxy, $(C_1\text{-}C_4)$-alkyl, $(C_1\text{-}C_4)$-alkoxy, mono- or di-$(C_1\text{-}C_4)$-alkylamino, amino-$(C_1\text{-}C_4)$-alkyl, hydroxy-$(C_1\text{-}C_4)$-alkyl or carboxy, whereby alkyl, alkoxy, alkylamino, aminoalkyl, hydroxyalkyl and carboxy in turn may be substituted with a substituent selected from the group consisting of halogen, $(C_1\text{-}C_4)$-alkyl and carbonyl, and l represents an integer 0, 1, 2 or 3, and the salts thereof, the hydrates thereof and the hydrates of the salts thereof.

2. Compound according to claim 1, characterized in that $R^1$ and $R^2$ independently of one another represent hydrogen or $(C_1\text{-}C_4)$-alkyl, or $R^1$ and $R^2$ together with the carbon atom to which they are bonded form a $(C_3\text{-}C_8)$-cycloalkyl, $R^3$ represents $-(CH_2)_m-(SO_2)OH$ or $-O-(CH_2)_o-(SO_2)OH$, wherein m and o independently of one another represent an integer 0 or 1 and wherein any $CH_2$-group contained in the residues which $R^3$ represents may be substituted with one or two $(C_1\text{-}C_4)$-alkyl-residues, X represents $CR^4$ or N, $R^4$ represents hydrogen or halogen, Z represents a bond or an alkyl-chain having one, two or three carbon atoms, whereby the alkyl-chain may be substituted with one, two or three substituents, selected independently of one another from the group consisting of carboxy, aminocarbonyl and $(C_1\text{-}C_4)$-alkyl, whereby alkyl in turn may be substituted with a substituent selected from the group consisting of hydroxy and carboxy, Y represents a bond, O, NH or S, A represents $(C_6\text{-}C_{10})$-aryl or 5- to 10-membered heteroaryl, whereby aryl and heteroaryl are substituted with a substituent of the following formula

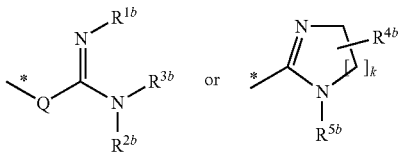

wherein $R^{1b}$, $R^{2b}$ and $R^{33b}$ independently of one another represent hydrogen, amino, hydroxy, $(C_1\text{-}C_4)$-alkyl, 4-, 5-, 6- or 7-membered heterocyclyl or 5- or 6-membered heteroaryl, whereby heterocyclyl and heteroaryl may be substituted with one, two or three substituents selected independently of one another from the group consisting of halogen, hydroxy, amino, carbonyl, carboxy, $(C_1\text{-}C_4)$-alkylcarbonyl, $(C_1\text{-}C_4)$-alkoxy, mono- or di-$(C_1\text{-}C_4)$-alkylamino, mono- or di-$(C_1\text{-}C_4)$-alkylaminocarbonyl, $-NH-CH(=NH)$, $-NH-C(=NH)(NH_2)$, $-C(=NH)CH_3$ and $(C_1\text{-}C_4)$-alkyl, and whereby alkyl may be substituted with one, two or three substituents selected independently of one another from the group consisting of halogen, hydroxy, amino, carbonyl, carboxy, carbonyloxy, aminocarbonyl, carbonylamino, $(C_1\text{-}C_4)$-alkylcarbonyl, $(C_1\text{-}C_4)$-alkoxy, mono- or di-$(C_1\text{-}C_4)$-alkylamino, mono- or di-$(C_1\text{-}C_4)$-alkylaminocarbonyl, $-NH-CH(=NH)$, $-NH-C(=NH)-(NH_2)$, $-CH(=NH)CH_3$, $(C_6\text{-}C_{10})$-aryl, 5- or 6-membered heteroaryl and 5- or 6-membered heterocyclyl, whereby heteroaryl and heterocyclyl in turn may be substituted with $(C_1\text{-}C_4)$-alkyl or $R^{2b}$ and $R^{3b}$ together with the nitrogen atom to which they are bonded form a 5- to 7-membered heterocycle including one, two or three further heteroatoms selected from the series N, O and S and $R^{1b}$ is as defined above, $R^{4b}$ represents hydrogen, amino, hydroxy, $(C_1\text{-}C_4)$-alkyl or $(C_1\text{-}C_4)$-alkoxy, whereby amino and hydroxy may be substituted with one or two substituents selected independently of one another from the group consisting of $(C_1\text{-}C_4)$-alkylcarbonyl, mono- or di-$(C_1\text{-}C_4)$-alkylaminocarbonyl and $(C_1\text{-}C_4)$-alkyl, and whereby alkyl may be substituted with one, two or three substituents selected independently of one another from the group consisting of halogen, hydroxy, amino, carbonyl, carboxy, aminocarbonyl, $(C_1\text{-}C_4)$-alkylcarbonyl, $(C_1\text{-}C_4)$-alkoxy, mono- or di-$(C_1\text{-}C_4)$-alkylamino, mono- or di-$(C_1\text{-}C_4)$-alkylaminocarbonyl, $-NH-CH(=NH)$, $-NH-C(=NH)(NH_2)$, $-CH(=NH)CH_3$, $(C_1\text{-}C_4)$-alkyl, $(C_6\text{-}C_{10})$-aryl and 5- or 6-membered heteroaryl, $R^{5b}$ represents hydrogen or $(C_1\text{-}C_4)$-alkyl, Q represents a bond, $CH_2$ or NH, k represents an integer 1 or 2, and

* is the linkage site to the residue represented by A, and whereby aryl and heteroaryl further may be substituted with one or two substituents selected independently of one another from the group consisting of halogen, cyano, amino, hydroxy, $(C_1\text{-}C_4)$-alkyl, $(C_1\text{-}C_4)$-alkoxy, mono- or di-$(C_1\text{-}C_4)$-alkylamino, amino-$(C_1\text{-}C_4)$-alkyl, hydroxy-$(C_1\text{-}C_4)$-alkyl or carboxy, whereby alkyl, alkoxy, alkylamino, aminoalkyl, hydroxyalkyl and carboxy in turn may be substituted with a substituent selected from the group consisting of halogen, $(C_1\text{-}C_4)$-alkyl and carbonyl, and l represents an integer 0 or 1 and the salts thereof, the hydrates thereof and the hydrates of the salts thereof.

3. Compound according to claim 1, characterized in that $R^1$ and $R^2$ independently of one another represent hydrogen or $(C_1\text{-}C_4)$-alkyl, or $R^1$ and $R^2$ together with the carbon atom to which they are bonded form a $(C_3\text{-}C_8)$-cycloalkyl, $R^3$ represents $-(SO_2)OH$ or $-O-(CH_2)_o-(SO_2)OH$, wherein o is an integer 0 or 1, and wherein any $CH_2$-group contained in the residues which $R^3$ represents may be substituted with one or two $(C_1\text{-}C_4)$-alkyl-residues, X represents CH, Z represents an alkyl-chain having two or three carbon atoms, whereby the alkyl-chain may be substituted with one or two substituents selected independently of one another from the group consisting of carboxy, aminocarbonyl, methyl, hydroxymethyl, hydroxyethyl, Y represents O A represents phenyl or 5- or 6-membered heteroaryl,
whereby phenyl and heteroaryl are substituted with a substituent of the following formula

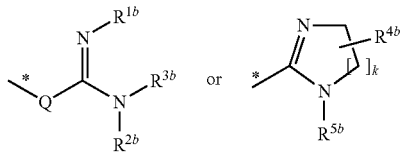

wherein
$R^{1b}$, $R^{2b}$ and $R^{3b}$ independently of one another represent hydrogen, amino, hydroxy, $(C_1-C_4)$-alkyl or 4-, 5-, 6- or 7-membered heterocyclyl,
whereby heterocyclyl may be substituted with one or two substituents selected independently of one another from the group consisting of amino, carboxy, mono- or di-$(C_1-C_4)$-alkylamino, and $(C_1-C_4)$-alkyl, and
whereby alkyl may be substituted with one or two substituents selected independently of one another from the group consisting of hydroxy, amino, carboxy, carbonyloxy, aminocarbonyl, carbonylamino, mono- or di-$(C_1-C_4)$-alkylamino, mono- or di-$(C_1-C_4)$-alkylamino carbonyl, —NH—CH(=NH), —NH—C(=NH)(NH$_2$), phenyl, 6-membered heteroaryl and 5- or 6-membered heterocyclyl, or,
$R^{2b}$ and $R^{3b}$ together with the nitrogen atom to which they are bonded form a 6-membered heterocycle including one or two nitrogen atoms and $R^{1b}$ is hydrogen,
$R^{4b}$ represents hydrogen or amino,
whereby amino may be substituted with one or two $(C_1-C_4)$-alkyl substituents,
$R^{5b}$ represents hydrogen,
Q represents a bond,
k represents an integer 1 or 2, and
* is the linkage site to the residue represented by A, and
whereby phenyl and heteroaryl further may be substituted with one or two substituents selected independently of one another from the group consisting of halogen, cyano, amino, hydroxy, $(C_1-C_4)$-alkyl or hydroxy-$(C_1-C_4)$-alkyl,
whereby hydroxyalkyl in turn may be substituted with a carbonyl substituent, and
l represents 0
and the salts thereof, the hydrates thereof and the hydrates of the salts thereof.

4. Compound according to claim 1, characterized in that
$R^1$ and $R^2$ independently of one another represent hydrogen or methyl,
$R^3$ represents —(SO$_2$)OH or —O—(SO$_2$)OH,
X represents CH,
Z represents an alkyl-chain having two or three carbon atoms,
whereby the alkyl-chain may be substituted with one or two substituents, selected independently of one another from the group consisting of carboxy and methyl, Y represents O,
A represents phenyl or 6-membered heteroaryl,
whereby phenyl and heteroaryl are substituted with a substituent of the following formula

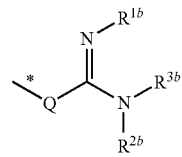

wherein
$R^{1b}$ and $R^{2b}$ represent hydrogen,
$R^{3b}$ represents hydrogen, amino, hydroxy, $(C_1-C_4)$-alkyl or 4-, 5- or 6-membered nitrogen-containing heterocyclyl,
whereby alkyl may be substituted with a substituent selected from the group consisting of hydroxy, amino, carboxy, carbonyloxy, mono- or di-$(C_1-C_4)$-alkylamino, —NH—CH(=NH), —NH—C(=NH)(NH$_2$), 5- or 6-membered nitrogen-containing heteroaryl and 5- or 6-membered nitrogen-containing heterocycl heterocyclyl,
Q represents a bond,
* is the linkage site to the residue represented by A, and
whereby aryl and heteroaryl further may be substituted with one substituent selected from the group consisting of halogen, cyano, amino, hydroxy, $(C_1-C_4)$-alkyl or hydroxy-$(C_1-C_4)$-alkyl, and
l represents 0
and the salts thereof, the hydrates thereof and the hydrates of the salts thereof.

5. Compound according to claim 1, characterized in that
$R^1$ and $R^2$ represent methyl,
$R^3$ represents —O—(SO$_2$)OH,
X represents CH,
Z represents an alkyl-chain having two carbon atoms,
whereby the alkyl-chain may be substituted with a carboxy substituent,
Y represents O,
A represents phenyl substituted with a substituent of the following formula

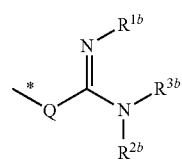

wherein
$R^{1b}$ and $R^{2b}$ represent hydrogen,
$R^{3b}$ represents aminoethyl, azetidine, pyrrolidine or piperidine,
Q represents a bond,
* is the linkage site to the residue represented by A, and
l represents 0
and the salts thereof, the hydrates thereof and the hydrates of the salts thereof.

6. Compound according to claim 1 characterized in that
R¹ and R² represent methyl,
R³ represents —O—(SO₂)OH,
X represents CH,
Z represents a two carbon alkyl-chain, substituted with a carboxy substituent,
Y represents O,
A represents phenyl substituted with a substituent of the following formula

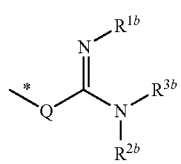

wherein
R$^{1b}$ and R$^{2b}$ represent hydrogen,
R$^{3b}$ represents aminoethyl, azetidine, pyrrolidine or piperidine,
Q represents a bond,
* is the linkage site to the residue represented by A, and
l represents 0
and the salts thereof, the hydrates thereof and the hydrates of the salts thereof.

7. Compound according to claim 1, characterized in that A represents a group selected from the following formulae

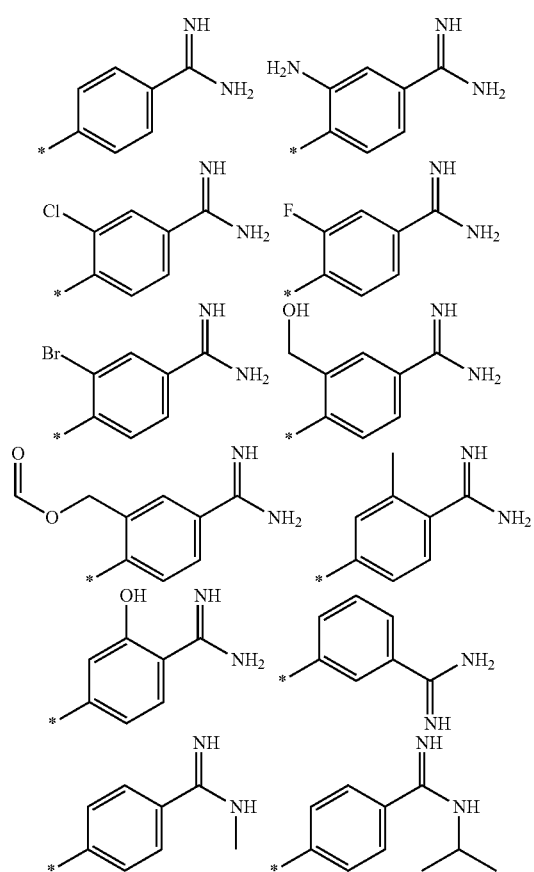

-continued

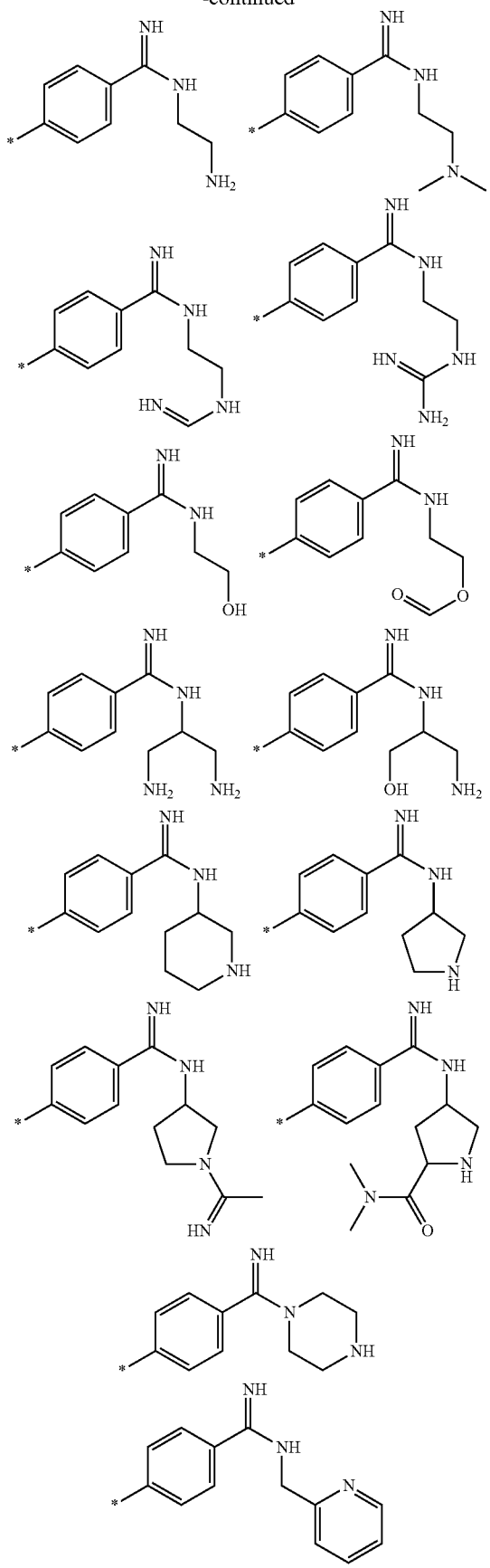

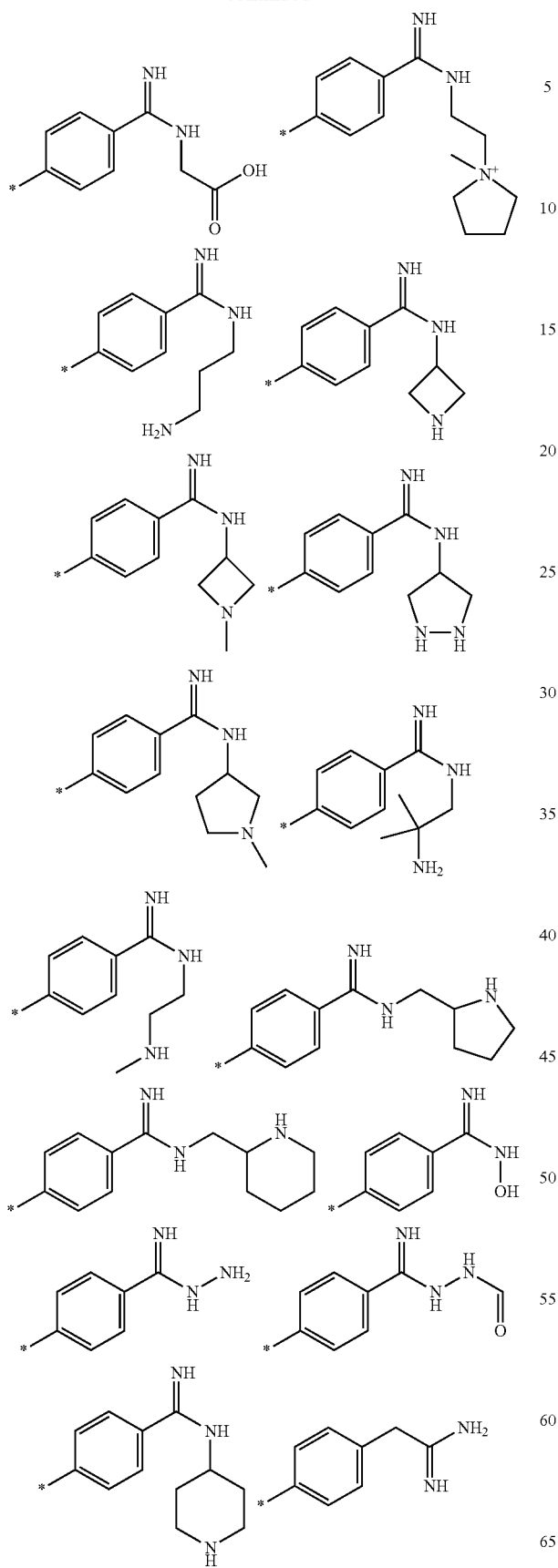
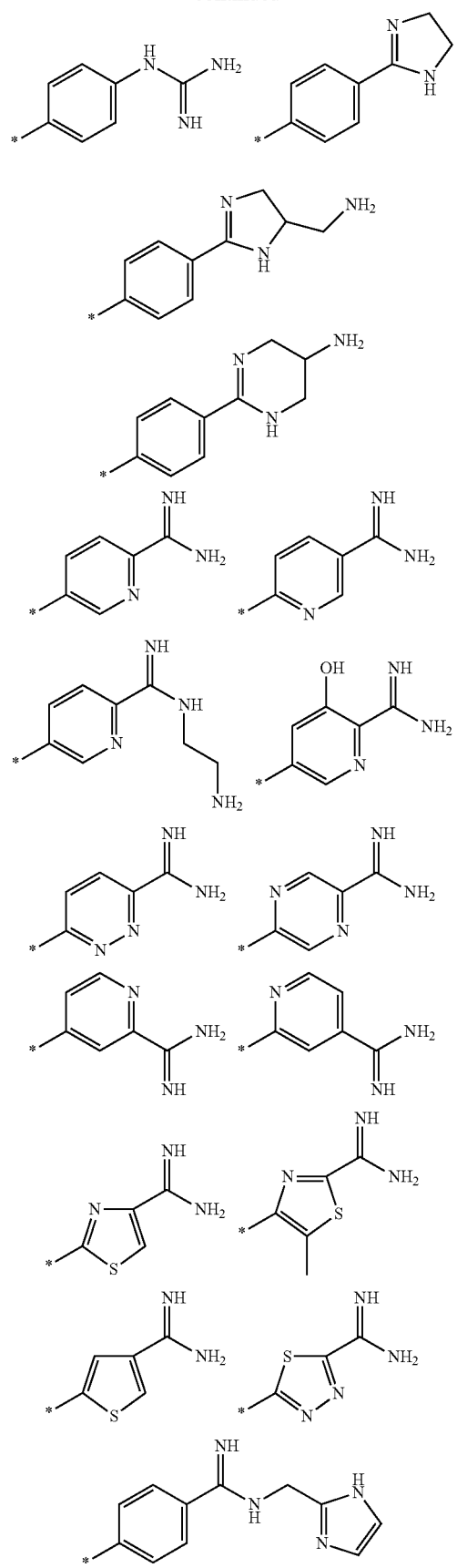

-continued

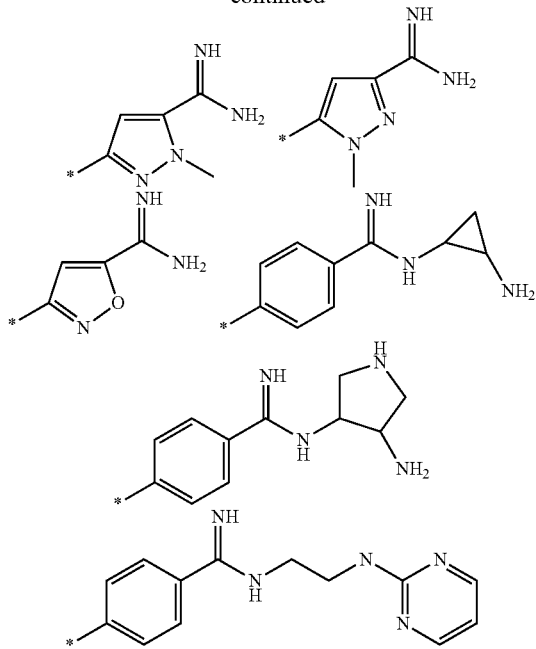

and the salts thereof, the hydrates thereof and the hydrates of the salts thereof.

8. Compound which is selected from:
(2Z)-2-(2-Amino-1,3-thiazol-4-yl)-2-{[2-(4-carbamimidoyl-3-hydroxyphenoxy)-ethoxy]imino}-N-[(3S)-2,2-dimethyl-4-oxo-1-(sulfooxy)azetidin-3-yl]ethanamide
(2S,3S)-3-{[(2Z)-2-(2-Amino-1,3-thiazol-4-yl)-2-{[2-(4-carbamimidoyl-3-hydroxy-phenoxy)ethoxy]imino}acetyl]amino}-2-methyl-4-oxoazetidine-1-sulfonic acid
(2S,3S)-3-{[(2Z)-2-(2-Amino-1,3-thiazol-4-yl)-2-({2-[(6-carbamimidoylpyridin-3-yl)oxy]ethoxy}imino)acetyl]amino}-2-methyl-4-oxoazetidine-1-sulfonic acid
(2Z)-2-(2-Amino-1,3-thiazol-4-yl)-2-({2-[(6-carbamimidoylpyridin-3-yl)oxy]ethoxy}imino)-N-[(3S)-2,2-dimethyl-4-oxo-1-(sulfooxy)azetidin-3-yl]ethanamide
(2S,3S)-3-{[(2Z)-2-(2-Amino-1,3-thiazol-4-yl)-2-({2-[(5-carbamimidoylpyridin-2-yl)oxy]ethoxy}imino)acetyl]amino}-2-methyl-4-oxoazetidine-1-sulfonic acid
(2S,3S)-3-{[(2Z)-2-(2-Amino-1,3-thiazol-4-yl)-2-({2-[(4-carbamimidoylphenyl)-sulfanyl]ethoxy}imino)acetyl]amino}-2-methyl-4-oxoazetidine-1-sulfonic acid
(2Z)-2-(2-Amino-1,3-thiazol-4-yl)-2-({2-[(4-carbamimidoylphenyl)sulfanyl]ethoxy}imino)-N-[(3S)-2,2-dimethyl-4-oxo-1-(sulfooxy)azetidin-3-yl]ethanamide
(2S,3S)-3-{[(2Z)-2-(2-Amino-1,3-thiazol-4-yl)-2-({2-[(4-carbamimidoylphenyl)-amino]ethoxy}imino)acetyl]amino}-2-methyl-4-oxoazetidine-1-sulfonic acid
(2S,3S)-3-{[(2Z)-2-(2-Amino-1,3-thiazol-4-yl)-2-{[2-(4-carbamimidoylphenoxy)-ethoxy]imino}acetyl]amino}-2-methyl-4-oxoazetidine-1-sulfonic acid
(2Z)-2-(2-Amino-1,3-thiazol-4-yl)-2-{[2-(4-carbamimidoylphenoxy)ethoxy]imino}-N-[(2R,3S)-2-methyl-4-oxo-1-(sulfooxy)azetidin-3-yl]ethanamide
(2R,3S)-3-{[(2Z)-2-(2-Amino-1,3-thiazol-4-yl)-2-{[2-(4-carbamimidoylphenoxy)ethoxy]imino}acetyl]amino}-2-methyl-4-oxoazetidine-1-sulfonic acid
{[(2S,3S)-3-{[(2Z)-2-(2-Amino-1,3-thiazol-4-yl)-2-{[2-(4-carbamimidoylphenoxy)-ethoxy]imino}acetyl]amino}-2-methyl-4-oxoazetidin-1-yl]oxy}methanesulfonic acid
(2Z)-2-(2-Amino-1,3-thiazol-4-yl)-2-{[2-(4-carbamimidoyl-3-methylphenoxy)ethoxy]imino}-N-[(3S)-2,2-dimethyl-4-oxo-1-(sulfooxy)azetidin-3-yl]ethanamide
(2S,3S)-3-{[(2Z)-2-(2-Amino-1,3-thiazol-4-yl)-2-{[2-(4-carbamimidoyl-3-methylphenoxy)ethoxy]imino}acetyl]amino}-2-methyl-4-oxoazetidine-1-sulfonic acid
(2Z)-2-(2-Amino-1,3-thiazol-4-yl)-2-({2-[(2-carbamimidoylpyridin-4-yl)oxy]ethoxy}imino)-N-[(3S)-2,2-dimethyl-4-oxo-1-(sulfooxy)azetidin-3-yl]ethanamide
(2Z)-2-(2-Amino-1,3-thiazol-4-yl)-2-{[2-(4-carbamimidoylphenoxy)ethoxy]imino}-N-[2-oxo-1-(sulfooxy)-1-azaspiro[3.4]oct-3-yl]ethanamide
(2S,3S)-3-{[(2Z)-2-(2-Amino-1,3-thiazol-4-yl)-2-{[2-(4-carbamimidoylphenoxy)-2-methylpropoxy]imino}acetyl]amino}-2-methyl-4-oxoazetidine-1-sulfonic acid
(2S,3S)-3-{[(2Z)-2-(2-Amino-1,3-thiazol-4-yl)-2-({[1-(4-carbamimidoylphenoxy)-2-methylpropan-2-yl]oxy}imino)acetyl]amino}-2-methyl-4-oxoazetidine-1-sulfonic acid
(2S,3S)-3-{[(2Z)-2-(2-Amino-1,3-thiazol-4-yl)-2-{[2-(4-carbamimidoyl-2-fluorophenoxy)ethoxy]imino}acetyl]amino}-2-methyl-4-oxoazetidine-1-sulfonic acid
(2S,3S)-3-{[(2Z)-2-(2-Amino-1,3-thiazol-4-yl)-2-{[2-(4-carbamimidoyl-2-chlorophenoxy)ethoxy]imino}acetyl]amino}-2-methyl-4-oxoazetidine-1-sulfonic acid
(2S,3S)-3-{[(2Z)-2-(2-Amino-1,3-thiazol-4-yl)-2-({2-[4-(N-hydroxycarbamimidoyl)-phenoxy]ethoxy}imino)acetyl]amino}-2-methyl-4-oxoazetidine-1-sulfonic acid
(2Z)-2-(2-Amino-1,3-thiazol-4-yl)-2-({2-[(4-carbamimidoylpyridin-2-yl)oxy]ethoxy}imino)-N-[(3S)-2,2-dimethyl-4-oxo-1-(sulfooxy)azetidin-3-yl]ethanamide
(2Z)-2-(2-Amino-1,3-thiazol-4-yl)-N-[(3S)-2,2-dimethyl-4-oxo-1-(sulfooxy)azetidin-3-yl]-2-[(2-{4-[N-(piperidin-4-yl)carbamimidoyl]phenoxy}ethoxy)imino]ethanamide
(2Z)-2-[(2-{4-[N-(2-Aminoethyl)carbamimidoyl]phenoxy}ethoxy)imino]-2-(2-amino-1,3-thiazol-4-yl)-N-[(3S)-2,2-dimethyl-4-oxo-1-(sulfooxy)azetidin-3-yl]ethanamide
(2Z)-2-(2-Amino-1,3-thiazol-4-yl)-2-({2-[4-(4,5-dihydro-1H-imidazol-2-yl)phenoxy]ethoxy}imino)-N-[(3S)-2,2-dimethyl-4-oxo-1-(sulfooxy)azetidin-3-yl]ethanamide
(2S and 2R)-2-({[(1Z)-1-(2-Amino-1,3-thiazol-4-yl)-2-{[(2S,3S)-2-methyl-4-oxo-1-sulfoazetidin-3-yl]amino}-2-oxoethylidene]amino}oxy)-3-(4-carbamidinoyl-phenoxy)propanoic acid
(2S and 2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-carbamimidoyl-phenoxy)propanoic acid
(2S,3S)-3-{[(2Z)-2-(2-Amino-1,3-thiazol-4-yl)-2-({2-[(6-carbamimidoylpyridazin-3-yl)oxy]ethoxy}imino)acetyl]amino}-2-methyl-4-oxoazetidine-1-sulfonic acid
(2Z)-2-(2-Amino-1,3-thiazol-4-yl)-2-({2-[(6-carbamimidoylpyridazin-3-yl)oxy]-ethoxy}imino)-N-[(3S)-2,2-dimethyl-4-oxo-1-(sulfooxy)azetidin-3-yl]ethanamide (2S,3S)-3-{[(2Z)-2-(2-Amino-1,3-thiazol-4-yl)-2-({2-[(5-carbamimidoylpyrazin-2-yl)oxy]ethoxy}imino)acetyl]amino}-2-methyl-4-oxoazetidine-1-sulfonic acid (2S,3S)-3-{[(2Z)-2-(2-Amino-1,3-thiazol-4-yl)-2-({2-[(4-carbamimidoyl-1,3-thiazol-2-yl)oxy]ethoxy}imino)acetyl]amino}-2-methyl-4-oxoazetidine-1-sulfonic acid (2S,3 S)-3-{[(2Z)-2-(2-Amino-1,3-thiazol-4-yl)-2-(2-[(4-carbamimidoylthiophen-2-yl)methoxy]imino)acetyl]amino}-2-methyl-4-oxoazetidine-1-sulfonic acid (2Z)-2-(2-Amino-1,3-thiazol-4-yl)-2-({2-[(6-carbamimidoyl-5-hydroxypyridin-3-yl)oxy]ethoxy}imino)-N-[(3S)-2,2-dimethyl-4-oxo-1-(sulfooxy)azetidin-3-yl]ethanamide (2S and 2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-carbamimidoyl-3-hydroxyphenoxy)propanoic acid (2S,3S)-3-{[(2Z)-2-{[2-(2-Amino-4-carbamimidoylphenoxy)ethoxy]imino}-2-(2-amino-1,3-thiazol-4-yl)acetyl]amino}-2-methyl-4-oxoazetidine-1-sulfonic acid (2S and 2R)-2-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-3-[(6-carbamimidoylpyridin-3-yl)oxy]propanoic acid (2S,3S)-3-{[(2Z)-2-(2-Amino-1,3-thiazol-4-yl)-2-[{3-(4-carbamimidoylphenoxy)-propoxy]imino}-acetyl]-amino}-2-methyl-4-oxoazetidine-1-sulfonic acid (2Z)-2-(2-Amino-1,3-thiazol-4-yl)-N-[(3S)-1-hydroxy-2,2-dimethyl-4-oxoazetidin-3-yl]-2-({2-[4-(N-{2-[(iminomethyl)amino]ethyl}carbamimidoyl)phenoxy]ethoxy}-imino)ethanamide (2Z)-2-(2-Amino-1,3-thiazol-4-yl)-N-[(3S)-2,2-dimethyl-4-oxo-1-(sulfooxy)azetidin-3-yl]-2-{[2-(4-{N-[(3S)-pyrrolidin-3-yl]carbamimidoyl}phenoxy)ethoxy]imino}-ethanamide (2Z)-2-(2-Amino-1,3-thiazol-4-yl)-2-{[2-(4-{N-[2-(dimethylamino)ethyl]-carbamimidoyl}phenoxy)ethoxy]imino}-N-[(3S)-2,2-dimethyl-4-oxo-1-(sulfooxy)azetidin-3-yl]ethanamide (2Z)-2-(2-Amino-1,3-thiazol-4-yl)-2-{[2-(4-carbamimidoylphenoxy)ethoxy]imino}-N-[(3S)-2,2-dimethyl-4-oxo-1-(sulfooxy)azetidin-3-yl]ethanamide (4S)-4-{[{4-[2-({[(1Z)-1-(2-Amino-1,3-thiazol-4-yl)-2-{[(3S)-2,2-dimethyl-4-oxo-1-(sulfooxy)-azet-idin-3-yl]amino}-2-oxo-ethylidene]-amino}-oxy)-ethoxy]-phenyl}-(imino)methyl]amino}-N,N-dimethyl-L-prolinamide (2Z)-2-(2-Amino-1,3-thiazol-4-yl)-N-[(3S)-2,2-dimethyl-4-oxo-1-(sulfooxy)azetidin-3-yl]-2-{[2-(4-{N-[(3S)-1-ethanimidoylpyrrolidin-3-yl]carbamimidoyl}phenoxy)-ethoxy]imino}ethanamide (2R and 2S)-3-{4-[N-(2-Aminoethyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}-oxy)-propanoic acid (2Z)-2-(2-Amino-1,3-thiazol-4-yl)-2-({[(2R and 2S)-1-(4-carbamimidoylphenoxy)-3-hydroxypropan-2-yl]oxy}imino)-N-[(3S)-2,2-dimethyl-4-oxo-1-(sulfooxy)azetidin-3-yl]ethanamide 3-({[(1Z)-1-(2-Amino-1,3-thiazol-4-yl)-2-{[(3S)-2,2-dimethyl-4-oxo-1-(sulfooxy)-azetidin-3-yl]amino}-2-oxoethylidene]amino}oxy)-4-(4-carbamimidoylphenoxy)butanoic acid (2Z)-2-(2-Amino-1,3-thiazol-4-yl)-2-{[2-(4-carbamimidoylphenoxy)ethoxy]imino}-N-[(2S,3S)-2-methyl-4-oxo-1-(sulfooxy)azetidin-3-yl]ethanamide (2R,3S)-3-{[(2Z)-2-(2-Amino-1,3-thiazol-4-yl)-2-{[3-(4-carbamimidoylphenoxy)-propoxy]imino}acetyl]amino}-2-methyl-4-oxoazetidine-1-sulfonic acid (2S,3S)-3-{[(2Z)-2-(2-Amino-1,3-thiazol-4-yl)-2-{[2-(2-bromo-4-carbamimidoylphenoxy)ethoxy]imino}acetyl]amino}-2-methyl-4-oxoazetidine-1-sulfonic acid (2S,3S)-3-{[(2Z)-2-(2-Amino-1,3-thiazol-4-yl)-2-{[2-(4-carbamimidamidophenoxy)-ethoxy]imino}acetyl]amino}-2-methyl-4-oxoazetidine-1-sulfonic acid (2S,3S)-3-{[(2Z)-2-(2-Amino-1,3-thiazol-4-yl)-2-{[3-(4-carbamimidamidophenoxy)-propoxy]imino}acetyl]amino}-2-methyl-4-oxoazetidine-1-sulfonic acid (2Z)-2-(5-Amino-1,2,4-thiadiazol-3-yl)-2-{[2-(4-carbamimidoylphenoxy)ethoxy]-imino}-N-[(2S,3S)-1-hydroxy-2-methyl-4-oxoazetidin-3-yl]ethanamide (2S,3S)-3-{[(2Z)-2-(2-Amino-1,3-thiazol-4-yl)-2-{[2-(3-carbamimidoylphenoxy)-ethoxy]imino}acetyl]amino}-2-methyl-4-oxoazetidine-1-sulfonic acid (2S,3S)-3-({(2Z)-2-(2-Amino-1,3-thiazol-4-yl)-2-[(2-{4-[N-(propan-2-yl)carbamimidoyl]phenoxy}ethoxy)imino]acetyl}amino)-2-methyl-4-oxoazetidine-1-sulfonic acid (2S,3S)-3-{[(2Z)-2-(2-Amino-1,3-thiazol-4-yl)-2-{[(4-carbamimidoylbenzyl)oxy]-imino}acetyl]amino}-2-methyl-4-oxoazetidine-1-sulfonic acid (2S,3S)-3-{[(2Z)-2-(2-Amino-1,3-thiazol-4-yl)-2-({2-[(4-carbamimidoylthiophen-2-yl)methoxy]ethoxy}imino)acetyl]amino}-2-methyl-4-oxoazetidine-1-sulfonic acid (2Z)-2-(2-Amino-1,3-thiazol-4-yl)-2-{[(4-carbamimidoylbenzyl)oxy]imino}-N-[(3S)-2,2-dimethyl-4-oxo-1-(sulfooxy)azetidin-3-yl]ethanamide (2Z)-2-(2-Amino-1,3-thiazol-4-yl)-2-{[3-(4-carbamimidoylphenoxy)propoxy]imino}-N-[(3S)-2,2-dimethyl-4-oxo-1-(sulfooxy)azetidin-3-yl]ethanamide (2S,3S)-3-{[(2Z)-2-(2-Amino-1,3-thiazol-4-yl)-2-({2-[4-carbamimidoyl-2-(hydroxy-methyl)phenoxy]ethoxy}imino)acetyl]amino}-2-methyl-4-oxoazetidine-1-sulfonic acid (2S,3S)-3-({(2Z)-2-(2-Amino-1,3-thiazol-4-yl)-2-[(2-{4-carbamimidoyl-2-[(formyloxy)methyl]phenoxy}ethoxy)imino]acetyl}amino)-2-methyl-4-oxoazetidine-1-sulfonic acid (2S,3S)-3-{[(2Z)-2-(2-Amino-5-chloro-1,3-thiazol-4-yl)-2-{[2-(4-carbamimidoylphenoxy)ethoxy]imino}acetyl]amino}-2-methyl-4-oxoazetidine-1-sulfonic acid (2S,3 S)-3-{[(2Z)-2-({2-[4-(2-Amino-2-iminoethyl)phenoxy]ethoxy}imino)-2-(2-amino-1,3-thiazol-4-yl)acetyl]amino}-2-methyl-4-oxoazetidine-1-sulfonic acid (2S,3S)-3-({(2Z)-2-(2-Amino-1,3-thiazol-4-yl)-2-[(2-{4-[(2-formylhydrazinyl)-(imino)methyl]phenoxy}ethoxy)imino]acetyl}amino)-2-methyl-4-oxoazetidine-1-sulfonic acid (2S,3 S)-3-({(2Z)-2-(2-Amino-1,3-thiazol-4-yl)-2-[(2-{4-[hydrazinyl(imino)methyl]-phenoxy}ethoxy)imino]acetyl}amino)-2-methyl-4-oxoazetidine-1-sulfonic acid (2S,3S)-3-{[(2Z)-2-(2-Amino-1,3-thiazol-4-yl)-2-({2-[(5-carbamimidoyl-1,3,4-thiadiazol-2-yl)oxy]ethoxy}imino)acetyl]amino}-2-methyl-4-oxoazetidine-1-sulfonic acid (2S,3S)-3-{[(2Z)-2-(2-Amino-1,3-thiazol-4-yl)-2-{[2-(4-carbamimidoylphenoxy)ethoxy]imino}acetyl]amino}-2-carbamoyl-4-oxoazetidine-1-sulfonic acid (2S,3S)-3-{[(2Z)-2-(2-Amino-1,3-thiazol-4-yl)-2-({2-[(3-carbamimidoyl-1,2-oxazol-5-yl)oxy]ethoxy}imino)acetyl]amino}-2-methyl-4-oxoazetidine-1-sulfonic acid (2S,3S)-3-{[(2Z)-2-(2-Amino-1,3-thiazol-4-yl)-2-({2-[4-(N-methylcarbamimidoyl)phenoxy]ethoxy}imino)acetyl]amino}-2-methyl-4-oxoazetidine-1-sulfonic acid (2S,3S)-3-({(2Z)-2-(2-Amino-1,3-thiazol-4-yl)-2-[(2-{4-[N-(2-hydroxyethyl)carbamimidoyl]phenoxy}ethoxy)imino]acetyl}amino)-2-methyl-4-oxoazetidine-1-sulfonic acid (2S,3S)-3-{[(2Z)-2-(2-Amino-1,3-thiazol-4-yl)-2-{[2-(4-{N-[2-(formyloxy)ethyl]-carbamidoyl}phenoxy)ethoxy]imino}acetyl]amino}-2-methyl-4-oxoazetidine-1-sulfonic acid (2S,3S)-3-{[(2Z)-2-(2-Amino-1,3-thiazol-4-yl)-2-({2-[(3-carbamimidoyl-1-methyl-1H-pyrazol-5-yl)oxy]ethoxy}imino)acetyl]amino}-2-methyl-4-oxoazetidine-1-sulfonic acid (2S,3S)-3-{[(2Z)-2-(2-Amino-1,3-thiazol-4-yl)-2-({2-[(5-carbamimidoyl-1-methyl-1H-pyrazol-3-yl)oxy]ethoxy}imino)acetyl]amino}-2-methyl-4-oxoazetidine-1-sulfonic acid N-[{4-[2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)ethoxy]phenyl}(imino)methyl]glycine (2Z)-2-(2-Amino-1,3-thiazol-4-yl)-2-({2-[(2-carbamimidoyl-5-methyl-1,3-thiazol-4-yl)oxy]ethoxy}imino)-N-[(3S)-2,2-dimethyl-4-oxo-1-(sulfooxy)azetidin-3-yl]ethanamide 2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-carbamimidoylphenoxy)propanamide (2Z)-2-(2-Amino-1,3-thiazol-4-yl)-N-[(3S)-2,2-dimethyl-4-oxo-1-(sulfooxy)azetidin-3-yl]-2-[(2-{4-[N-(pyridin-2-ylmethyl)carbamimidoyl]phenoxy}ethoxy)imino]ethanamide {[(2S,3S)-3-{[(2Z)-2-[(2-{4-[N-(2-Aminoethyl)carbamimidoyl]phenoxy}ethoxy)imino]-2-(2-amino-1,3-thiazol-4-yl)acetyl]amino}-2-methyl-4-oxoazetidin-1-yl]oxy}methanesulfonic acid (2Z)-2-(2-Amino-1,3-thiazol-4-yl)-2-[(2-{4-[N-(2-carbamimidamidoethyl)-carbamimidoyl]phenoxy}ethoxy)imino]-N-[(3S)-2,2-dimethyl-4-oxo-1-(sulfooxy)azetidin-3-yl]ethanamide 1-(2-{[{4-[2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)ethoxy]phenyl}(imino)-methyl]amino}ethyl)-1-methylpyrrolidinium chloride (2Z)-2-(2-Amino-1,3-thiazol-4-yl)-N-[(3S)-2,2-dimethyl-4-oxo-1-(sulfooxy)azetidin-3-yl]-2-[(2-{4-[imino(piperazin-1-yl)methyl]phenoxy}ethoxy)imino]ethanamide (2Z)-2-(2-Amino-1,3-thiazol-4-yl)-2-({[1-(4-carbamimidoylphenoxy)-(2R and 2S)-4-hydroxybutan-2-yl]oxy}imino)-N-[(3S)-2,2-dimethyl-4-oxo-1-(sulfooxy)azetidin-3-yl]ethanamide (2Z)-2-{[2-({6-[N-(2-Aminoethyl)carbamimidoyl]pyridin-3-yl}oxy)ethoxy]imino}-2-(2-amino-1,3-thiazol-4-yl)-N-[(3S)-2,2-dimethyl-4-oxo-1-(sulfooxy)azetidin-3-yl]ethanamide (2Z)-2-[(2-{4-[N-(3-Aminopropyl)carbamimidoyl]phenoxy}ethoxy)imino]-2-(2-amino-1,3-thiazol-4-yl)-N-[(3S)-2,2-dimethyl-4-oxo-1-(sulfooxy)azetidin-3-yl]ethanamide (2Z)-2-(2-Amino-1,3-thiazol-4-yl)-2-[(2-{4-[N-(1,3-diaminopropan-2-yl)carbamimidoyl]phenoxy}ethoxy)imino]-N-[(3S)-2,2-dimethyl-4-oxo-1-(sulfooxy)azetidin-3-yl]ethanamide (2Z)-2-{[2-(4-{N-[(2R)-1-Amino-3-hydroxypropan-2-yl]carbamimidoyl}phenoxy)-ethoxy]imino}-2-(2-amino-1,3-thiazol-4-yl)-N-[(3S)-2,2-dimethyl-4-oxo-1-(sulfooxy)azetidin-3-yl]ethanamide (2Z)-2-({2-[4-(5-Amino-1,4,5,6-tetrahydropyrimidin-2-yl)phenoxy]ethoxy}imino)-2-(2-amino-1,3-thiazol-4-yl)-N-[(3S)-2,2-dimethyl-4-oxo-1-(sulfooxy)azetidin-3-yl]-ethanamide (2R and 2S) 3-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-2-(4-carbamimidoyl-phenoxy)propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[(3R)-piperidin-3-yl]carbamimidoyl}phenoxy)propanoic acid (2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[(3R)-piperidin-3-yl]carbamimidoyl}phenoxy)propanoic acid {[(3S)-3-{[(2Z)-2-(2-Amino-1,3-thiazol-4-yl)-2-{[(4-carbamimidoylbenzyl)oxy]imino}acetyl]amino}-2,2-dimethyl-4-oxoazetidin-1-yl]oxy}methanesulfonic acid (2Z)-2-[(2-{4-[5-(Aminomethyl)-4,5-dihydro-1H-imidazol-2-yl]phenoxy}ethoxy)-imino]-2-(2-amino-1,3-thiazol-4-yl)-N-[(3S)-2,2-dimethyl-4-oxo-1-(sulfooxy)azetidin-3-yl]ethanamide (3S)-3-({(2Z)-2-(2-Amino-1,3-thiazol-4-yl)-2-[(2-{4-[N-(pyrazolidin-4-yl)carbamimidoyl]phenoxy}ethoxy)imino]acetyl}amino)-2,2-dimethyl-4-oxoazetidine-1-sulfonic acid (2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3S)-pyrrolidin-3-yl]carbamimidoyl}phenoxy)propanoic acid (2S)-3-{4-[N-(2-Amino-2-methylpropyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[2-(methylamino)ethyl]carbamimidoyl}phenoxy)propanoic acid (2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3R)-pyrrolidin-3-yl]carbamimidoyl}phenoxy)propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(piperidin-3-yl)carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(pyrrolidin-2-ylmethyl)carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(piperidin-2-ylmethyl)carbamimidoyl]phenoxy}propanoic acid (2S)-3-{4-[N-(trans-(R,R and S,S)-2-Aminocyclopropyl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid (2S)-2-({[(1Z)-1-(2-Amino-1,3-thiazol-4-yl)-2-{[(3S)-2,2-dimethyl-4-oxo-1-sulfoazetidin-3-yl]amino}-2-oxoethylidene]amino}oxy)-3-(4-{N-[(3S)-1-methylpyrrolidin-3-yl]carbamimidoyl}-phenoxy)-propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1,3-diaminopropan-2-yl)carbamimidoyl]phenoxy}propanoic acid (2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1,3-diaminopropan-2-yl)carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1H-imidazol-2-ylmethyl)carbamimidoyl]phenoxy}propanoic acid (2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(1H-imidazol-2-ylmethyl)carbamimidoyl]phenoxy}propanoic acid (2S)-3-{4-[N-(4-Aminopyrrolidin-3-yl)carbamimidoyl]phenoxy}-2-({[(1Z)-1-(2-amino-1,3-thiazol-4-yl)-2-{[(3S)-2,2-dimethyl-4-oxo-1-(sulfooxy)azetidin-3-yl]amino}-2-oxoethylidene]amino}oxy)propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(azetidin-3-yl)-carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(piperidin-4-yl)carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-{4-[N-(azetidin-3-yl)carbamimidoyl]phenoxy}propanoic acid (2S)-2-({[(1Z)-1-(2-Amino-1,3-thiazol-4-yl)-2-{[(3S)-2,2-dimethyl-4-oxo-1-(sulfo-oxy)azetidin-3-yl]amino}-2-oxoethylidene]amino}oxy)-3-(4-{N-[2-(pyrimidin-2-ylamino)ethyl]carbamimidoyl}phenoxy)propanoic acid (2R)-2-({[(1Z)-1-(2-Amino-1,3-thiazol-4-yl)-2-{[(3S)-2,2-dimethyl-4-oxo-1-(sulfooxy)azetidin-3-yl]amino}-2-oxoethylidene]amino}oxy)-3-(4-{N-[2-(pyrimidin-2-ylamino)ethyl]carbamimidoyl}phenoxy)propanoic acid and the salts thereof, the hydrates thereof and the hydrates of the salts thereof.

9. A method for treating a bacterial infection in a human or animal comprising administering an antibacterially effective amount of at least one compound according to claim 1 to the human or animal.

10. Method for the preparation of a compound of formula (I) according to claim 1 comprising removing the protecting group from a compound of formula

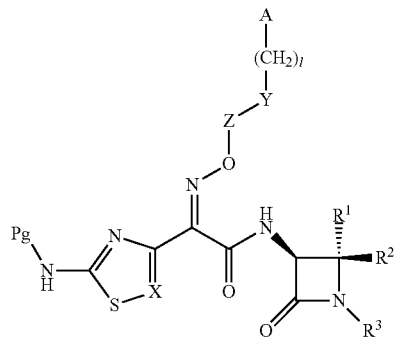

in which Pg represents a protecting group and $R^1$-$R^3$, A, l, X, Y and Z are as defined in claim 1.

11. Method according to claim 10, characterized in that compound (II) is prepared by reacting a compound of formula

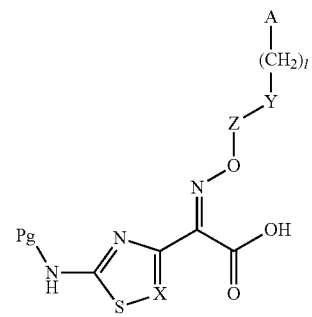

in which Pg represents a protecting group, with a compound of formula

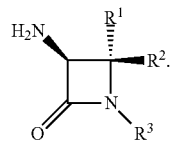

12. A composition comprising at least one compound according to claim 1 in combination with at least one further active compound.

13. A composition according to claim 12, characterized in that the further active compound is a β-lactamase inhibitor.

14. A composition comprising at least one compound according to claim 1 in combination with at least one inert, non-toxic, pharmaceutically acceptable excipient.

15. A method for treating a bacterial infection in a human or animal comprising administering an antibacterially effective amount of at least one medicament composition according to claim 12 to the human or animal.

16. A method for treating a bacterial infection in a human or animal comprising administering an antibacterially effective amount of at least one medicament composition according to claim 13 to the human or animal.

17. The method of claim 9, wherein the bacterial infection is a gram-negative bacterial infection.

* * * * *